(12) United States Patent
Chander

(10) Patent No.: US 11,007,528 B2
(45) Date of Patent: May 18, 2021

(54) SYSTEMS, METHODS AND DEVICES FOR MEASURING GROWTH/ONCOGENIC AND MIGRATION/METASTATIC POTENTIAL

(71) Applicant: CELLANYX DIAGNOSTICS, LLC, Beverly, MA (US)

(72) Inventor: Ashok C. Chander, Boston, MA (US)

(73) Assignee: CELLANYX DIAGNOSTICS, LLC, Beverly, MA (US)

(*) Notice: Subject to any disclaimer, the term of this patent is extended or adjusted under 35 U.S.C. 154(b) by 71 days.

(21) Appl. No.: 15/629,639

(22) Filed: Jun. 21, 2017

(65) Prior Publication Data

US 2019/0255526 A1 Aug. 22, 2019
US 2020/0276584 A9 Sep. 3, 2020

Related U.S. Application Data

(63) Continuation of application No. 13/878,080, filed as application No. PCT/US2011/055444 on Oct. 7, 2011, now abandoned.

(Continued)

(51) Int. Cl.
*G01N 33/50* (2006.01)
*B01L 3/00* (2006.01)
(Continued)

(52) U.S. Cl.
CPC ... *B01L 3/502761* (2013.01); *B01L 3/502746* (2013.01); *C12M 41/14* (2013.01);
(Continued)

(58) Field of Classification Search
CPC ............... C12N 2503/02; C12M 41/46; G01N 33/5091
See application file for complete search history.

(56) References Cited

U.S. PATENT DOCUMENTS 5,840,507 A 11/1998 Fruehauf
7,101,976 B1 9/2006 Kilpatrick et al.
(Continued)

FOREIGN PATENT DOCUMENTS

WO 2009005770 A1 1/2009
WO 2009032164 A1 3/2009

OTHER PUBLICATIONS

Albini, A., "Tumor and endothelial cell invasion of Basement membranes. The matrigel chemoinvasion assay as a tool for dissecting molecular mechanisms," Pathology Oncology Research, 1998, vol. 4, pp. 230-241.

(Continued)

*Primary Examiner* — Jonathan M Hurst
(74) *Attorney, Agent, or Firm* — Rimôn, P.C.

(57) ABSTRACT

Systems, methods, and devices for determining various properties of cells are provided herein. In one aspect, the method includes measuring one or more variables based on physical and/or chemical characteristics of a cell or its environment. The method further includes calculating one or more quantifiable metrics based on a mathematical expression including one or more of the variables, where those metrics correlate with at least one of the growth characteristics of the cell, the motility characteristics of the cell, the oncogenic potential of the cell, or the metastatic potential of the cell. Various aspects of systems and devices for determining various properties of cells are also provided herein.

2 Claims, 73 Drawing Sheets

Related U.S. Application Data

(60) Provisional application No. 61/391,340, filed on Oct. 8, 2010.

(51) Int. Cl.
    *G01N 33/574*    (2006.01)
    *G01N 33/49*     (2006.01)
    *C12M 1/00*     (2006.01)

(52) U.S. Cl.
    CPC ....... *G01N 33/492* (2013.01); *G01N 33/5091* (2013.01); *G01N 33/574* (2013.01); *B01L 2300/087* (2013.01); *B01L 2300/089* (2013.01); *B01L 2300/0819* (2013.01); *B01L 2300/0893* (2013.01); *B01L 2300/16* (2013.01)

(56) References Cited

U.S. PATENT DOCUMENTS

| | | |
|---|---|---|
| 7,160,687 B1 | 1/2007 | Kapur et al. |
| 8,012,744 B2 | 9/2011 | Gibbons et al. |
| 8,372,629 B2 | 2/2013 | Southern et al. |
| 8,790,891 B2 | 7/2014 | Irimia |
| 2003/0206901 A1 | 11/2003 | Chen |
| 2005/0019798 A1 | 1/2005 | Kattan |
| 2005/0244843 A1 | 11/2005 | Chen et al. |
| 2006/0083720 A1 | 4/2006 | Fraser et al. |
| 2006/0134599 A1 | 6/2006 | Toner et al. |
| 2006/0270032 A1 | 11/2006 | Bhatia et al. |
| 2007/0059718 A1 | 3/2007 | Toner et al. |
| 2007/0092876 A1 | 4/2007 | Xu |
| 2008/0039419 A1 | 2/2008 | Dedhar et al. |
| 2008/0166804 A1 | 7/2008 | Shamblott et al. |
| 2009/0061422 A1 | 3/2009 | Linke et al. |
| 2009/0269767 A1 | 10/2009 | Soderlund et al. |
| 2010/0022626 A1 | 1/2010 | Geiger et al. |
| 2010/0304485 A1 | 12/2010 | Karnik et al. |
| 2011/0003324 A1 | 1/2011 | Durack |
| 2012/0094325 A1* | 4/2012 | Irimia ............... B01L 3/502746 435/34 |

OTHER PUBLICATIONS

Lo C-N. et al., "Cell movement is guided by the rigidity of the substrate," Biophysical Journal, 2000, vol. 79, pp. 144-152.

Wozniak et al., Focal Adhesion Regulation of Cell Behavior, Biochimica et Biophysica Acta, 2004, 1692, 103-109.

Mei Y et al, "Gradient substrate assembly for quantifying cellular response to biomaterials", Journal of Biomedical Materials Research Part A, 2006, vol. 79A, pp. 974-988.

Alovskaya et al., Fibronectin, Collagen, Fibrin—Components of Extracellular Matrix for Nerve Regeneration, Chapter 12, Topics in Tissue Engineering, N Ashammakhi, ed., 2007, 3, 1-27.

Alexandrova et al., Comparative Dymanics of Retrograde Actin Flow and Focal Adhesions: Formation of Nascent Adhesions Triggers Transition From Fast to Slow Flow, PLoS One, 2008, 3(9), 1-9.

Gardel et al., Traction Stress in Focal Adhesions Correlates Biphasicaly With Actin Regrograde Flow Speed, J. Cell Biol., 2008, 183(6), 999-1005.

Mori et al., Anchorage-Independent Cell Growth Signature Identified Tumors with Metastatic Potential, Oncogene, 2009, 28, 2796-2805.

Cai K. et al., "Regulation of endothelial cells migration on poly (d, l-lactic acid) films immobilized with collagen gradients," colloids and surfaces. B, Biointerfaces, 2010, vol. 79, pp. 291-297.

Aratyn-Schaus et al., Transient Frictional Slip Between Integrin and the ECM in Focal Adhesions Under Myosin II Tension, Current Biology, 2010, 20, 1145-1153.

Deer et al., Phenotype and Genotype of Pancreatic Cancer Cell Lines, Pancreas, 2010, 39(4), 425-435.

Kraning-Rush et al., Cellular Traction Stresses Increase With Increasing Metastatic Potential, PLoS One, 2012, 7(2), 1-10.

Chander, Ashok; Integrin-Linked Kinase, ECM Composition and Substrate Rigidity Regulate Focal Adhesion-Actin Coupling, Modulating Survival, Proliferation and Migration: Towards a Biophysical Cancer Biomaker, Dissertation, Columbia University, 2012, 1-329.

International Search Report dated Jun. 10, 2013, in related International Patent Application No. PCT/US2011/055444.

* cited by examiner

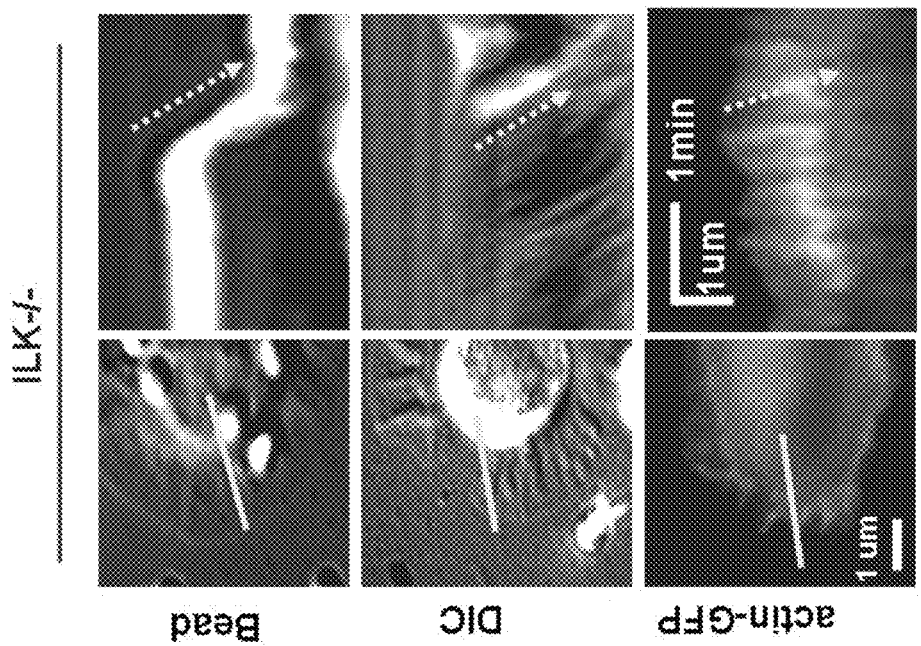
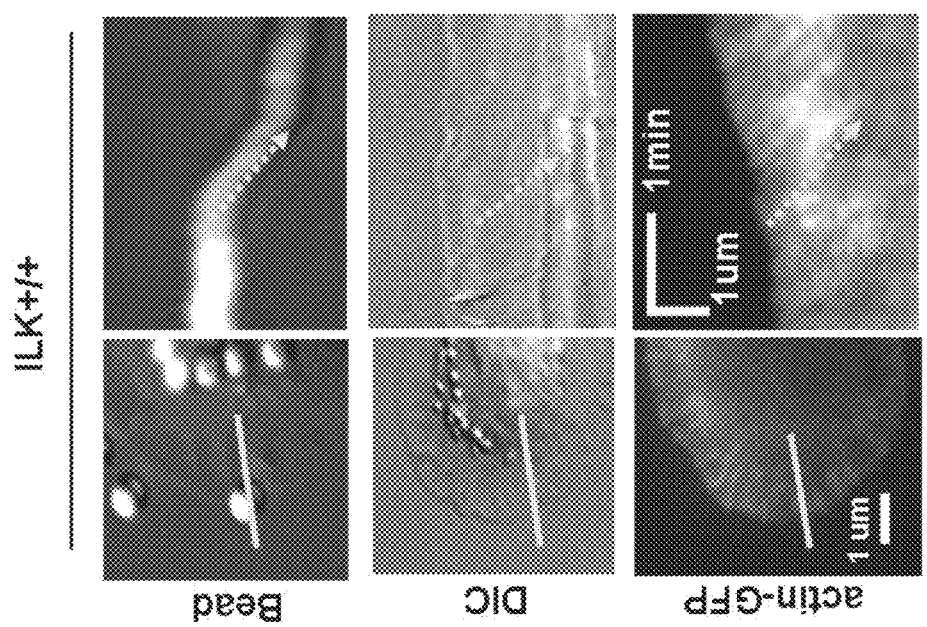
FIG. 2A
FIG. 2B

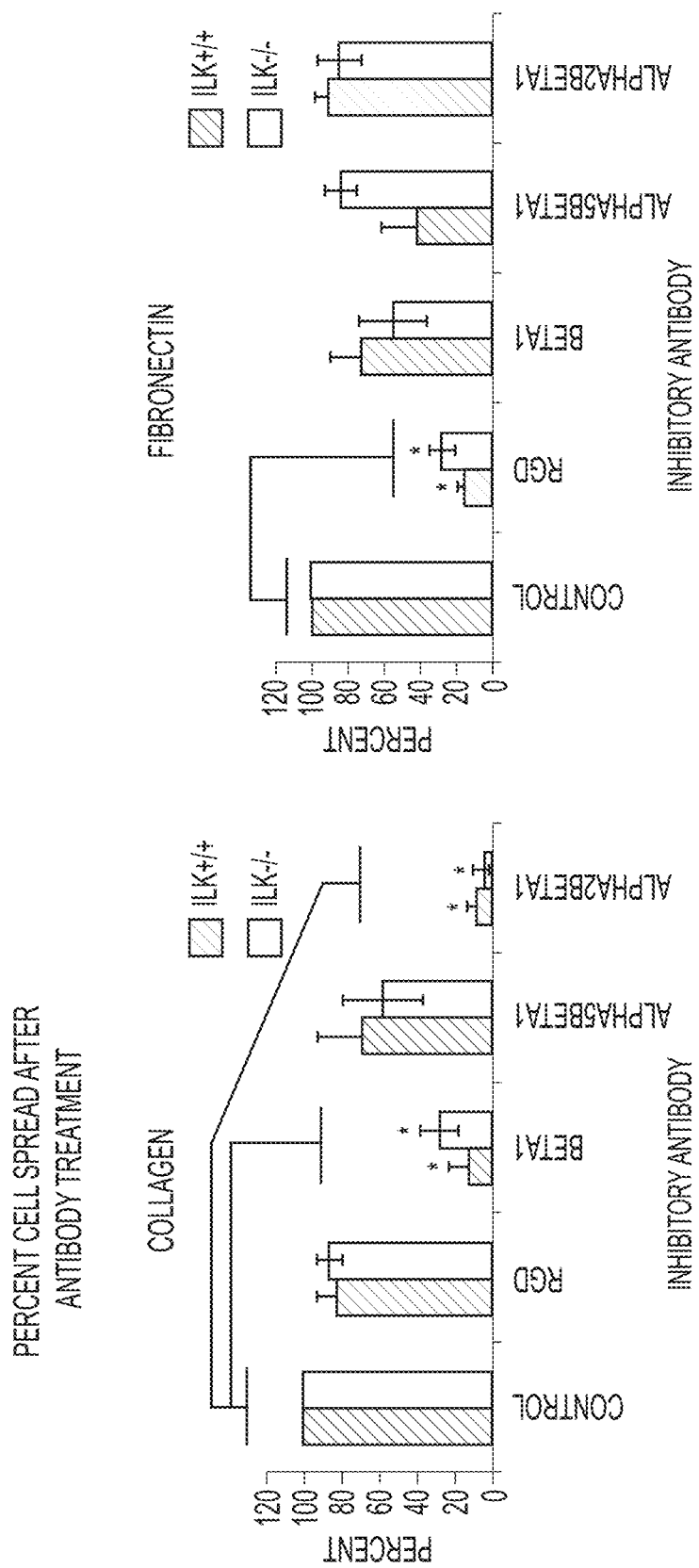

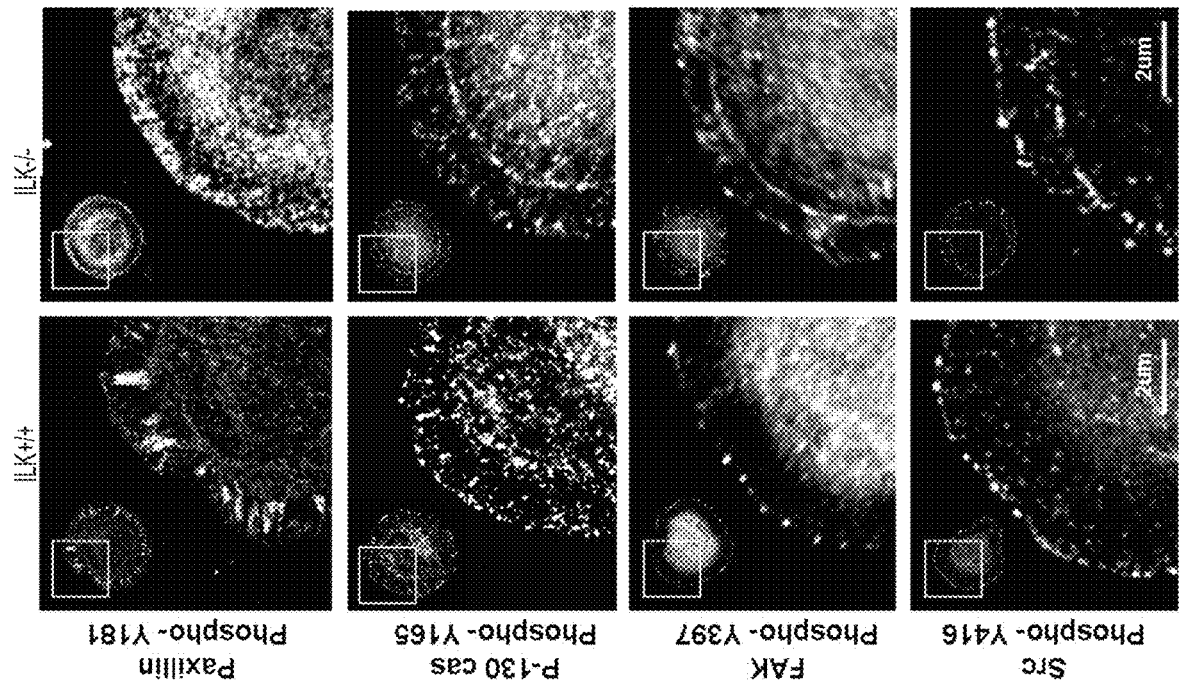
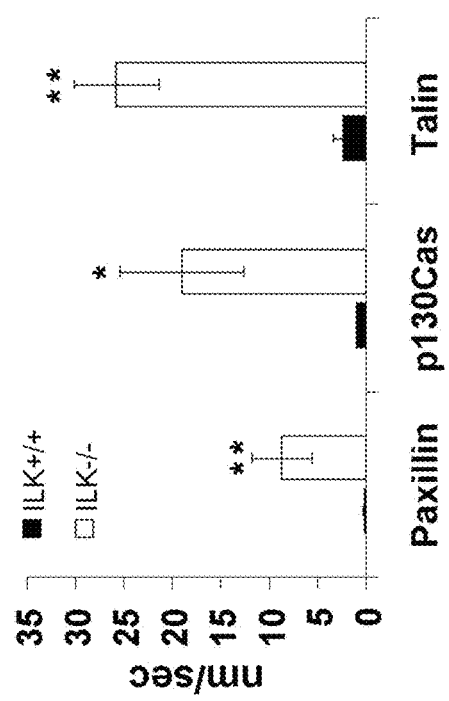
FIG. 4D
FIG. 4E

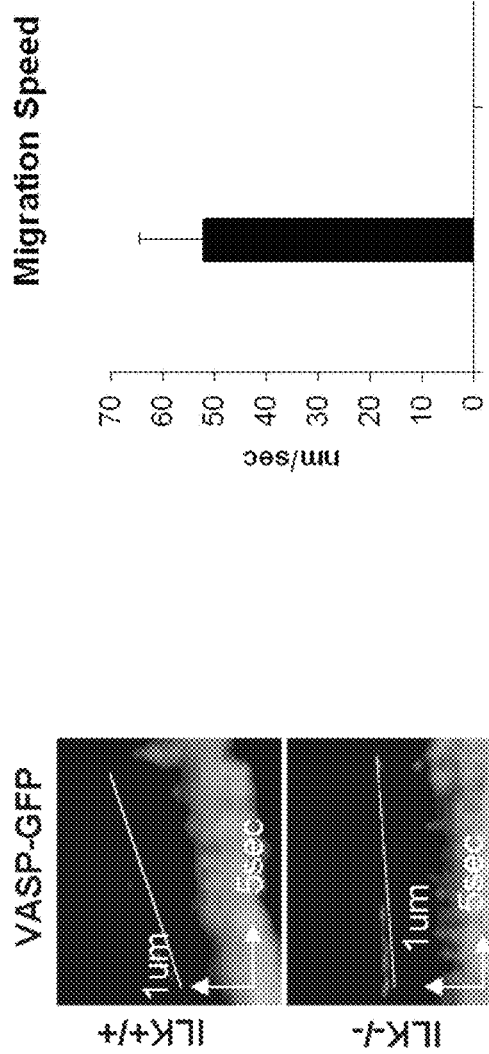
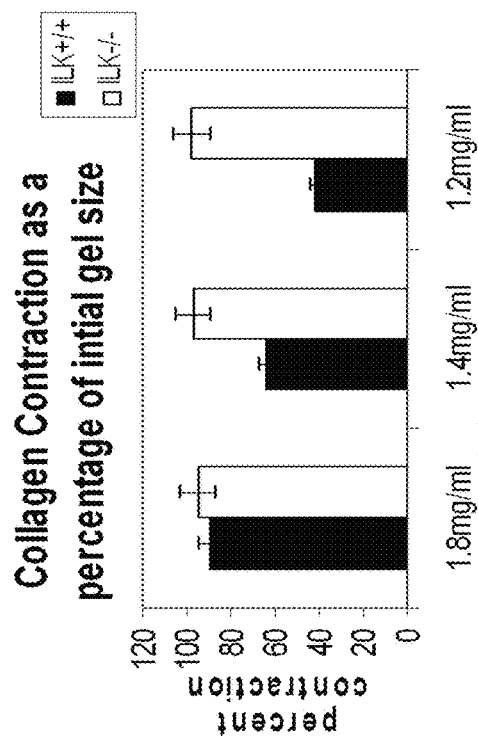
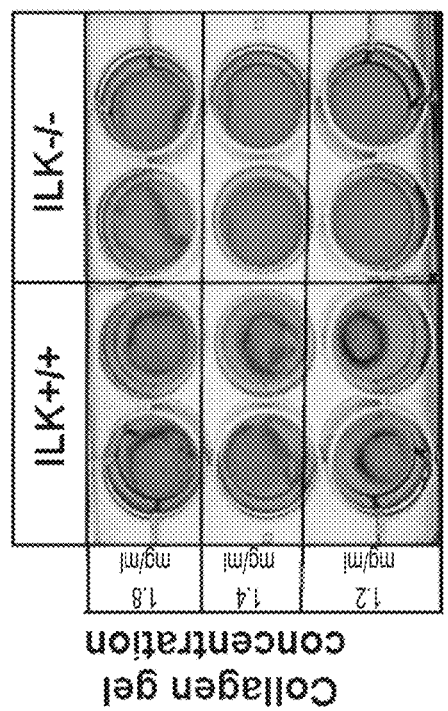
FIG. 5A  FIG. 5B  FIG. 5C  FIG. 5D

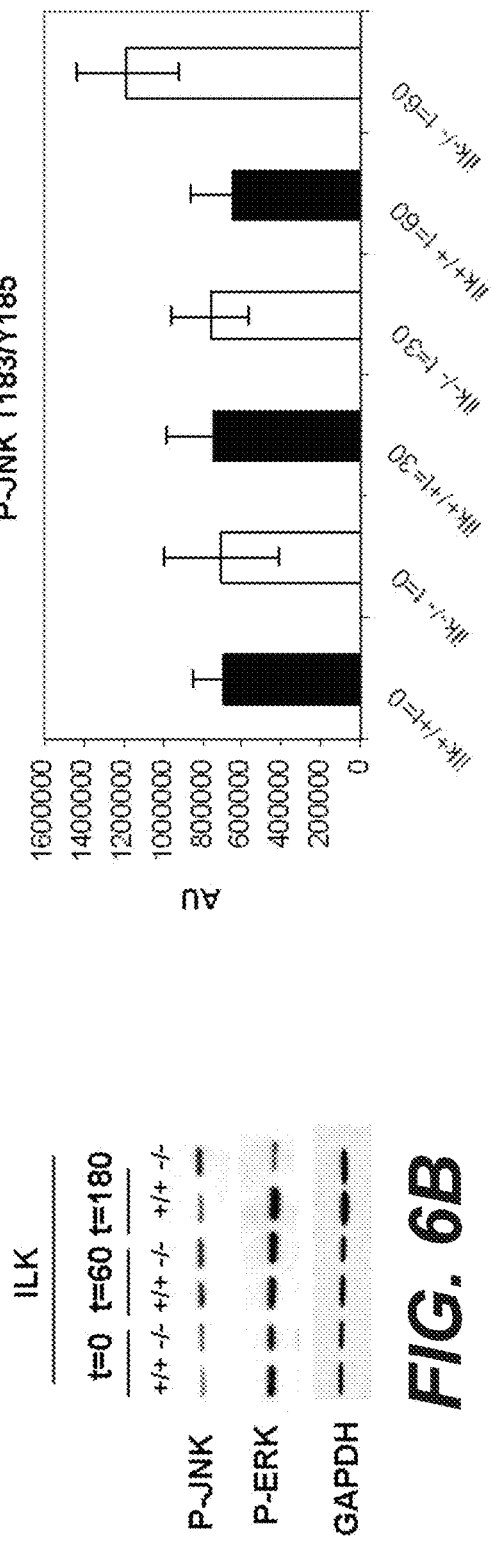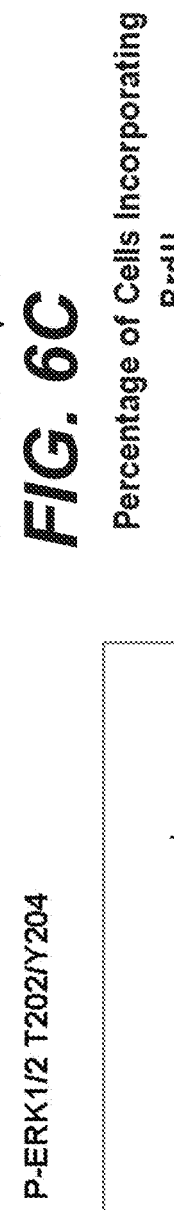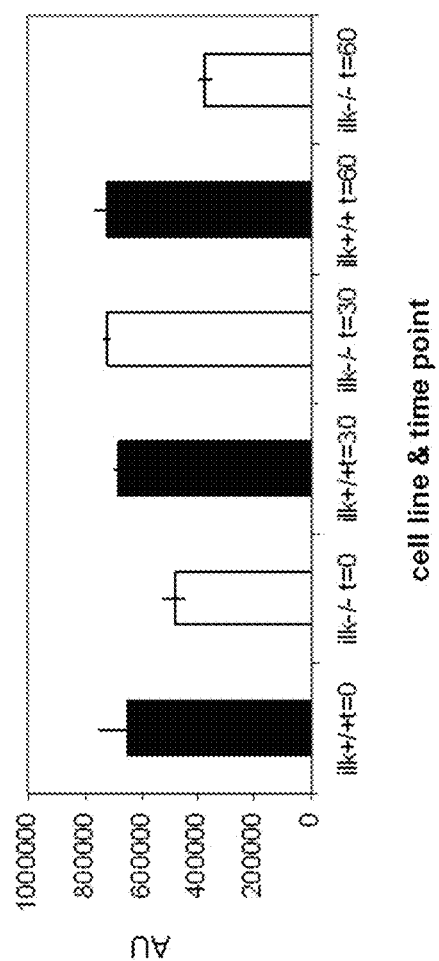

MEF Knockout Screen

Ratios of Collagen & Fibronectin Needed for Spreading

| Collagen : Fibronectin | Total # of Proteins (10^16) | C:F Ratio | C:Total Ratio | F:Total Ratio | Cell Area /100 |
|---|---|---|---|---|---|
| 1ug:1ug | 3.505 | 1.56 | 0.61 | 0.39 | 1.68 |
| 1ug:5ug | 8.977 | 0.312 | 0.24 | 0.76 | 1.75 |
| 5ug:1ug | 12.053 | 7.811 | 0.89 | 0.11 | 1.54 |
| 5ug:5ug | 17.525 | 1.562 | 0.6 | 0.4 | 1.83 |
| 5ug:10ug | 24.365 | 0.78 | 0.44 | 0.56 | 1.74 |
| 10ug:5ug | 26.978 | 2.94 | 0.75 | 0.25 | 5.78 |
| 10ug:10ug | 33.817 | 1.47 | 0.6 | 0.4 | 5.19 |

FIG. 22E

SYSTEMS, METHODS AND DEVICES FOR MEASURING GROWTH/ONCOGENIC AND MIGRATION/METASTATIC POTENTIAL

RELATED APPLICATION

This application claims priority to U.S. Provisional Application No. 61/391,340, filed Oct. 8, 2010, which is incorporated herein by reference in its entirety.

FIELD

The systems, methods, and devices provided herein relate to the field of medical testing/diagnostics, cell-based assays, and compound discovery, in particular the determination of the growth, and/or oncogenic potential, migration rate, and/or metastatic potential of cells obtained from mammalian cells or patient's cells respectively.

BACKGROUND

Prognosis and lifestyle of diagnosed cancer patients can be improved. Mortality rates for heart disease, influenza, and cancer have decreased in the past 25 years 30%, 50%, and 16% respectively. That is to say, much more progress has been made in treating other acute/chronic diseases than cancer. This fact may be a result of the complex nature of cancer, as well as the current treatment methods. In 2009 there were approximately 1.4 million cancer cases in the United States, with the probability of 1 in 2 men eventually developing cancer and 1 in 3 women developing cancer in their lifetime. The expected survival rate for those diagnosed with cancer is 60%.

Currently, once cancer is detected, the practicing physician starts the process of 'cancer staging.' Cancer staging describes the extent of the disease at the time of diagnosis and offers very little, if any, information about how the cancer is likely to progress or any specific indication about the optimal treatment strategies. Currently there are two main types of cancer staging. The first is known as the TNM staging system, in which the physician qualitatively judges the extent of primary tumor (T), assesses the absence or presence of regional lymph nodes (N), and finally explores via surgery or scanning methods the absence or presence of distant metastasis (M).

The second staging method is termed "in situ, local, regional and distant" and is also largely a descriptive, qualitative staging technique. This technique uses the following criteria: if cancer cells are present only in the layer of cells where they developed and have not spread then the cancer is termed "in situ;" if they have spread to other parts of the body the cancer is termed "invasive." The practicing physician utilizes a number of surgical and imaging, techniques to determine whether "in situ" or "invasive" should be applied to the patient's biopsy.

These existing methods for cancer staging are qualitative and therefore limited in applicability. For example, diagnoses made by different physicians or of different patients using the existing methods can be difficult to compare in a meaningful manner due to the subjective nature of these methods. The subjectivity of the existing methods of cancer staging often results in overly aggressive treatment strategies. For example, in the absence of better data, the most drastic, potentially invasive, strategy is often recommended, which can lead to overtreatment, poor patient quality of life, and increased medical costs.

Accordingly, there remains a need for systems, methods, and devices for determining the growth, and/or oncogenic, migration rate, and/or metastatic potential of cells obtained from a patient to better characterize the aggressiveness of a given cancer.

SUMMARY

The systems, methods, and devices disclosed herein generally involve determining the growth, and/or oncogenic, migration rate, and/or metastatic potential of cells obtained from a patient to better characterize the aggressiveness of a given cancer. A determination of these characteristics can, among other things, aid in the discovery of therapeutics that alter and/or perturb a cells characteristics that engender its cancer-like, or oncogenic and metastatic phenotype.

In aspects of the invention, cellular samples, and/or biopsy tissue can be used to provide quantitative metrics that correlate with the malignant and/or metastatic potential of the tissue. In such aspects, these metrics can facilitate treatment decision steps taken by a physician after patients present with symptoms of cancer.

For example, quantitative prognostic metrics according to aspects of the invention can improve the accuracy of diagnosis by supplementing a physician's decision-making process with clinical data to support the available treatment options. As a result, embodiments of the invention can provide numerous advantages, for example, reduced healthcare costs, reduced risk associated with treatment, improved patient quality of life, and increased patient survival.

As will be described in more detail below, one aspect of the invention provides a diagnostic chip or device including microfluidic channels and a substrate to culture any mammalian cell, for example, cells obtained from a patient. For example, the cells can be obtained by a biopsy or any other means. In related aspects, the chip can be analyzed using a light/fluorescent microscope. In other aspects, a suite of biomarkers is provided that can be used to characterize biopsy tissue. These biomarkers are sensitive, robust, functional, and easily quantifiable using the diagnostic chip or device. In another aspect, interpretation software is provided to acquire images from the device and measure biomarkers. For example, microscope images can be uploaded and analyzed using image acquisition software, measurements based on biomarkers can be quantified from image sequences and built-in algorithms can use the measurements taken as input values to return a quantitative prediction, or metric, of a cell and/or the biopsy tissue's oncogenic and metastatic potential with its resultant confidence interval.

In related aspects, an information database of derived metrics from biopsy samples, associated treatment regimes and patient outcomes can be built. This information database can be mined and used as a knowledge database to provide another level of prognostic accuracy.

In another aspect, the systems, methods and devices of the invention can be used as a cell-based assay. In some embodiments, lead compounds that slow or impede the growth and metastatic capabilities of epithelial cancer cells and other disease states such as cardiac hypertrophy can be analyzed and studied. Thus, the biomarkers, algorithm and metrics according to embodiments of the invention can identify compounds that modulate metastasis and growth, which can lead to treatments for epithelial born cancers and other diseases involving fibroblasts and extracellular matrix (ECM) maintenance.

In one aspect, the invention provides a method for determining a property of a cell. The cell can be of any cell type.

For example, the cell can be a cancer cell, a heart cell, a kidney cell, a lung cell, a pancreatic cell, a brain cell, a skin cell, a prostate cell, a breast cell, or any cell derived from a tissue biopsy. In some embodiments, the method can include obtaining a matrix material capable of receiving a cell and disposing at least one cell on the matrix material. The matrix material can be any suitable material for culturing the cell. For example, the matrix can include one or more proteins, peptides, or chemicals, such as fibronectin, collagen type I, laminin, vitronectin, and collagen type IV, or any combinations thereof. In other embodiments, the method can include culturing a cell on a matrix, homogenizing a cell, imaging a cell in a tissue or biopsy sample, or imaging a cell in vivo. However, one of skill in the art will appreciate that any means of measuring the variables discussed below can be used in the disclosed methods.

In an exemplary embodiment, the method includes measuring one or more variables related to the physical characteristics of the cell, the physical characteristics of an environment surrounding the cell, the chemical characteristics of the cell or the chemical characteristics of an environment surrounding the cell. These variables can be used in mathematical expressions to determine and/or predict one or more of a growth rate, migration rate, oncogenic potential, or metastatic potential of the cell. In some embodiments, a single variable, or a mathematical relationship involving that single variable can be used to make such a determination or prediction. In other embodiments, any number of variables can be used in combination to make the determination or prediction of, for example, one or more of a growth rate, migration rate, oncogenic potential, or metastatic potential of the cell.

For example, the one or more variables can include a focal adhesion size, actin retrograde flow speed within the cell, a force generated by the cell, a cell area, a migration velocity of the cell, a polarization time of the cell, a endocytic rate of the cell, a exocytic rate of the cell, a nucleus/cell area, a microtubule density, a kinesin velocity, a focal adhesion retrograde flow speed or combinations thereof. In some embodiments, the one or more variables can include a proliferation indicator average, a metabolic indicator average, an ILK expression level, a Western titrated average of P-FAK (Y397), a Western titrated average of P-PAX (S181), a Western titrated average of P-p130Cas (Y165), a Western titrated average of a protein of interest, a Micron Scale ELISA average of a protein of interest, NFkappaB transcription average, a Ratio of Tyrosine Phosphorylated Adhesion Kinase to Focal Adhesion Phosphatase, an ECM Composition of Dissassociated Tissue, an Immuno-stain of Phospho-Protein, am mRNA Localization Intensity, a Ratio of NFKappaB transcription factor and p53 activation state, a Ratio of STAT transcription factor and p53 activation state or combinations thereof.

The method further includes calculating one or more quantifiable metrics based on a mathematical expression or relationship that includes one or more of the variables. For example, the quantifiable metrics that can be calculated based on mathematical expressions including one or more of the variables can correlate with at least one of the growth characteristics of the cell, the motility characteristics of the cell, the oncogenic potential of the cell, or the metastatic potential of the cell.

In an exemplary embodiment, the one or more variables can include a focal adhesion size of the cell and a retrograde flow speed of the cell. One or more of the quantifiable metrics can then include a ratio of the focal adhesion size to the retrograde flow speed. For example, the ratio of the focal adhesion size to the retrograde flow speed can correlate with at least one of the growth characteristics of the cell, the motility characteristics of the cell, the oncogenic potential of the cell, or the metastatic potential of the cell. For another example, the ratio of the focal adhesion size to the retrograde flow speed can be proportional to other ones of said one or more variables such that a mathematical expression including one or more of those variables and the ratio of the focal adhesion size to the retrograde flow speed can correlate with at least one of the growth characteristics of the cell, the motility characteristics of the cell, the oncogenic potential of the cell, or the metastatic potential of the cell.

In another exemplary embodiment, the one or more variables can include a force generated by the at least one cell, a focal adhesion size of the at least one cell, and a retrograde flow speed of the at least one cell. In such an embodiment, the force generated by the cell can be proportional to the ratio of the focal adhesion size to the retrograde flow speed. The force generated by the cell can, for example, correlate with at least one of the growth characteristics of the cell, the motility characteristics of the cell, the oncogenic potential of the cell, or the metastatic potential of the cell. In other aspects, the invention provides a system for determining a property of a cell.

The system includes a microfluidic device including a plurality of cell culture locations and a detection device configured to measure one or more properties of a cell cultured on one of the plurality of cell culture locations. For example, the properties can include the physical characteristics of a cell, the physical characteristics of an environment surrounding a cell, the chemical characteristics of a cell, or the chemical characteristics of an environment surrounding a cell. In some embodiments, the microfluidic device can include a plurality of geometric sites arranged across a substrate in a defined pattern. For example, each site can be dimensioned and configured to culture one or more cells. In some embodiments, the plurality of geometric sites can be arranged in an array.

In some embodiments, the plurality of geometric sites can include at least one first site having a first diameter and a first height corresponding to a first rigidity and at least one second site having a second diameter and a second height corresponding to a second rigidity. For example, any of the diameter, height and rigidity of the first site can be any of greater than, less than or the same as any of the diameter, height and rigidity of the second site. In some embodiments, the plurality of geometric sites can include at least one first site having a first extracellular matrix coating and at least one second site having a second extracellular matrix coating. For example, the first and second extracellular matrix coatings can provide different cell culture conditions.

These and other embodiments, features and advantages will become apparent to those skilled in the art when taken with reference to the following more detailed description of various exemplary embodiments of the invention in conjunction with the accompanying drawings that are first briefly described.

(C) Coating the softest gels that stay solid (below 0.01% Bis, gels become fluid) with 10 ug/ml collagen+fibronectin rescues spreading. (D) Titration of collagen and fibronectin show that a minimum of 10 ug/ml collagen to 5 ug/ml fibronectin is needed to rescue spreading on soft surfaces. (Ratios are Collagen:Fibronectin). (E) Titrating collagen and fibronectin identify a minimum total number of molecules as well suggests an optimal ratio of collagen to fibronectin to rescue spreading on soft surfaces and culture primary cells in vitro. This data is important in understanding how to prepare and coat the device as to optimize the ability to culture cancer biopsies, explants in vitro.

Figure 23:
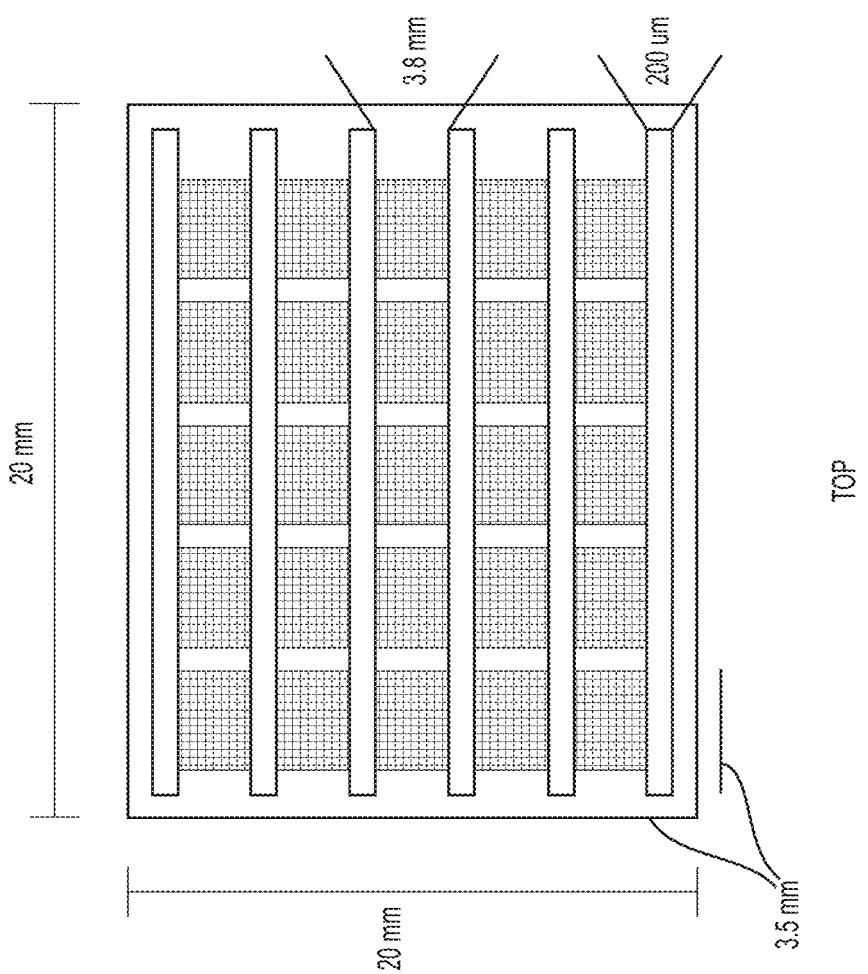

FIG. 23. Top view of an example general schematic of PDMS, or similar moldable, imprintalbe polymer, chip that details the overall dimensions of the chip and general design. The chip is composed of a 5×5 matrix of 3.5 mm×3.5 mm surfaces, here after termed substrates, that can be fabricated with different micron-sub micron features allowing for cancer cells extracted from a biopsy/explant to adhere, spread, proliferate and allow for measurements to be made.

Figure 24:
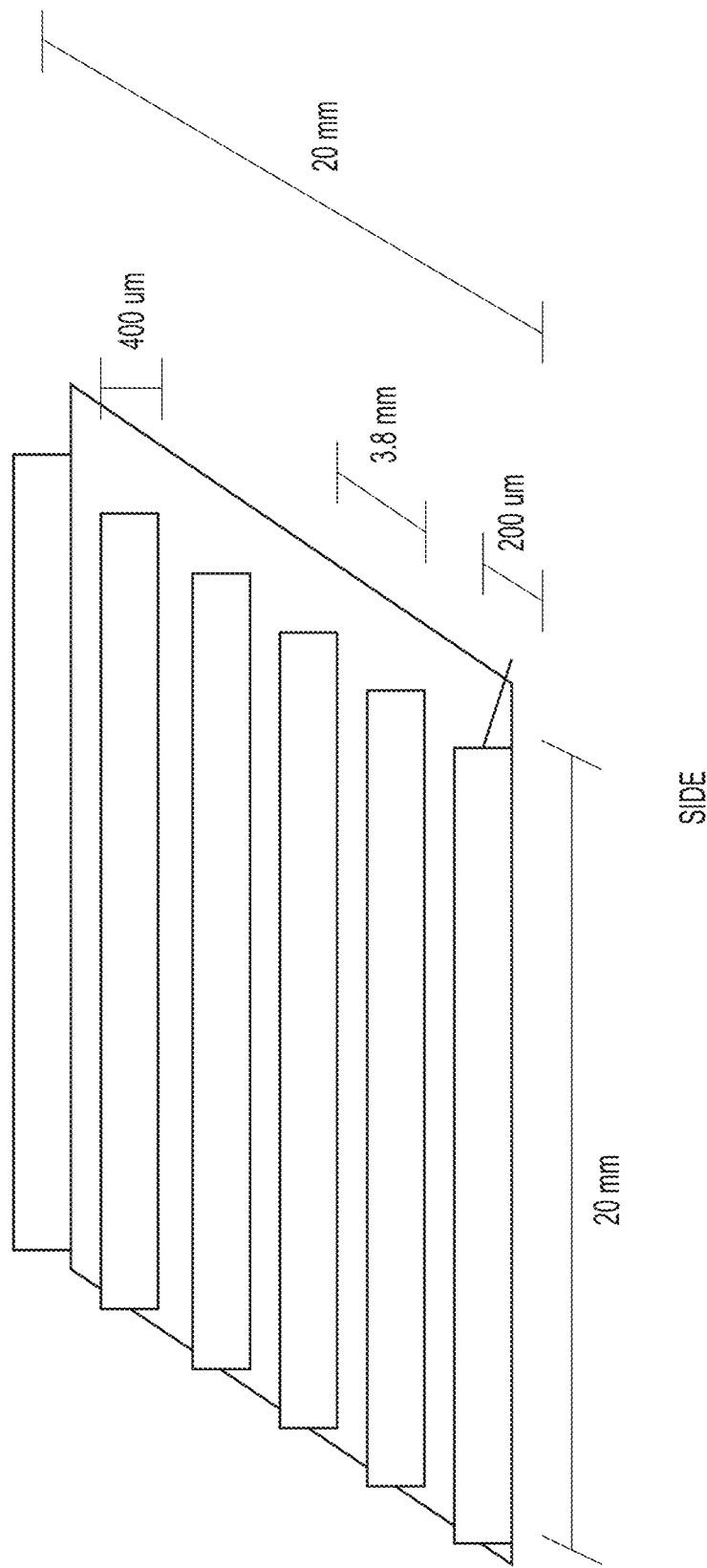

FIG. 24. An example side view of PDMS chip, highlighting features that separate the rows of five substrates. These features are 350 um-500 um in height and 200 um in wide. The feature form macrochannels that allow for different reagents to be flowed through the row of 5 substrates.

Figure 25:
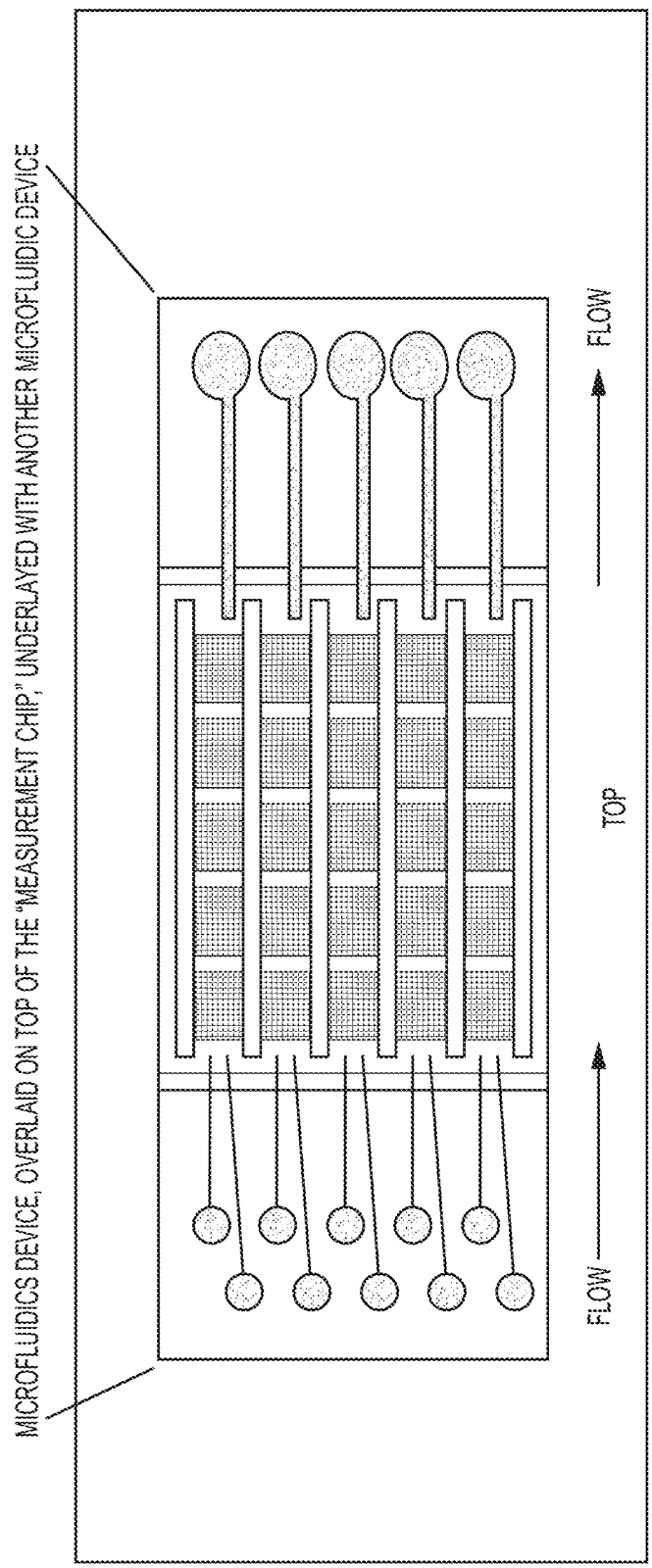

FIG. 25. Top view of an example of overall device. The device is composed of the chip containing the array of 25 individual substrates, a PDMS or similar polymer microfluidic manifold that fits over and around the chip and a glass substrate that seals the top of the chip and bottom of the microfluidic manifold.

Figure 26:
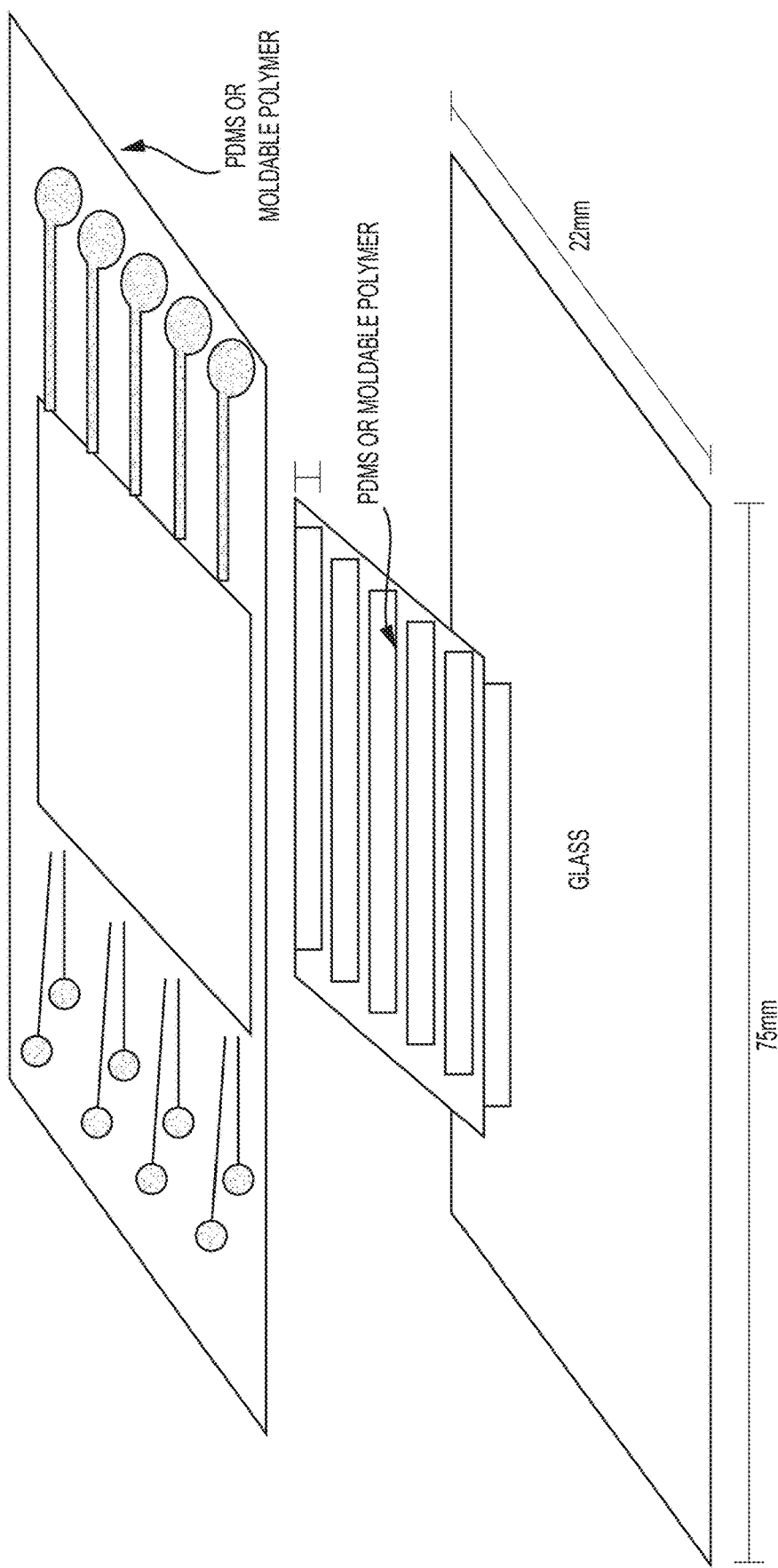

FIG. 26. Example schematic of how the three parts of the device are overlaid on one another to construct the working device.

Figure 27:
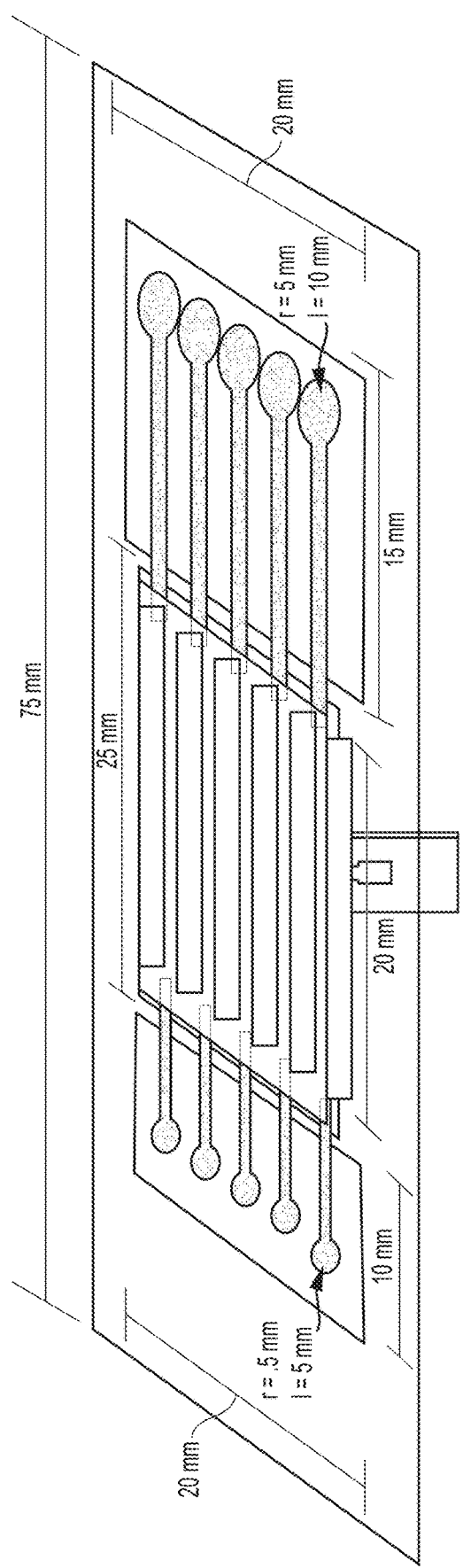

FIG. 27. Example schematic of how the device will be imaged as well as general dimensions of the device. The device would be placed on a microscope with white, transmitted light illuminated from the top polarized light from the bottom, to image both in DIC and excitable fluorescent light of wavelengths from 300-800 nm, respectively.

Figure 28:
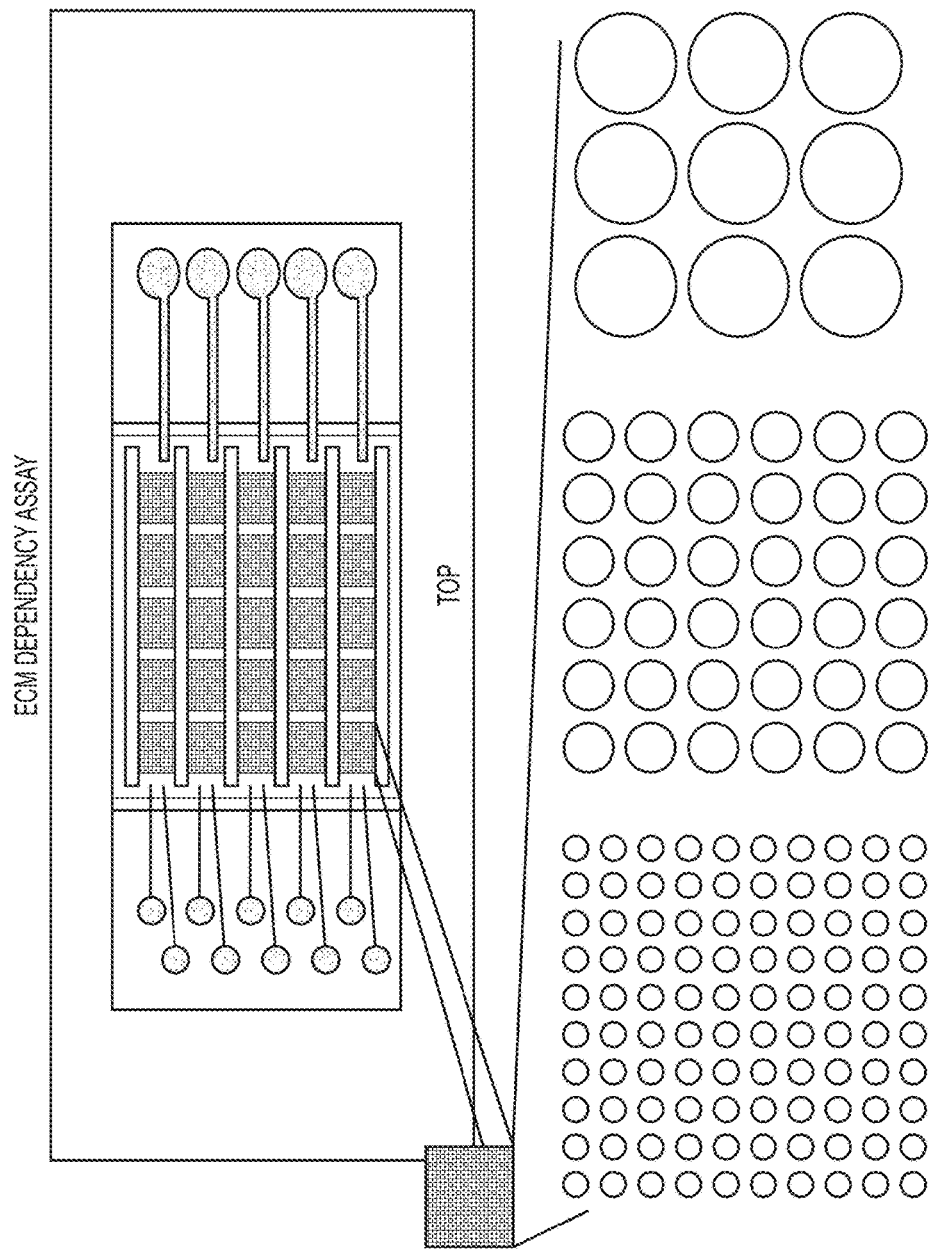

FIG. 28. Example of the substrate features used for an ECM dependency assay. The ECM dependency assay will allow for validation of the in vitro conditions needed to culture the biopsy/explant in vitro. Different ECM components, collagen, fibronectin, laminin, will be flowed through the five macro channels, coating each row of five substrates. The substrates will be fabricated to contain pillars of increasing heights, from 2 um, 4 um, 6 um, 8 um, and 10 um. Within each substrate, the pillars will have different radii, 0.5 um, 1 um, 2 um, 4 um, 6 um. This configuration will allow for an array of matrix coatings and rigidities to be tested and force generated to be measured to determine the ideal conditions to culture a given biopsy in vitro as well as the force generated in each of the viable conditions.

Figure 29:
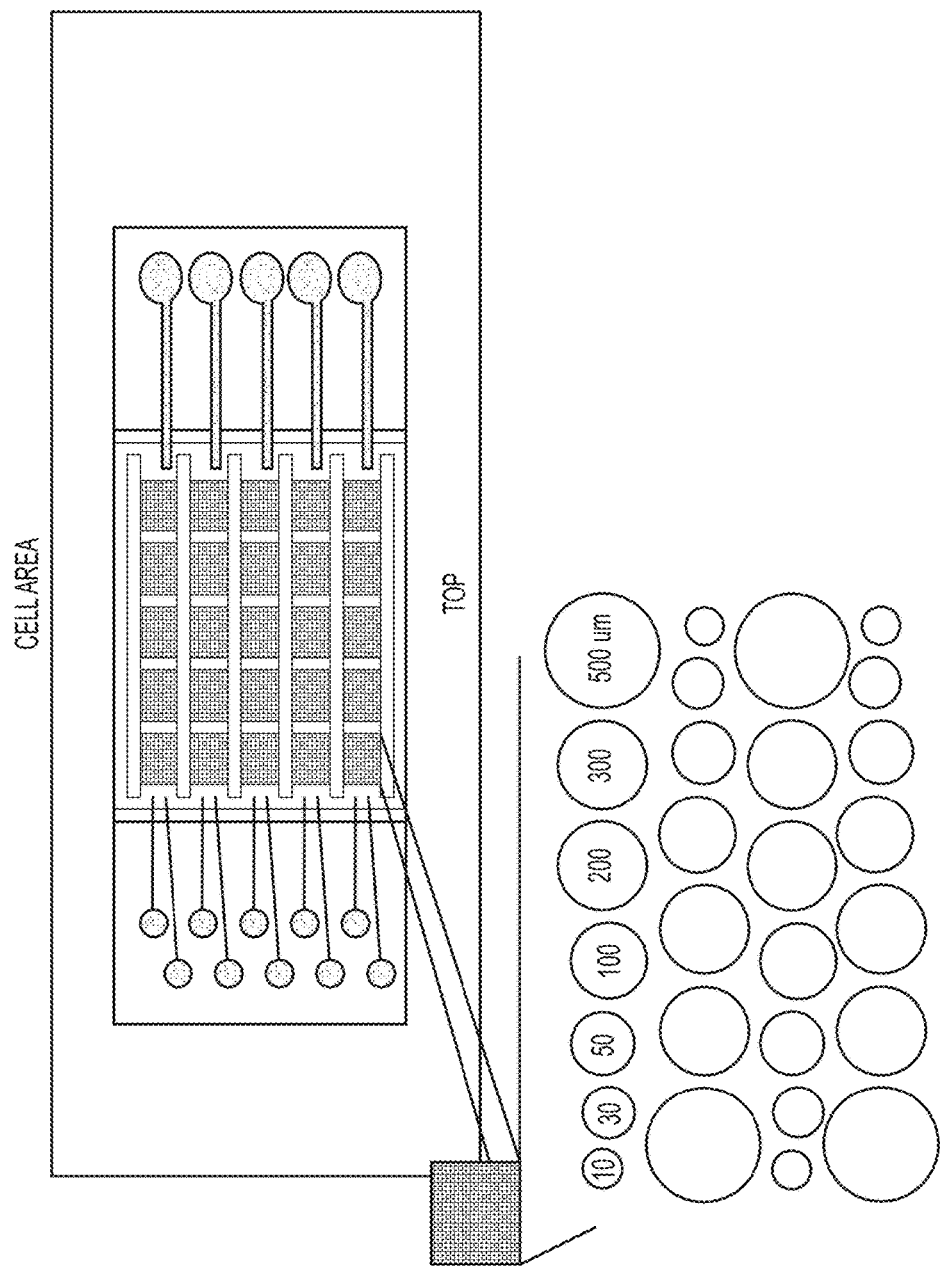

FIG. 29. Example of the substrate features used to determine cell area. Each substrate would be composed of an array of pillars of different diameters and similar heights that correspond to different rigidities of in vivo and in vitro relevance, with the appropriate ECM molecules. For example, the pillars could have diameters of 10, 30, 50, 100, 200, 300, 500 um's. The different sized pillars will provide a surface for cells to spread to their maximum area.

Figure 30:
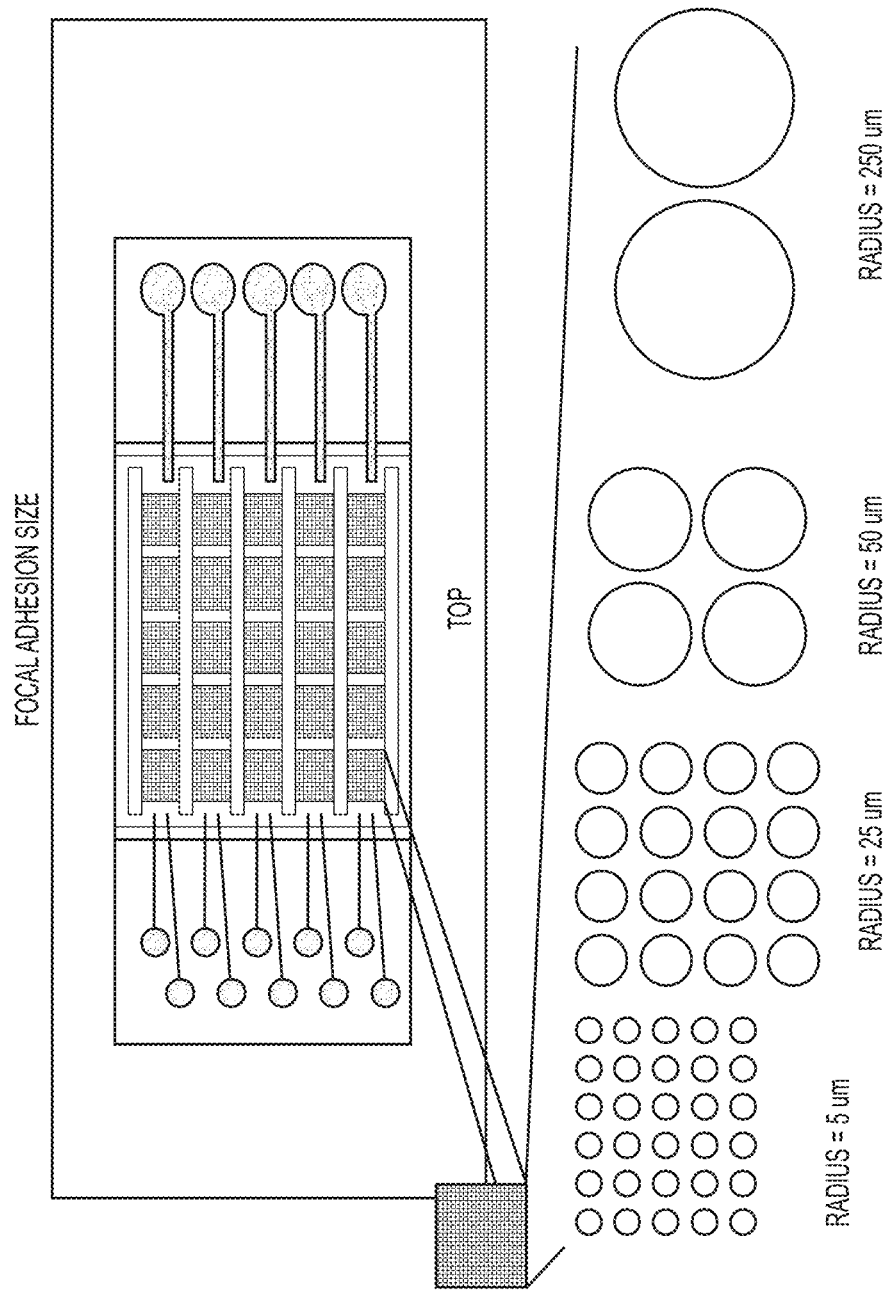

FIG. 30. Example of substrate features used to determine focal adhesion size. Each substrate would be composed of an array of pillars of the same height, but different diameters such as 5 um, 25 um, 50 um, 250 um. These pillars will serve as surfaces for cells to spread and attach to, forming focal adhesion. Focal adhesions will be imaged via fluorescently labeled antibodies or quantum dots conjugated to recognize focal adhesion proteins such as paxillin, p130Cas, FAK, and vinculin.

Figure 31:
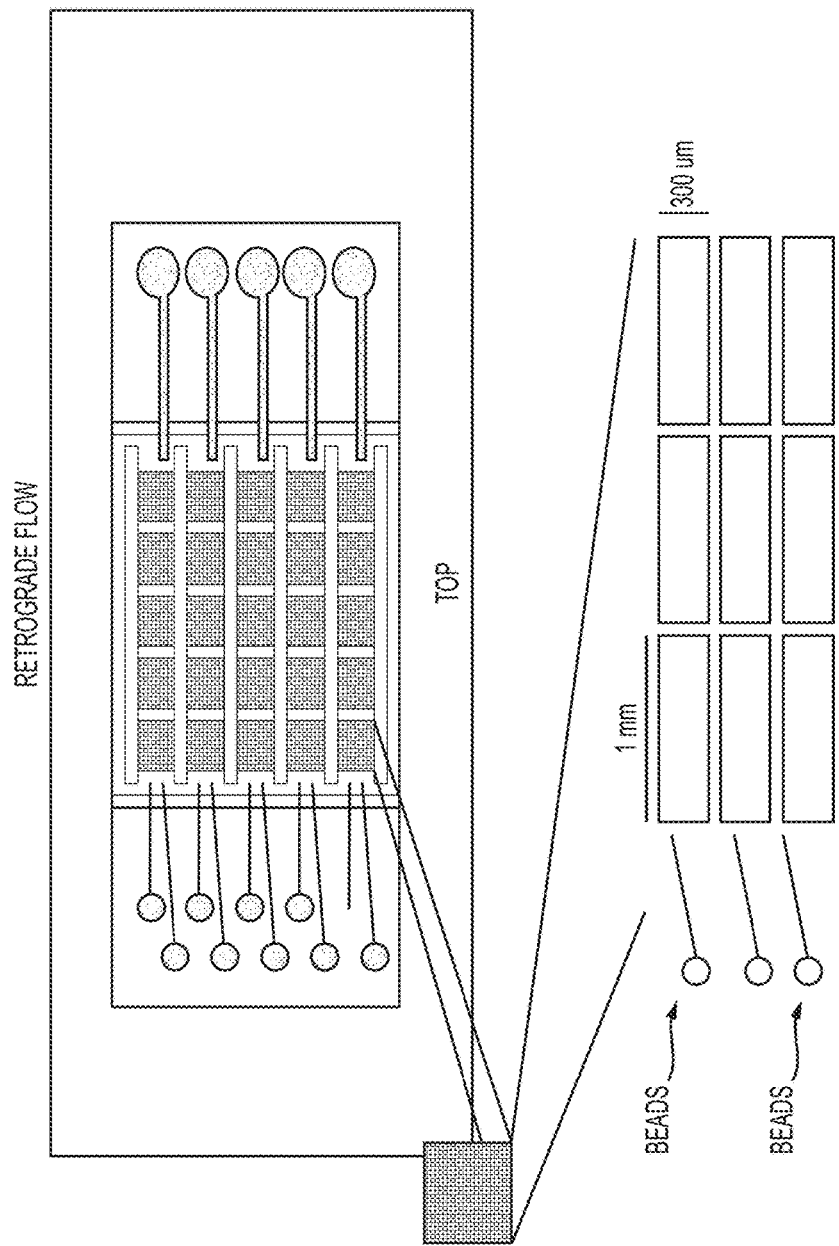

FIG. 31. Example of substrate features used to determine actin retrograde flow speed. Each substrate would be composed of an array of rectangular platforms that correspond to different rigidities of in vivo and in vitro relevance, will be coated in different ECM molecules, while 1-3 um diameter glass, polystyrene, magnetic or other type of beads are flowed in and images using differential interference contrast (DIC) microscopy over time to measure the velocity of beads at the leading edge of cells. Alternatively, measurements of membrane deformation, or turbulence at the leading edge as imaged via DIC can be used to determine the actin retrograde flow speed or velocity.

Figure 32:
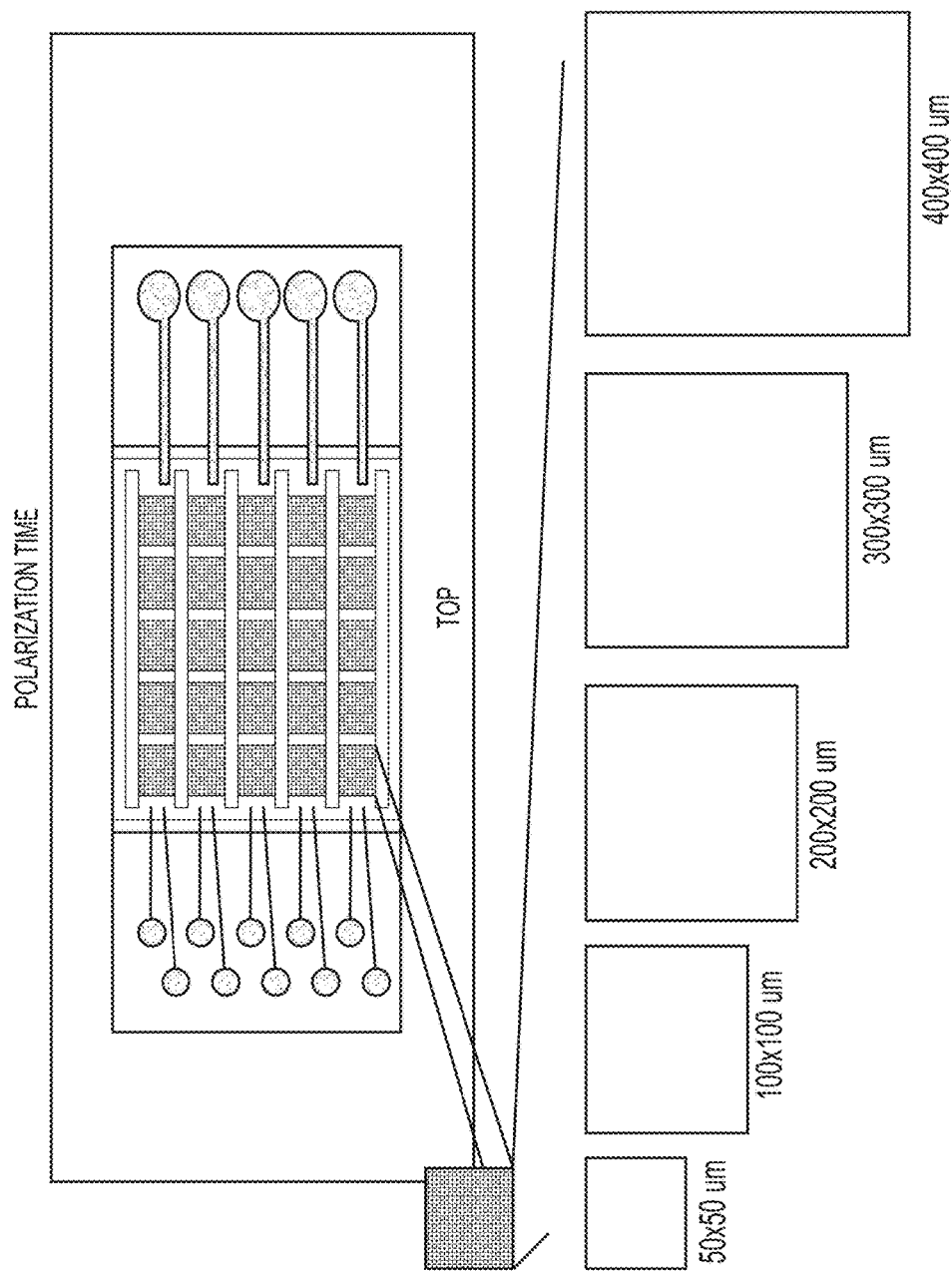

FIG. 32. Example of substrate features used to determine polarization time. An array of squares of similar heights and dimensions of 50×50 um, 100×100 um, 200×200 um, 300×300 um, 400×400 um will allow cells to spread and polarize in a given, defined area, allowing for separation of cells to best measure polarization time.

Figure 33:
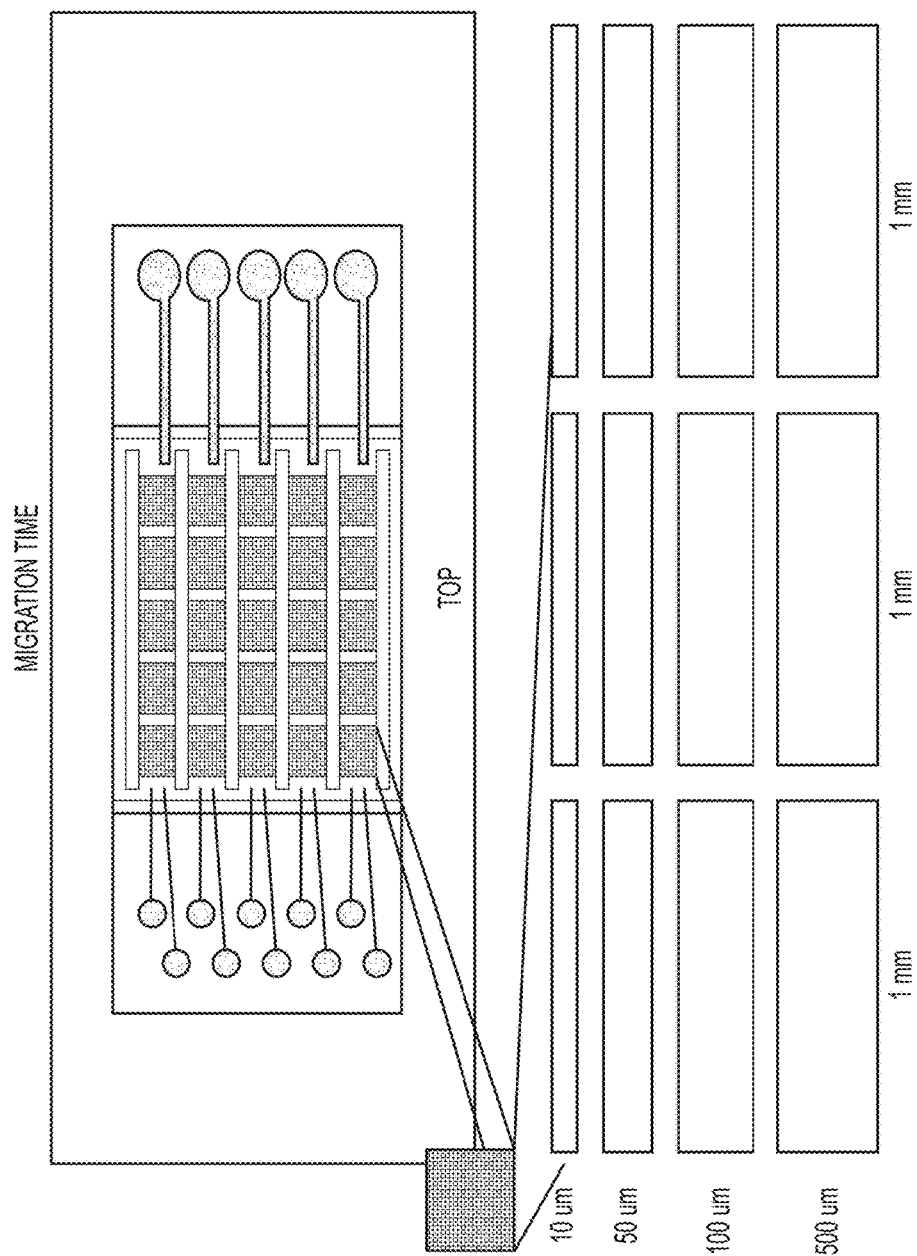

FIG. 33. Example of substrate features used to determine migration time. An array of rectangles of similar height, and length, but varying widths of 10 um, 50 um, 100 um, 500 um, will allow for cells to spread and migrate a specific distance while imaged over time to measure and calculate their migration time.

Figure 34:
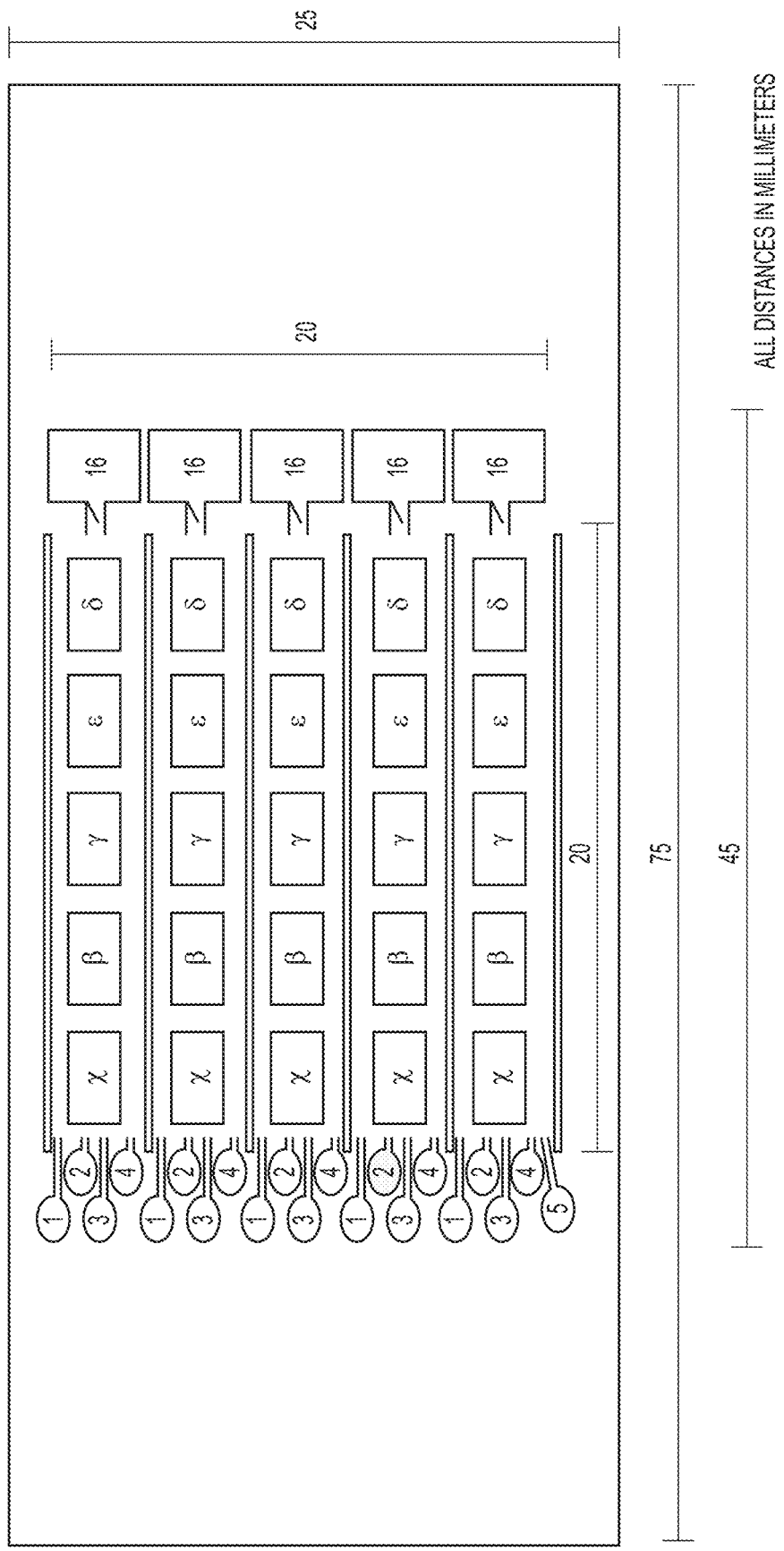

FIG. 34. Schematic of an exemplary device according to an embodiment of the invention with dimensions and general features, including microfluidic channels on the periphery, macrochannels that contain five individual substrates.

Figure 35:
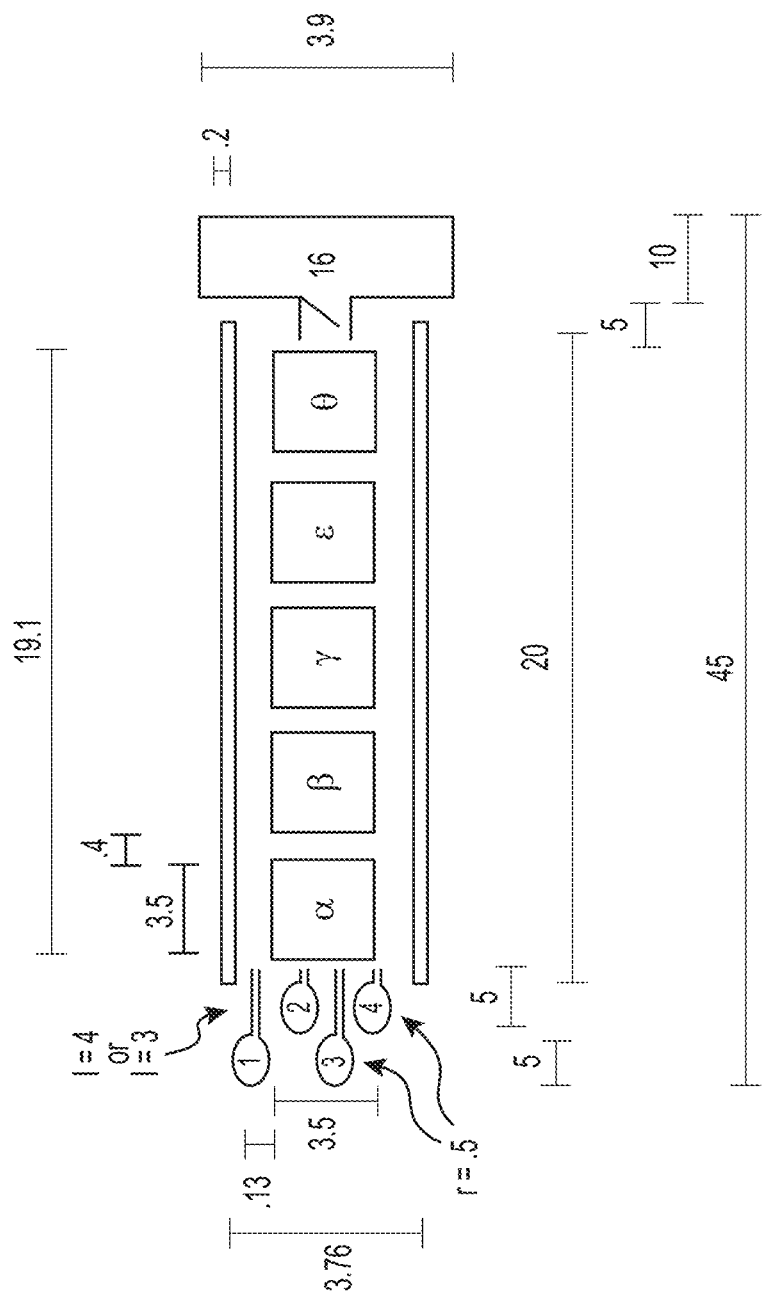

FIG. 35. Schematic of an exemplary macrochannel according to an embodiment of the invention with dimensions and general features. Each substrate denoted by the Greek letters alpha, beta, gamma, epsilon, and theta can be engineered to have features necessary to test each one of the measurements of interest.

Figure 36:
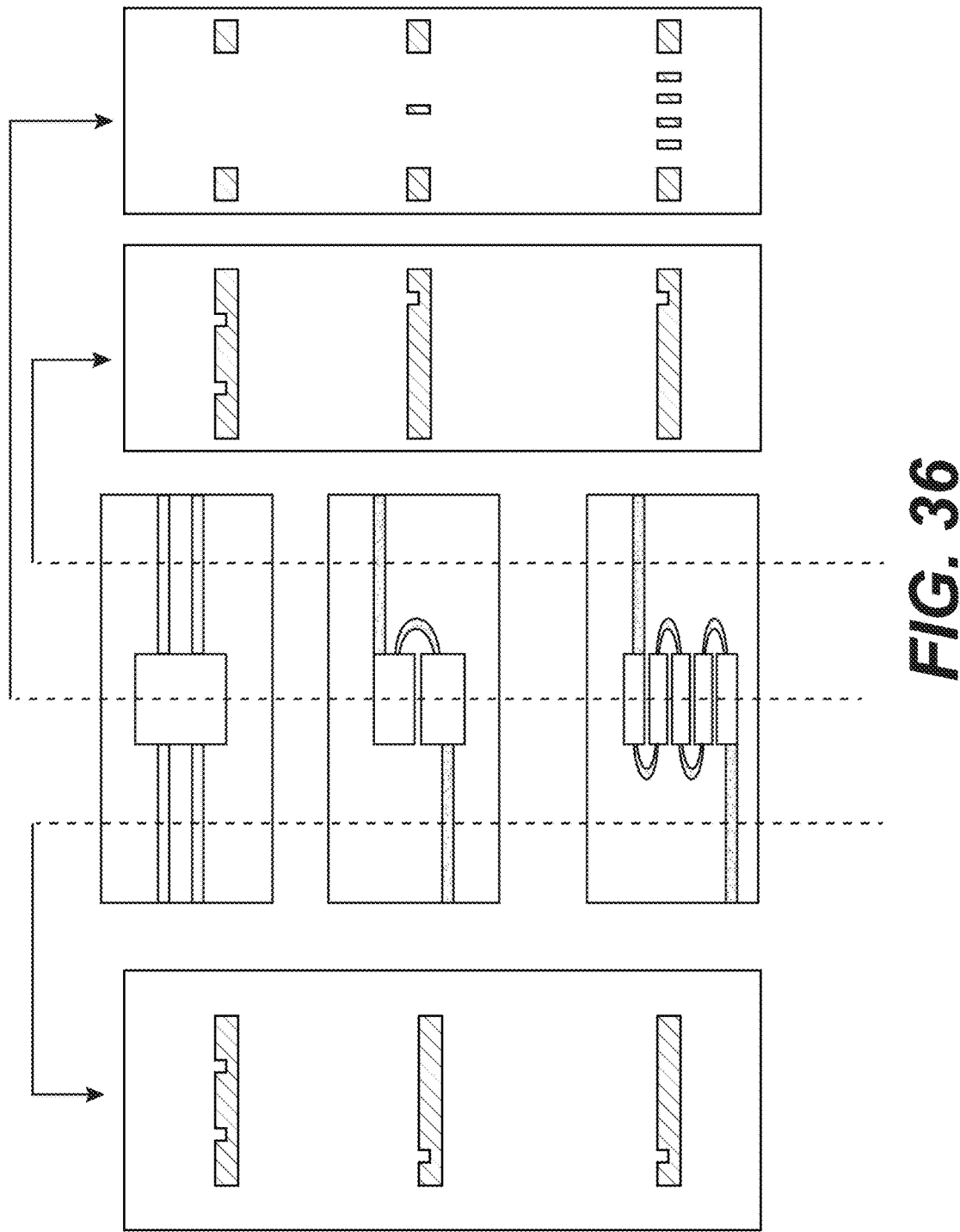

FIG. 36. Schematic of exemplary prototypes according to an embodiment of the invention made from aluminum and plastic tubes. Both top views and cross-sectional views are presented.

Figure 37:
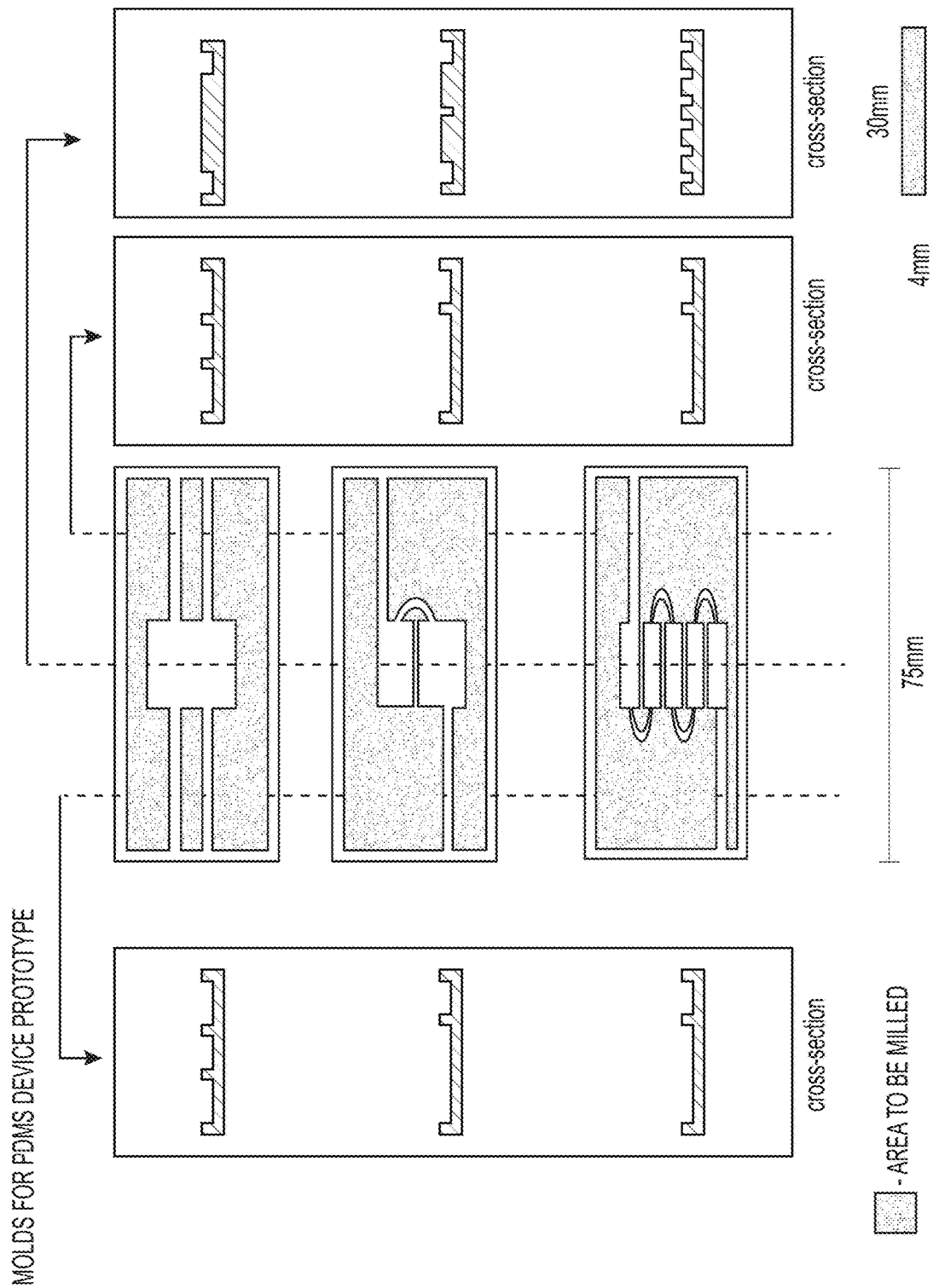

FIG. 37. Schematic of exemplary prototypes according to an embodiment of the invention made from aluminum to provide molds for PDMS. Both top views and cross-sectional views are presented.

Figure 38:
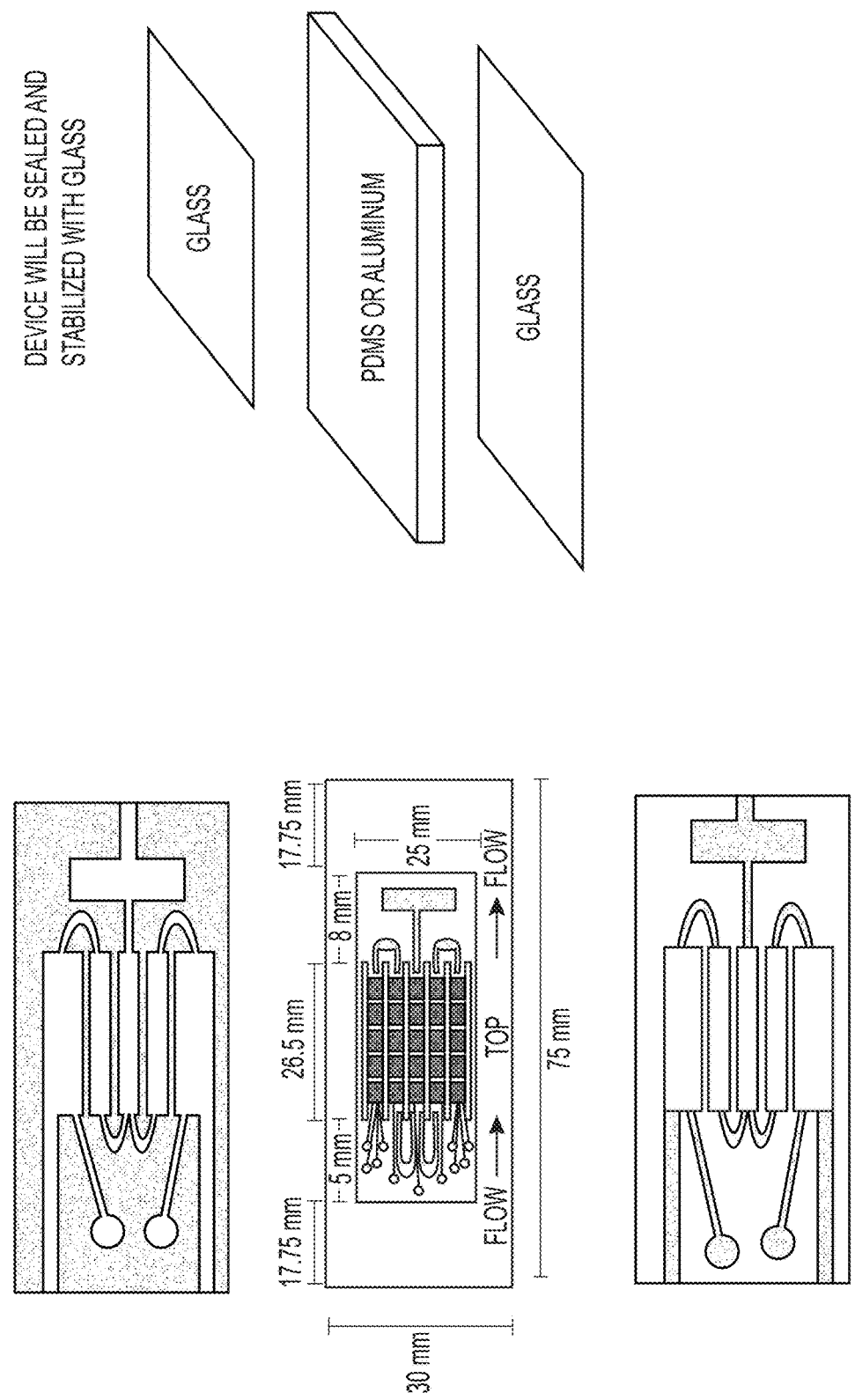

FIG. 38. Schematic of exemplary prototypes according to an embodiment of the invention made from aluminum and plastic tubes to act as device and to provide a mold for PDMS. Both top views and cross-sectional views are presented.

Figure 39:
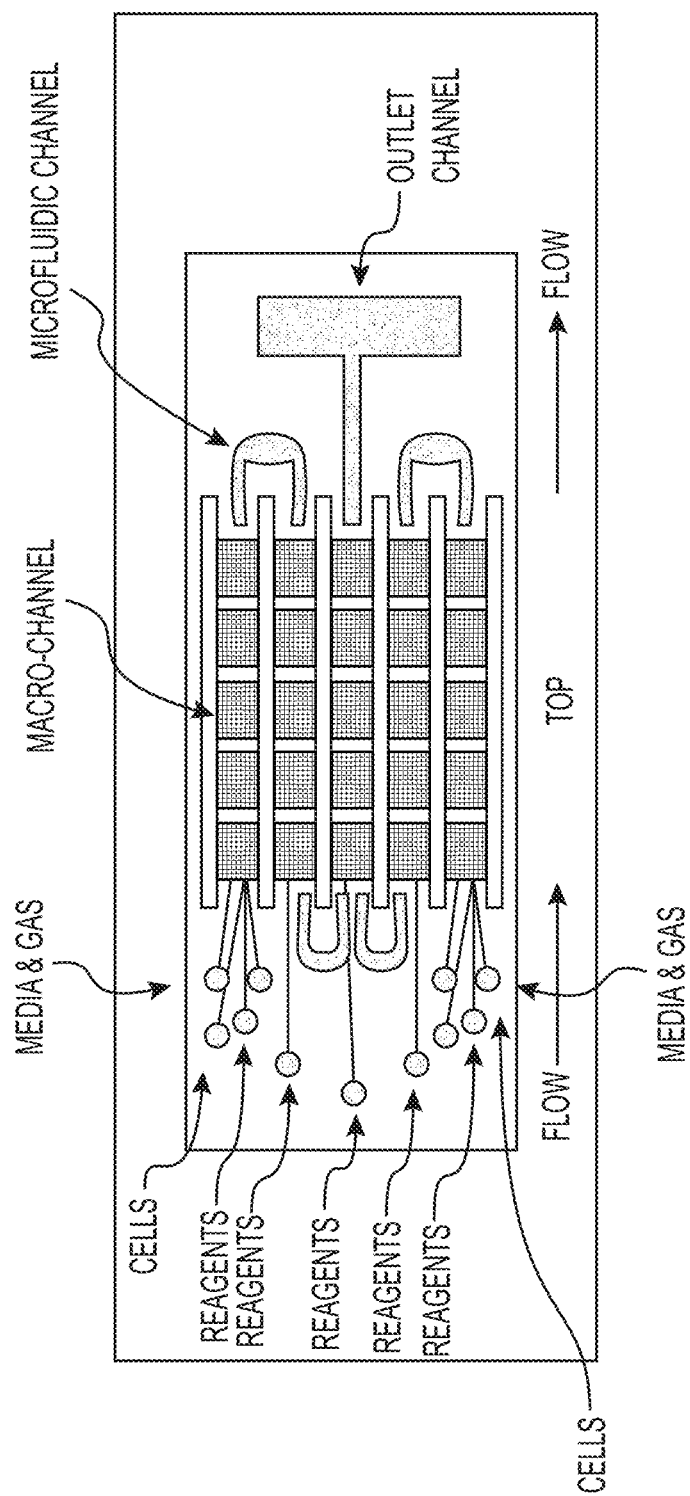

FIG. 39. Schematic drawing of an exemplary device according to an embodiment of the invention that can be used to measure biomarkers in 5 macrochannels, with 5 substrates inside each macrochannel.

Figure 40:
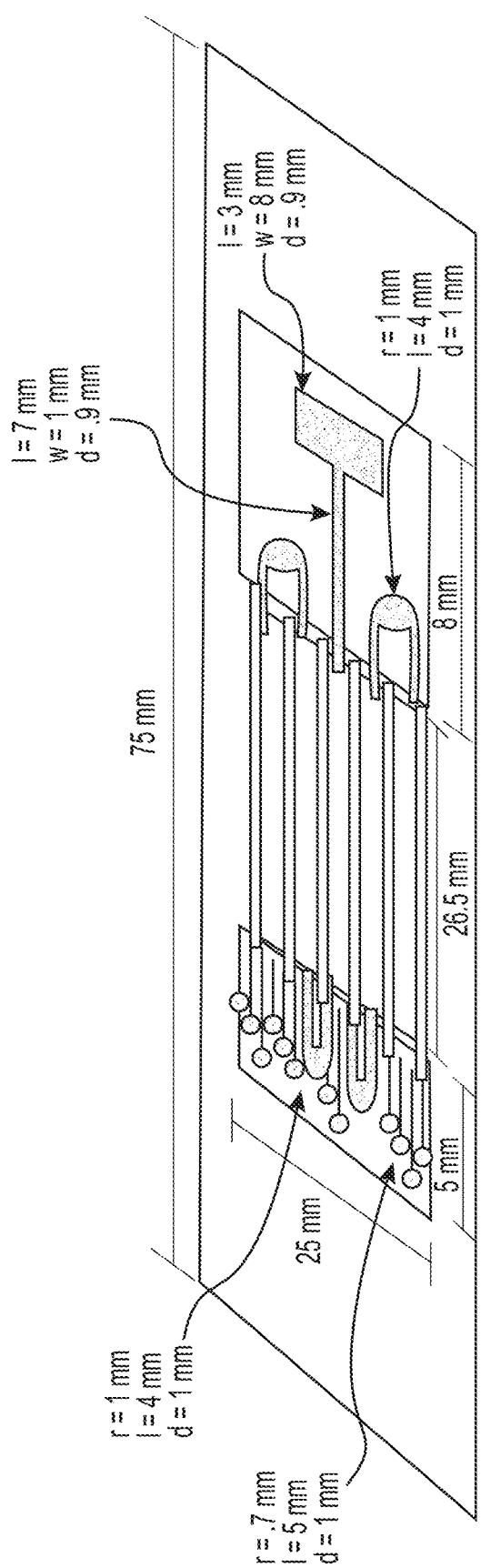

FIG. 40. Schematic drawing of an exemplary device according to an embodiment of the invention that can be used to measure biomarkers in 5 macrochannels, with 5 substrates inside each macrochannel.

Figure 41:
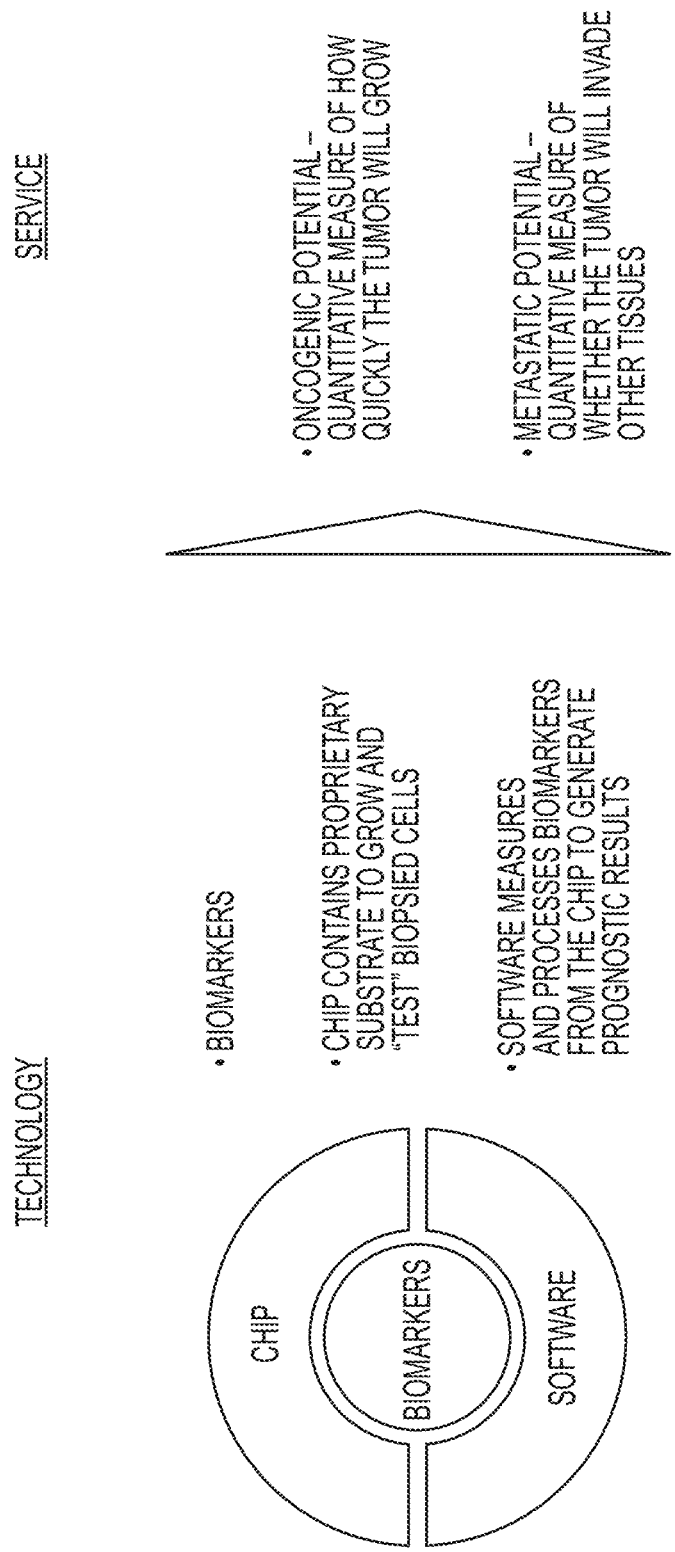

FIG. 41. Description of exemplary technology according to an embodiment of the invention and example of possible implementation.

Figure 42:
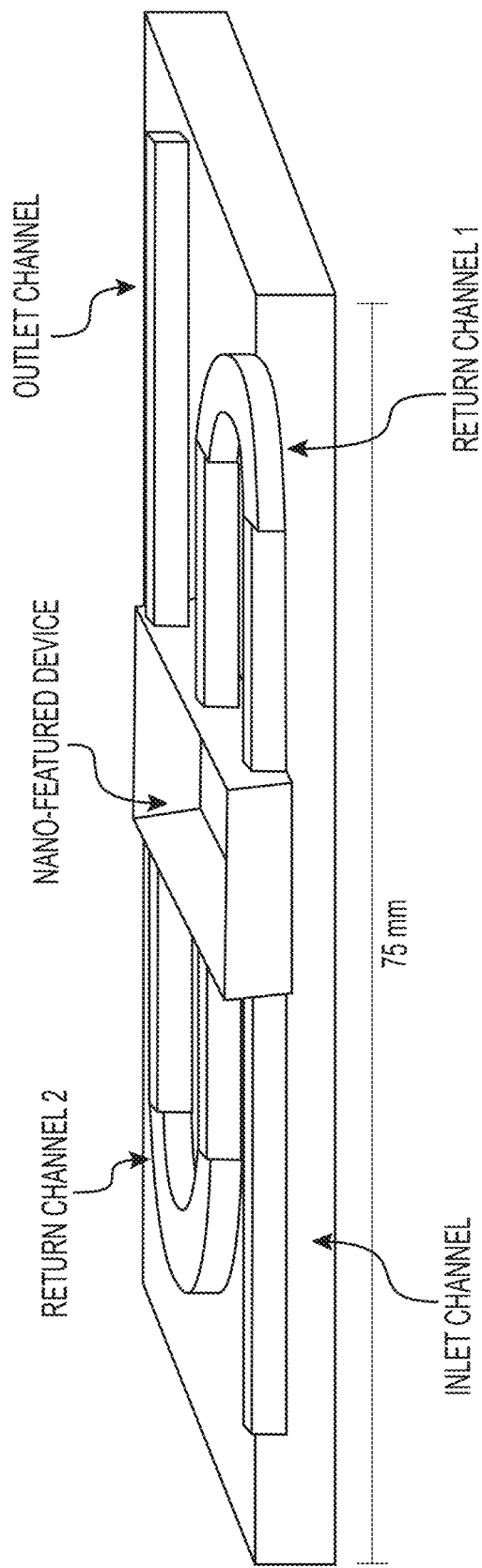

FIG. 42. General schematic of an example of a device according to an embodiment of the invention.

Figure 43:
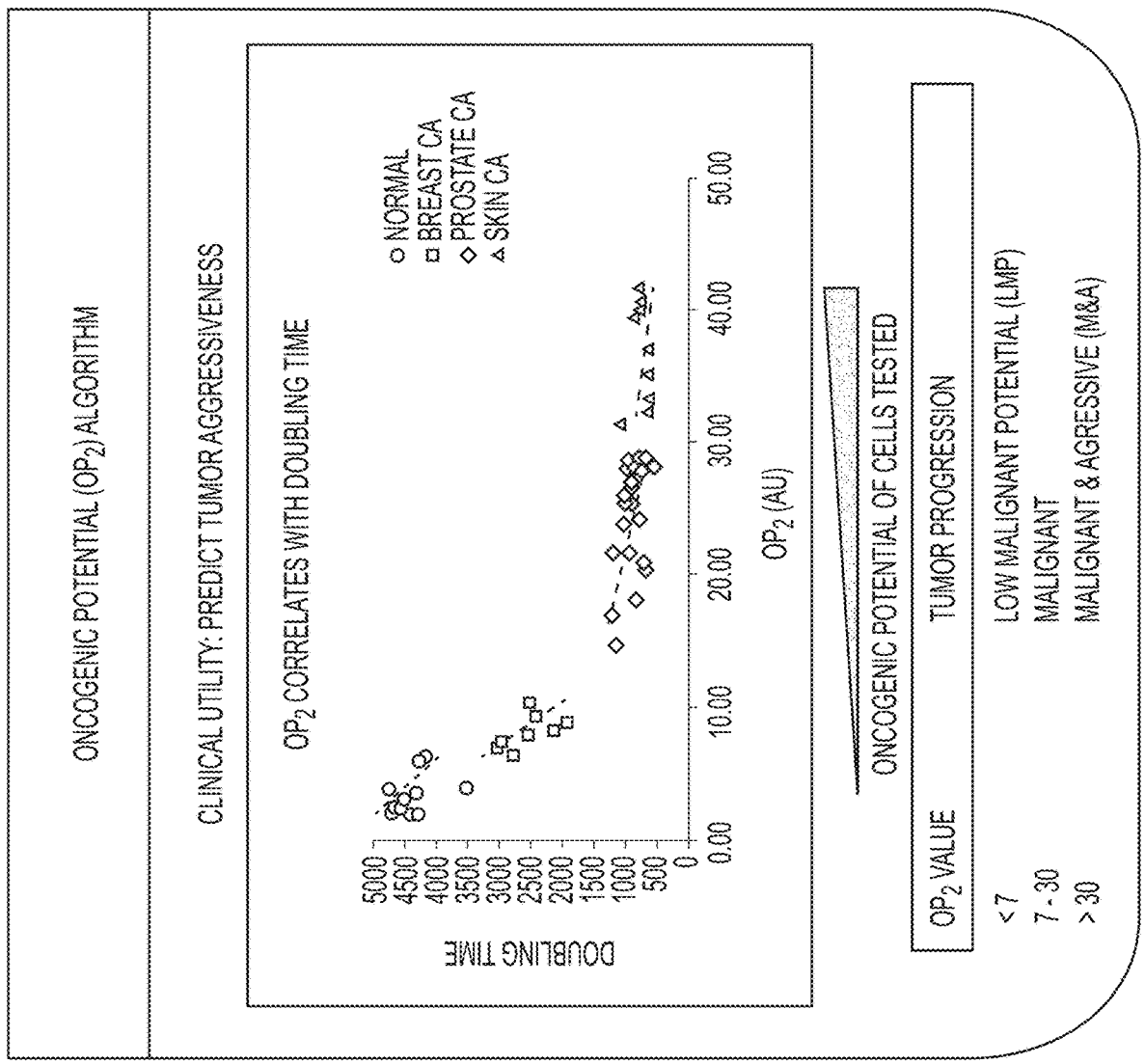
Figure 43:
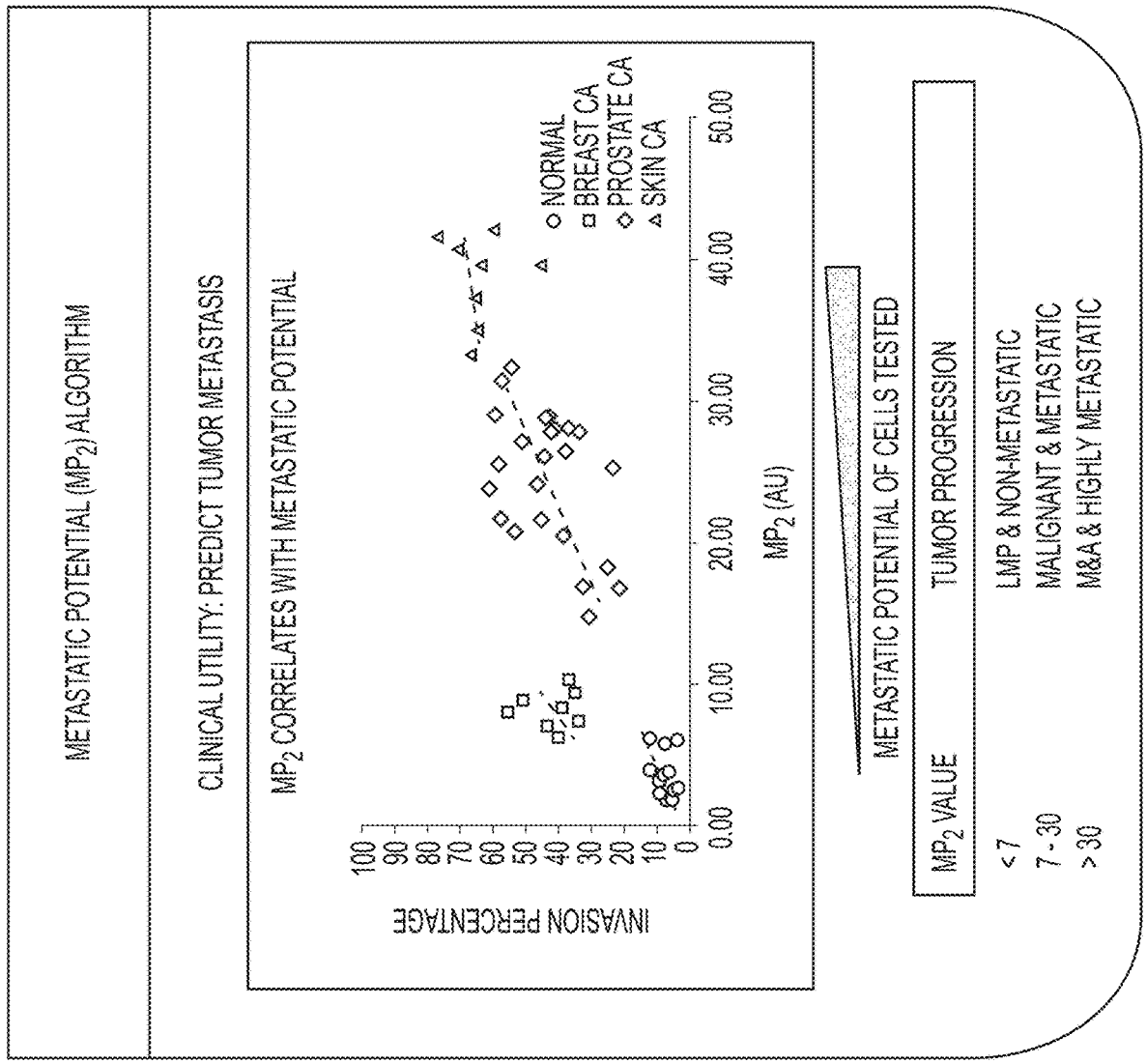

FIG. 43. Examples of how two algorithms correlate with doubling time (oncogenic potential), and metastatic potential of a different cancer cell lines according to an embodiment of the invention.

Figure 44:
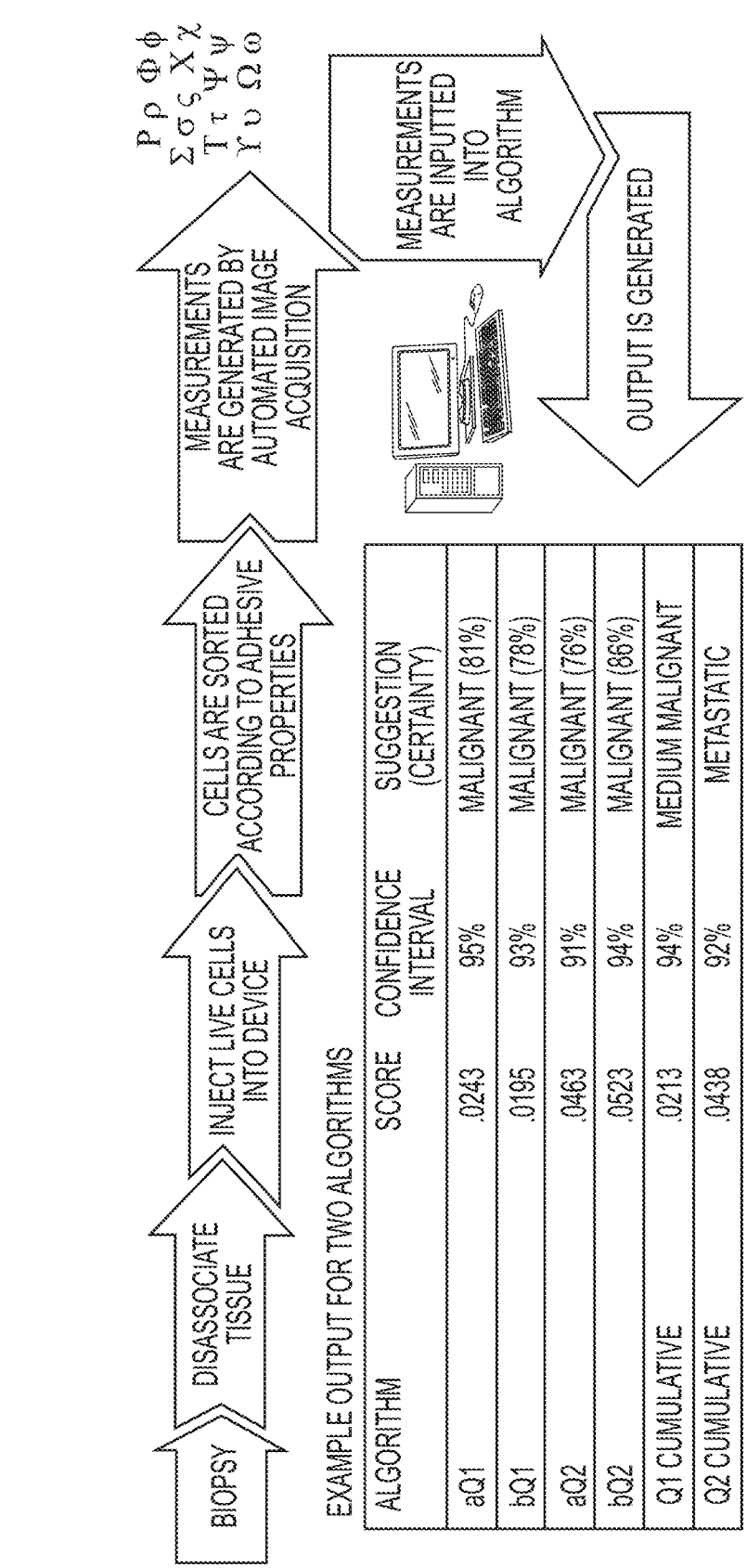

FIG. 44. Example of how prognostic results will be transmitted to end user according to an embodiment of the invention.

Figure 45:
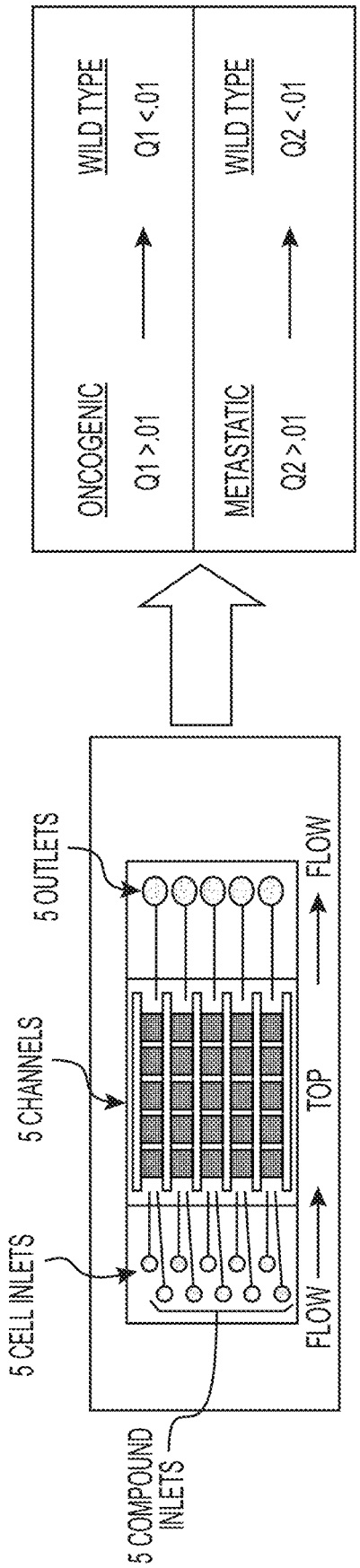

FIG. 45 Example of how cell based assay results can be useful according to an embodiment of the invention.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention.

Unless defined otherwise, technical and scientific terms used herein have the same meaning as commonly understood by one of ordinary skill in the art to which the invention belongs. Singelton et al., Dictionary of Microbiology and Molecular Biology $2^{nd}$ ed., J. Wiley & Sons (New York, N.Y. 1994); and Webster's New World Medical Dictionary, $2^{nd}$ Edition, Wiley Publishing Inc., 2003. provide one skilled in the art with a general guide to many of the terms used in the present application. For purposes of the present invention, the following terms are defined below.

The terms "biomarkers," "markers," "measurements," and "variables" are used interchangeably and refer to the an observation that can be used as an indicator of a particular disease state, for example, but not limited to, cancer or some other physiological state of a tissue, or organism.

The term "biophysical variable" refers to a subset or type of variable or biomarker that is a measurable physical characteristic of the cell and/or component inside or outside the cell including but not limited to length, area, mass, velocity, density and combinations thereof.

The term "biochemical variable" refers to a subset or type of variable or biomarker that is a measurable chemical or enzymatic entity or event inside or outside the cell that can be further characterized by the specific units of the method of their measurement including, but not limited to optical density, arbitrary units of fluorescence intensity, molecular weight and combinations thereof.

The term "oncogenic" means taking on or resembling the cellular properties of cancer cells, mostly with regards to uncontrolled cell growth.

The term "metastatic" means taking on or resembling the cellular properties of invasive cancer cells, mostly with regards to their ability to invade surrounding tissue or blood vessels.

The term "oncogenic potential" is a term that describes the ability of a cell, due to its biochemical and biophysical state, to grow in an uncontrolled manner, in addition to the ability of an existing tumor to become more aggressive, or achieve a faster growth rate.

The term "metastatic potential" of a cell is a term that describes the ability of a cell, due to its current biochemical and biophysical state, to invade, migrate and generate force in its immediate environment, in addition to the ability of an existing tumor to grow in different layers of tissues, and parts of the body than from where the tumor originally formed.

The term "prognostic" is used herein to refer to the likelihood of cancer-attributable death of cancer progression, including recurrence and metastatic spread of a neoplastic disease.

The terms "epithelial cancers" refer to or describe the physiological condition in mammals that is typically characterized by unregulated cell growth. Examples of epithelial cancers include, but are not limited to, breast cancer, ovarian cancer, colon cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer.

The terms "cytoskeletal dynamics" refer to the molecular dynamics of actin, and microtubules inside a cell.

The term "focal adhesions" refers to protein aggregates, or complexes that associate with integrins that are bound to extra-cellular matrix proteins.

The term "proliferation" refers to the process of doubling and division of a cell, or population of cells.

The term "growth" refers to the process of a cell or population of cells surviving and maintaining cellular functions.

The term "migration" refers to the process of a cell or population of cells moving from one physical point to another, and exhibiting physical displacement of the entire cell or subsets of a population of cells.

The term "motility" refers to the physical motion of a cell that often results in migration or movement of a cell or population of cells from one physical point to another and can refer to finite movements that do not result in a net physical displacement.

The terms "extracellular matrix" refers to the immediate external environment around a cell. The extracellular matrix (ECM) exhibits both biochemical and physical properties. Biochemical properties, include, but are not limited to protein composition, and modification state of proteins. Physical properties of the ECM include, but are not limited to, rigidity, geometry, and topology.

The term "retrograde flow" refers to the flow of actin, unless otherwise stated, inward from the leading edge of the cell, within but not limited to the lamellipodia, lamella, and cell body.

The term "integrins" refers to the protein receptor complex involved in binding the extracellular matrix.

The term "β integrins" refers to the β subunit of protein receptors whose main function is to bind ECM molecules and aggregate proteins within the cell to form focal adhesions.

The term "α integrins" refers to the a subunit of protein receptors whose main function is to bind ECM molecules and aggregate proteins within the cell to form focal adhesions.

The term "mouse embryonic fibroblasts" refers to an in vitro cell line that was derived from mouse embryonic fibroblasts (MEF)

The term "Polydimethylsiloxane" (PDMS) refers to a group of polymeric, organosilicon compounds that are commonly referred to as silicones. PDMS serves as an example of a material suitable for, and optimal for its rheological (or flow) properties, optically clear, and, in general, is considered to be inert, non-toxic and non-flammable.

The term "brightfield" refers to a specific mode of microscopy that employs transillumination to image the sample.

The term "immunofluorescence" refers to the imaging cells via fluorescent microscopy. Cells, subcellular structures, and proteins can be imaged via labeling with fluorescent dyes, antibodies, or proteins. Fluorescent molecules are excited at a given wavelength and emit light at another wavelength.

The term "pillar" refers to a micropost or structure that resembles a pillar structure on the spatial scale of nanometers or micrometers.

The term "fibronectin" refers to a specific protein that is a constituent of the extracellular matrix.

The term "collagen" refers to a specific protein that is a constituent of the extracellular matrix.

The term "laminin" refers to a specific protein that is a constituent of the extracellular matrix.

The term "kymograph" refers to a graphical representation of a microscopic image over space and time.

The term "coupling" refers to the interaction of protein components in dynamic structures. For example, but not limited to, coupling refers to the degree with which focal adhesion proteins bind and interact with the adjacent actin cytoskeleton.

The term "extracellular" refers to the space outside of a cell.

The term "localization" refers to the position of a protein or group of proteins inside a cell.

The term "modification" refers to post-translational modification of proteins, lipids, or other molecules found inside cells. For example, but not limited to, phosphorylation, acetylation, farsenylation.

The term "scaffold" refers to a protein's ability to bind other protein(s) to facilitate other protein-protein interactions and/or modifications.

The term "cancer" refers to or describes the physiological condition in mammals that is typically characterized by unregulated cell growth.

The term "kinase" refers to a protein that exhibits catalytic activity, in that it is able to phosphorylate other proteins, or in other words add a phosphate group to a protein.

The term "actin" refers to a protein constituent of a cells cytoskeleton.

The term "phosphatase" refers to a protein that exhibit catalytic activity, in that it is able to remove a phosphate group from a protein.

The term "isolate" refers to the process of purification of cells, proteins, or other molecules from a heterogeneous mixture of cells, proteins or other molecules.

The term "traction force" refers to the force generated by a cell on its external environment. Proteins are referred to herein using their common acronyms, below.

| Acronym | Protein Name |
| --- | --- |
| ILK | Integrin Linked Kinase |
| FAK | Focal Adhesion Kinase |
| Pax | Paxillin |
| p130Cas | p130 Crk associated substrate |
| ERK | Extracellular signal-regulated kinase |
| JNK | c-Jun N-terminal Kinase |
| β integrin | Beta Integrin |
| α integrin | Alpha Integrin |
| NFκB | nuclear factor kappa-light-chain-enhancer of activated B cells |
| Src | Src |
| Fyn | FYN |
| Yes | YES |
| MLC | Myosin Light Chain |
| PAK | p21 activated kinase |
| cdc42 | cell division control protein 42 homolog |
| rac | Ras-realted C3 botulinum toxin substrate 1 |
| rho | RHO |

-continued

| Acronym | Protein Name |
| --- | --- |
| Vav2 | VAV |
| αPix | alphaPIX |
| Crk | CRK |
| Sos | SOS |
| GSK3 | Glycogen synthase kinase 3 beta |
| CREB | cAMP response element-binding |
| Cylin D | CYCLIN D |
| Nck | Non-Catalytic region of tyrosine Kinase adaptor protein 1 |
| Dock | Dedicator of cytokinesis |
| PI3K | Phosphatidylinositol 3-kinases |
| AKT | Protein Kinase B |
| Bcl-2 | B-cell lymphoma 2 |
| p38MAPK | P38 mitogen-activated protein kinases |
| PTP-PEST | protein tyrosine phosphatase |
| C3G | C3G |
| MAPK | mitogen-activated protein kinases |

Abbreviations used are listed below.

| Abbreviation | Full name |
| --- | --- |
| ECM | extra-cellular matrix |
| FA | focal adhesion |
| FAS | focal adhesion size |
| ARFS | actin retrograde flow speed |
| FARFS | focal adhesion retrograde flow speed |
| FG | force generation |
| CA | cell area |
| MV | migration velocity |
| PT | polarization time |
| PIA | proliferation indicator average |
| MIA | metabolic indicator average |
| IEL | Integrin-Linked Kinase expression level |
| WTA | western titrated average |
| MSEA | micon scale ELISA average |
| NFTA | NFkB titratration average |
| ELISA | Enzyme-linked immunosorbent assay |
| mRNALI | mRNA localization intensity |
| ISPP | Immuno-stain of PhosphoProtein |
| ECMCDT | ECM Composition of Dissassociated Tissue |
| KV | Kinesin Velocity |
| MD | Microtubule Density |
| N/CA | Nuclear/Cell Area |
| EnR | Endocytic Rate |
| ExR | Exocytic Rate |
| BrDU | Bromodeoxyuridine |
| FN | Fibronectin |
| C | Collagen |
| F | Fibronectin |
| PDMS | Polydimethylsiloxane |
| um | micrometer |
| nm | nanometer |
| mm | millimeter |
| GEFs | Guanine nucleotide exchange factors |
| PIP2 | Phosphatidylinositol 4,5-bisphosphate or PtdIns(4,5)P$_2$, |
| Ca++ | Calcium cation |
| H+ | Hydrogen cation |
| GTPases | Guanosine Tri-Phosphate |
| MAP kinases | mitogen activated protein kinases |
| LD motifs | leucine-aspartate repeat motif |
| nN | nano Newton |
| pN | pico Newton |
| FERM domain | F for 4.1 protein, E for ezrin, R for radixin and M fo moesin |

In one aspect, the present invention provides a cell-based, biophysical cancer diagnostic tool. Among the advantages provided by the systems, methods, and devices discussed herein is the ability to assign number values to a given biopsy. These number values are proportional to the aggressiveness and invasiveness (oncogenic & metastatic potential) of the biopsy and correlates with a patient's prognosis. Furthermore, upon some clinical investigation, these numbers can be used, e.g., by a practicing physician, to determine further diagnostic and treatment strategies/methods. In some aspects, exemplary embodiments of these numbers, hereinafter "Q", can be derived from discrete-emerging biophysical measurements as well as biochemical techniques. For example, in one exemplary embodiment, Q can be extrapolated from data taken from a model cancer line system termed the Integrin-Linked-Kinase (ILK) Mouse Embryonic Fibroblast line, and confirmed with the human breast cancer cell line termed the MCF cell line, as well as other cancer cell lines including A431, Hec1, LnCap, NCI-NIH460, MDA-MB-231, DU14, T47D, PC3, SHS-Y5Y (FIG. 8-12). In one aspect, the present invention provides systems and methods of determining Q using certain biophysical and biochemical biomarkers that will be discussed in more detail below. In related aspects, the invention provides a physical device that can be used to take appropriate biophysical and biochemical measurements from a patient, for example, but not limited to a biopsy. In another related aspect, the invention provides methods of using this device as well as methods of determining the growth, and/or oncogenic, migration rate, and/or metastatic potential of cells obtained from a patient using the determined value of Q.

Biomarkers & Quantification of 'Q'

There are many ways to determine a value for Q. As will be discussed in more detail below, various formulas can be used to determine Q. These formulas can incorporate various biophysical measurements, biochemical measurements, and/or other variables. Using various ones of these measurements, variables, formulas, and/or combinations thereof, a discrete set of Q values can be determined that can enumerate the oncogenic and metastatic potential of a given tissue. For convenience, the various different Q values will be denoted herein with a leading lower case letter. Subsets of a given Q value will be denoted with a following number. In some embodiments, the various different Q values and subsets thereof can be used in combination, e.g., to better approximate the tissues' oncogenic and/or metastatic potential.

As discussed above, there are numerous biophysical and biochemical markers that can be used to obtain Q. Quantification of these biomarkers can allow them to be used in various algorithms that output values for Q corresponding to an oncogenic and/or metastatic potential.

For example, biomarkers can be measurements of physical properties of the cell, or components inside or outside the cell. In an exemplary embodiment, a biophysical marker could be the measure of the area of the punctuate foci when a cell is stained with a known focal adhesion protein. In another exemplary embodiment, a biophysical marker could be the measure of the rearward velocity of actin from the leading cell edge.

Biomarkers can also be measurements of chemical properties of the cell, or components inside or outside the cell. In an exemplary embodiment, a biochemical marker could be the expression level of Integrin Linked Kinase (ILK) as determined by but not limited to western blot, northern blot or reverse transcriptase polymerase chain reaction, mass spectrometry analysis of ILK protein or mRNA synthesis. In another exemplary embodiment, a biochemical marker could be the activity level of an activated transcription factor NFkappaB as determined by but not limited to the measurement of a reporter construct that expresses a fluorescent molecule proportional to the activity of NFkappaB's transcriptional activity.

Crucially, these biophysical and biochemical markers are quantified and utilized in one aspect of the invention as inputs into mathematical expressions and/or algorithms which ultimate yield Q. Q is ultimately a function of, but not limited to, individual biomarkers, sets of biomarkers, or combinations of biomarkers expressed as mathematical functions.

In one aspect, these biophysical biomarkers can be referred to as oncogenic biophysical variables (OBPV). The following are exemplary oncogenic biophysical variables:

1. Focal Adhesion Size (FAS). In an exemplary embodiment, Focal Adhesion Size refers to a measure of, but not limited to the area of the punctuate foci when a cell is stained with a known focal adhesion protein such as talin, vinculin, paxillin, p130Cas, or FAK using immunohistochemical techniques. Focal Adhesion Size can be expressed in units of square micrometers ($\mu m^2$).

2. Retrograde Flow Speed (RFS). In an exemplary embodiment, Retrograde Flow Speed refers to a measure of the rearward velocity of actin from the leading cell edge, through the lamellipodia, into the cell interior by using, but not limited to DIC microscopy, measuring membrane deformation, beads, or fluorescent microscopy, measuring actin or actin associated protein—fusion proteins that allows for live imaging such as GFP. Tracking the membrane deformation, bead movement or actin-GFP or actin related protein-GFP movement over time allows one to generate a value for the retrograde flow speed of actin. Retrograde Flow Speed can be expressed in units of micrometers per second ($\mu m/s$).

3. Force Generated (FG). In an exemplary embodiment, Force Generated is a measure of the force generated in proportion to the surface area of the cell edge. In some embodiments, FG can be measured using, but not limited to elastic deformable substrates, where the force generated is proportional to the distance the substrate is deformed at contact points the cells makes with the substrate. Force Generated can be expressed in units of nano-Newtons over a given area, (e.g, $\eta N/\mu m^2$).

4. Cell Area (CA). In an exemplary embodiment, Cell Area can be a measure of, but is not limited to, the two dimensional (2D) cell area when cells are plated on 2D substrates. Cell Area can be expressed in units of square micrometers ($\mu m^2$).

5. Migration Velocity (MV). In an exemplary embodiment, Migration Velocity refers to a measure of, but not limited to, the rate of migration or lateral movement of a cell across a 2D substrate. Migration Velocity can be expressed in units of micrometers per second ($\mu m/s$), or nanometers per second.

6. Polarization Time (PT). In an exemplary embodiment, Polarization Time is a measure of, but not limited to, how long it takes 70% of cells to polarize, e.g., to form a defined migrating edge and triangle shape on a 2D substrate. Polarization Time can be expressed in seconds, or other unit of time such as minutes, or hours.

7. Focal Adhesion Retrograde Flow Speed (FARFS). In an exemplary embodiment, Focal Adhesion Retrograde Flow Speed refers to a measure of, but not limited to, the rearward velocity of focal adhesion proteins (ex. Paxillin, p130Cas, talin, vinculin, zyxin) from the leading cell edge, through the lamellipodia, into the cell interior by using DIC microscopy, measuring membrane deformation, internally bound beads or dots, or fluorescent microscopy, measuring fluorescent proteins that are visualized using a fused fluorescent protein, fluorescently conjugated protein. Tracking the membrane deformation, bead/dot movement or fusion or fluorescently conjugated protein movement over time allows one to generate a value for the retrograde flow speed of the focal adhesion protein in question. Retrograde Flow Speed can be expressed in units of micrometers per second (μm/s).

8. Kinesin Velocity (KV). In an exemplary embodiment, Kinesin Velocity is the velocity of the molecular motor known as kinesin along microtubules as measured by means of a fluorescent marker that enables the tracking of the kinesin protein within the cell and can be expressed in units of nanometers per second.

9. Microtubule Density (MD). In an exemplary embodiment, Microtubule Density is the density of microtubules in a cells periphery and perinuclear region. Microtubule Density can be measured by, but not limited to, immunostaining of the microtubules alpha or beta subunits. Microtubule Density can be expressed in arbitrary units that have been scaled over the linear range of fluorescent emission/detected by a specific charge-coupled device.

10. Nucleus/Cell Area (N/CA). In an exemplary embodiment, Nucleus/Cell Area is the ratio of the size, 2D and/or 3D area of the nucleus and cell area. Nucleus and Cell Area can be measured in square nanometers while the ratio will be unitless.

11. Endocytic Rate (EnD). In an exemplary embodiment, the Endocytic Rate is the rate of endocytosis as measured by, but not limited to, a lypophillic dye or external vesicle incorporation dye, and can be measured in units of a given arbitrary unit, decided based upon a given threshold value, per second.

12. Exocytic Rate (ExR). In an exemplary embodiment, the Exocytic Rate is the rate of exocytosis as measured by, but not limited to, a lypophillic dye over time and can be measured in units of a given arbitrary unit, decided upon a given threshold value, per second.

As discussed above, there are also numerous biochemical biomarkers that can to be used to obtain Q. In one aspect, these biochemical biomarkers can be referred to as oncogenic biochemical variables (OBCV). The following are exemplary oncogenic biochemical variables:

1. Proliferation Indicator Average (PIA). In an exemplary embodiment, Proliferation Indicator Average is a measurement derived from a colormetric or fluorescent assay based on, but not limited to, enzyme activity or incorporation of a fluorescent molecule into dividing cells, that assesses how fast a cell divides, and or replicates it DNA. Proliferation Indicator Average can be expressed in arbitrary units that have been scaled over the linear range of fluorescent emission/detected by a specific charge-coupled device.

2. Metabolic Indicator Average (MIA). In an exemplary embodiment, Metabolic Indicator Average is a measurement derived from, but not limited to, a colormetric assay that assesses how fast a cell metabolizes critical, or limiting reagents in its environment such as carbohydrates such as glucose, amino acids such as glutamate, and lipids such as triglycerides. Metabolic Indicator Average can be expressed in arbitrary units that have been scaled over the linear range of fluorescent emission/detected by a specific charge-coupled device.

3. ILK Expression Level (IEL). In an exemplary embodiment, ILK Expression Level is a semi quantitative measurement derived from, but not limited to, western blot, northern blot or reverse transcriptase polymerase chain reaction, mass spectrometry analysis of ILK protein or mRNA synthesis. ILK Expression Level can be expressed in arbitrary units that have been scaled over the linear range of the given measurement.

4. Western Titrated Average of P-FAK (Y397) (WTA-P-FAK). In an exemplary embodiment, Western Titrated Average is a semi quantitative measurement derived from, but not limited to, western blot analysis of the Phosphorylated-FAK (Y397) (P-FAK) epitope. Western Titrated Average of P-FAK can be expressed in arbitrary units that have been scaled over the linear range of blot pixel-density over multiple blot exposures, as measured by a program such as NIH's Image J.

5. Western Titrated Average of P-PAX (S181). In an exemplary embodiment, Western Titrated Average of the Phosphorylated-PAX (S181) (P-Pax) is a semi quantitative measurement derived from, but not limited to, western blot analysis of the of P-PAX (Y181) epitope that is a measure of how well cells can recruit important signaling molecules to focal adhesions. This Western Titrated Average can be expressed in arbitrary units that have been scaled over the linear range of blot pixel-density over multiple blot exposures, as measured by a program such as NIH's Image J.

6. Western Titrated Average of P-Cas (Y165). In an exemplary embodiment, Western Titrated Average of Phosphorylated-p130Cas(Y165) (P-Cas) is a semi quantitative measurement derived from, but not limited to, western blot analysis of the of P-Cas (Y165) epitope. This Western Titrated Average can be expressed in arbitrary units that have been scaled over the linear range of blot pixel-density over multiple blot exposures, as measured by a program such as NIH's Image J.

7. Western Titrated Average of protein of interest (WTA). In an exemplary embodiment, Western Titrated Average of protein of interest is a semi quantitative measurement derived from, but not limited to, western blot analysis of other proteins of interest. This Western Titrated Average can be expressed in arbitrary units that have been scaled over the linear range of blot pixel-density over multiple blot exposures, as measured by a program such as NIH's Image J.

8. Micron Scale ELISA Average of protein of interest (MSEA). In an exemplary embodiment, Micron Scale ELISA Average of a protein of interest is a quantitative measurement of, but not limited to, soluble extracellular protein levels in the in vitro cultured media in the device via a variation of the ELISA technique. The levels of any protein of interest can be measured, for example, but not limited to, EGF or TGFB. Micron Scale ELISA Average of Protein of Interest (MSEA) can be expressed in arbitrary units that have been scaled over the linear range of fluorescent emission/detected by a specific charge-coupled device.

9. NFkappaB Transcription Average (NFTA). In an exemplary embodiment, NFkappaB Transcription Average is a semi-quantitative measure of NFkappaB's activity as measured by, but not limited to, a reporter construct that expresses a fluorescent molecule proportional to the activity of NFkappaB's transcriptional activity. NFkappaB Transcription Average can be expressed in arbitrary units that have been scaled over the linear range of fluorescent emission/detected by a specific charge-coupled device.

10. mRNA Localization Intensity (mRNALI). In an exemplary embodiment, mRNA Localization Intensity refers to a measure of, but not limited to, the area of the punctuate foci when a cell is stained for the mRNA of a known focal adhesion protein, such as talin, vinculin, paxillin, p130Cas, or FAK, mRNA via fluorescent in situ hybridization or similar techniques. mRNA Localization Intensity can be expressed in units of square micrometers ($\mu m^2$) or fluorescent intensity expressed in arbitrary units that have been scaled over the linear range of fluorescent emission/detected by a specific charge-coupled device.

11. Immuno-stain of PhosphoProtein (ISPP). In an exemplary embodiment, Immuno-stain of PhosphoProtein refers to a measure of, but not limited to, the area of the punctuate foci when a cell is stained for a phosphorylated form of a known focal adhesion protein, such as talin, vinculin, paxillin, p130Cas, or FAK, via immunohistochemical techniques. Immuno-stain of PhosphoProtein can be expressed in units of square micrometers ($\mu m^2$) or fluorescent intensity expressed in arbitrary units that have been scaled over the linear range of fluorescent emission/detected by a specific charge-coupled device.

12. ECM Composition of Disassociated Tissue (ECMCDT). In an exemplary embodiment, ECM Composition of Disassociated Tissue refers to a measure of, but not limited to, the protein content of the ECM isolated or purified from the biopsy tissue, such as collagen types I-X, fibronectin, vitronectin, and laminin, via immunohistochemical, and or mass spectrometry techniques. ECM Composition of Disassociated Tissue can be expressed in units of mass or as a ratio of intensities expressed in arbitrary units that have been scaled over the linear range of fluorescent emission/detected by a specific charge-coupled device.

13. Ratio of Tyrosine Phosphorylated Adhesion Kinase to Focal Adhesion Phosphatase (RTFAPP). In an exemplary embodiment, Ratio of Tyrosine Phosphorylated Adhesion Kinase to Focal Adhesion Phosphatase refers to a measure of, but not limited to, the tyrosine phosphorylated protein content within focal adhesions, purified from the biopsy tissue. RTFAPP can be calculated after measuring isolated kinases and phosphatases from focal adhesions and measuring the amount of phosphorylated forms of protein. Ratio of Tyrosine Phosphorylated Adhesion Kinase to Focal Adhesion Phosphatase can be expressed in units of mass or as a ratio of intensities expressed in arbitrary units that have been scaled over the linear range of fluorescent emission/detected by a specific charge-coupled, photographic, or luminometric device.

14. Ratio of STAT transcription factor and p53 activation state (RSTFp53). In an exemplary embodiment, Ratio of STAT transcription factor and p53 activation state refers to a measure of, but not limited to, the postranslationally modified STAT and p53 protein content within the cell, purified from the biopsy tissue. Ratio of STAT transcription factor and p53 activation state can be calculated after measuring the amount of post-translation modified forms of protein STAT and p53. Ratio of STAT transcription factor and p53 activation state can be expressed in units of mass or as a ratio of intensities expressed in arbitrary units that have been scaled over the linear range of fluorescent emission/detected by a specific charge-coupled, photographic, or luminometric device.

14. Ratio of NFKappaB transcription factor and p53 activation state (RNTFp53). In an exemplary embodiment, Ratio of NFKappaB transcription factor and p53 activation state refers to a measure of the modified forms of NFKappaB and p53, purified from the biopsy tissue. RNTFp53 can be calculated after measuring, but not limited to, the amount of post-translation modified forms of protein NFKappaB and p53. Ratio of NFKappaB transcription factor and p53 activation state can be expressed in units of mass or as a ratio of intensities expressed in arbitrary units that have been scaled over the linear range of fluorescent emission/detected by a specific charge-coupled, photographic, or luminometric device.

As will be discussed in more detail below, the biophysical biomarkers, and biochemical biomarkers discussed above can be used to derive one or more number values, or metrics, that are proportional to and correlate with the aggressiveness and invasiveness (oncogenic & metastatic potential) of a tissue sample. These numerical metrics can then be correlated with a patient's prognosis. The derivation of these formulas comes from experimental data described in more detail below.

The identity of the aforementioned biomarkers is related to the idea that focal adhesions are protein complexes that concentrate signaling molecules. The following data presented demonstrates that focal adhesions and actin retrograde flow actually regulate the localization, modification, and activation of proteins involved in important cellular functions such as stress fiber formation, endocytosis, exocytosis survival, growth, transcription, translation, endocytosis, exocytosis.

In one exemplary embodiment, ILK+/+ embryonic cells (cells with ILK) have been shown to grow faster and migrate faster than embryonic cells without ILK (ILK−/−). As will be discussed in more detail below, this suggests that ILK+/+ cells have a tendency to be more oncogenic and metastatic than ILK−/− cells. The results demonstrating that the properties of ILK cells correlates with their growth and migration potential have also been confirmed and validated using the human breast cancer MCF cell line and other cell lines, as mentioned below.

| Cell Line | Cell Description |
| --- | --- |
| A431 | Human epidermoid carcinoma cell line |
| Hec1 | Human uterin, endometrial, adenomacarcinoma cancer. |
| LnCap | Human prostate carcinoma |
| NCI-H460 | Human lung carcinoma |
| MDA-MB231 | Human breast adenocarcinoma |
| ILK+/+ | Mouse Embryonic Fibroblast containing Integrin-Linked Kinase |
| ILK−/− | Mouse Embryonic Fibroblast not containing Integrin-Linked Kinase |
| FAK+/+ | Mouse Embryonic Fibroblast containing Focal Adhesion Kinase |
| FAK−/− | Mouse Embryonic Fibroblast not containing Focal Adhesion Kinase |
| MCF7 | Human breast adenocarcinoma |
| MCF10 | Human breast fibrocystic disease |
| Wi38 | Human normal Lung fibroblast |
| NIH3T3 | Human Embryo Fibroblast |
| RPTPα+/+ | Mouse Embryonic Fibroblast containing Receptor Protein Tyrosine Phosphatase |
| β1 integrin+/+ | Mouse Embryonic Fibroblast containing Beta 1 Integrin |
| β1 integrin−/− | Mouse Embryonic Fibroblast not containing Beta 1 Integrin |
| SYF | Mouse Embryonic Fibroblast not containing Src, Yes, or Fyn |
| E503 | Mouse Embryonic Fibroblast containing Src, Yes, Fyn |
| hMSC | Human Mesencymal Stem Cell |
| IEC18 | Human Intestinal epithelial cell line |
| DU145 | Prostate cancer cell derived from brain metastasis |
| PC3 | Prostate cancer cell derived from bone metastasis |
| SH-SY5Y | Human neuroblastoma |
| T47D | Human breast cancer cell |

Figure 1A:
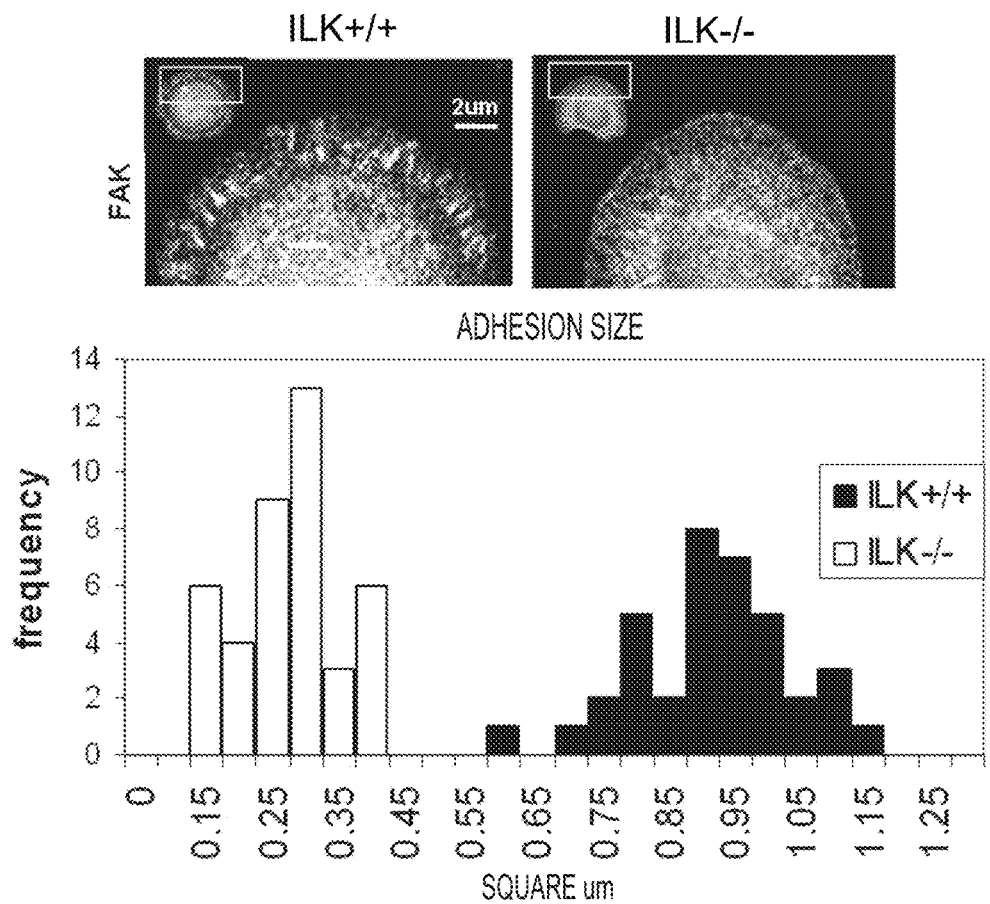
FIG. 1. Mouse Embryonic Fibroblasts ILK−/− cells form smaller focal adhesions when cells are immunostained for FAK, p130Cas, paxillin, talin,& vinculin on collagen coated glass. (a-e) Confocal images of cells plated on collagen coated glass for 60 min, fixed and stained for indicated proteins and quantification of focal adhesion sizes.
Figure 1B:
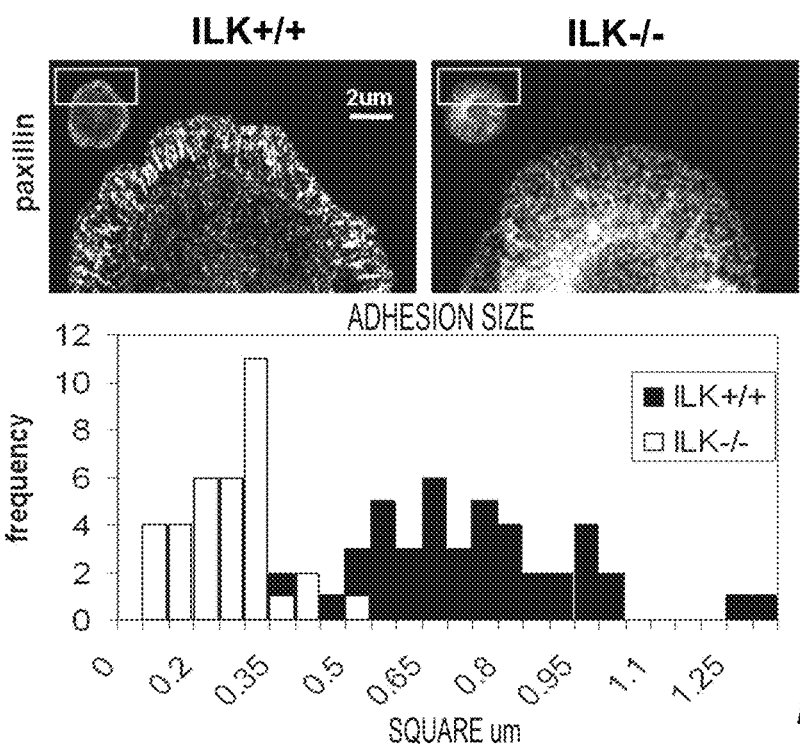
Figure 1C:
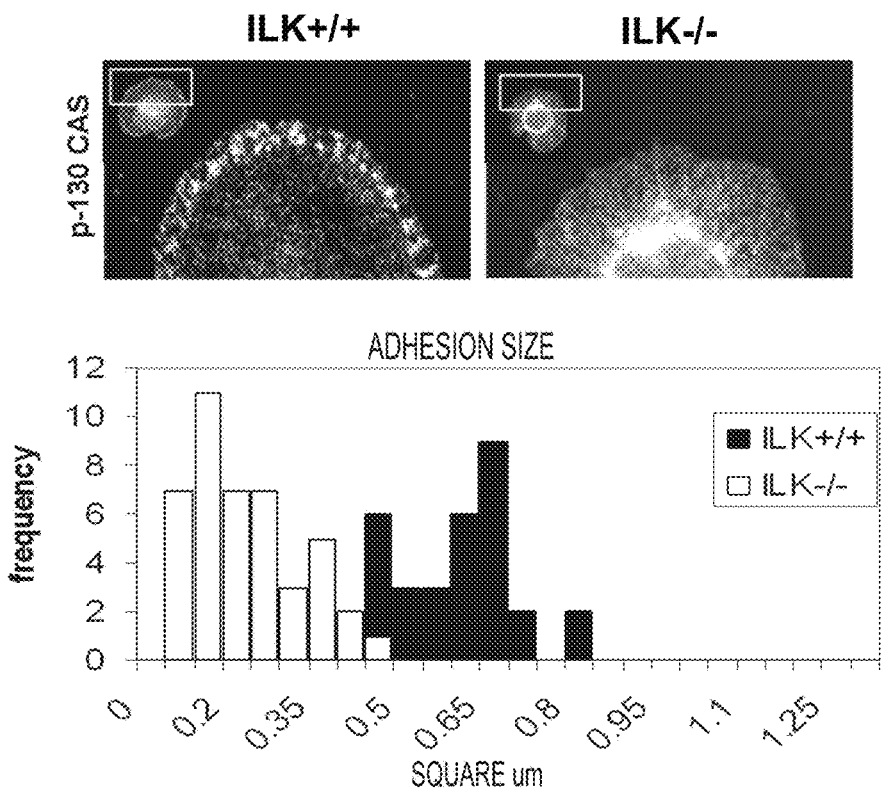
Figure 1D:
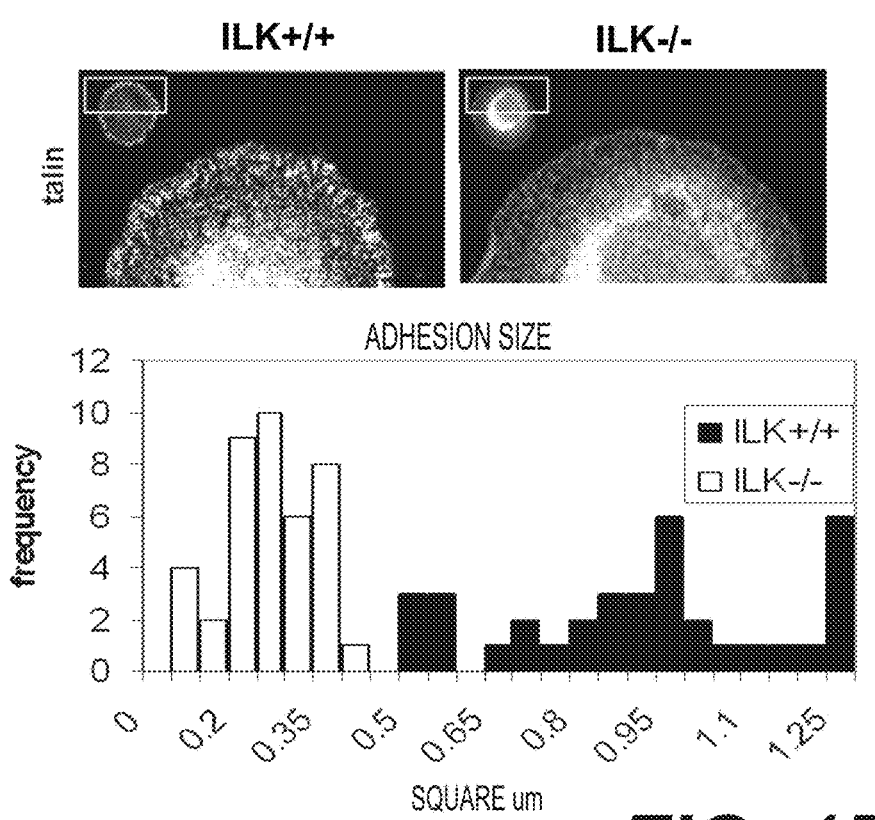
Figure 1E:
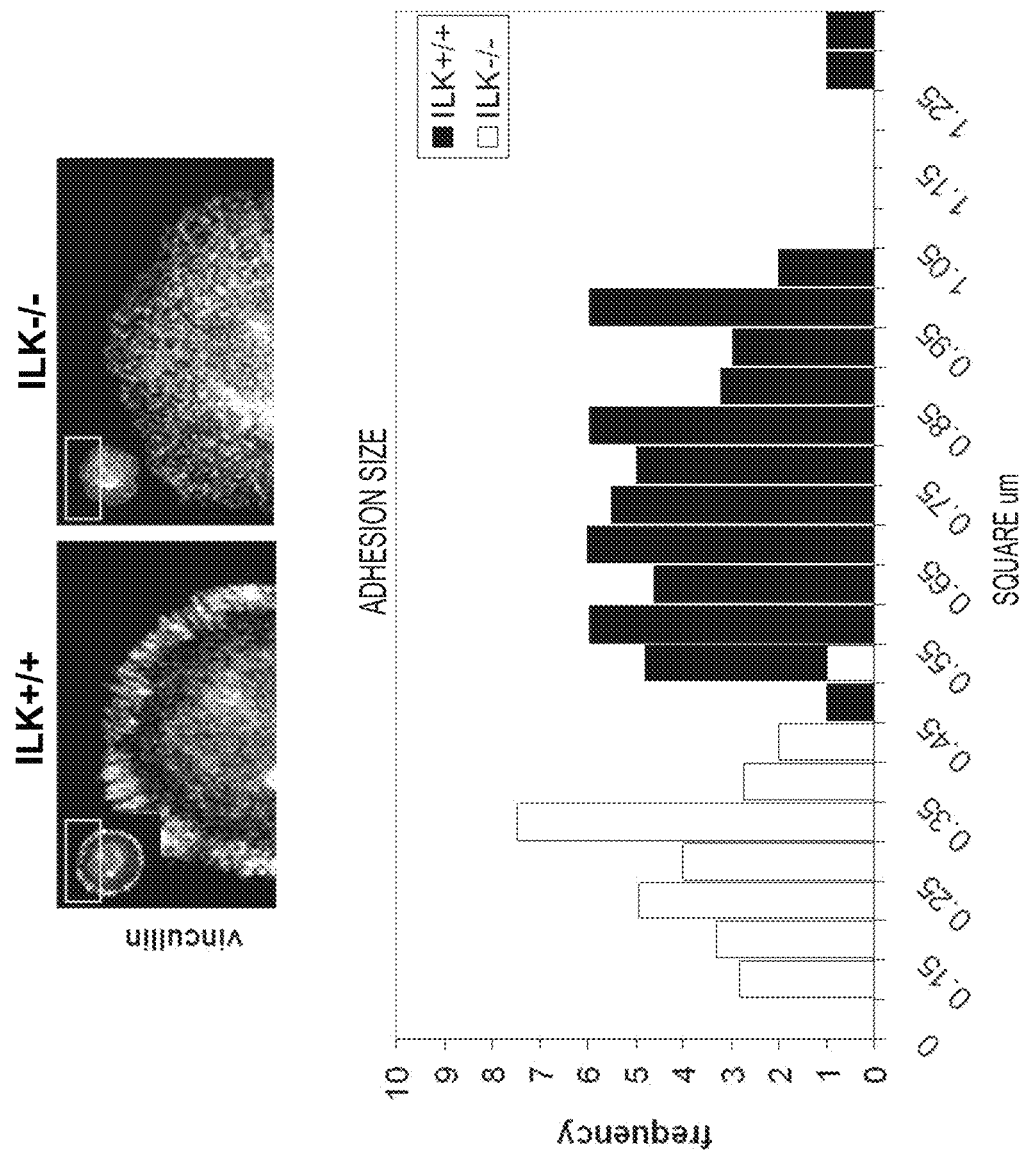
Figure 2C:
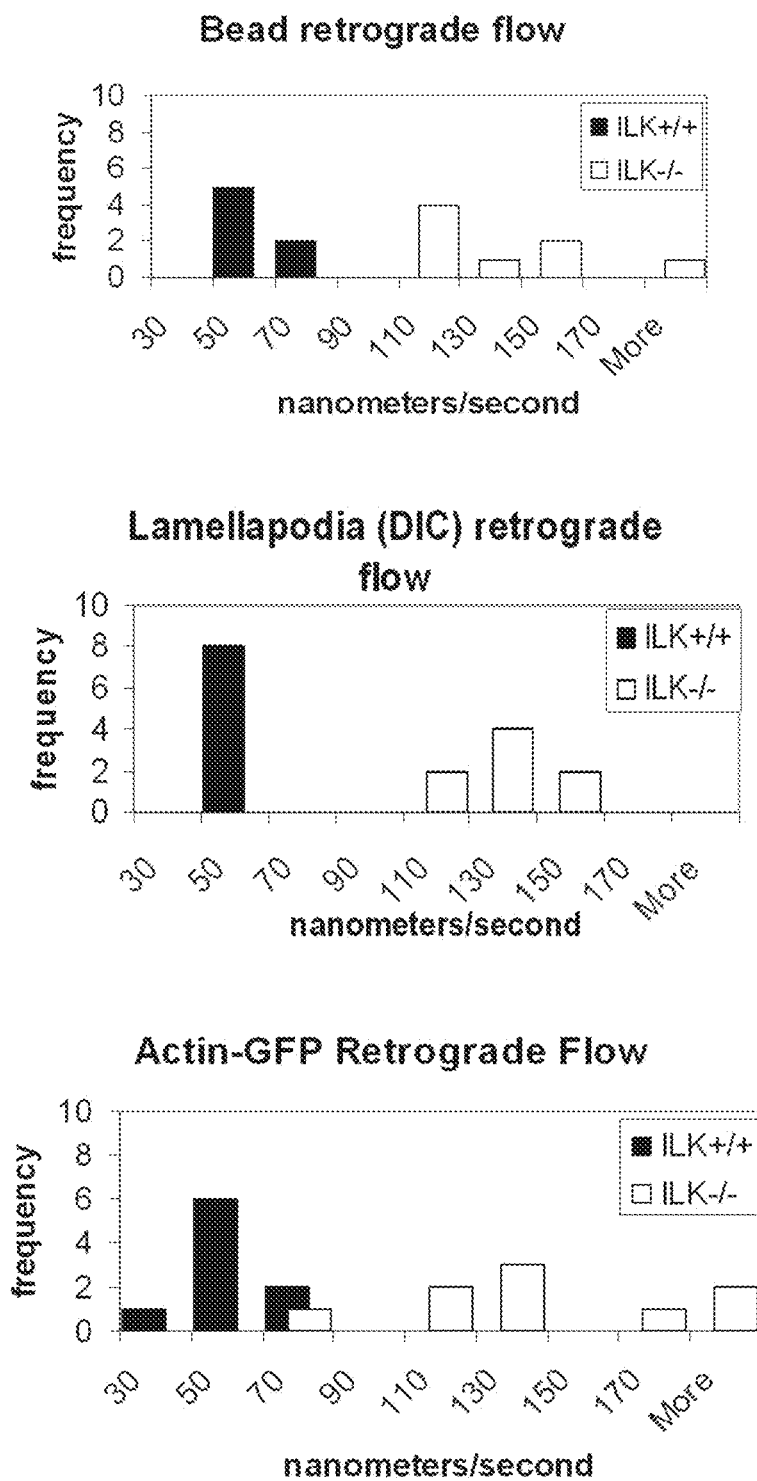
FIG. 2. Mouse Embryonic Fibroblasts ILK+/+ exhibits slower actin retrograde flow than ILK−/− cells. (a) Kymographs of ILK+/+ cells. Retrograde flow velocities were calculated by measuring the speed of laminin & collagen coated beads, actin-gfp and membrane displacement (via differential interference contrast microscopy (DIC)). (b) Kymographs of ILK−/− cells. Retrograde flow velocities were calculated by measuring the speed of laminin & collagen coated beads, actin-gfp and membrane displacement (via DIC). (c) Quantification of retrograde flow velocities over the three techniques employed.
Figure 3A:
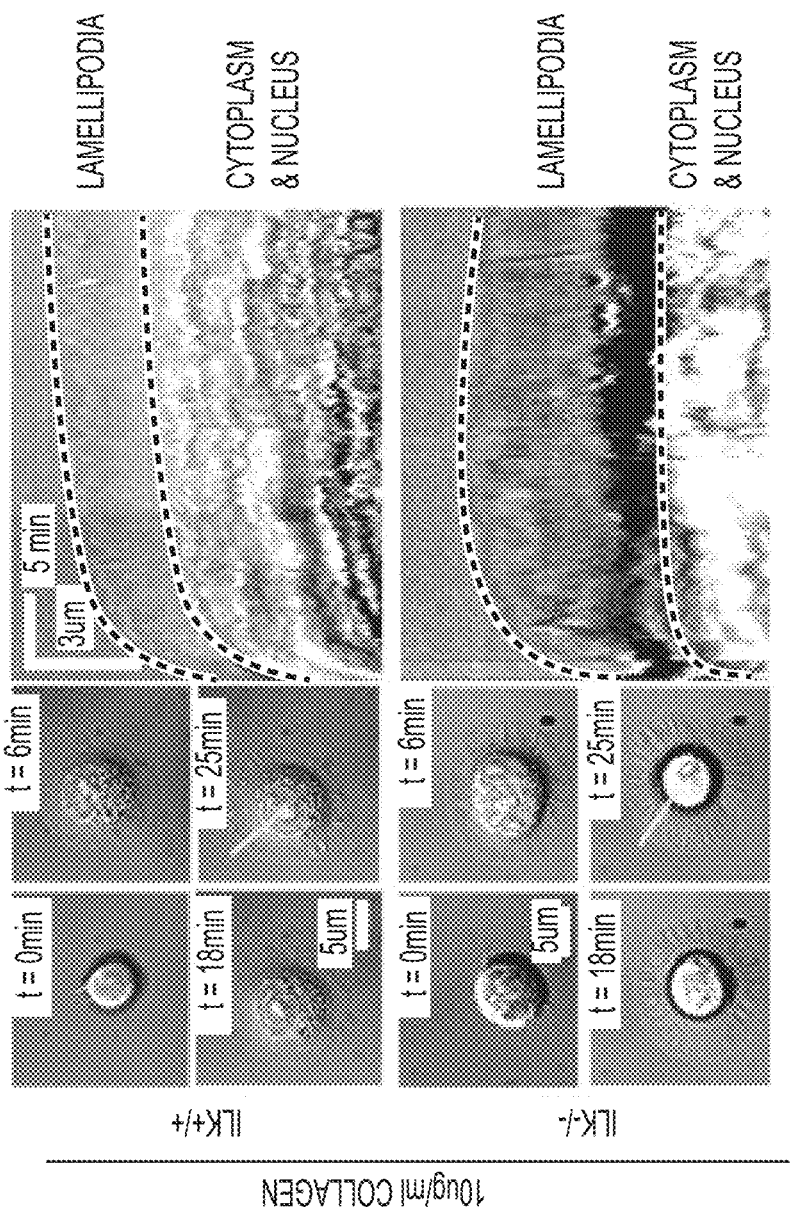
FIG. 3. ILK+/+ exhibits slower myosin-light-chain (MLC) retrograde flow and greater MLC persistence at the leading edge compared to ILK−/− cells. ILK+/+ and ILK−/− cells exhibit different early integrin-mediated Cell-ECM interactions, dynamics, and phenotype on collagen and fibronectin. (A) DIC microscopy of ILK+/+ and ILK−/− cells spread on collagen coated glass showed ILK−/− cells are unable to spread their cytoplasm and exhibit wider lamellipodia. (B) DIC microscopy of ILK+/+ and ILK−/− cells spread on fibronectin coated glass showed ILK−/− cells are unable to maintain late forming, stable adhesions. (C) Antibodies specific for β1 and α2β1 integrins block spreading of Mouse Embryonic Fibroblast's on collagen. Quantification of cell areas after treatment with inhibitory antibodies as indicated. Data represents mean±SEM of three individual experiments. A Student's t-test was used for statistical analyses, *=P<0.05. (D) Cyclic RGD peptides specific for alphaVBeta3 block spreading of MEF's on fibronectin. Data represents mean±SEM of three individual experiments. A Students t-test was used for statistical analyses, *=P<0.05. (E) DIC microscopy of ILK+/+ and ILK−/− cells on soft or rigid collagen and fibronectin show ILK−/− cells do not sense rigidity on collagen but do sense rigidity on fibronectin. (F) Quantification of cell areas when ILK+/+ and ILK−/− cells are spread on soft and rigid gels coated with collagen and fibronectin. Unlike wildtype cells, ILK−/− cells do not sense rigidity on collagen and spread to similar areas on soft and rigid substrates. ILK−/− cells do sense rigidity on fibronectin. Data represents mean±SEM of three individual experiments. A Student's t-test was used for statistical analyses, **=P<0.001. (G) Kymographs of ILK+/+ and ILK−/− cells transfected with myosin-light-chain-GFP (MLC-GFP) to show myosin light chain flow velocities. (H) Summary of myosin-light-chain (MLC) velocities shows MLC flows rearward at greater velocity in ILK−/− cells. (I) TIRF image of ILK+/+ and ILK−/− transfected with myosin-light-chain-GFP demonstrating localization of myosin at leading edge in ILK+/+ versus ILK−/−. MLC-GFP localizes to and persists at ~0.9 um inward of the leading edge in ILK+/+ cells, while it is localized throughout the basal portion of the cytoplasm in ILK null cells and perisists ~3.8 um inward of the leading edge. (J) Line intensity plot of MLC localization in ILK+/+ and ILK−/− cells shows MLC localizes >3 um inward of leading edge in ILK−/− cells while MLC localizes <1 um inward of leading edge in ILK+/+ cells.
Figure 3B:
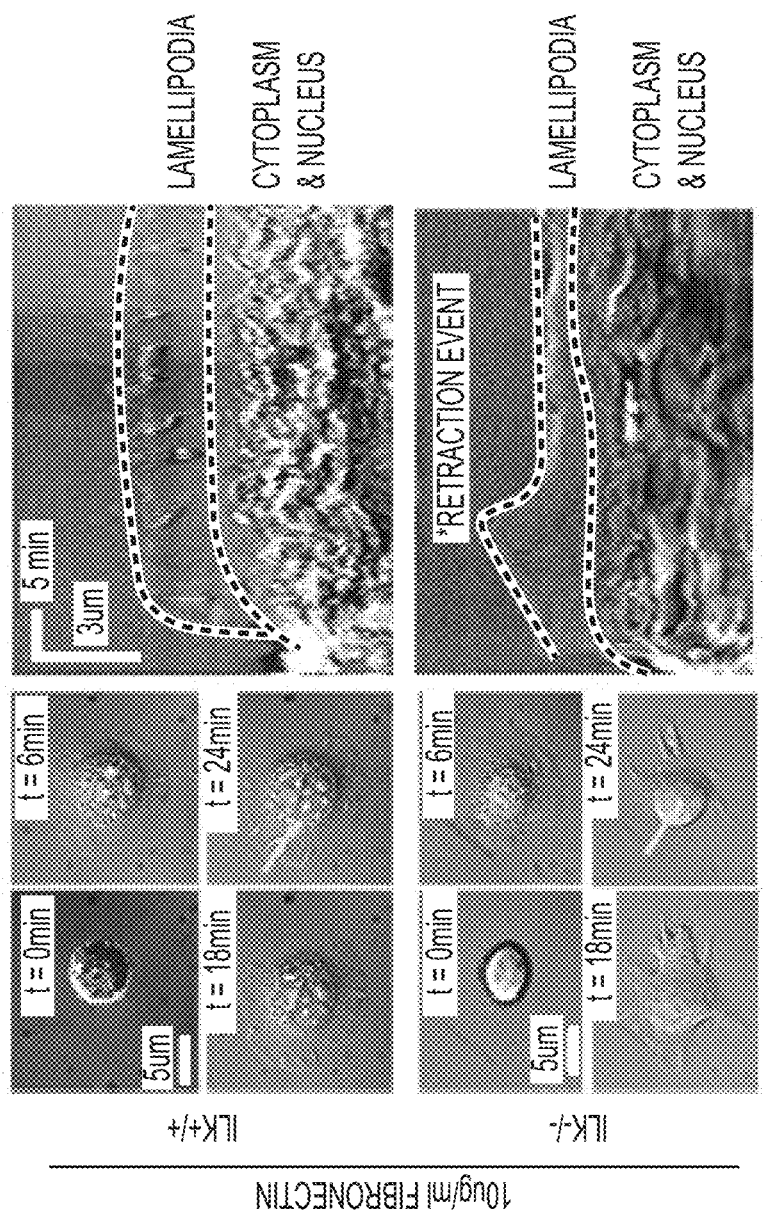
Figure 3F:
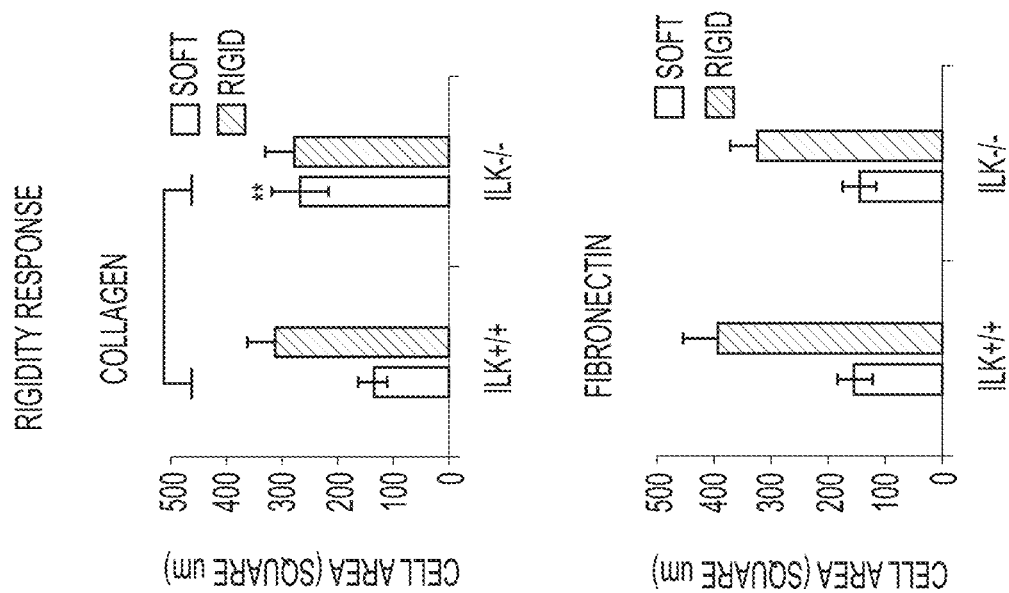
Figure 3E:
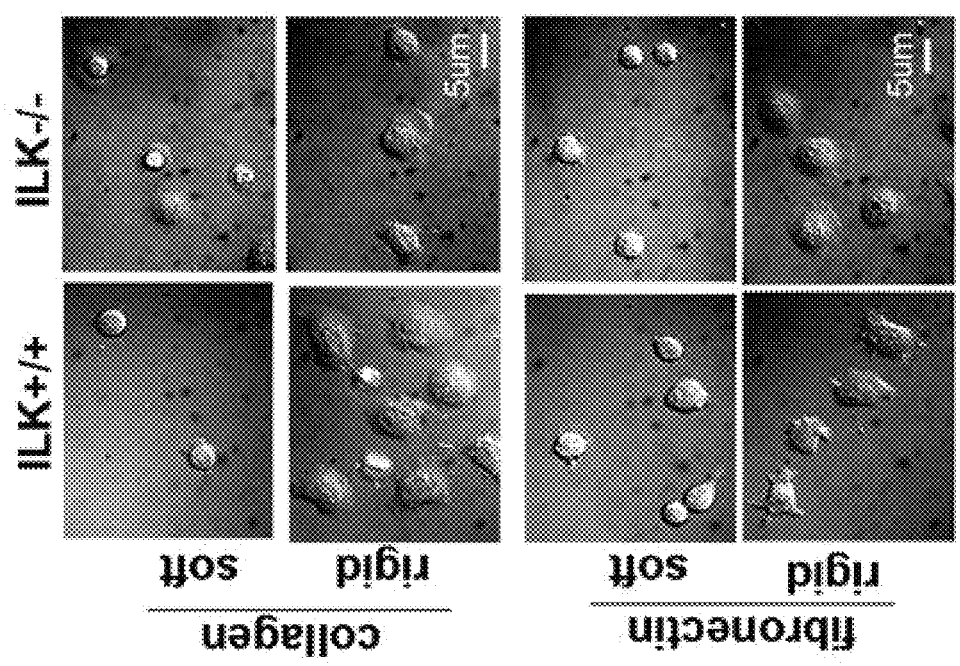
Figure 3G:
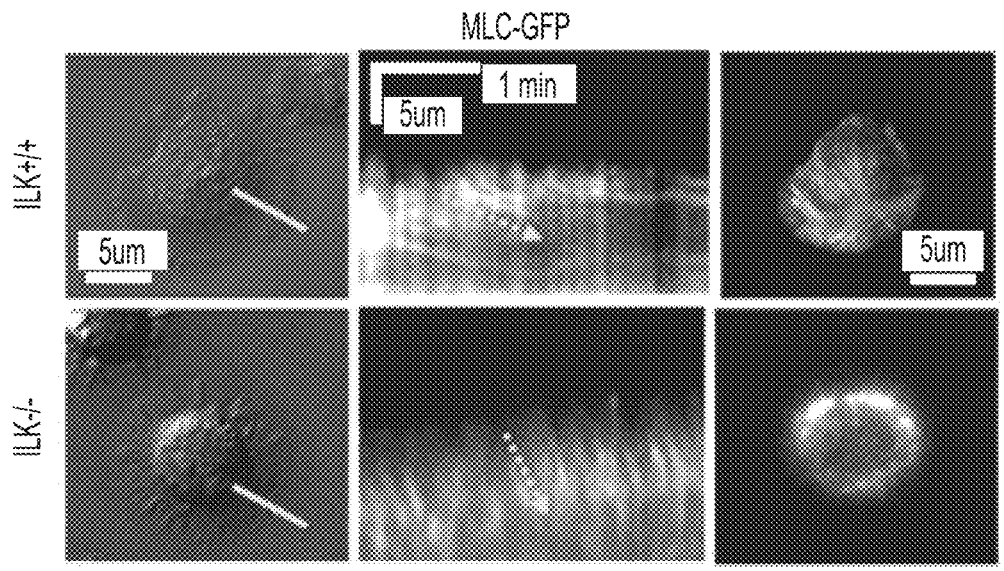
Figure 3H:
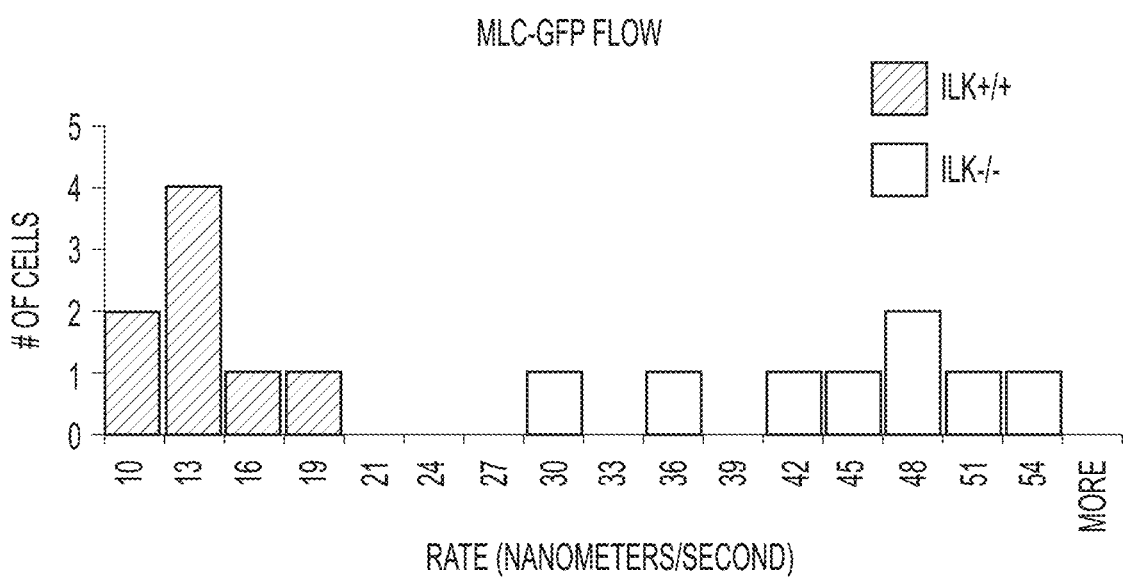
Figure 3I:
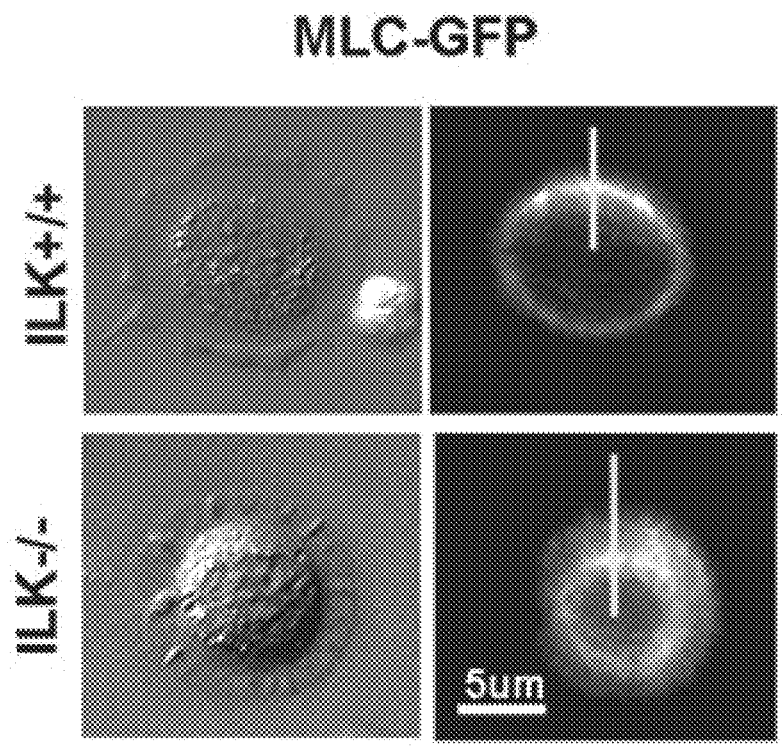
Figure 3J:
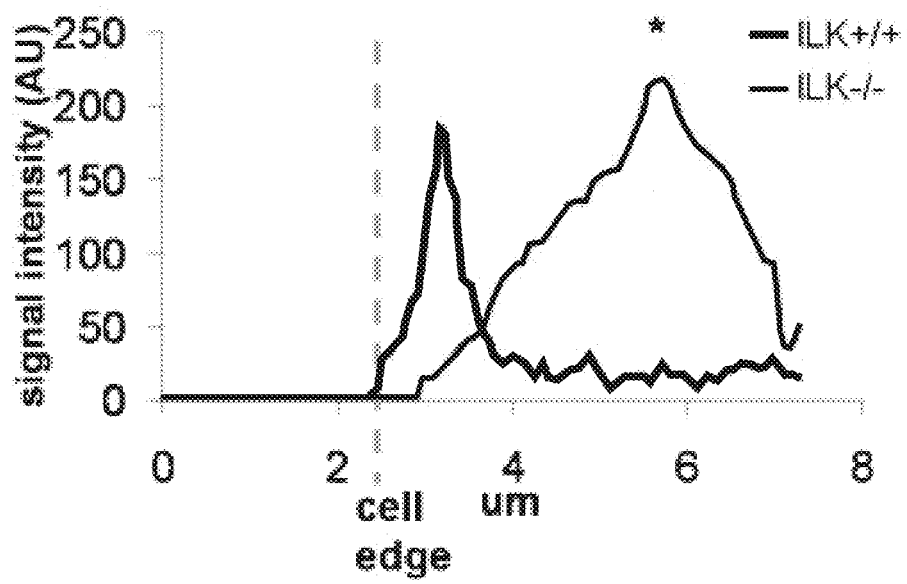
Figure 8:
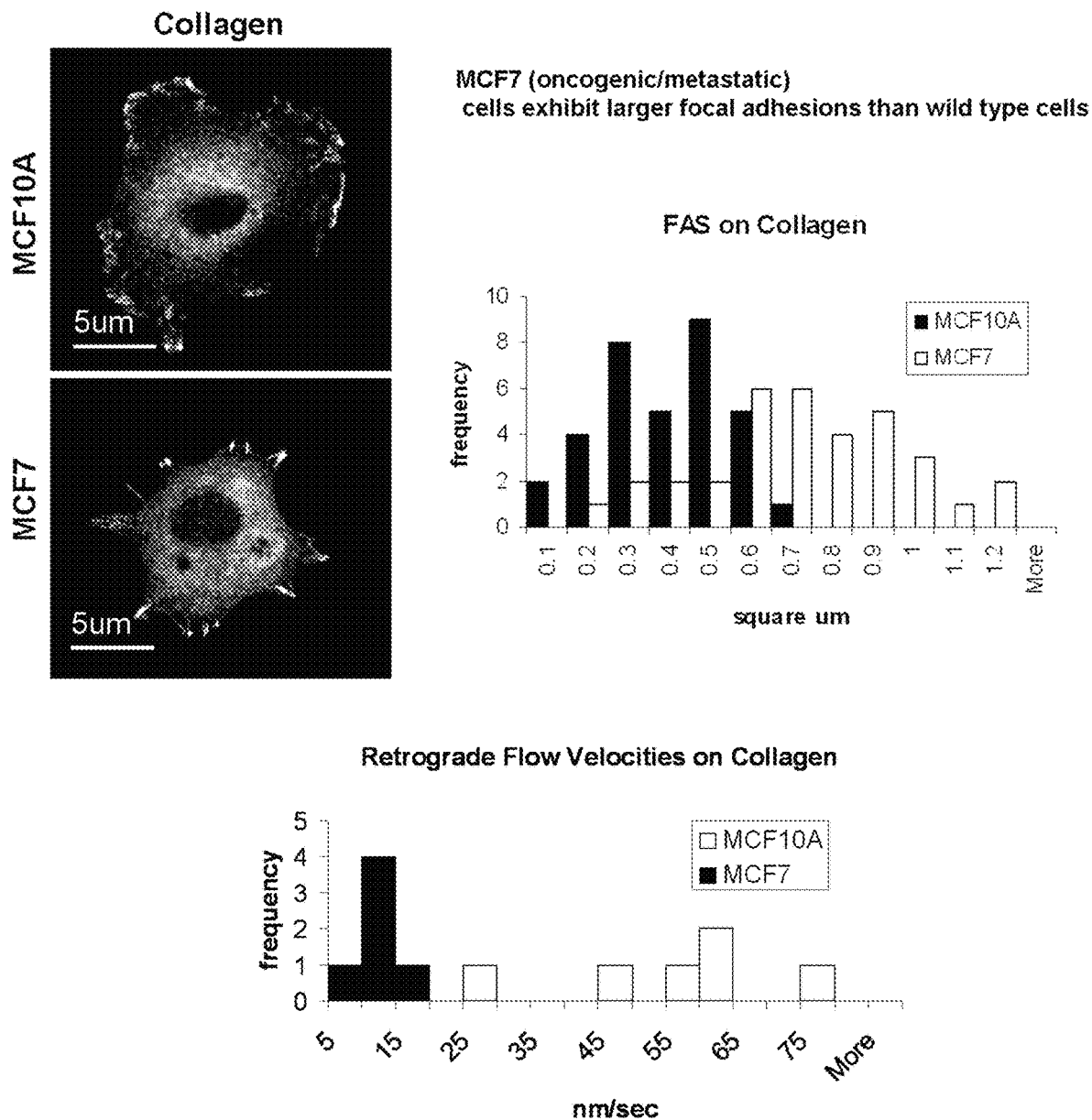
FIG. 8. Summary quantification of retrograde flow velocities or speeds for MCF7, MCF10A cells on collagen and fibronectin. MCF7 cells exhibit slower retrograde flow velocities or speeds. Moreover, this data demonstrates that retrograde flow speed, focal adhesion, and traction force index maintain their relative differences over different extracellular matrix molecules. For example, focal adhesion size is still larger for cancer cells whether they are plated on collagen or fibronectin. When plated on 10 ug/ml of fibronectin coated glass, the oncogenic, metastatic MCF7 breast cancer cell line form larger focal adhesions than normal, wild type MCF10A breast cell line. This observation is consistent with the previous observations with the ILK cell line, in that cells with larger focal adhesions grow faster and exhibit faster migration rates. Moreover, this supports the idea that cells with larger focal adhesions exhibit greater oncogenic and metastatic potential.
Figure 8:
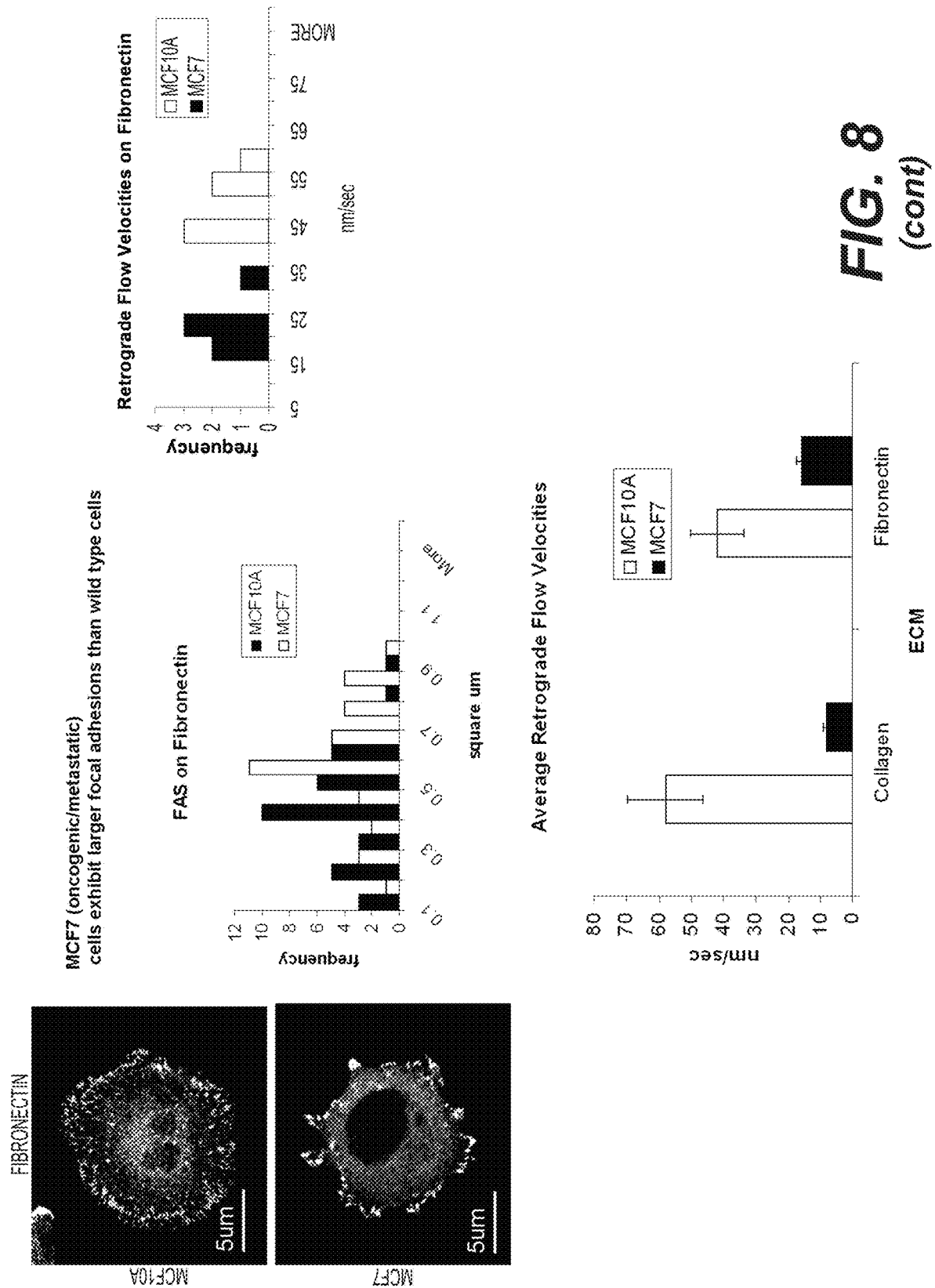
Figure 9A:
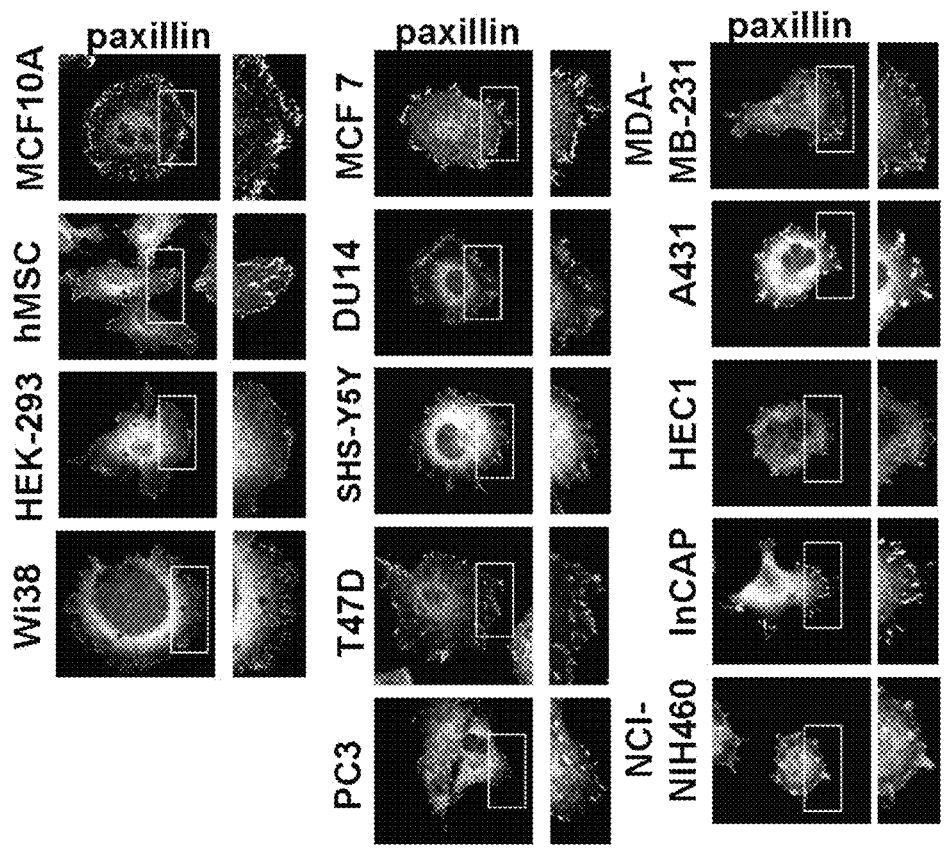
FIG. 9. Focal Adhesion sizes of human wildtype and cancer cell lines. (A) Cells were plated on 10 ug/ml collagen+fibronectin coated glass, fixed at 60 minutes, stained for paxillin, and imaged via confocal microscopy. (B) Summary quantification of focal adhesion sizes. Error bars are +−1 Standard Deviation. Data represent mean±1 SD from a minimum of 50 cells. When plated on 10 ug/ml of collagen coated glass, the oncogenic, metastatic MCF7 breast cancer cell line form larger focal adhesions than normal, wild type MCF10A breast cell line. This observation is consistent with the previous observations with the ILK cell line, in that cells with larger focal adhesions grow faster and exhibit faster migration rates. Moreover, this supports the idea that cells with larger focal adhesions exhibit greater oncogenic and metastatic potential.
Figure 9B:
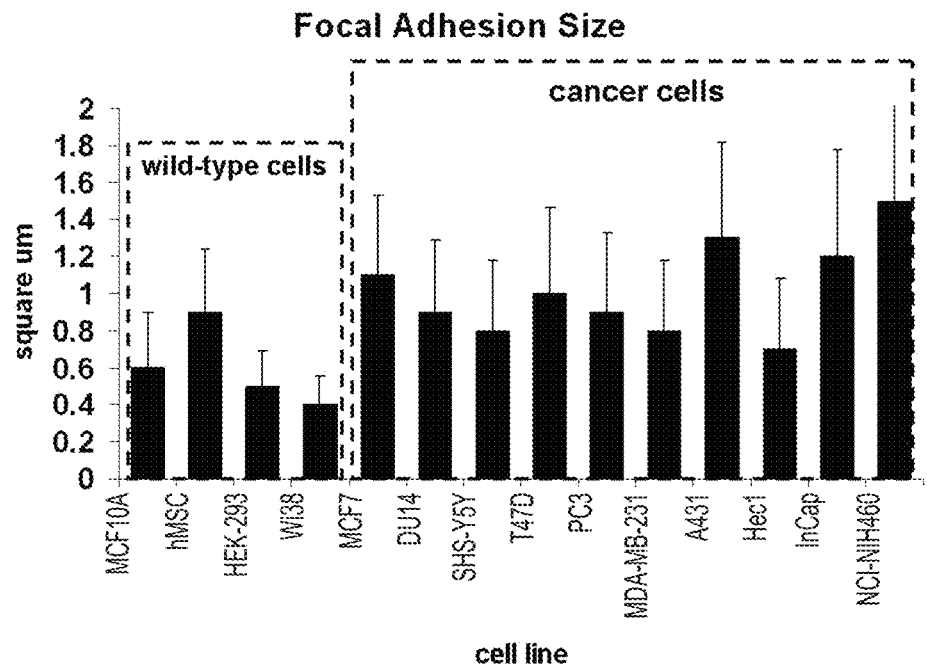
Figure 10A:
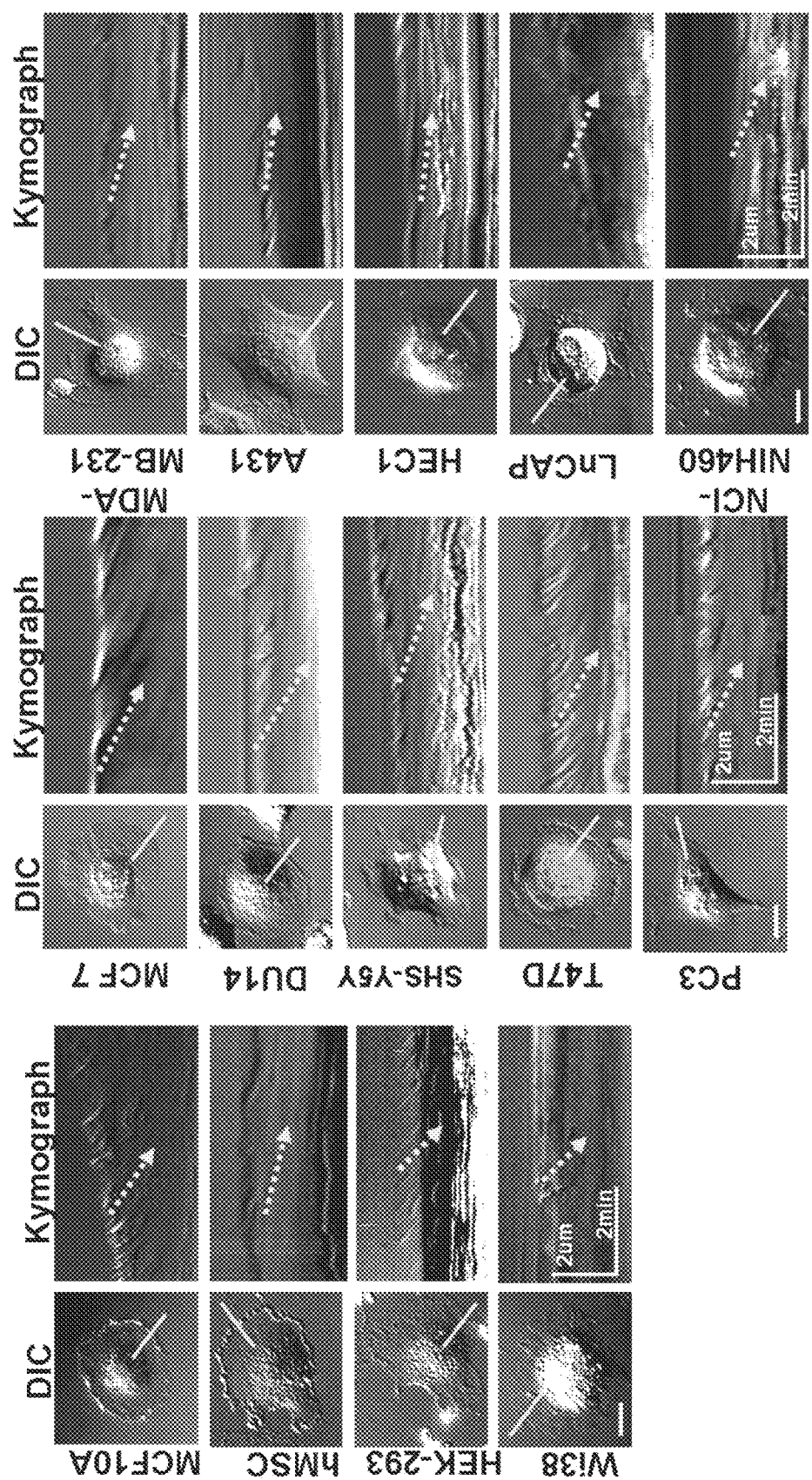
FIG. 10. Actin retrograde flow velocities of wildtype and cancer cells. (A) Cells were plated on 10 ug/ml collagen+fibronectin coated glass on imaged via time-lapse DIC. Actin retrograde flow was calculated by observing dorsal feature flow. (B) Summary quantification of actin retrograde flow velocities. Data represent mean±1 SD from a minimum of 20 cells for retrograde flow speed for each individual ECM condition. Oncogenic, and metastatic cells, such as MCF7, exhibit slower actin retrograde flow than normal, wild type cells, such as MCF10A cells. This observation is consistent with results obtained from the ILK model system: cells with larger focal adhesions and slower retrograde flow exhibit greater growth/oncogenic, migration/metastatic potential.
Figure 10B:
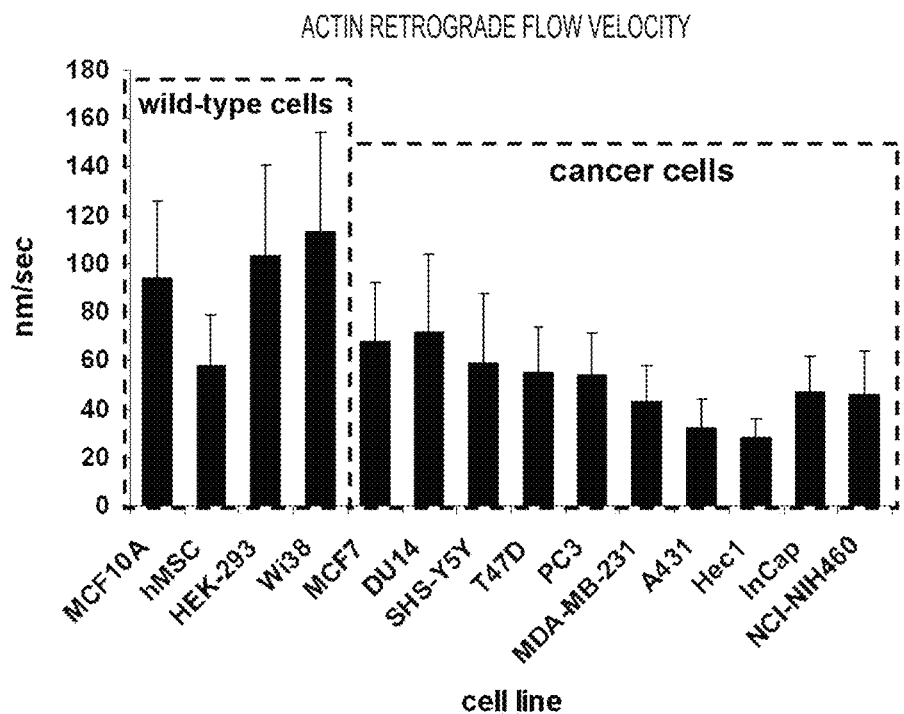
Figure 11:
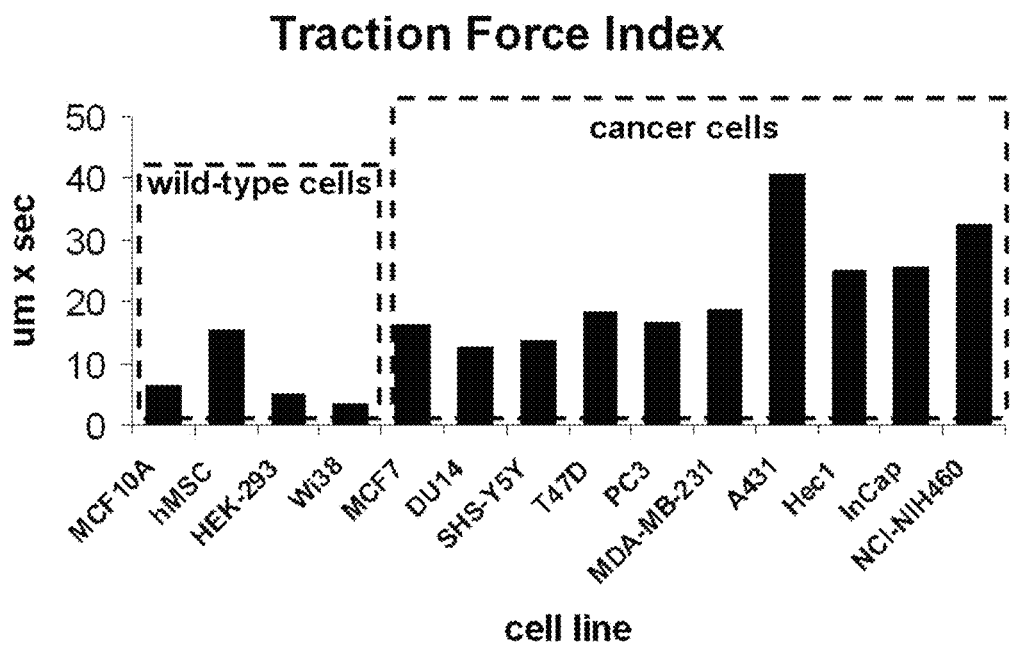
FIG. 11. Summary of the calculation of the Traction Force Index for wild-type and cancer cell lines. Traction Force Index is calculated by dividing focal adhesion size, and retrograde flow speed. Cells that have greater growth/oncogenic potential and migration/metastatic potential exhibit larger Traction Force Indexes. (A) Cell were plated on 10 ug/ml collagen+fibronectin coated tissue culture plastic and TFI was calculated.

Focal adhesions (FAs) can exist in different sizes and primarily reside at the leading edge of cells (FIGS. 1, 4 and 8). After observing FAs are smaller in ILK−/− cells compared to ILK+/+, it was investigated whether cellular consequences may result from smaller FAs. It was found that smaller FAs result in a contracted cytoplasm (FIG. 3A) and faster actin retrograde flow (FIG. 2). Interestingly, a contracted cytoplasm phenotype has been shown to result in reduced endocytosis and lack of microtubule extension. More cellular consequences of altered FA size and actin retrograde flow speed were subsequently investigated. FIG. 3G-H demonstrates that increased actin flow in ILK−/− cells results in the mislocalization of myosin toward the interior of the cell. This mislocalization of myosin subsequently results in the rearward localization of actin stress fibers necessary for force generation, polarization, migration and invasion.

Figure 4A:
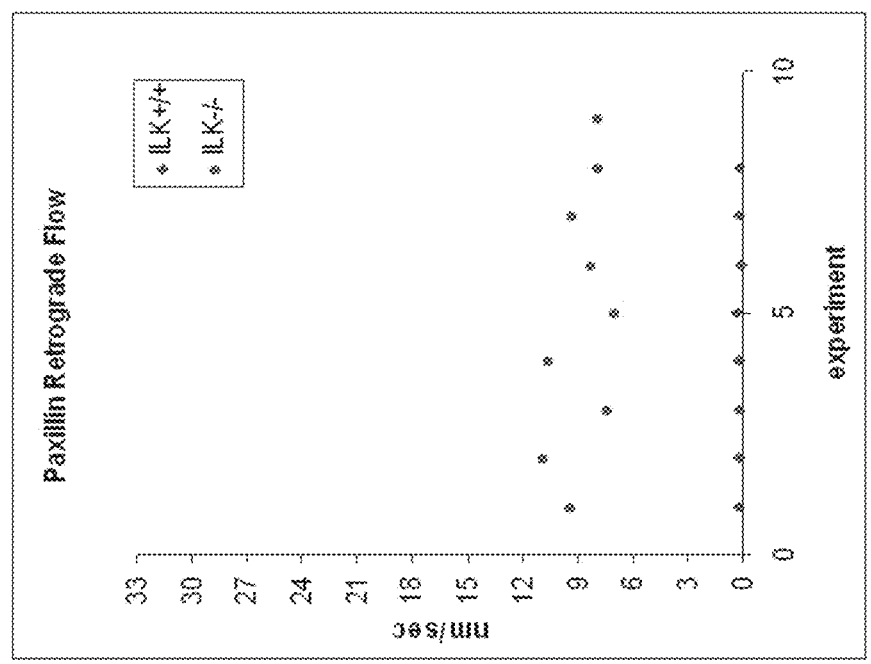
FIG. 4. Adhesions Move Inward Rapidly without ILK. These Kymographs show the dramatic difference between the velocity of p130Cas, paxillin, and talin rearward movement (see slopes in kymographs) between ILK+/+ and ILK−/− cells when plated on collagen. (a) Kymograph of ILK+/+ and ILK−/− cells transfected with paxillin-GFP, demonstrating paxillin's increased rate of rearward flow in ILK−/− (ILK+/+: 20 nm/sec±0.05 (n=8); for ILK−/−: 8.7 nm/sec±3.1 (n=9) (b) Kymograph of ILK+/+ and ILK−/− cells transfected with p130Cas-GFP, demonstrating p130Cas's increased retrograde flow in ILK−/− cells. ILK+/+: 0.91 nm/sec±0.04 (n=9); for ILK−/−: 19.0 nm/sec±6.4 (n=11) (c) Kymograph of ILK+/+ and ILK−/− cells transfected with talin-gfp, demonstrating talin's increased rate of reward flow in ILK−/− cells. ILK+/+: 2.38 nm/sec±0.90 (n=4) ILK−/−: 25.8 nm/sec 4.4 (n=5) (d) Localization of indicated proteins in ILK+/+ and ILK−/− backgrounds, demonstrating phosphorylated proteins localize at the leading edge in ILK+/+ background, and localize toward the interior of the cell and endo-exoplasmic border in ILK−/−. Cells were plated on collagen coated glass for 60 min, fixed, stained, and imaged via confocal microscopy. (E) Summary quantification of retrograde velocities of FA proteins. (F) Total western analysis of phosphorylated focal adhesion proteins for p130Cas, FAK, and Src when ILK+/+ and ILK−/− cells are compared after being spread on 10 ug/ml collagen coated tissue culture plastic for indicated time points. This is in contrast to phospho staining at sites of adhesion, where ILK+/+ cells exhibit greater staining for phospho—FAK, Src, Pax, and p130Cas at sites of adhesion compared to ILK−/− cells.
Figure 4A:
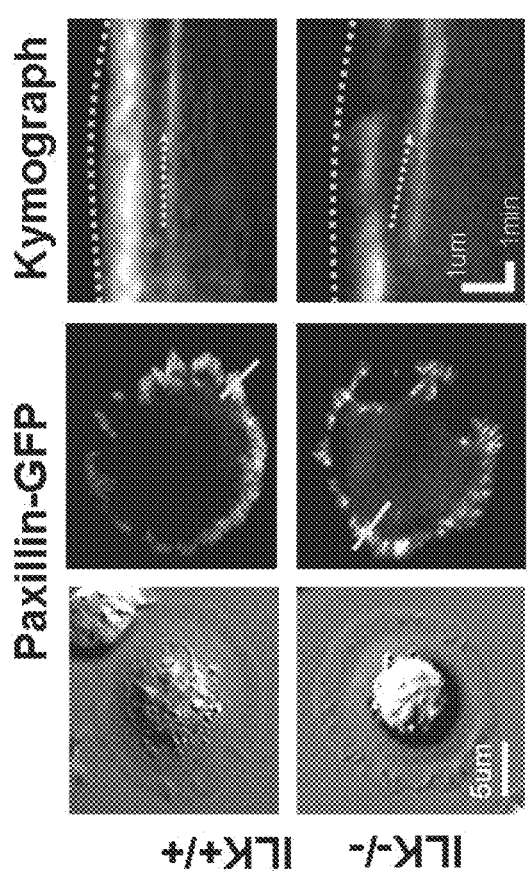
Figure 4B:
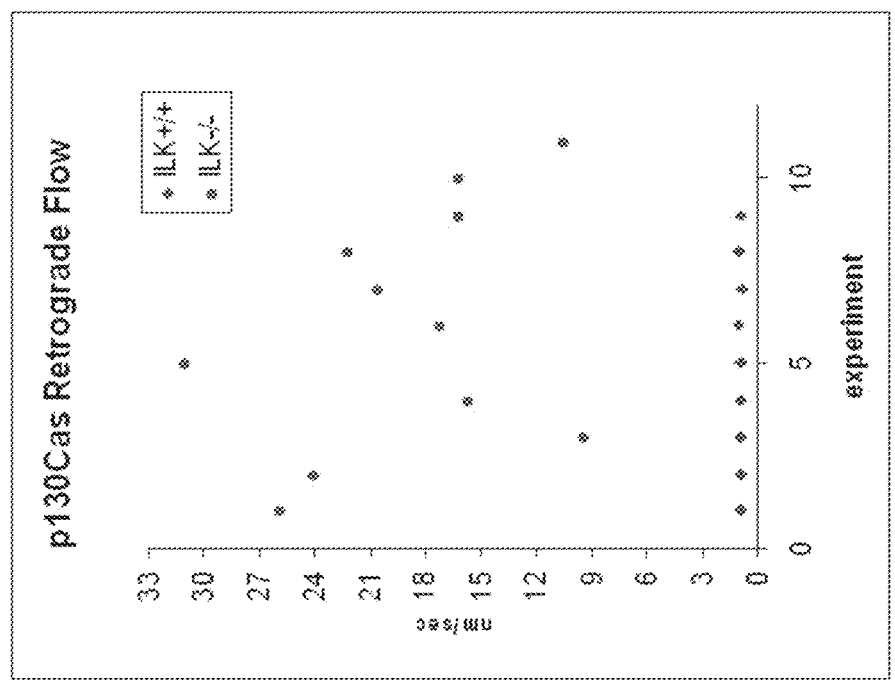
Figure 4B:
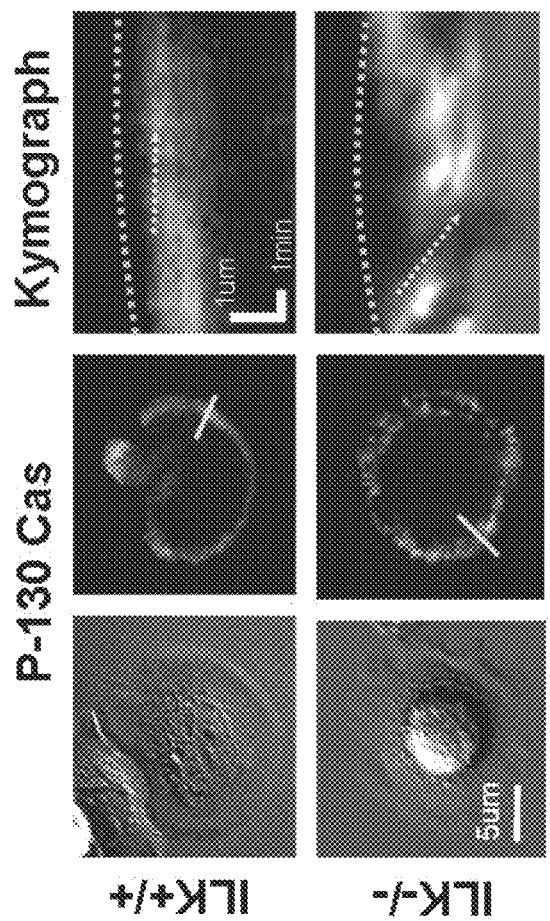
Figure 4C:
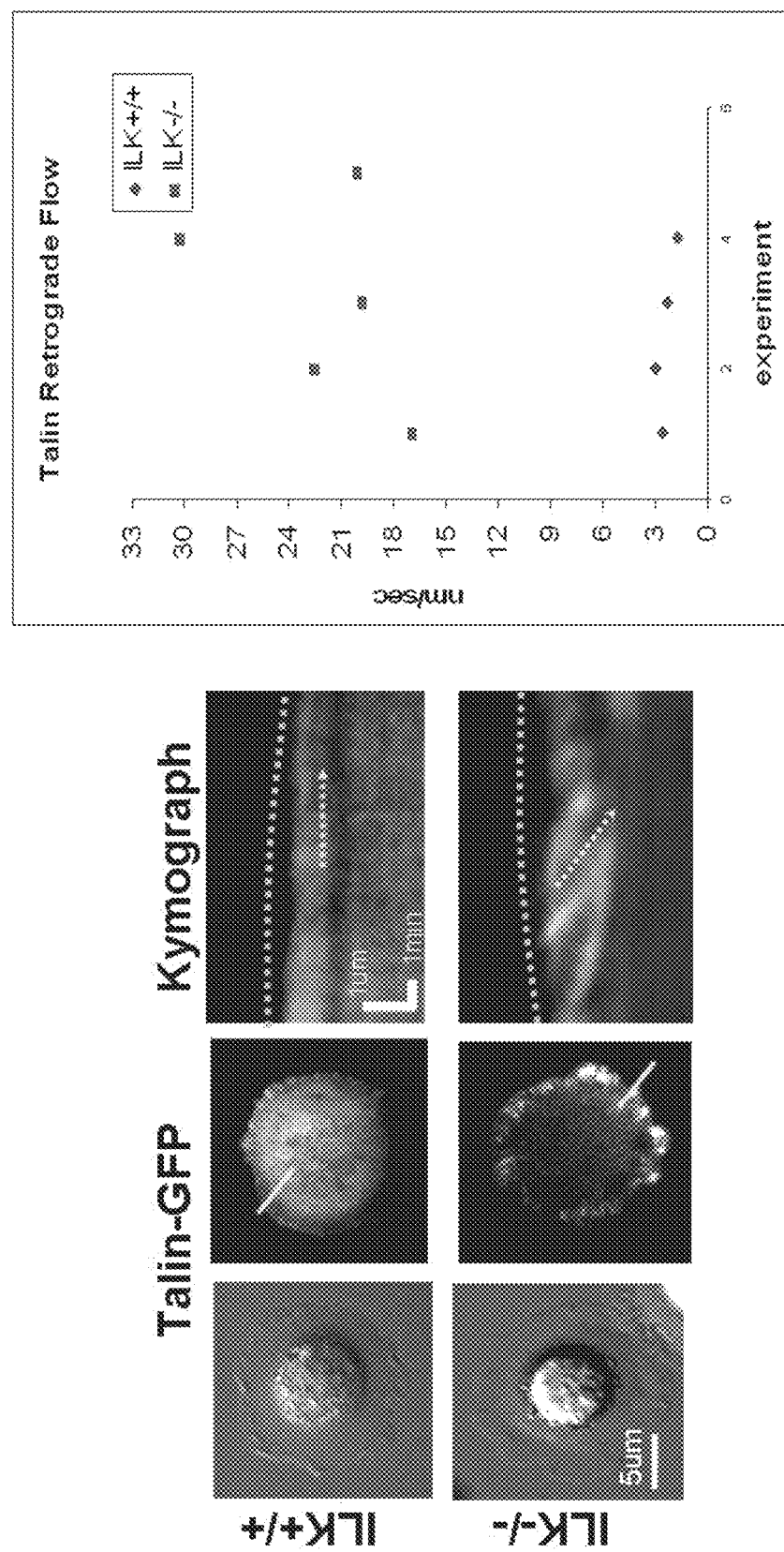
Figure 4E:
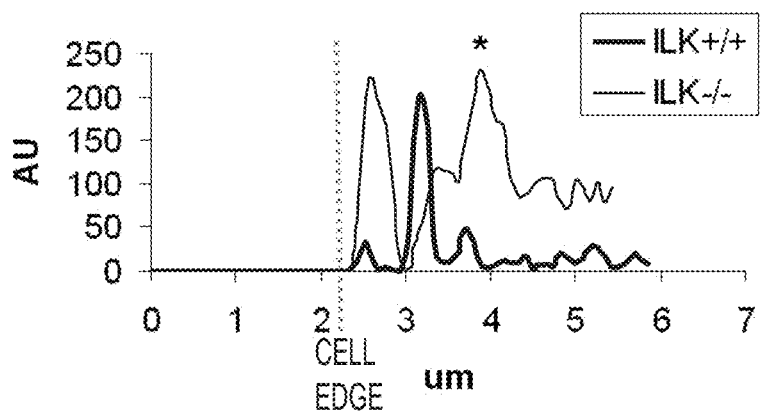
Figure 4E:
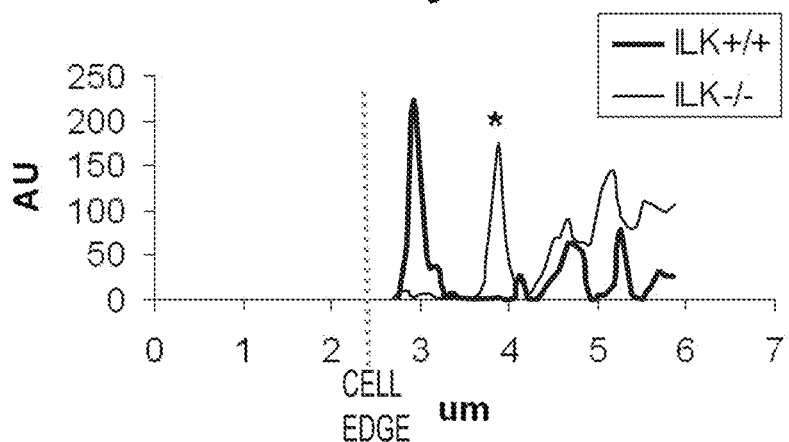
Figure 4E:
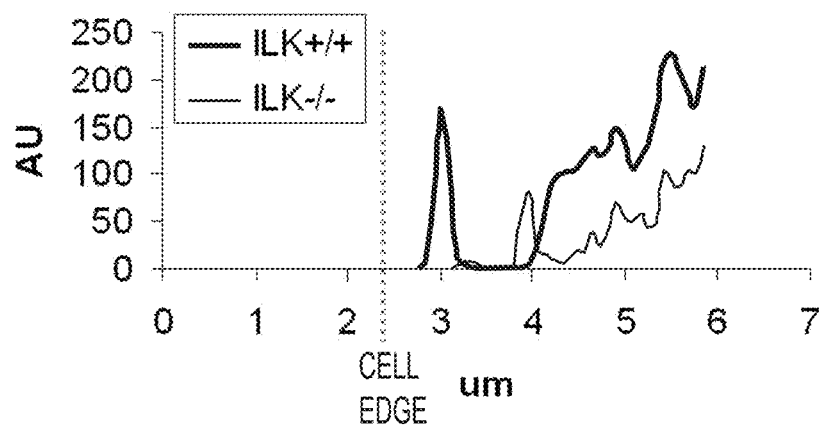
Figure 4E:
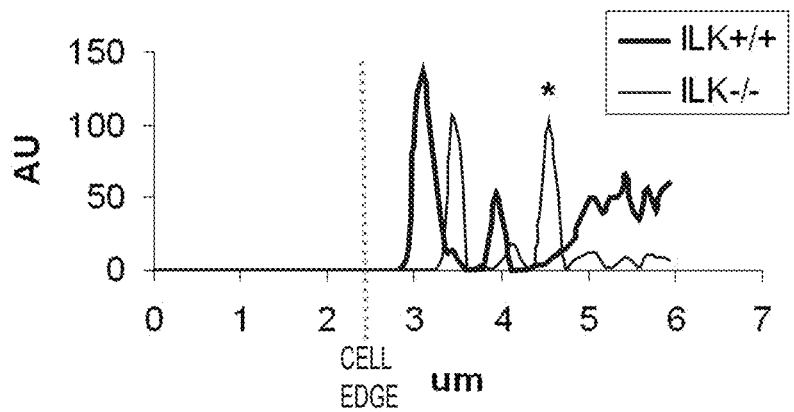
Figure 5E:
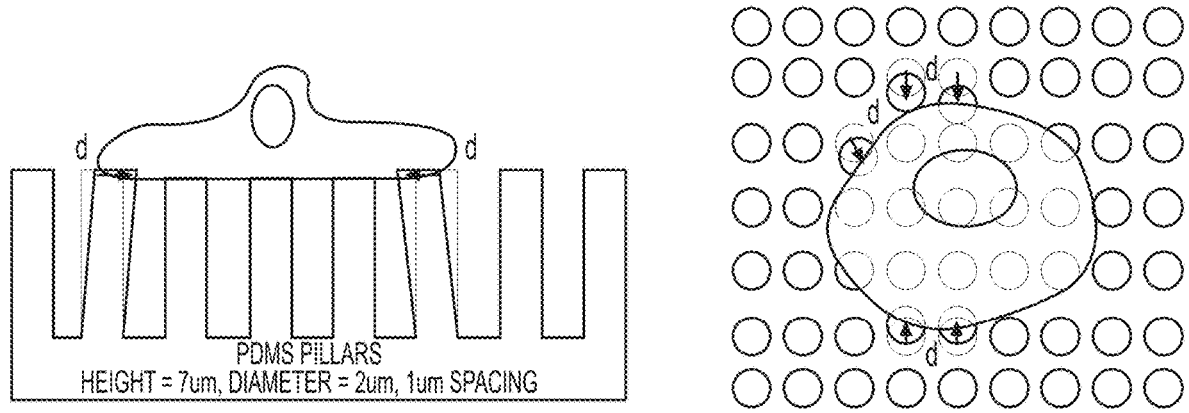
FIG. 5. ILK null cells exhibit slower migration velocities and reduced collagen contraction. (a) ILK+/+ and ILK−/− cells were transfected with VASP-GFP and plated on collagen coated glass, imaged via TIRFM at 0.2 Hz. (b) Summary of quantification of migration velocities. (c) ILK+/+ and ILK−/− cells were seeded in collagen gels of different densities and allowed to contract the gel for ~two weeks in culture. (d) Summary of quantification of percent contraction of collagen gels. ILK null mouse embryonic fibroblasts (MEF's) exert less force on both substrates than wild-type MEF's. Cells were plated on PDMS pillars coated with either 10 ug/ml collagen or 10 ug/ml fibronectin, allowed to spread for 30 minutes and imaged via brightfield microscopy. (E) Side and top view cartoon depiction of PDMS pillar assay to measure traction force generation. Cells were plated on PDMS pillars and allowed to spread for 60-90 minutes. (F) Brightfield Images (inset) and force vector maps of ILK+/+ and ILK−/− cells plated on 2 um diameter, 7 um height pillars coated with 10 ug/ml collagen and 10 ug/ml fibronectin. ILK+/+ and ILK−/− cells were plated on PDMS pillars and imaged at 1 Hz for 30 min. Using a nanotracker program, pillar displacement was calculated and a vector force map was generated using MatLab. (G) Quantification of individual pillar displacement for ILK+/+ and ILK−/− cells (n=359, n=231 collagen coated pillars, respectively) and quantification of individual pillar displacement for ILK+/+ and ILK−/− cells (n=294, n=211 fibronectin coated pillars, respectively).
Figure 5F:
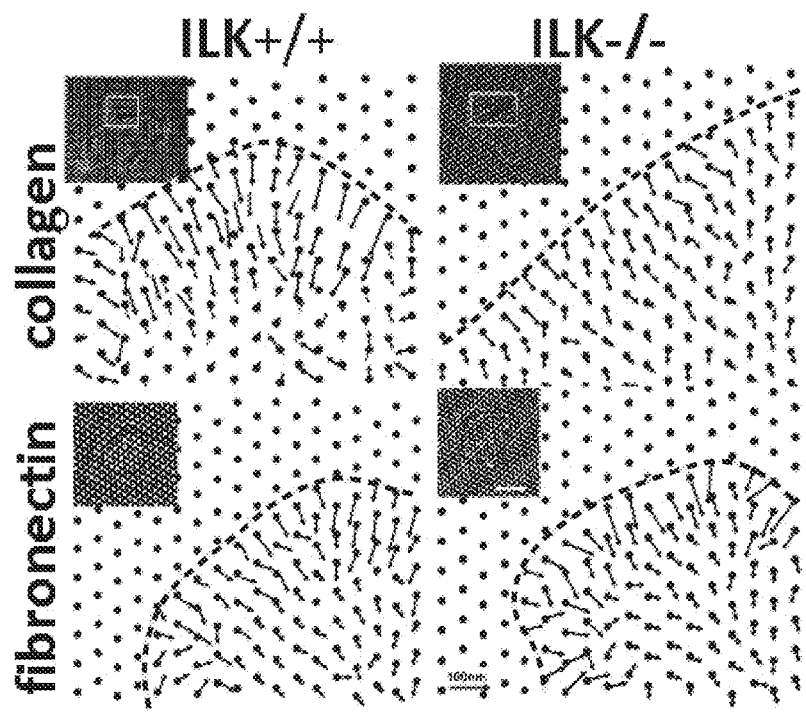
Figure 5G:
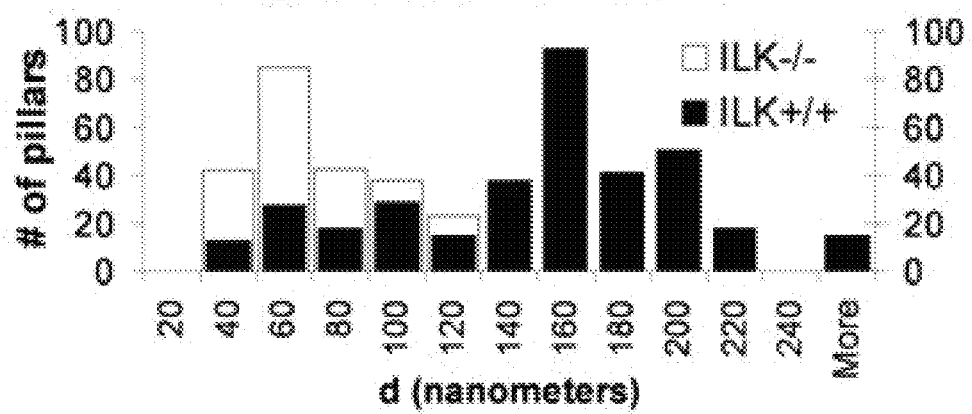
Figure 5G:
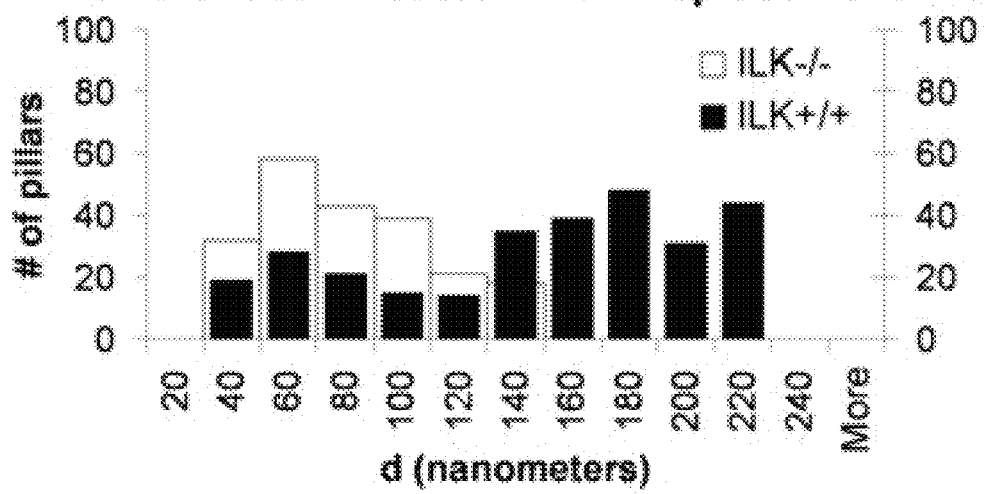
Figure 6A:
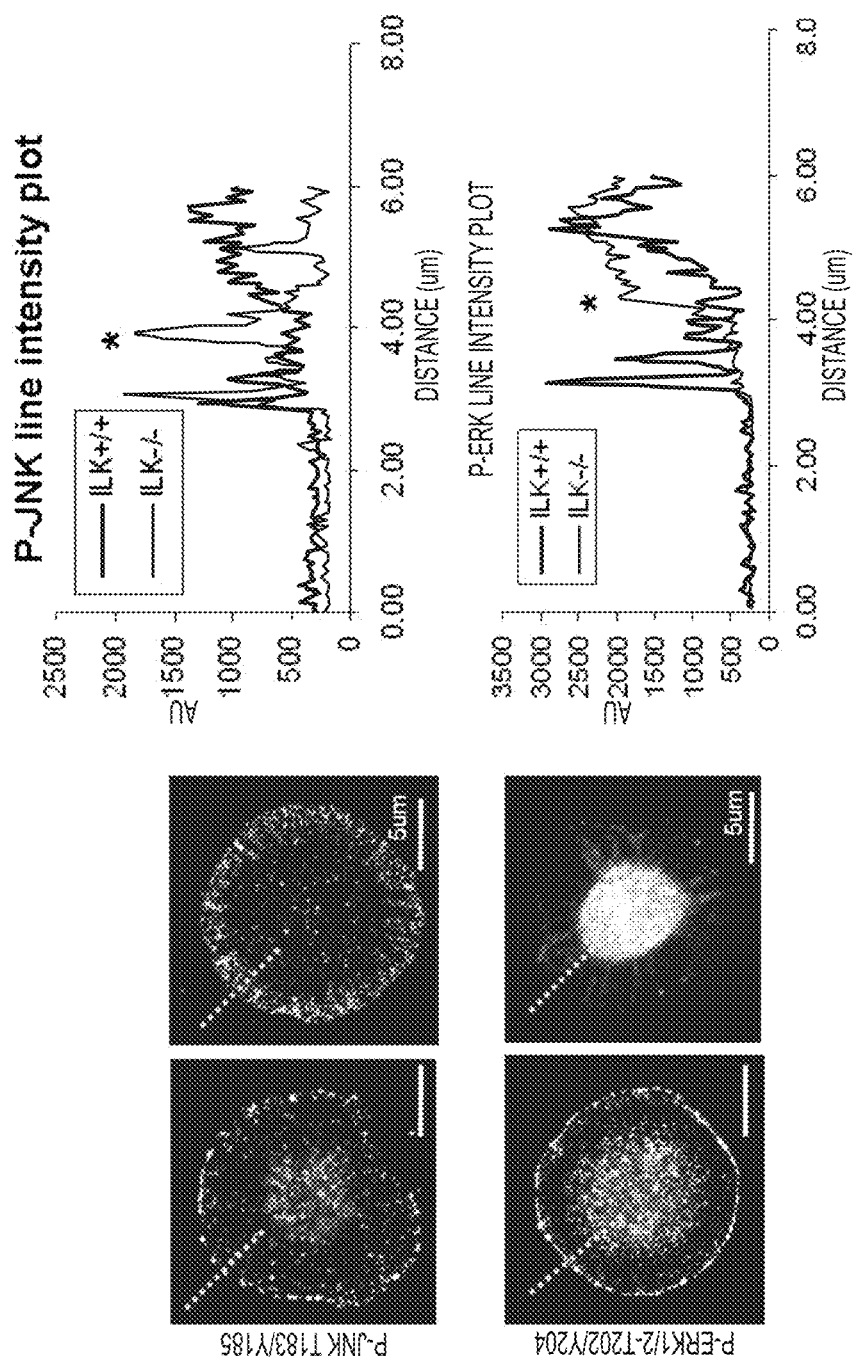
FIG. 6. ILK−/− mislocalize MAPK's inward, in the direction of actin retrograde flow and exhibit slower proliferation and growth. (a) ILK+/+ and ILK−/− cells were plated on collagen coated glass for 60 min, fixed and stained indicated proteins and imaged via confocal microscopy. (b) Fluorescent-Line Intensity plots demonstrates the localization of phosphorylated protein with respect to the edge and interior of the cell. (c) Western blot of phospho-JNK T183/Y185 and phospho-ERK1/2 T202/Y204, showing lower level of phospho-JNK, and elevated levels of phospho-ERK. (d) Quantification of phospho-MAPK's western blot. (e) ILK+/+ and ILK−/− cells were incubated with BrDU for the indicated times, fixed, stained and imaged confocal microscopy Summary of quantification of fluorescent intensity of BrDU signal.

After observing that small focal adhesion size and fast actin retrograde flow resulted in mislocalization of myosin, it was investigated if other proteins were mislocalized. FIG. 4 demonstrates that proteins necessary for ECM-cell contacts, and the recruitment of important signaling molecules were mislocalized rearward, approximately 1-2 micrometers. FIG. 4E demonstrates that given increased actin retrograde flow, activated forms of important signaling molecules are mislocalized. Interestingly, this mislocalization effects protein binding partners that are necessary for growth, proliferation, and transcriptional events (FIG. 6). Moreover, as proteins necessary for ECM-cell contacts are also displaced with large actin rearward flow, defects in migration, collagen contraction, and force generation are also reported (FIG. 5).

The following table summarizes the biophysical variables that are related to, and affected by focal adhesion size and retrograde flow. ILK+/+ cells represent cellular conditions of large FAs and slow actin retrograde flow, while ILK−/− cells represent cellular conditions of small FAs and fast actin retrograde flow.

As previously mentioned, the biophysical measurements, biochemical measurements, and other variables discussed above can be used to determine various number values that are proportional to and correlate with the aggressiveness and invasiveness (oncogenic & metastatic potential) of a tissue. For example, a traction force index (TFI) can be determined as a ratio of focal adhesion size to retrograde flow, i.e., focal adhesion size (square micrometer)/retrograde flow speed (micrometers per second)=TFI (micron seconds).

For example, exemplary ILK+/+ cells having an average focal adhesion size (FAS) of 1 square micrometer and a actin retrograde flow speed (RFS) of 0.05 micrometers per second would have a TFI of 20 micrometer seconds. In comparison, exemplary ILK−/− cells having an average FAS of 0.1 square micrometers and a RFS of 0.1 micrometers per second would have a lower TFI of 1 micrometer seconds. In this exemplary embodiment, a lower TFI indicates lower ECM—focal adhesion—actin coupling and correlates with lower force generation, altered activation of intracellular signaling, slower cell proliferation, and slower migration rate. Data presented in FIG. 6 demonstrated that decreased TFI leads to mislocalization of the important growth signaling molecules ERK and INK. This resultant mislocalization leads to altered modification leading to slower growth.

|  | ILK+/+ | (n) | ILK−/− | (n) |
|---|---|---|---|---|
| lamellapodia width | 2.2 µm ± .4 | (23) | 4.2 µm ± .6 | (26) |
| focal adhesion size | 1.1 µm² ± .4 | (31) | .19 µm² ± .06 | (32) |
| edge velocity in P1 | 86.0 nm/sec | (16) | 61.6 nm/sec | (18) |
| actin retrograde velocity* | 43.1 nm/sec ± 9 | (21) | 128.6 nm/sec ± 22 | (20) |
| myosin retrograde velocity* | 15 nm/sec ± 6 | (8) | 44 nm/sec ± 11 | (8) |
| ILK retrograde velocity* | 0.4 nm/sec +− .1 | (6) | NA | |
| ILK-PBS-GFP retrograde vel.* | NA | | 8.0 nm/sec ± 4.3 | (9) |
| paxillin retrograde velocity * | 20 nm/sec ± .05 | (8) | 8.7 nm/sec ± 3.1 | (9) |
| p130-Cas retrograde velocity* | .91 nm/sec ± .04 | (9) | 19.0 nm/sec ± 6.4 | (11) |
| talin retrograde velocity* | 2.38 nm/sec ± .90 | (4) | 25.8 nm/sec ± 4.4 | (5) |
| collagen coated pillar displacement | 164.5 nm ± 22.3 | (16) | 62.5 nm ± 24.4 | (19) |
| fibronectin coated pillar disp. | 167.3 nm ± 31.6 | (24) | 52.2 nm ± 38.1 | (19) |
| collagen bead disp. (external ipN) | 45.3 nm ± 6.2 | (10) | 74.4 nm ± 15.4 | (12) |
| fibronectin bead displ. (external1pN) | 37.5 nm ± 7.0 | (11) | 41.3 nm ± 8.4 | (11) |
| polarization time** | 130 min ± 30 | | 340 min ± 40 | |
| migration velocity | 51 nm/sec ± 21 | (5) | 10 nm/sec ± 2 | (4) |
| doubling time** | 640 mins ± 54 | | 820 mins ± 52 | |

Figure 7A:
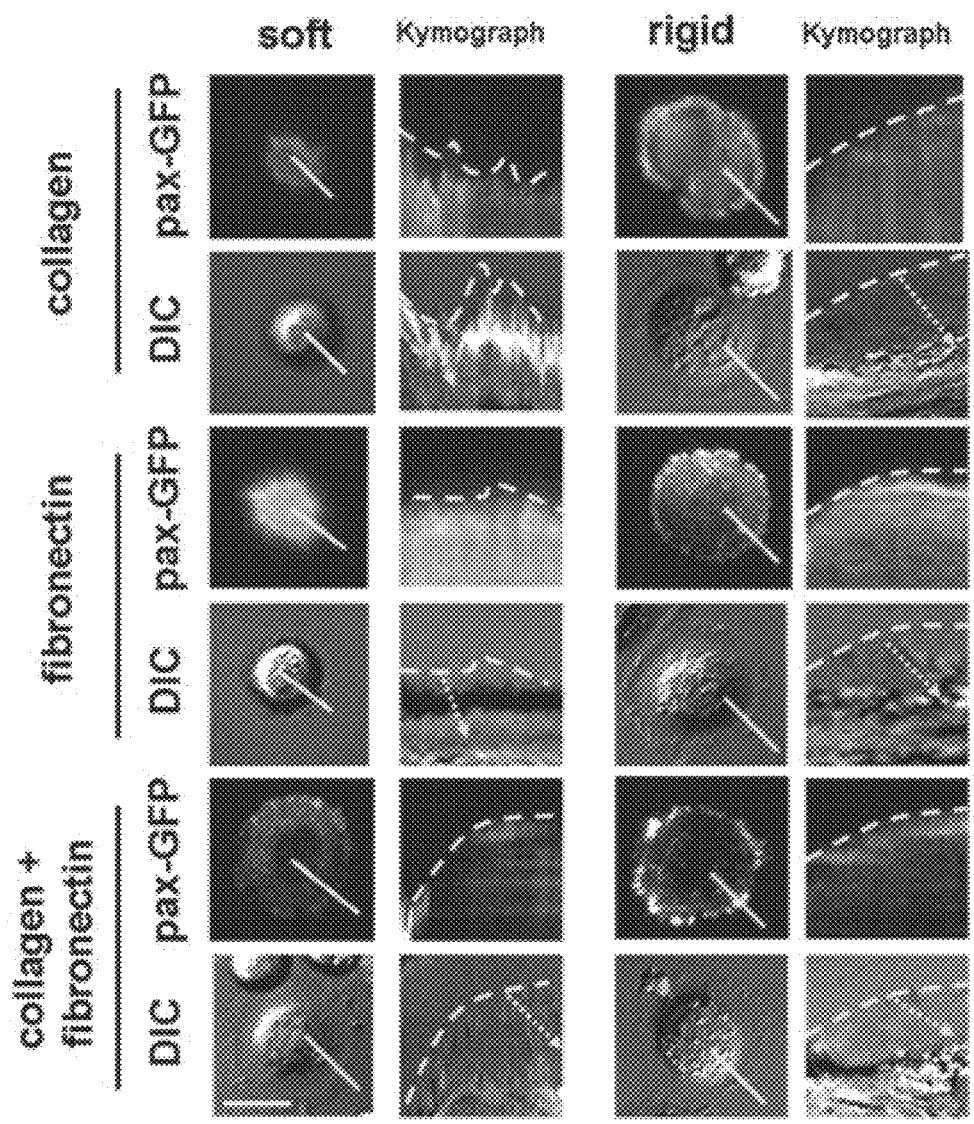
FIG. 7. The ratio of focal adhesion size and retrograde flow velocity is inversely proportional to doubling time. (A) Cells were transfected with paxillin-gfp and imaged via confocal microscopy on indicated substrates. Retrograde flow velocities and focal adhesion sizes were measured for individual cells. (B) Summary quantification of measurements made in (A). (C) Plot of traction force index vs. doubling time over indicated substrates. (C-collagen, F-fibronectin)
Figure 12:
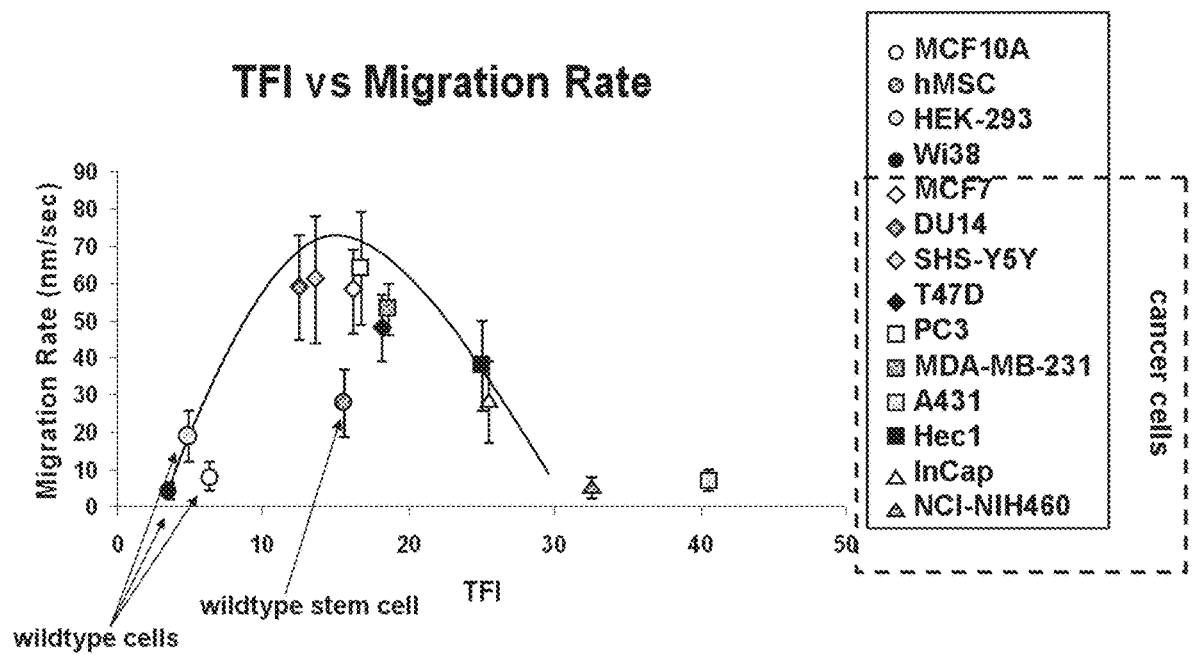
FIG. 12. Migration rate correlates with the Traction Force Index (TFI). (A) The Traction Force Index (TFI) was calculated by dividing the average focal adhesion size (FAS) by the average retrograde flow speed (RFS) for each cell line. The TFI was then plotted against the migration rate. Cells that migrate faster, have a larger TFI. The value of the Traction Force Index correlates with migration velocity. Cells with slower to faster migration velocities (ILK−/−, MCF10A, ILK+/+, MCF7, respectively) exhibit smaller to larger TFI, respectively. Again, ILK−/− cells are growth deficient, slow migrating mouse embryonic fibroblasts; MCF10A cells are normal, wild type human breast epithelium cells; ILK+/+ are fast growing, fast migrating mouse embryonic fibroblasts; MCF7 cells are oncogenic, highly metastatic human breast cancer cells.
Figure 13:
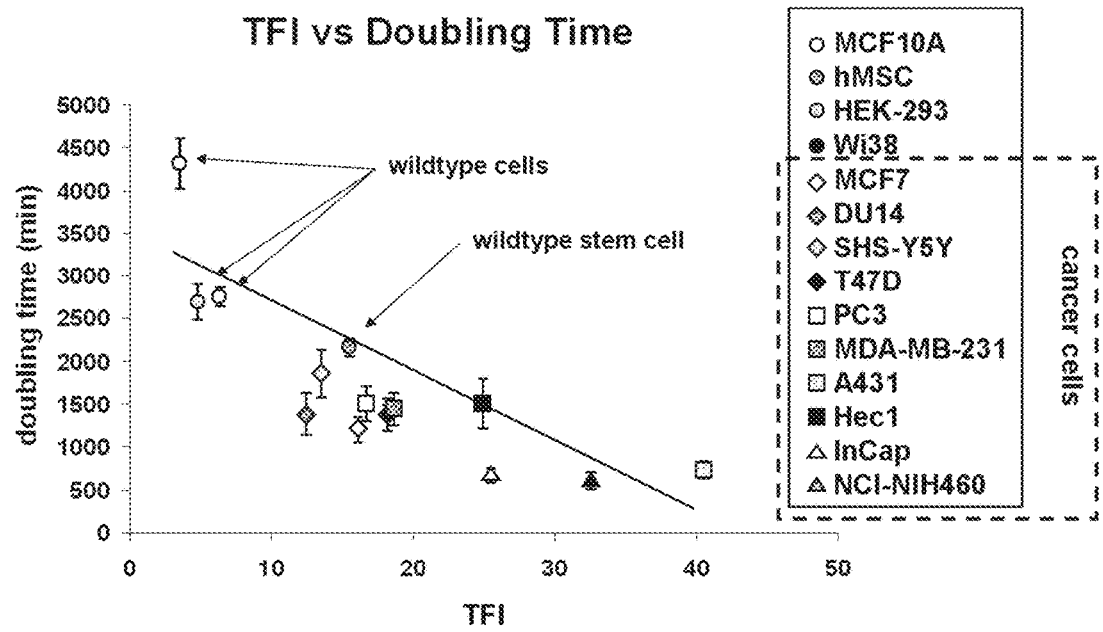
FIG. 13. Doubling time inversely correlates with the Traction Force Index (TFI). (A) The Traction Force Index (TFI) was calculated by dividing the average focal adhesion size (FAS) by the average retrograde flow speed (RFS) for each cell line. The TFI was then plotted against the doubling time. Cells that divide faster, have a larger TFI. The value of the Traction Force Index correlates with growth rate (1/doubling time). Cells with slower to faster doubling times or growth rates (i.e. ILK−/−, MCF10A, ILK+/+, MCF7, respectively) exhibit smaller to larger TFI, respectively. Again, ILK−/− cells are growth deficient, slow migrating mouse embryonic fibroblasts; MCF10A cells are normal, wild type human breast epithelium cells; ILK+/+ are fast growing, fast migrating mouse embryonic fibroblasts; MCF7 cells are oncogenic, highly metastatic human breast cancer cells.

After it was observed that cells with altered FA size, and actin retrograde flow exhibited the above differences in cellular function, the correlation between FA size, retrograde flow speed and cellular functions was further investigated. In FIG. 7 it is shown that by increasing the rigidity and ECM concentration of substrates, FA size is increased and actin retrograde flow speed decreases. Furthermore, FIG. 7 is the first correlation of growth rates or doubling times with the ratio of FA size and actin retrograde flow speed. FIGS. 8-13 details the validation of FA size and actin retrograde flow and the related measurements as biomarkers, FIG. 8 was the initial demonstration that a cancer cell, MCF7, exhibits different FA sizes and actin retrograde flow speeds when compared to a normal cell from the same tissue, MCF10A. Building on this result, 10 different human cancer cell lines were compared to 4 different human wild-type cell lines (FIGS. 9-13). After measuring FA size (FIG. 11), and actin retrograde flow speed (FIG. 12) in both cancer and normal human cells, the ratio of the two measurements was calculated as the Traction Force Index (TFI) (FIG. 13). FIG. 12 demonstrates that the TFI can be correlated with motility of cancer cells while FIG. 13 demonstrates that the TFI correlates with the growth rate of cancer cells.

These observations are further confirmed in FIGS. 8 and 13 with known cancer cell lines. Put more simply, ILK+/+ cells exhibit larger focal adhesions and slower retrograde flow than ILK−/− cells. In other words, focal adhesion size (FAS) is inversely proportional to retrograde flow speed (RFS), a relationship which can be expressed as:

$$FAS \sim 1/RFS$$

Therefore, in one embodiment, the ratio of focal adhesion size to retrograde flow speed can be used as a first proliferation quotient (Q1):

$$FAS/RFS \sim Q1$$

Using the first proliferation quotient (Q1) based on the above relationship between focal adhesion size and retrograde flow speed, ILK+/+ cells will have a higher Q1 than ILK−/− cells (FIG. 7). Thus, Q1 provides a measure of both the oncogenic and metastatic potential of tissue, confirmed by the higher oncogenic and metastatic potential of ILK+/+ cells in comparison to ILK−/− cells (FIG. 7) and investigation using cancer cell lines (FIG. 8-14). This observation is further supported by cancer cell lines in FIGS. 12 & 13, where cancer cells with higher TFI exhibit faster growth.

For another example, ILK+/+ cells also exhibit greater force generation (FIG. 5), and as the force is transmitted to the extracellular matrix (ECM) via focal adhesions, the ratio focal adhesion size (FAS) is proportional to force generation (FG), a relationship which can be expressed as:

$$FAS \sim FG$$

Therefore, in one embodiment, the ratio of force generation (FG) to retrograde flow speed (RFS) can be used as a migration quotient (Q2):

$$FG/RFS \sim Q2$$

Via substitution of variables, Q2 can also be expressed as a product of traction force index (TFI) and the ration of force generation (FG) to focal adhesion size (FAS):

$$Q2 \sim TFI \times (FG/FAS)$$

Thus, Q2 provides a measure of the migration and/or metastatic potential of tissue. This relationship is confirmed by the higher migration potential of ILK+/+ cells in comparison to ILK−/− cells and further confirmed via a parabolic correlation with 13 other cell lines, as shown in FIG. 12. This non-linear correlation can be explained, for example, by the correlation between increased FAS and the inability of a cell to detach from the substrate and migrate forward.

Given the data collected with cancer cell lines (FIG. 8-13), the following exemplary embodiments are well suited for use in a clinical, diagnostic environment in methods, systems, and devices that can be used to assess the oncogenic and metastatic potential of a biopsy sample. As discussed above:

$$Q1 = \text{proliferation quotient}$$

$$Q2 = \text{migration quotient}$$

The following relationships can be used as substitutions with the following equations as a means to calculate Q values using different variables as needed or dictated by experimental measurements. The data in the above table listing experimental values for both ILK+/+ and ILK−/− cells, as well as data from FIGS. 1-22, provides evidence for the following relationships.

In a first aspect, various Proliferation Quotient relationships can be used, for example, to derive a measure of the growth or oncogenic potential of a cell. In one exemplary embodiment, the ratio of focal adhesion size (FAS) and cell area (CA) is proportional to the proliferation/oncogenic rate of the cell:

$$Q1 \sim (FAS/CA)$$

In another exemplary embodiment, the ratio of focal adhesion size (FAS) and retrograde flow speed of actin, multiplied by a western titrated average of FAK, Paxillin, p130Cas, or other known focal adhesion proteins is proportional to the proliferation/oncogenic rate of the cell:

$$Q1 \sim (FAS/RFS)(WTA)$$

In another exemplary embodiment, ILK expression level is proportional to the proliferation/oncogenic rate of the cell:

$$Q1 \sim IEL$$

In another exemplary embodiment, the micron scale ELISA average (MSEA) is proportional to the proliferation/oncogenic rate of the cell:

$$Q1 \sim MSEA$$

In another exemplary embodiment, the mRNA Localization Intensity (mRNALI) is proportional to the proliferation/oncogenic rate of the cell:

$$Q1 \sim mRNALI$$

In another exemplary embodiment, the Immuno-stain of PhosphoProtein (ISPP) is proportional to the proliferation/oncogenic rate of the cell:

$$Q1 \sim ISPP$$

In another exemplary embodiment, the ECM Composition of Disassociated Tissue (ECMCDT) is proportional to the proliferation/oncogenic rate of the cell:

$$Q1 \sim ECMCDT$$

In another exemplary embodiment, the Proliferation Indicator Average (PIA) is proportional to the proliferation/oncogenic rate of the cell:

$$Q1 \sim PIA$$

In another exemplary embodiment, the Metabolic Indicator Average (MIA) is proportional to the proliferation/oncogenic rate of the cell:

$$Q1 \sim MIA$$

In another exemplary embodiment, the NFKappaB Transcription Average (NFTA) is proportional to the proliferation/oncogenic rate of the cell:

$$Q1 \sim NFTA$$

In another exemplary embodiment, the Kinesin Velocity (KV) is proportional to the proliferation/oncogenic rate of the cell:

$$Q1 \sim KV$$

In another exemplary embodiment, the Microtubule Density (MD) is proportional to the proliferation/oncogenic rate of the cell:

$$Q1 \sim MD$$

In another exemplary embodiment, the Nucleus/Cell Area (N/CA) is proportional to the proliferation/oncogenic rate of the cell:

$$Q1 \sim N/CA$$

In another exemplary embodiment, the Endocytic Rate (EnR) is proportional to the proliferation/oncogenic rate of the cell:

$$Q1 \sim EnR$$

In another exemplary embodiment, the Exocytic Rate (ExR) is proportional to the proliferation/oncogenic rate of the cell:

$$Q1 \sim ExR$$

In another exemplary embodiment, the Ratio of Tyrosine Phosphorylated Adhesion Kinase to Focal Adhesion Phosphatase (RTFAPP) is proportional to the proliferation/oncogenic rate of the cell:

$$Q1 \sim RTFAPP$$

In another exemplary embodiment, the Focal Adhesion Retrograde Flow Speed is proportional to the proliferation/oncogenic rate of the cell:

$$Q1 \sim FARFS$$

In another exemplary embodiment, the Ratio of STAT transcription factor and p53 activation state (RSTFp53) is proportional to the proliferation/oncogenic rate of the cell:

$$Q1 \sim RSTFp53$$

In another exemplary embodiment, the Ratio of NFKappaB transcription factor and p53 activation state (RNTFp53) is proportional to the proliferation/oncogenic rate of the cell:

$$Q1 \sim RNTFp53$$

In another aspect, various Migration Quotient relationships can be used, for example, to derive a measure of the migration or metastatic potential of a cell.

In one exemplary embodiment, the ratio of force generation (FG) and retrograde flow speed (RFS) is proportional to the migration/metastatic rate of the cell (FIGS. 5 & 12):

$$Q2 \sim (FG/RFS)$$

In another exemplary embodiment, the ratio of focal adhesion size (FAS), and retrograde flow speed (RFS), is proportional to the migration/metastatic rate of the cell (FIG. 12):

$$Q2 \sim (FAS/RFS)$$

In another exemplary embodiment, the ratio of focal adhesion size (FAS), and retrograde flow speed (RFS), is proportional to the migration rate and in vivo metastatic potential of the cell:

$$Q2 \sim (FAS/MV)$$

In another exemplary embodiment, the ILK expression level (IEL) is proportional to the migration/metastatic rate of the cell (FIG. 7):

$$Q2 \sim IEL$$

In another exemplary embodiment, the mRNA Localization Intensity (mRNALI) is proportional to the migration/metastatic rate of the cell:

$$Q2 \sim mRNALI$$

In another exemplary embodiment, the Immuno-stain of PhosphoProtein (ISPP) is proportional to the migration/metastatic rate of the cell:

$$Q2 \sim ISPP$$

In another exemplary embodiment, the ECM Composition of Disassociated Tissue (ECMCDT) is proportional to the migration/metastatic rate of the cell:

$$Q2 \sim ECMCDT$$

In another exemplary embodiment, the Metabolic Indicator Average (MIA) is proportional to the migration/metastatic rate of the cell:

$$Q2 \sim MIA$$

In another exemplary embodiment, the NFKappaB Transcription Average (NFTA) is proportional to the migration/metastatic rate of the cell:

$$Q2 \sim NFTA$$

In another exemplary embodiment, the Kinesin Velocity (KV) is proportional to the migration/metastatic rate of the cell:

$$Q2 \sim KV$$

In another exemplary embodiment, the Microtubule Density (MD) is proportional to the migration/metastatic rate of the cell:

$$Q2 \sim MD$$

In another exemplary embodiment, the Nucleus/Cell Area (N/CA) is proportional to the migration/metastatic rate of the cell:

$$Q2 \sim N/CA$$

In another exemplary embodiment, the Endocytic Rate (EnR) is proportional to the migration/metastatic rate of the cell:

$$Q2 \sim EnR$$

In another exemplary embodiment, the Exocytic Rate (ExR) is proportional to the migration/metastatic rate of the cell:

$$Q2 \sim ExR$$

In another exemplary embodiment, the Ratio of Tyrosine Phosphorylated Adhesion Kinase to Focal Adhesion Phosphatase is proportional to the migration/metastatic rate of the cell:

$$Q2 \sim RTFAPP$$

In another exemplary embodiment, the Focal Adhesion Retrograde Flow Speed is proportional to the migration/metastatic rate of the cell:

$$Q2 \sim FARFS$$

In another exemplary embodiment, the Ratio of STAT transcription factor and p53 activation state is proportional to the migration/metastatic rate of the cell:

$$Q2 \sim RSTFp53$$

In another exemplary embodiment, the Ratio of NFKappaB transcription factor and p53 activation state (RNTFp53) is proportional to the migration/metastatic rate of the cell:

$$Q2 \sim RNTFp53$$

In another aspect, various relationships between variables can be used, for example, to allow for the above Q relationships to be derived from a number of experimental values. These relationships between variables may be of interest in the instances where some experimental values are more easily obtained than others or where some experimental values are unobtainable.

In one exemplary embodiment, actin retrograde flow speed (RFS) is inversely proportional to migration velocity and the inverse of polarization time (PT):

$$RFS \sim 1/MV \sim 1/PT$$

In another exemplary embodiment, the western titrated average of phosphorylated proteins such ad P-FAK, P-Cas, and P-PAX (WTA), is proportional to focal adhesion size (FAS) and polarization time (PT):

$$WTA \sim FAS \sim PT$$

In another exemplary embodiment, force generations (FG), focal adhesion size/actin retrograde flow, or the Traction Force Index, is proportional to ILK expression level as well as migration velocity.

$$FG \sim (FAS/RFS) \sim IEL \sim MV \sim ExR \sim EnR \sim (1/MIA) \sim N/CA$$

In another exemplary embodiment, focal adhesion size (FAS) is proportional to the inverse of retrograde flow speed (RFS) multiplied by the western titrated average (WTA) and proportional to ILK expression level as well as migration velocity.

$$FAS \sim (1/RFS)(WTA) \sim IEL \sim MV \sim ISPP \sim mRNALI \sim ECMCDT$$

In another exemplary embodiment, the western titrated average (WTA) multiplied by the actin retrograde flow speed (RFS) is proportional to migration velocity, polarization time (PT) and ILK expression level:

$$(WTA)(RFS) \sim MV \sim IEL \sim ISPP$$

The following equations, which use the aforementioned variables and relationships, can be used to calculate numerical Q values that can be used to determine the growth/oncogenic and migration/metastatic potential of a cell or population of cells. In the various embodiments below, Q1 correlates with growth/oncogenic potential and Q2 correlates with migration/metastatic potential. For example, the greater the calculated value for Q1, the more oncogenic the cancer, e.g., faster growth or larger growth, and the greater the value of Q2, the more metastatic the cancer.

The embodiments of Q1 and Q2 discussed below represent exemplary embodiments of possible relationships between the measurements and variables discussed above. Applicants note that other substitutions for equivalent variables and relationships can be used to determine other useful Q values.

One embodiment of a set of proliferation and migration quotients, aQ1, and aQ2 respectively, can be expressed by the following relationships:

$$aQ1 = FAS/RFS \text{ (or } TFI = FAS/RFS \text{ or } aQ1 \sim FG)$$

$$aQ2 = FG/RFS$$

Another embodiment of a set of proliferation and migration quotients, bQ1, and bQ2, can be expressed by the following relationships:

$$bQ1 = ((FAS/RFS) \times (MIA/CA))(WTA)$$

$$bQ2 = ((FAS/RFS) \times (MV/CA))(WTA)$$

Another embodiment of a set of proliferation and migration quotients, cQ1, and cQ2, can be expressed by the following relationships:

$$cQ1 = (1/aQ1)(MIA) \text{ or } cQ1 = (1/aQ1)(WTA)$$

$$cQ2 = (aQ1)(MV) \text{ or } cQ2 = aQ1$$

Another embodiment of a set of Q values can be expressed using the following relationships:

$$dQ1 = ((FAS/RFS) \times (MIA/WTA))/CA,$$

$$dQ1 = (TFI \times (MIA/MTA))/CA, \text{ or}$$

$$dQ2 = ((FG/RFS) \times (MV/IEL))/CA$$

Another embodiment of a set of Q values can be expressed using the following relationships:

$$eQ1 = (CA \times PIA)$$

$$eQ2 = (CA \times MV)$$

Another embodiment of a set of Q values can be expressed using the following relationships:

$$fQ1 = (A1)(TFI) + B1$$

$$fQ2 = -(A2)(TFI^2) + B21(TFI) + C2$$

where A1, B1, A2, B2, and C2 are constant rational numbers.

Using the above embodiments of Q values, a Z1 and Z2 value can be derived that can be used to determine if the cells, or population of cells, (e.g., from a biopsy) are predisposed to growing more than migrating, oncogenic more than metastatic, or vice versa for each scenario.

For example, if given a Z1 and Z2 whose identity are rational numbers that are initially determined by measurements made by, for example, ILK+/+ cells, or a wild type cell that is extracted from the patient, or another cell line that can be used as a standard, where $$Z1 = Q1/Q2, \text{ and}$$

$$Z2 = Q2/Q1,$$

Then, for a given Q1 and Q2 (aQ, bQ, cQ, dQ, eQ, fQ, etc.), if, for example, $aQ1/aQ2 \geq Z1$, where Z1 equals the ratio of aQ1 and aQ2 of another known cell line, or biopsy with known oncogenic or metastatic potential, then the tendency of the cell in question to proliferate is greater than that of the known cell.

Moreover, if from the same cell, or sample of cells, $Z2 \leq Z1$ then that cell or sample of cells has a greater potential to migrate and invade than to grow and the cell or sample of cells can be described as metastatic and not aggressive. That is to say if $aQ2/aQ1 \geq aQ1/aQ2$, then the tendency of the cell in question to migrate is greater than its tendency to proliferate.

Applicant notes that the logic discussed above can be applied to all embodiments of Q1 and Q2 (i.e. aQ1, aQ2, bQ1, bQ2 ... eQ1, eQ2, etc.), for example:

If Q1/Q2 of the biopsy tissue $\leq Z1$ of the standard tissue, then the cancer or population of cells has high growth/oncogenic potential

AND/OR

If Q2/Q1 of the biopsy tissue $\geq Z2$ of the standard tissue, then the cancer, or population of cells has high migration/metastatic potential.

Given the above relationships and equations, substitutions can be made to better approximate a given tissues oncogenic and metastatic potential depending on what measurements potentially made using the diagnostic device based on any number of variables, such as, for example, the tissue type, time of diagnosis, ease of culturing or other practical considerations. Moreover, these metrics and ratios can be used to diagnose other disease states such as cardiac hypertrophy and renal diseases.

The above details the biomarkers and provides examples of algorithms used to determine numerical values, or metrics, that correlate with the ability of biopsy tissue to grow, proliferate and metastasize as well as a method to compare oncogenic and metastatic potentials of cells, populations of cells, and tissue samples.

Device

In another aspect, the present invention provides a device that can be used to measure the aforementioned variables. In an exemplary embodiment tissue (e.g. biopsy tissue) or cells (e.g. cancer cells) are cultured within the device and the aforementioned variables are measured utilizing techniques discussed below. The device can be fabricated using nanotechnology methods, emerging techniques such as microcontact printing or multi-layer soft lithography methods, or traditional photolithographic techniques. The devices can be composed of rigid materials such as glass or silicon, or soft materials such as PDMS or similar polymers. Device feature sizes are in the millimeter, micron, and nanometer range with channel, chamber, and substrate feature sizes sufficient to measure variables from tissues and cells ranging from millimeters to sub-micron in size. Device geometries are designed such that different regions of the device can be selectively isolated and treated with, for example, different substrate coatings (e.g. ECM proteins fibronectin and collagen), culture media, or other reagents necessary to measure the desired biophysical or biochemical variables.

For measuring the desired biophysical or biochemical variables, techniques such as immunohistochemistry using antibodies or quantum dots can be used to measure FAS, IPPS, while DIC and fluorescent microscopy can be used to measure velocities, in addition to employing um and rim scaled beads coated with ECM molecules to measure Retrograde Flow Speed (RFS). Moreover, RFS can be calculated using DIC microscopy without beads and actin-gfp. Furthermore, enzymes and catalytic molecules can be used to measure MIA, and PIA, with a relevant chemical product collected in a reservoir.

FIGS. 23-33, 37 are schematics of an exemplary device. FIGS. 35, 36 are schematics of prototypes of this device. The device features inlet and outlet ports for the introduction and collection of various reagents including but not limited to tissues, cells, cell culture media, and protein coatings. The device also features channels and chambers designed for the culturing and imaging of tissues and cells via the aforementioned techniques. Any channel or chamber surface can be designed and fabricated to exhibit specific rigidities by, for example, varying the composition of the device material (e.g. cross-linking density or composition of PDMS) or including microstructures such as pillars, posts, or similar structures with sizes ranging from microns to nanometers as seen in FIGS. 28-30. Similarly, such structures can be used to create geometries and topologies to influence cell growth and motility (e.g. creating channels for cells to grow into, or posts for cells to grow around). The microstructures themselves can be monitored as they interact with the cells and tissues as a way to measure the desired biophysical and biochemical variables. Finally, any of the surfaces within the device can be treated with various coatings including but not limited to fibronectin and collagen. Examples of different chambers within the device that exhibit different rigidities, geometries, and ECM coatings are shown in FIGS. 28-35, with the squares labeled with greek symbols: alpha, beta, gamma, epsilon, theta representing chambers containing structures with different rigidities, geometric features, and ECM coatings As seen in FIGS. 32 and 33, five macro channels enable the device to be functionalized with as many as five different macro environments with at least 4 different solutions at a given time. The macro environments not only can be functionalized by different liquids passed through the microfluidic channels but by the engineering of each individual 3.5 mm×3.5 mm substrate. This modular, multifunctional design allows for maximizing the capability to culture multiple biopsies at a time while taking multiple measurements to acquire as many values for the oncogenic biophysical and biochemical variables used to quantify both Q and Z values.

Dissassociation of Tissue

In another aspect, the invention provides a method of using the device to acquire measurements that can be used to determine Q. For example, mammalian tissue (e.g. cancer biopsy tissue) can be titrated and plated on different substrates, with as many as 25 different rigidities, coated with 5 different ECM molecules or combinations of ECM molecules (laminin, collagen type I, collagen type IV, vitronectin, fibronectin) to assess the necessary coating of the other chips used to acquire the aforementioned measurements. This will allow the person handling the tissue to decide what ECM molecules to coat the device with and to use a media containing no serum, or fortified with serum or hormones. The aforementioned process has also been validated experimentally. Interestingly, cells, in particular cancer cells, grow, proliferate, differentiate and metastasize in a specific microenvironment. This microenvironment is characterized by insoluble, and soluble proteins, and molecules, physical attributes such as rigidity, and neighboring cells that regulate a given cell's behavior. One of the hallmarks of cancer cells derived from tumors is that they have the ability to grow and spread on soft surfaces (ex. 0.05 kPa). ILK+/+ cells cannot spread on soft surfaces, unless the surface is coated with collagen and fibronectin (FIG. 14-22). Accordingly, different stages of cancer will have different abilities of spreading on different rigidities (0.05 kPa-50 GPa) coated with different ECM molecules (Collagen type I, & IV, Fibronectin Laminin and vitronectin,). However, cells removed from a patient can be challengint to culture. The devices and methods described herein address and ameliorate this problem.

Culturing Cells on Device

Figure 16B:
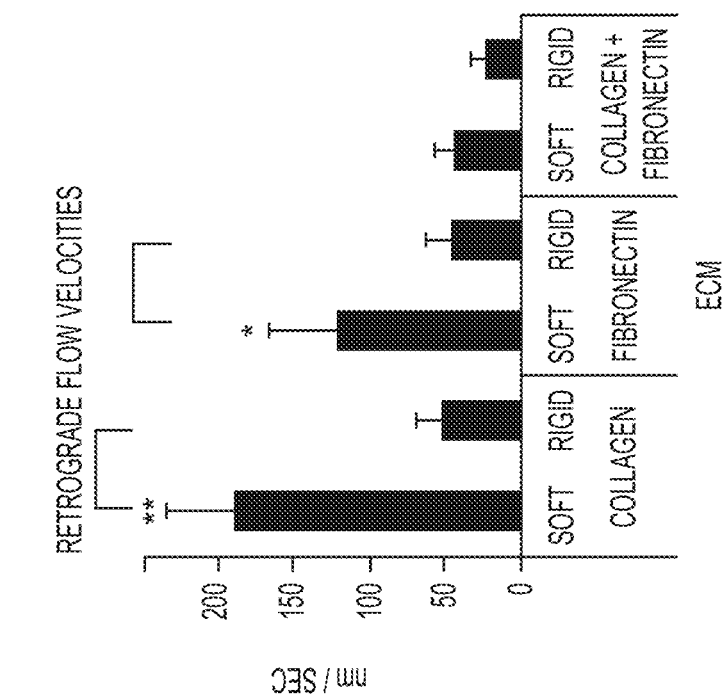
FIG. 16. Cells spread on soft collagen+fibronectin coated substrates, exhibit similar focal adhesion size and actin retrograde flow velocity as cells spread on rigid substrates coated with collagen or fibronectin. (A) Cells were plated on indicated substrates and imaged via time-lapse DIC. Kymographs graphically represent the feature flow at the lamellipodia, indicating retrograde flow velocity. (B) Summary quantification of actin retrograde flow velocity as measured by feature flow. Data represent mean±1 SD from a minimum of 50 cells for focal adhesion size, and 20 cells for retrograde flow speed for each individual ECM condition. A Student's t-test was used for statistical analyses, *=P<0.05. Cells plated on rigid collagen and fibronectin, soft collagen and fibronectin, rigid fibronectin, rigid collagen, exhibit slower actin retrograde flow speeds respectively. Interestingly, this observation taken with the observation that cells plated on rigid collagen and fibronectin, soft collagen and fibronectin, rigid fibronectin, rigid collagen, grow and proliferate faster, respectively, supports the assertion that cells with slower retrograde flow speeds grow faster.
Figure 16A:
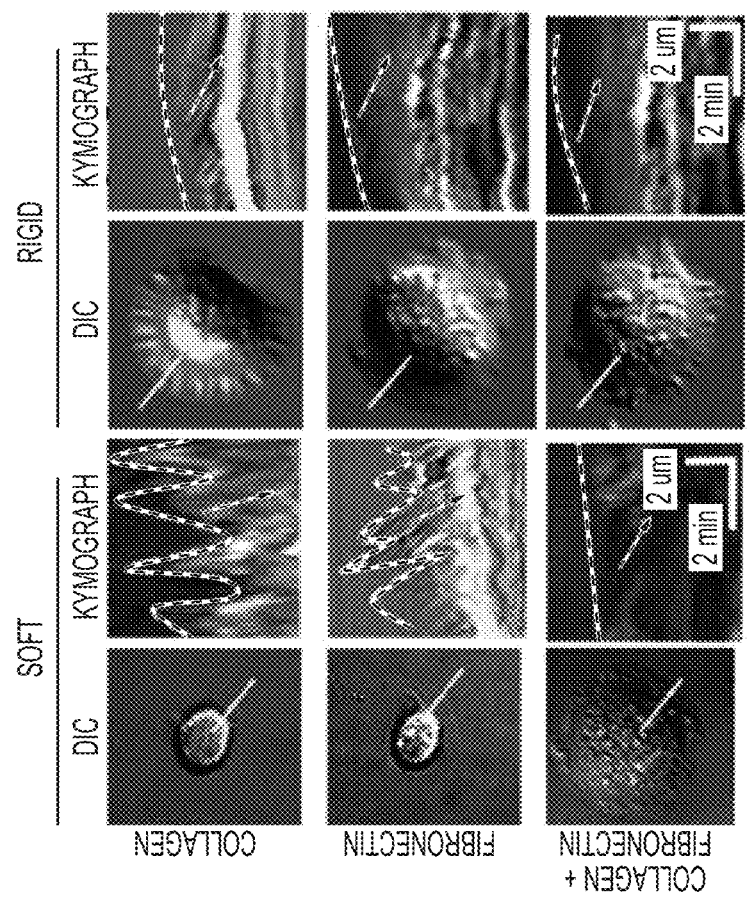

Applicants have surprisingly discovered that coating soft polyacrylamide gels with 10 ug/ml collagen and 10 ug/ml fibronectin enables spreading and proliferation of mammalian embryonic fibroblasts (FIG. 14) on soft surfaces. Accordingly, varying the rigidity and ECM coating of the device creates a permissive environment to culture, image, and take measurements on cells that would otherwise not grow on a 2D-glass, plastic, PDMS or other polymer based substrate and serum free environment. Moreover, the recruitment of more paxillin on surfaces coated with 10 ug/ml collagen and 10 ug/ml fibronectin indicates that focal adhesions cluster integrins and focal adhesion proteins more readily (FIG. 15). Moreover, cells spread and grown on 2D substrates coated with collagen and fibronectin exhibit slower actin retrograde flow. The slower actin retrograde flow on surfaces coated with 10 ug/ml collagen and 10 ug/ml fibronectin indicates that focal adhesion coupling to actin is increased compared to substrates coated with just collagen and fibronectin alone (FIG. 16). These results are consistent with cells spread and grown on substrates coated with just collagen or fibronectin and indicate that focal adhesion-actin coupling is a determinant of growth and proliferation as well as migration.

Moreover, the signaling involved in regulating cell spreading and growth on otherwise non-permissive substrates, are involved in growth, proliferation, migration, oncogenesis and metastasis. $\beta 1$ integrins are necessary for the rescue of spreading on soft surfaces coated with 10 ug/ml collagen and 10 ug/ml fibronectin suggesting that $\beta 1$ is sufficient for activation of actin polymerization, and adhesion formation. $\beta 3$ integrins are necessary for the rigidity response and that is why blocking $\beta 3$ is still permissive for spreading on soft surfaces (FIG. 17). Furthermore, a knock out cell line screen implicates proteins involved in cancer progression, such as $\beta 1$ integrin, ILK, FAK, Src, Yes or Fyn, and p130Cas are also needed for the collagen and fibronectin rigidity response (FIG. 18).

Figure 19A:
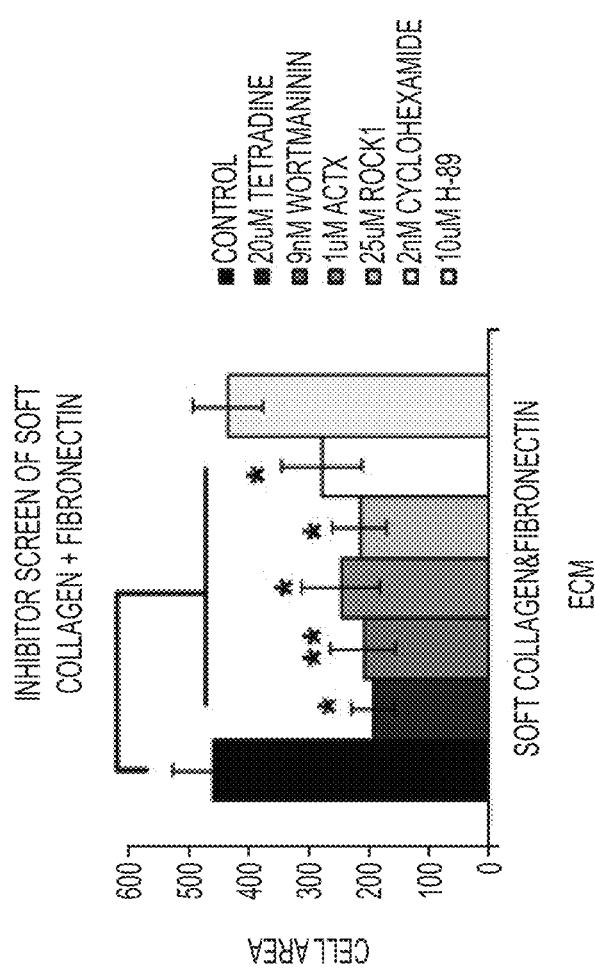
FIG. 19. Small molecule screen implicates the proliferation PI3K pathway and calcium signaling in rescuing spreading on soft gels coated with collagen and fibronectin The PI3K pathway has also been implicated in numerous cancers, supporting the idea that the signaling pathway triggered by cells interacting with collagen and fibronectin recapitulates the signaling needed to grow cancer cells in vitro. Cells were incubated with indicated inhibitors at indicated concentrations and plated on soft substrates coated with 10 ug/ml collagen+fibronectin, fixed, and cell areas were calculated. Summary quantification show that inhibitors of P-type Ca++ channels, PI3K, Akt, Rock1, and translation inhibit spreading. An inhibitor of PKA did not inhibit spreading. Data represent mean±SEM from a minimum of three individual experiments. A Student's t-test was used for statistical analyses, *=P<0.05.
Figure 19B:
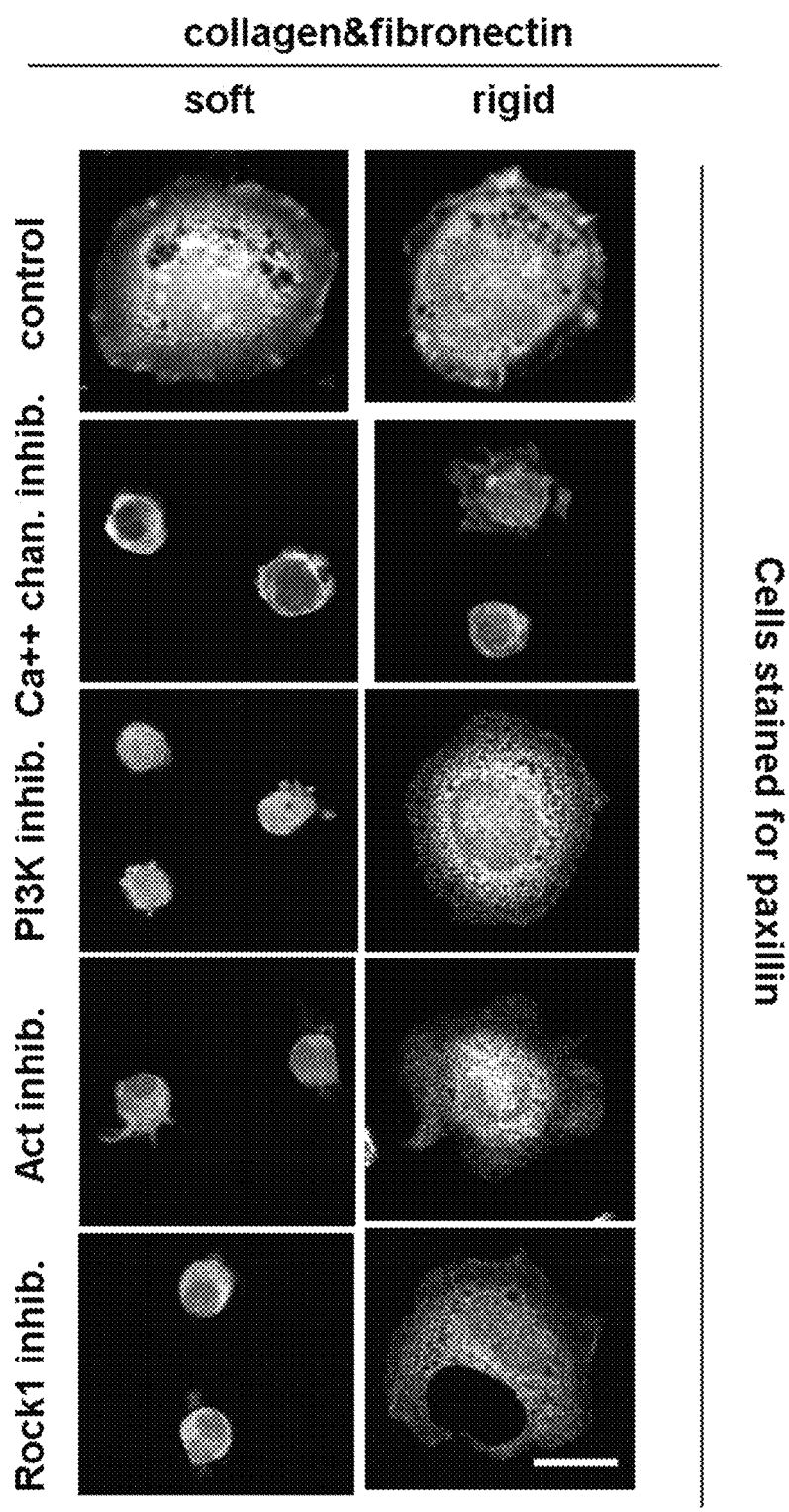

Supporting the knock out cell line screen, a small molecule screen implicates the proliferation PI3K pathway and calcium signaling in rescuing spreading on soft gels coated with collagen and fibronectin (FIG. 19). It is therefore possible to culture cells responsive to oncogenic and metastatic signaling in vitro utilizing various substrates of differing rigidities and ECM coatings.

Figure 20A:
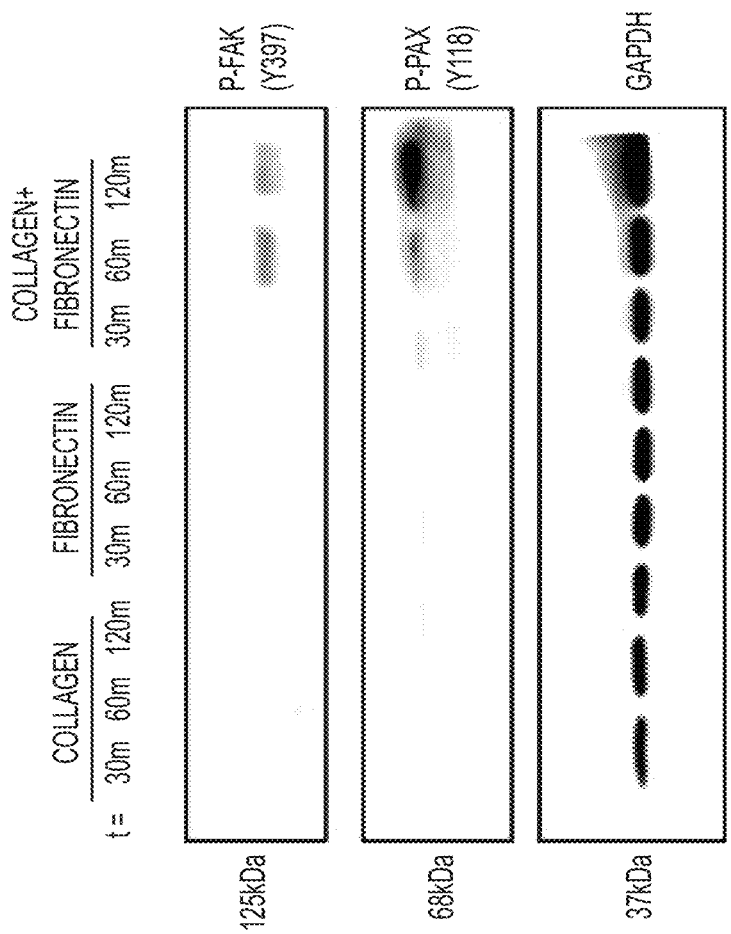
FIG. 20. Phosphorylation of focal adhesion proteins occurs only on soft surfaces coated with 10 ug/ml collagen+ fibronectin after 30 minutes and not on soft surfaces coated with 10 ug/ml collagen or 10 ug/ml fibronectin alone. (A) Western blot of Phospho-(Y397) FAK, and Phospho-(Y118) Paxillin, with GAPDH loading control. (B) Western blot quantification of Phospho-(Y397) FAK. (C) Western blot quantification of Phospho-(Y118) PAX. Data represent mean±SEM from a minimum of three individual experiments. A Student's t-test was used for statistical analyses, *=P<0.05.
Figure 20B:
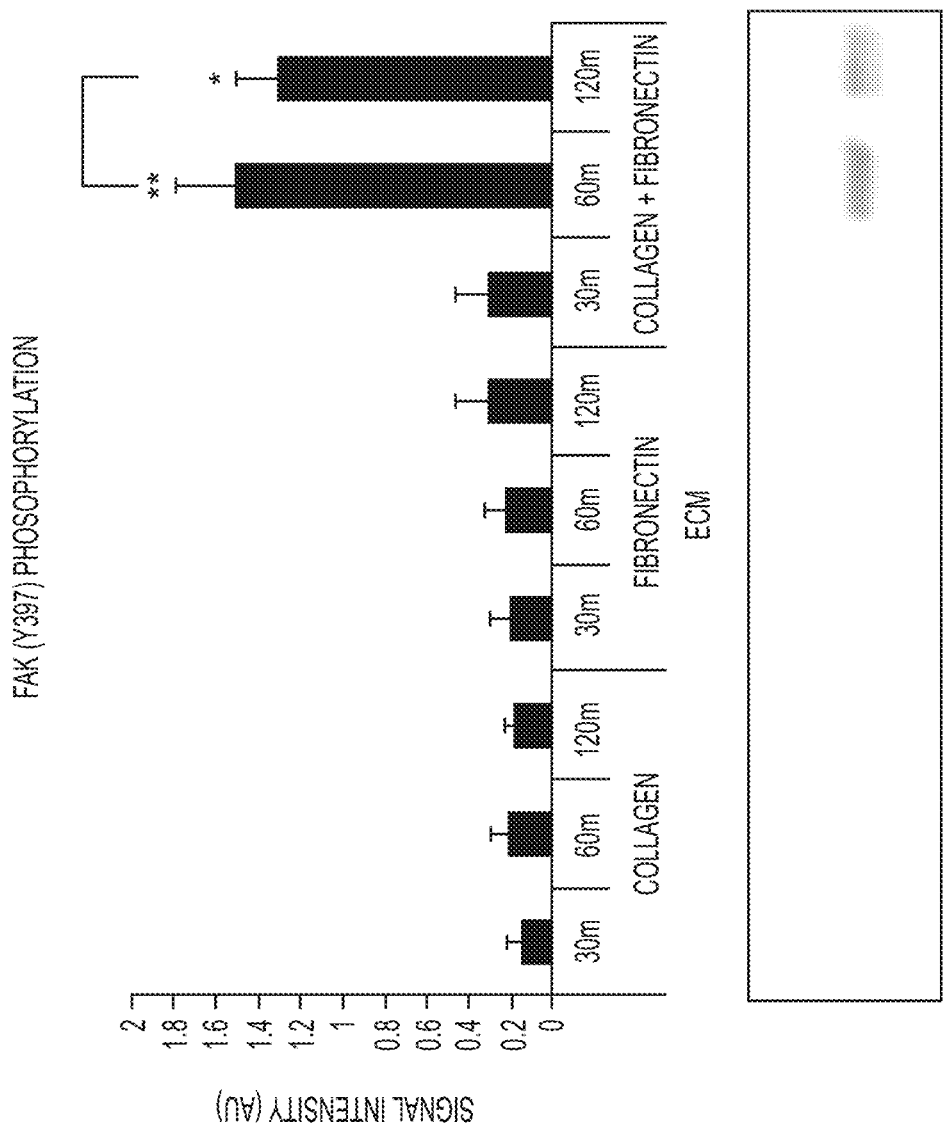
Figure 20C:
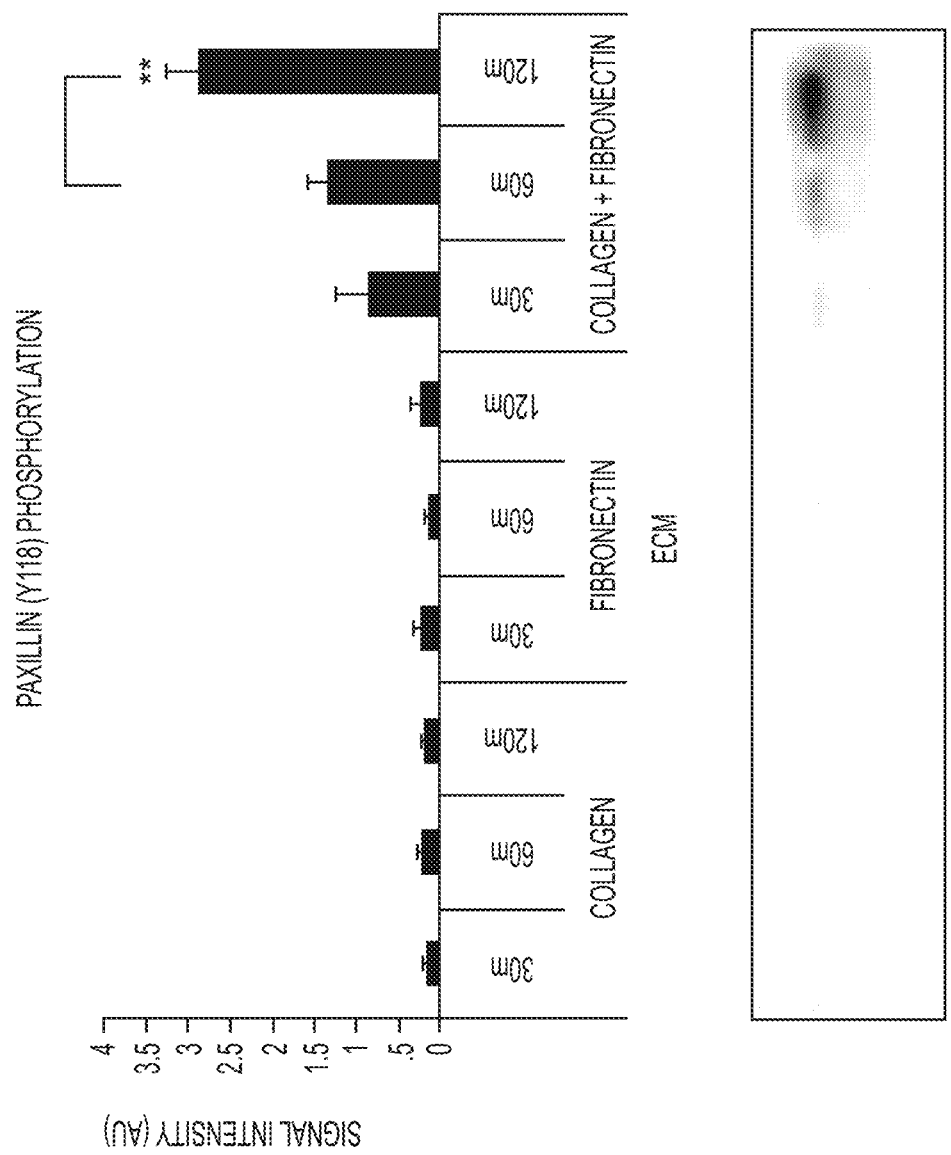
Figures 21A, 21B:
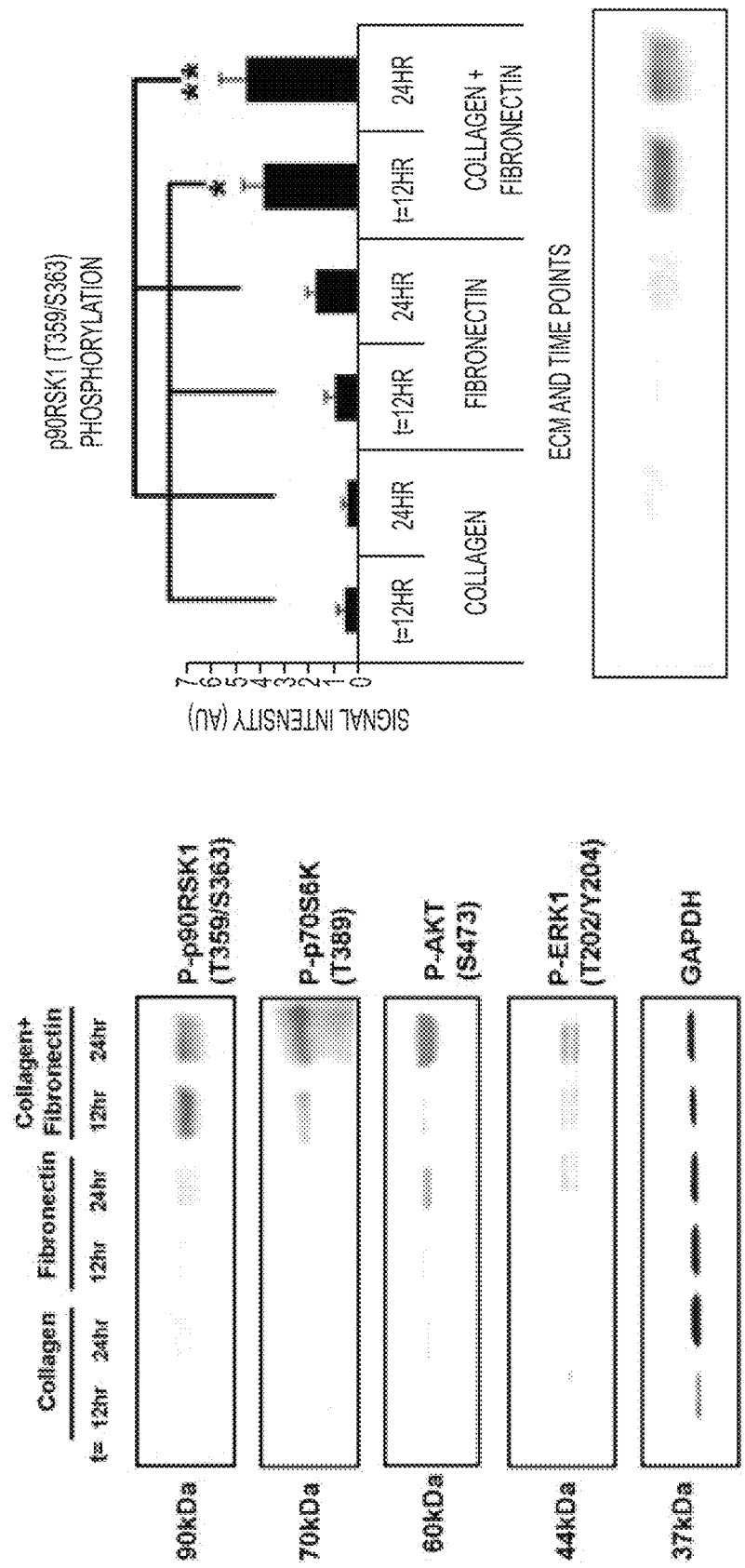
FIG. 21. Western blot analysis shows cells spread on soft surfaces coated with 10 ug/ml collagen+fibronectin activate ERK and the PI3K-AKT pathway, activating the translational regulator p90RSK1. (A) Western blot of Phospho-(T359/S363) p90RSK1, Phospho-(T389) p70S6K, Phospho-(S473) AKT, Phospho-(T202/Y204) ERK, and GAPDH loading control. (B-E) Summary quantification of western blots. Data represent mean±SEM from a minimum of three individual experiments. A Student's t-test was used for statistical analyses, *=P<0.05.
Figure 21D:
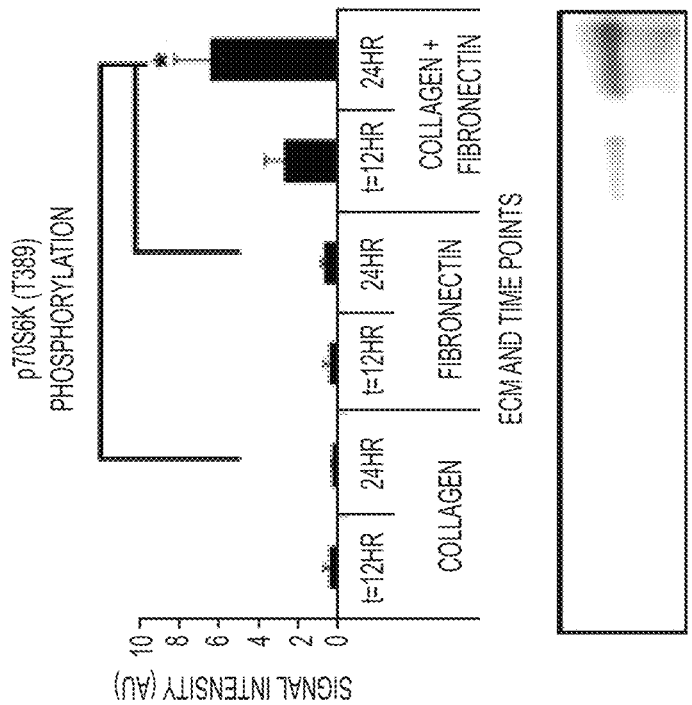
Figure 21C:
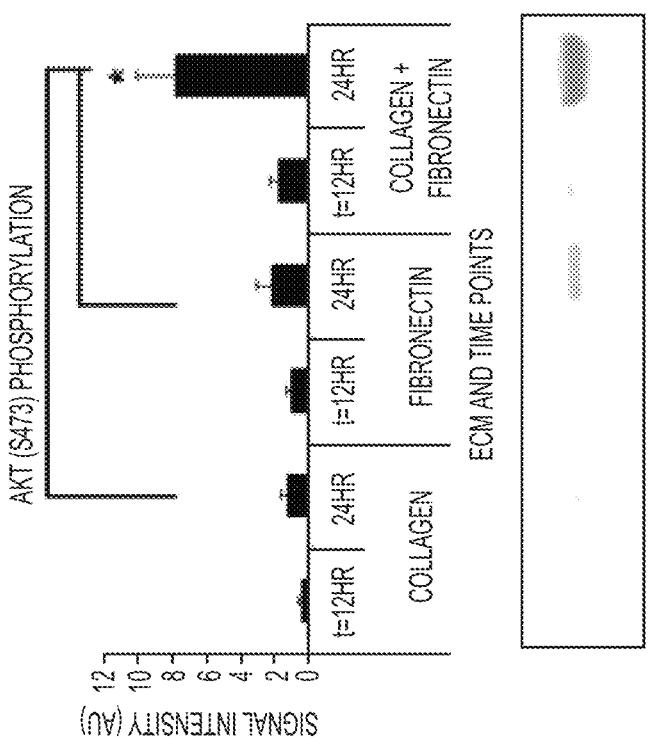
Figure 21E:
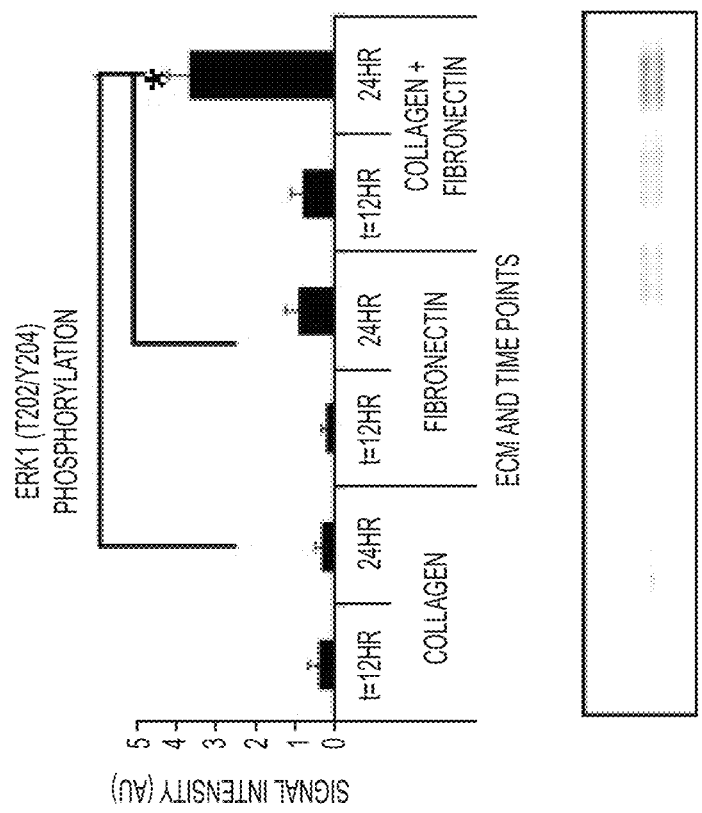
Figure 22A:
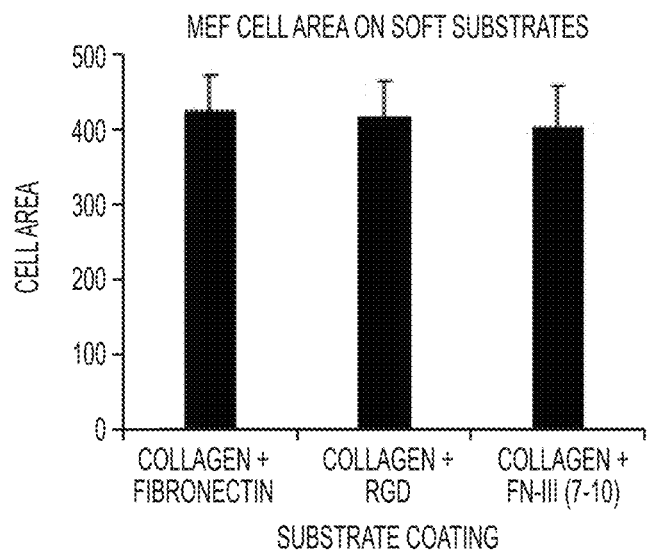
FIG. 22. Spreading on soft substrates is dependent on the availability of $\beta 1$ and $\beta 3$ binding sites. (A) Cells were spread on soft substrates coated with 10 ug/ml collagen+fibronectin, 10 ug/ml collagen+RGD peptide, and 10 ug/ml collagen+FN-III (7-10) show that cells were able to spread. (B) Total protein concentration does not effect cell spreading on soft surfaces. Coating substrates with 20 ug/ml of collagen or fibronectin does not rescue spreading on soft substrates.
Figure 22B:
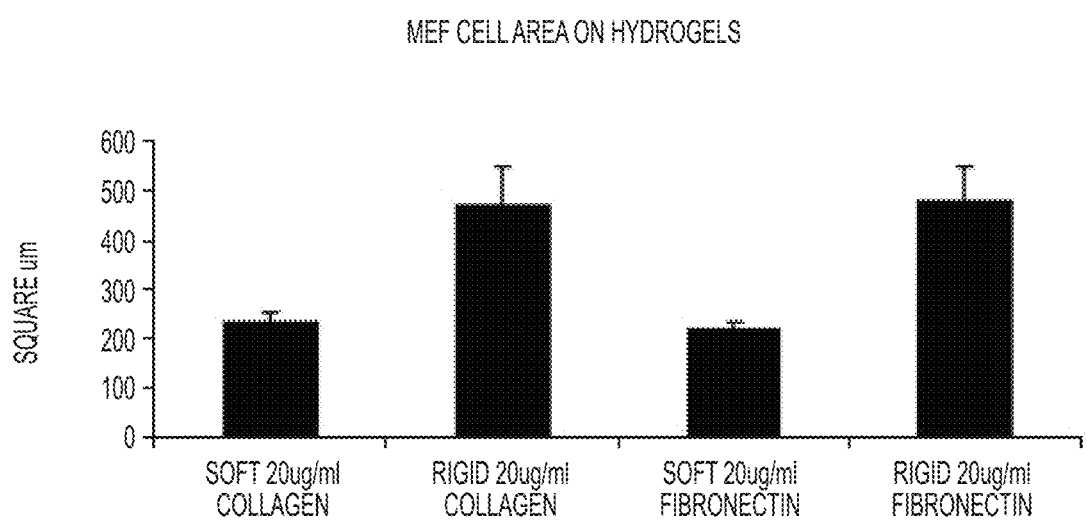
Figure 22C:
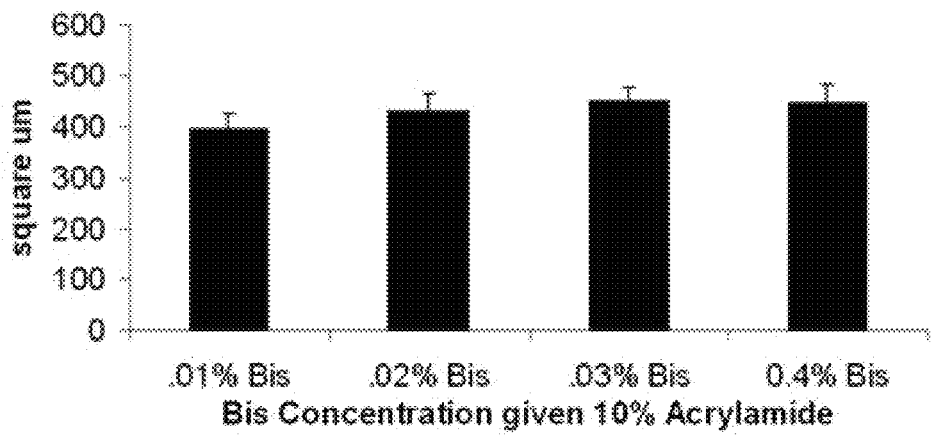
Figure 22D:
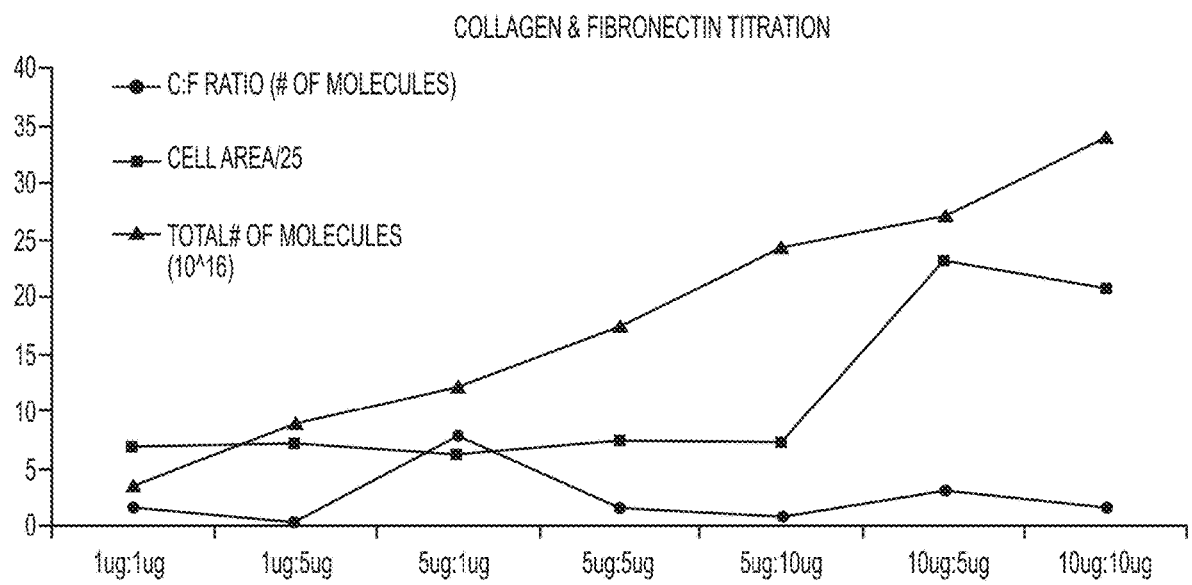

FIG. 20 illustrates that a given concentration and ratio of ECM proteins, collagen and fibronectin, is needed to allow for a permissive in vitro microenvironment to culture cancer cells in vitro. Specifically, titrating collagen and fibronectin identify a minimum total number of molecules ($\sim 2.5*10^{20}$ proteins), as well as suggests an optimal ratio of collagen to fibronectin (3:2) necessary to rescue spreading on soft surfaces and culture cells derived from in vivo samples, in vitro (FIG. 20). Once the ECM and rigidity of the substrate optimal for the removed tissue to grow in vitro is identified more measurements can be made to allow for further insights into the identity of the ECM molecule(s) and/or rigidity of the oncogenic niche environment.

Furthermore, as oncogenic and metastatic cells operate in both an ECM and cellular niche, the devices can be coated not only with varying ECM molecules over varying rigidities, but can be coated with cells from a given tissue, allowing for a co-culture system that would allow measurements to be made on biopsy tissue that has been plated on a layer of cells. For example, lung cancer cells often migrate out of the lung into the pericardium, or breast cancer cells migrate to the lung, resulting in morbity and mortality. Culturing biopsy tissue on cells types where they typically metastasize would allow for an even more "in vivo" measurement to be made. In this case the biopsy tissue would be titrated and labeled with a lypophillic dye that is covalently incorporated into the potentially oncogenic or metastatic tissue. This dye would allow the researcher or technician to differentiate the biopsy tissue with the monolayer of cells that have been grown on the device, allowing for measurements to be made in a more "in vivo-in vitro" measurement.

To maximize in vitro culturing, the device is designed such that it can accommodate the necessary rigidity, ECM molecule, or cellular environment the tissue needs to grow and interact with the device. One possible advantage of this diagnostic is that it would afford the capability, with the patient's consent, to test another tissue, of "non-suspect" origin for comparison. This would enable the practicing physician to compare and contrast the Q's and Z's of each tissue to determine a patient's particular cellular phenotype.

Once the tissue is on the device and the measurements are made, a 'Q' can be determined and a treatment plan decided upon. For example, looking at FIGS. 12 & 13, one may bin TFI values in such a way that specific ranges of TFIs predict the growth and metastatic potential of a cell. TFIs between 0-7 suggest low malignant and metastatic potential; TFIs between 7-30 suggests moderate malignant and high metastatic potential; TFIs greater that 30 correspond to high malignant potential, and low metastatic potential (FIG. 43).

Applicants note that the systems, devices, and methods of the invention can be used with any cell type for diagnosis of any disease, for example, epithelial cancers, carcinomas, sarcomas, adenomas (i.e. mouth, laryngeal, esophageal, lung, breast, prostate, cervical, testicular, and skin), blood born cancers, and neuronal cancers (FIGS. 41, 43, and 44).

In addition to its use as a diagnostic this method can be used to screen compounds that slow or impede the growth and metastatic capabilities of epithelial cancer cells. Compounds can be identified for their ability to change the values of measured biomarkers and Q values (FIG. 45).

Results from the ILK model system and cancer cell lines provide the cellular and molecular basis for using the TFI index and the related/proportional variables as a biomarker for growth, proliferation and migration potential.

Simply, the resultant mislocalization of adapter and signaling proteins such as paxillin, p130Cas, FAK, and Src, leading to the mislocalization and mismodification of MAPKs ERK and JNK that result due to the increased actin retrograde flow, due to decreased focal adhesion-actin coupling, leads to altered cellular growth, proliferation and migration (FIGS. 2-8, and 13). Taken with our observations that larger TFIs engender growth and proliferation (FIGS. 14-23), as well as our observation that TFI correlates with cancer cell line growth and migration (FIGS. 26-29), the data support the use of TFIs and related variables as biomarkers.

Briefly, the data presented in FIGS. 1-8 is the first evidence to suggest focal adhesion-actin coupling can induce changes in MAPK localization and activity and tyrosine phosphorylation patterns. Data presented in FIGS. 5-8 and 13 show that FAs are necessary for both growth and migration as well as motility. Interestingly, data in FIGS. 1-7 highlight the molecular consequences that result under conditions of small TFI values. Data in FIGS. 8-15 confirm that cancer cells exhibit different TFI values than normal cells. Data in FIGS. 14-22 further confirm that modulating the TFI can modulate growth, proliferation, and signaling events necessary for translation, transcription, and motility.

Because deficits in coupling the ECM, focal adhesions (FA) and actin can arise from many cellular perturbations and anomalies, it may be of value to have a single metric based on two simple experimentally derived metrics to quantify and better characterize these phenomena. One metric can include, but is not limited to the traction force index. Deriving the TFI (Traction Force Index) in different cell types can indicate an association with different pathological processes (e.g. oncogenesis, metastasis, cardiac hypertrophy). Namely, the proportional constant between the TFI and processes such as force generation, migration velocity and doubling time may be consistent and correlate to the phenotypic characteristics of a specific cell type. By way of example, and in no way limiting, a cell can exhibit an oncogenic and/or metastatic phenotype by yielding or exhibiting a larger TFI than a wild-type or non-malignant cell. Furthermore, cells derived from pathological tissue can also yield significantly different TFI values than cells derived from normal tissue. Similarly, stem-cells can yield different TFI values than differentiated tissues FIGS. 12 and 13.

Interestingly, increased tyrosine phosphorylation seems to accompany tumor cell invasion of adjacent extracellular matrix. Data presented in FIGS. 1, 2, 4, 6 and 20-21, 40 demonstrates that less tyrosine phosphorylated proteins are localized at the leading edge, altering MAPK signaling and growth and proliferation, and a cells oncogenic and metastatic potential.

As mentioned, the terms "traction force index" or "TFI" as used herein, refers to the ratio of focal adhesion size (um$^2$) and actin retrograde velocity (um/sec), yields a quantity with units um×sec, and a magnitude that is proportional to specific physiological phenomena such as force generation and collagen contraction. Measuring TFI can also be a metric associated with the ECM, focal adhesion and actin-cytoskeleton coupling.

The Traction Force Index is a direct indicator of ECM-FA-actin coupling, and localization of signaling molecules involved in growth, oncogenesis, migration and metastasis. As the localization of proteins regulates the activation state and function, the TFI is a metric that can approximate the activity and function of the many proteins involved in cancer progression that are localized to the leading edge. The traction force index can also be defined as being the inverse of intracellular traction force index (ITFI), that can be defined as the traction force exerted by actin dynamics on focal adhesion proteins inside the cell. In cells with small TFI, or large ITFI due to the cells inability to exert force generated by the acto-myosin contraction on the ECM, gross displacement of focal adhesion proteins within the lamellipodia and cell interior occur with increased retrograde flow of talin, paxillin, p130Cas, and mislocalization of FAK and Src.

To better understand the method to derive a biopsy's oncogenic and metastatic potential, there are many ways to measure the aforementioned biophysical biomarkers. Focal adhesions can be measured using immunofluorescence, by fixing and staining the cell using standard immunochemical procedures, with an antibody for focal adhesion proteins such as talin, vinculin, paxillin, p130Cas, and/or focal adhesion kinase (FAK) (FIG. 1). Actin retrograde flow can be measured by at least three methods as exhibited in FIG. 2. One, actin retrograde flow can be measured by taking DIC time-lapse video microscopy, two actin retrograde flow can be measured by applying 100 to 500 micron sized beads to the extracellular environment while imaging their movement rearward from the cells leading edge via DIC, three, actin retrograde flow can be measured using an actin fusion protein that enables live fluorescent imaging of the actin monomers within the cell; given sufficient resolution to image membrane deformation at 1 image every 5 seconds. Using image analysis software to generate a kymograph (space vs. time), the actin retrograde flow can be calculated by the movement of the membrane, bead, or actin-fusion protein from the leading edge into to the cell interior. Force generation can be measured a number of ways. Classically, force generated by a cell has been measured using deformable substrates such as hydro-gels, silicone gels, and polymers such as PDMS (Polydimethylsiloxane). As cells interact with a deformable substrate, the displacement generated at the cell substrate interface can be measured and approximating the cell-substrate interaction as a spring, with a given Young's modulus or stiffness, one can calculate the force generated on the substrate using Hooks law. Migration rate can be measured using time-lapse video microscopy. Taking images over time of a cell as it move along a substrate, one can calculate the distance the cell traveled, while knowing the time, one can calculate the migration rate as distance divide by time.

By establishing the traction force index, one of ordinary skill in the art can quantify a cellular interaction involved in the regulation and maintenance of numerous cellular, and physiological responses such as polarization, migration, and collagen contraction, as well as pathological states, such as oncogenesis, metastasis and cardiac hypertrophy. Furthermore, this index allows for the prediction of cellular processes such as force generation and in turn multicellular processes, such as wound healing, specific motility events during development or regeneration and pathological states such as cancer prognosis and cardiac hypertrophy.

Studies deriving the TFI in different wild type and pathological tissues can be drawn from direct correlations between the TFI value and the aforementioned cellular processes (FIGS. 7, 12, and 13). Namely, the proportional constant between the TFI and processes such as force generation, migration velocity and doubling time can be consistent and directly correlated to the phenotypic characteristics of a specific cell type. By way of example, a cell exhibiting an oncogenic and/or metastatic phenotype would yield or exhibit a larger TFI than a wild-type or non-malignant cell. Furthermore, cells derived from pathological tissue would yield significantly different TFI values than cells derived from normal tissue. Similarly, stem-cells would yield different TFI values than differentiated tissues (FIGS. 12 and 13).

As the Examples demonstrate, some proteins can indicate proper recruitment and intracellular dynamics of numerous focal adhesion proteins such as paxillin, p130Cas, and FAK, and mislocalization or changes in protein dynamics can affect many downstream consequences in molecules such as ERK, JNK, Akt, p70S6K, and p90RSK1 given the role of these proteins in the cell to growth, proliferation, migration, oncogenesis, metastasis, and activate protein translation, Using the data generated from the ILK model cancer system and cancer cell lines (FIGS. 1-13) and given the multitude of protein interactions present within a cell, the disruption of numerous signaling and actin-based processes can result in a small (ex. <7) TFI value (FIG. 40). A small TFI can be associated with weak focal adhesion and actin coupling, leading to the mislocalization of integral focal adhesion proteins. Cells exhibiting a small TFI, due to small focal adhesion size, may not be able to recruit actin binding proteins such as vinculin, CrkII-Dock180-ELMO complex via paxillin. This lack of function can result in excess unpolymerized actin and mislocalization of proteins at the leading edge. For example, phospho-paxillin (Y181), a modification necessary for paxillin-protein interactions, is mislocalized throughout the leading edge and interior of the cell as opposed to puncate foci at the leading edge. Other protein complexes can also be displaced, such as activate forms of FAK, Src, ERK and p38MAPK. As the focal adhesion complex is composed of ~125 different proteins, a small TFI value suggests mislocalization of numerous focal adhesions and their direct and in direct binding partners. This mislocalization leads to mismodification of proteins, altering their wild-type activation state, promoting faster growth, migration, invasion and oncogenic phenotype. For example, FIG. 40 gives an example of how cells can be classified as oncogenic and/or metastatic.

Q and Z values are calculated as discussed in the Examples below, which demonstrate how cell lines, using these formulas, can be quantitatively compared and assessed for their growth, migration, oncogenic and metastatic potential.

The device to measure the aforementioned variables will be fabricated using emerging nanotechnology methods, in a scalable, multifunctional manner, with features small enough to measure the necessary metrics from even the smallest of biopsies (FIGS. 21-37). The methods used for fabrication will be a combination of photo-lithography, dry etching and micro-contact printing, using a silicon master, producing a device with microfluidic capability, composed of PDMS, or similar polymer in a design suitable for high through-put capability. Immunohistochemistry using antibodies or quantum dots will be used to measure IPPS, FAS, DIC and fluorescent microscopy will be used to measure velocities, and micrometer and nanometer scaled beads coated with ECM molecules will be used to measure RFS. Moreover, RFS (retrograde flow speed) can be calculated using DIC microscopy without beads or a fluorescent protein 'fused' to an actin associated protein. The device is composed of three layered sections (FIG. 24). One, a central 20×20 mm PDMS chip (FIGS. 21 & 22), that is merged, or overlayed by a fluidic device, that is married with the chip, to allow for materials to be flowed in and out of the five macrochannels of the device (FIG. 22). The chip and fluidic device are then placed on top of a glass coverslip (FIG. 24), allowing for the fluidic channels to accessed from above, while the macrochannels and chip are enclosed on the cover glass. The device can then be mounted on a microscope to be imaged (FIG. 25).

In the schematic of the device (FIGS. 32 & 33) highlights the fact that the device is designed in a modular fashion in that the squares labeled with the Greek symbols: alpha, beta, gamma, epsilon, theta, can be engineered to contain PDMS structures with different rigidities, geometric features, and ECM coating. FIGS. 6-11 highlight the different geometries and parameters that can be engineered to better measure a given variable/metrics.

Moreover, these metrics and ratios can be used to diagnose other disease states such as cardiac hypertrophy, myopathy and renal diseases.

In order to culture cells on the device, sterile, freshly obtained solid human tumor specimens are mechanically dissociated with a scalpel to the size of 1 mm and then treated with ~0.75% collagenase HI and ~0.005% DNase in balanced salt solution with ~10% serum for ~16 h at 37° C. under continuous agitation to form single cell suspensions. Cells are then washed in a balanced salt solution. The number of viable cells is determined by a cytometric count of trypan blue-negative nucleated cells, excluding lymphocytes, granulocytes, and mesothelial cells using a phase-gradient imaging microscope at ×10 magnification. The single-cell suspension can be diluted with the attachment medium and incubated at 37° C. in a humidified 5% CO2-air atmosphere. Cells can be then placed on the device to make the necessary measurements.

To use the device, one would use appropriate surface chemistry techniques to covalently, or hydrophobically coat the macrochannels of the device with ECM molecules such as laminin, vitronectin, collagen type I, collagen type IV, and fibronectin. This coating will allow for a minimum density of protein (FIG. 20), at an appropriate ratio of ECM proteins if more than one ECM molecule is used to coat the macrochannel. After the channels are coated with an ECM, the channel can be washed with a balanced salt buffer, and culture media. The device will now be ready to culture cells. Single cell suspensions of will be injected into the macrochannels via micro fluidic channels and allowed to interact with each substrate for a given time. Cells can be imaged using phase, differential interference microscopy, fluorescent microscopy, using an objective with an appropriate numerical aperture to enable visualizing the substrate through 400-700 nm of aqueous buffer between the coverglass and chip. Once digital images are recorded using commercially available software, digital imaging processing software can be employed to automate and quantify the measurements of the various biophysical and biochemical variables. In the case of many biochemical variables, spectrometry may be employed to assess variables such as MIA, PIA. Utilizing metabolic reactions with colorimetric assays, spectrometry can be preformed on liquid from the microfluidic outflow reservoir.

Upon removal of the tissue, the tissue will be titrated and plated on different substrates, with as many as 15 different rigidities, coated with 12 different ECM molecule combinations to assess the necessary coating of the chip. This in it of itself will allow the person handling the tissue to decide what ECM molecules to coat the device with and to use a media containing no serum, or serum or hormones. The aforementioned has also been validated experimentally. One of the hallmarks of cancer cells is that they have the ability to grow and spread on soft surfaces (0.05 kPa). ILK+/+ cells cannot spread on soft surfaces, unless the surface is coated with collagen and fibronectin. This fact allows one to infer that different stages of cancer will have different abilities of spreading on different rigidities (3 kPa-50 GPa) coated with different ECM molecules (Collagen type 1, & 4, Fibronectin Laminin). One of the main problems of doing cell-based diagnostics is the fact that cells removed from a patient are hard to culture. The method described in this part of the invention is to ameliorate this problem. Once the ECM and rigidity of the substrate, optimal for the removed tissue to grow in vitro is identified, more measurements can be made as well as the insight gained from the identity of the ECM molecule(s) and/or rigidity of the substrate.

Furthermore, as oncogenic and metastatic cells operate in both an ECM and cellular niche, the devices can be coated not only with varying ECM molecules over varying rigidities, but can be coated with cells from a given tissue, allowing for a co-culture system that would allow measurements to be made on biopsy tissue that has been plated on a layer of cells. This would allow for an even more "in vivo" measurement to be made. In this case the biopsy tissue would be titrated and labeled with a lypophillic dye that is covalently incorporated into the potentially oncogenic or metastatic tissue. This dye would allow the researcher or technician to differentiate the biopsy tissue with the monolayer of cells that have been grown on the device, allowing for measurements to be made in the most "in vivo-in vitro" measurement.

The device will be designed such that it can accommodate the necessary rigidity, ECM molecule, or cellular environment the tissue needs to be cultured in vitro. A possible advantage of this diagnostic is that it would afford the capability, with the patient's consent, to test another tissue, of "non-suspect" origin for comparison. This would enable the practicing physician to compare and contrast the Q's and Z's of each tissue to determine what that patients particular cellular phenotype may be.

Once the tissue is on the device and the measurements are made, Q can be determined and a treatment plan can be decided upon. Specifically, this device may be best suited for epithelial cancers, blood born cancers, and neuronal cancers and can be extended towards cardiac hypertrophy, myopathy, and renal diseases.

Certain exemplary embodiments will now be described to provide an overall understanding of the principles of the structure, function, manufacture, and use of the systems, methods, and devices disclosed herein. One or more examples of these embodiments are illustrated in the accompanying drawings. Those skilled in the art will understand that the systems, methods, and devices specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. As used herein, the terms "about" or "approximately" for any numerical values or ranges indicate a suitable tolerance that allows the part or collection of components to function for its intended purpose as described herein.

Example 1

Experiment Data for the ILK MEF Line:

| Variable | +/+ | -/- |
|---|---|---|
| FAS | 1 um (+−.3) | .1 um (+−.2) |
| RFS | .05 um/sec (+−.02) | .1 um/sec (+−.02) |
| MV | .2 um/sec (+−.05) | .05 um/sec (+−.02) |
| CA | 350 um2 (+−80) | 250 um2 (+−70) |
| FG | .13 uN (+−.04) | .07 uN (+−04) |

-continued

| Variable | +/+ | -/- |
|---|---|---|
| PT | 5400 sec (+−1200) | 7200 sec (+−1000) |
| PIA | 2.5 C | C |
| MIA | C | 2 C |

Given the above experimental values, the formulas below were used to verify the proposed relationships and correlation with growth, migration, oncogenic and metastatic potential.

| Formula | ILK+/+ | ILK-/- | Values correlate relative growth & migration? |
|---|---|---|---|
| aQ1 = FAS/RFS | 20 | 1 | Yes |
| aQ2 = FG/RFS | 2.6 | 0.7 | Yes |
| bQ1 = ((FAS/RFS) × (MIA/CA))(WTA) | 0.057 C | 0.0008 C | Yes |
| bQ2 = ((FAS/RFS) × (MV/CA))(WTA) | 0.011 | 0.00002 | Yes |
| aZ1 = aQ1/aQ2 | 7.69 | 1.43 | |
| aZ2 = aQ2/aQ1 | 0.13 | 0.7 | |
| bZ1 = bQ1/bQ2 | 5.18 | 40 | |
| bZ2 = bQ2/bQ1 | 0.19 | 0.025 | |

Experiment Data for the MCF Breast Cancer Cell Line on Collagen:

| Variable | MCF7 | MCF10A |
|---|---|---|
| FAS | .9 um (+−.25) | .45 um (+−.3) |
| RFS | .009 um/sec (+−.002) | .055 um/sec (+−.03) |
| MV | .48 um/sec (+−.09) | .016 um/sec (+−.007) |
| CA | 380 um2 (+−60) | 480 um2 (+−90) |
| PT | 4300 sec (+−930) | 5200 sec (+−1020) |
| PIA | 1.5 C | C |

Given the above experimental values, the formulas below were used to verify the proposed relationships and correlation with growth, migration, oncogenic and metastatic potential.

| Formula | MCF7 | MCF10A | Values correlate relative growth & migration? |
|---|---|---|---|
| aQ1 = FAS/RFS | 100 | 8 | Yes |
| aQ2 = FG/RFS | 111 C | 18 C | Yes |
| bQ1 = ((FAS/RFS) × (MIA/CA))(WTA) | 0.26 | 0.017 | Yes |
| bQ2 = ((FAS/RFS) × (MV/CA))(WTA) | 0.126 | 0.00028 | Yes |
| aZ1 = aQ1/aQ2 | 0.9 | 0.44 | |
| aZ2 = aQ2/aQ1 | 1.11 | 2.25 | |
| bZ1 = bQ1/bQ2 | 2.06 | 60 | |
| bZ2 = bQ2/bQ1 | 0.48 | 0.016 | |

Upon solving for the initial Q1's, Q2's and Z1 and Z2 using the ILK line a standard of oncogenic and metastatic potential can be established by which other tissue samples can be measured. The initial Z1 and Z2 would be based on the above values with Q1/Q2=Z1 and Q2/Q1=Z2. Indeed the Z values of the cancer cell, MCF7 can be compared to the Z values of the ILK+/+ cell line, and as predicted for each Z1 and Z2, the MCF7 cell line would be predicted as more metastatic and oncogenic compared to the ILK+/+ cell line.

$MCF7aZ1 \leq ILK++aZ1$ i.e. MCF7 is oncogenic $MCF7aZ2 \geq ILK++aZ2$ i.e. MCF7 is metastatic $MCF7bZ1 \leq ILK++bZ1$ i.e. MCF7 is oncogenic $MCF7bZ2 \geq ILK++bZ2$ i.e. MCF7 is metastatic Example 2

Spreading on Collagen Versus FN (Integrin Dependence)

To determine if there is an integrin dependence in ILK−/− cells, the spreading of ILK−/− and control cells on collagen or fibronectin-coated surfaces were analyzed. When control suspension cells were added to collagen-coated glass, they spread primarily (~60%) in an isotropic fashion with a significant fraction spreading in an anisotropic fashion (40%) (Dubin-Thaler et al., 2004). In contrast, ILK−/− cells spread almost completely in an isotropic fashion (~90%) and had a greatly expanded lamellipodium (FIG. 3A-F). After 5-10 minutes, the ILK−/− cell area gradually decreased whereas the control cells continued to increase in area. If ILK−/− cells were placed on fibronectin, they spread almost normally for the first 5-10 minutes but then retracted their lamellipodia rapidly (FIG. 3B). In most cases the central cytoplasm remained spread on fibronectin, unlike on collagen where there was a dramatically contracted central cytoplasm (FIG. 3A). The morphology of the ILK−/− cells on collagen was similar to that of talin depleted cells where the central cytoplasm was contracted by myosin because integrins were not mechanically coupled to the actin-myosin network in the periphery and contraction collapsed the cytoplasm (Zhang et al., 2008). To test for the role of myosin contraction in the morphology of ILK null cells, the myosin inhibitor blebbistatin was added, which resulted in endoplasm spreading as well as rescue of normal morphology similar to the talin depleted MEF's. Thus, there appears to be a myosin mediated collapse of the actomyosin network due to weakened coupling to adhesions in ILK−/− cells.

To determine if the apparent lack of connection between collagen and the cytoskeleton had a functional consequence, the ability of the cells to sense rigidity was tested by determining if the cells spread less on soft surfaces. When the extent of spreading on soft versus rigid polyacrylamide gels was measured, ILK−/− cells showed the same degree of spreading on soft and rigid collagen (FIG. 3, E and F). In contrast, the control cells spread to larger areas on rigid collagen than soft. In the ILK−/− cells, similar to when they were spread on collagen-coated glass, there was again a highly contracted core of cytoplasm and broad lamellipodium on both soft and rigid collagen (FIG. 3E). With fibronectin-coated acrylamide, both ILK−/− and control cells spread to a larger area on rigid than on soft polyacrylamide. Thus, the rigidity response (rigidity sensing) of collagen was selectively lost in the ILK−/− cells (FIGS. 3E and F).

Increased Actin Flow in ILK−/− Cells and Decreased Force

If the condensed cytoplasm in the ILK−/− cells was due to a lack of attachment of the actomyosin cytoskeleton with the peripheral adhesions, then the rate of actin flow inward may have been increased as previously observed for talin-depleted cells (Zhang et al., 2008). Several methods were used to measure the actin flow rate, including the rate of dorsal bead transport, of fluorescent actin movement, and of dorsal wave movement. All three methods showed that the rate of movement of actin inward was increased in ILK−/− cells on collagen. As mentioned above, ILK+/+ cells spread faster than ILK−/− cells (86 nm/sec±21 (n=16) and 51 nm/sec±11 (n=18) for ILK+/+ and ILK−/−, respectively). When actin retrograde flow was measured via the transport of 1 μm diameter beads coated with collagen, the velocity in the ILK+/+ line of cells was 43 nm/sec±9 nm/sec (n=7) and in ILK−/− cells it was 128 nm/sec±22 (n=7) (FIG. 2). Another means of measuring actin retrograde flow was to track actin-based distortions in the membrane by DIC microscopy. In this assay, ILK+/+ cells exhibited an actin rearward flow rate of 37 nm/sec±5 nm/sec (n=6) while ILK−/− cells exhibited 117 nm/sec±15 nm/sec (n=8) (FIG. 2). Finally, the rearward flow rate of actin-gfp speckle patterns was measured by TIRF microscopy. In this assay, the actin retrograde flow rate was 44 nm/sec 9 nm/sec (n=9) in ILK+/+ cells, versus 143 nm/sec±20 nm/sec (n=9) in ILK−/− cells (FIG. 2). Taken together, the average actin retrograde flow rates for ILK+/+ and ILK−/− were 43 nm/sec±9 nm/sec (n=22) and 128 nm/sec±22 nm/sec (n=24), respectively (FIG. 2). This increased retrograde flow in ILK−/− cells indicated a defect in the ability of integrins to link to the cytoskeleton in ILK−/− cells, resulting in decreased attachment of actin to the adhesions and greater rate of contraction inward.

Myosin-Driven Inward Flow Causes Contracted Cytoplasm

A corollary of the increased actin flow is that myosin flow should be increased as well and myosin distribution should be altered. MLC-GFP localization was significantly altered in an ILK−/− background (FIG. 3G-J). MLC-GFP appeared at the basal membrane earlier in the initial spreading phase in the ILK−/− background, and the contractile ring was more prominent. There were also deficits in the formation of transverse stress fibers across the cell. Interestingly, in ILK−/− cells, the contractile ring maintained a position ~3.8 μm interior from the leading edge (FIG. 3G-J) compared to ~0.9 μm from the leading edge in ILK+/+ cells. Consistent with this observation, the small myosin foci that formed at the leading edge in ILK−/− cells flowed rearward at ~3× the velocity in ILK null cells, 44 nm/sec±11 nm/sec (n=8) versus 15 nm/sec±9 nm/sec (n=8) (FIG. 3G-J) in ILK+/+ cells.

β1 Integrin Function But Not β3 Appears Altered

To test whether ILK was playing a larger role in specific integrin mediated functions, β1 mediated binding was compared to β3 mediated binding, using inhibitory antibodies to integrins. MEFs were incubated in suspension with inhibitory antibodies and plated on glass substrates coated with 10 ug/ml fibronectin or collagen (FIGS. 3C and D). Cells were allowed to spread for 30 minutes, fixed and imaged via DIC microscopy. The early time point of fixation ensured that primarily early integrin-ECM interactions were observed. Consistent with previous studies, inhibition with a cyclic RGD peptide, specific for αvβ3 integrin blocked rapid spreading on fibronectin in both ILK+/+ and ILK−/− cells (FIGS. 3C and D). Interestingly, α5β1 blocking antibodies preferentially inhibited spreading of ILK+/+ cells on fibronectin and not ILK null cells, indicating that cells without ILK may preferentially utilized β3 integrin to spread on fibronectin. For cells interacting with collagen, MEF's were unable to spread on collagen when treated with inhibitory antibodies to β1 and α2β1 integrins (FIGS. 3C and D). These results confirmed the previous observations that early interactions with fibronectin and collagen were mediated by β3 and β1, respectively. The results also suggest that ILK preferentially mediates coupling of the ECM to the actin cytoskeleton via β1 integrins.

Decreased Traction Force Resulting from Decreased Coupling

An important consequence of decreased attachment to the integrins is that traction forces may be decreased. A pillar displacement assay was used to measure the traction forces of control and ILK−/− cells. Pillar displacement was determined for spread cells after 60 minutes of spreading. ILK+/+ cells produced an average pillar displacement of 164 nm±22 nm (n=17), while ILK−/− cells averaged 62 nm±24 nm (n=19) of displacement per pillar on collagen coated pillars (FIG. 6). Using a similar method pillar displacement by ILK+/+ and ILK null cells was investigated on an array of pillars coated with fibronectin. ILK+/+ cells produced an average pillar displacement of 167 nm±31 nm (n=24), while ILK−/− cells produced an average displacement of 52 nm±38 nm (n=19) (FIG. 5G). With collagen or fibronectin-coated pillars, ILK−/− cells generated considerably lower forces than ILK+/+ cells. These measurements were at later times after spreading where the fibronectin was bound by α5/β1 integrin. Spread areas were not sufficiently different to account for the differences in force. Thus, it appeared that ILK was selectively needed for the generation of β1 mediated traction forces on collagen and fibronectin.

Adhesion Size is Smaller in the Absence of ILK

To determine if adhesion formation was also altered in ILK null cells on collagen, different adhesion proteins were stained after 1 hour. The ILK null cells, on average, exhibited focal adhesions 5× smaller than wild type MEF's expressing ILK, with adhesion sizes of 1.1 μm2±0.4 for ILK+/+ and 0.19 μm2±0.06 for ILK−/− cells (FIG. 1). Not only actin-binding proteins such as vinculin, and talin were depleted from focal adhesions, but scaffolding and signaling molecules such as p130Cas, paxillin and FAK were depleted as well.

Adhesions Migrate More Rapidly in the Absence of ILK

To determine if smaller adhesions resulted from greater turnover or lower rates of assembly, the dynamics of talin, p130Cas and paxillin were observed during the rapid and contractile phases of cell spreading using total internal reflection fluorescence (TIRF) microscopy. Paxillin-GFP localized to focal complexes early on in the rapid spreading phase. During contractile spreading, in ILK+/+ cells, paxillin-GFP persisted at the leading edge and formed two stable fluorescent lines or borders at the leading and interior edge of the lamellipodia, presumably demarcating nascent focal contacts at the leading edge and more mature adhesions toward the interior of the lamellipodia. While paxillin-GFP was stable in adhesions in ILK+/+ cells, paxillin-GFP was remarkably more dynamic at the leading edge in ILK−/− cells (FIGS. 4A and D), moving rearward at a velocity of 9 nm/sec±3 nm/sec (n=9), paxillin-GFP in ILK+/+ cells moved rearward at 0.2 nm/sec±0.05 nm/sec (n=8) or 45-fold slower (FIGS. 4A and D). The retrograde flow of a focal adhesion protein was surprising. Using the same techniques, two other focal adhesion proteins, talin and p130Cas, were investigated to determine if they moved at the same or different rates in the ILK−/− background. Talin-GFP was directly bound to integrin as well as actin filaments and was present throughout the basal membrane region in small foci early in spreading. Subsequently, it was concentrated in adhesions in early rapid spreading that persisted into late contractile spreading. While talin-GFP in ILK−/− cells was localized to adhesions during early spreading, talin-gfp failed to form sharp, defined focal contacts in fully spread ILK−/− cells. It was observed that talin formed globular, fluorescent foci in spread ILK−/− cells that moved rearward at ~25 nm/sec±4 nm/sec (n=5) (FIGS. 4C and D). Talin-gfp in spread ILK+/+ cells persisted at the leading edge and moved slowly rearward at 2.4 nm/sec±0.9 nm/sec (n=4) on substrates coated with collagen. For comparison, movements of p130Cas were measured, a protein of the CAS (Crk-associated substrate) family that was only indirectly bound to integrins in adhesions. Qualitatively, p130Cas-GFP exhibited similar localization and dynamics to paxillin, except that it was recruited to the leading edge later in spreading than ILK and paxillin, concurrent with the start of contraction. p130Cas localized to focal adhesions and formed a characteristic fluorescent band, circumscribing the cell, spanning the length of the leading-edge in ILK+/+ cells spread on collagen and moved inward at a low rate of 0.91 nm/sec±0.04 run/sec (n=9) (FIGS. 4B and D). In contrast, p130Cas was more dynamic in the ILK−/− background and moved rearward at a rate of 19 nm/sec±6.4 nm/sec (n=11) (FIGS. 4B and D). Thus, consistent with the observed smaller focal adhesions in ILK null cells, the observed adhesion proteins move more rapidly inward at different rates in ILK−/− cells.

Consistent with observations that paxillin and p130Cas move rearward in cells ILK null cells, immunofluorescent staining of phosphopaxillin (Y118) show a diffuse staining pattern in ILK−/− cells as well as significant staining towards the interior of the cell. This is in contrast to the distinct punctate staining pattern found in ILK+/+ cells (FIG. 4F).

Figure 4F:
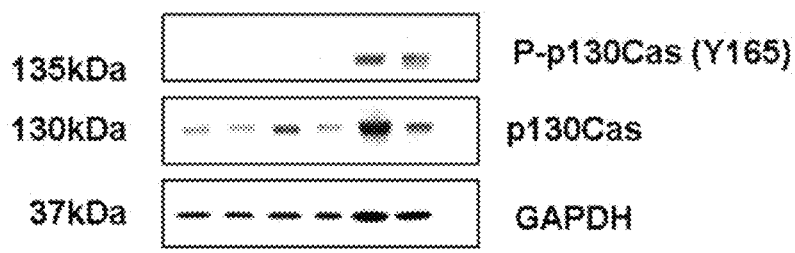
Figure 4F:

Staining of phospho-p130Cas (Y165) shows a distinct band ~2.5 μm interior to the leading edge in ILK−/− with diminished staining at the leading edge, in contrast to the punctate staining at the leading edge in ILK+/+ cells (FIG. 4F).

MAP Kinase Phosphorylation is Decreased in ILK−/− Cells

In contrast to what was found with other signaling molecules such as FAK, p130Cas, and src (FIG. 6), when absolute phosphorylation levels of JNK and p44ERK were studied using via western analysis, a difference was observed when compared ILK+/+ and ILK−/− lines were compared (FIG. 6). In addition to the difference in overall phosphorylation levels of JNK and p44ERK, a significant and consistent difference in the localization of the phosphorylated forms of JNK, and p44ERK was observed (FIG. 6). Phospho-JNK localizes to small foci at the leading edge in ILK+/+ cells, while it localizes along the entire width of the lamellipodia in ILK−/− cells. Similarly, phospho-p44ERK localized to foci at the leading edge of ILK+/+ cells but was unable to localize at any part of the lamellipodia, and remained in the endoplasm of ILK−/− cells (FIG. 6). This localization is consistent with the localization of their binding partners phospho-paxillin (Y118) and phospho-p130Cas (Y165). Finally, difference in proliferation between the ILK+/+ and ILK−/− lines was quantified using the BrdU assay. After serum starvation to synchronize both cell lines, each line was incubated with BrdU in the presence of serum for 30, 60 and 120 minutes. Upon staining for BrdU incorporation, significantly higher levels of incorporation of BrdU was observed in the ILK+/+ line with an estimated doubling time 640±54 minutes for ILK+/+, in contrast to ILK−/− line that had an estimated doubling time of 820±52 minutes. Taken with observations of actin and myosin retrograde flow, these observations suggest that the presence of ILK is critical for activation of the MAPK's involved in stimulation of growth.

Collagen Gel Contraction Requires ILK

Previous studies on migration of ILK−/− cells have shown decreased rates of movement on 2-D surfaces. Further, to determine if contraction of 3-D collagen networks would be altered in ILK−/− cells; 3D type I collagen-gel contraction was measured (Ngo, et al., 2006). An equal number of cells (5K) were seeded in gels of different collagen densities and allowed to grow in culture for 12 days. ILK−/− cells were unable to contract any gel of 1.8 mg/ml, 1.6 mg/ml, or 1.2 mg/ml collagen at day 12, and up to day 21, while ILK+/+ cells were able to contract gels of 1.2 mg/ml and 1.6 mg/ml to 60% and 40% of the original size, respectively, by day 12 (FIG. 5). This further underscored ILK's role in the physical linkage of the cytoskeleton to a collagen based ECM.

Discussion

These studies show that ILK−/− cells are particularly deficient in the coupling of matrix to the actin cytoskeleton through the collagen binding integrins and result in increased actin retrograde flow in the lamellipodia. From assays of early spreading to long-term assays of matrix contraction, there is consistently a defect in cytoskeleton-matrix linkage in ILK−/− cells (FIGS. 1, 3, and 5). The central cytoplasm fails to spread on collagen but spreads on fibronectin (FIG. 3). There is a greater rate of actomyosin transport inward and a lower force generated on collagen both on collagen coated pillars and 3-D collagen fibers (FIGS. 2 and 5). Although adhesions do form on collagen, they are typically smaller and more dynamic in ILK−/− cells (FIGS. 1 and 4). Moreover, actin and myosin dynamics are significantly altered with ILK−/− cells exhibiting rapid retrograde flows of actin and myosin. Perhaps the most striking defect is the weakness of the link between talin and integrins bound to collagen in the absence of ILK and the fact that paxillin has the lowest rate of transport inward. One possible explanation is that paxillin is associated with a complex of proteins more tightly coupled to the β1 integrin than talin and ILK would aid in forming a larger, more stable complex. Many of the other changes can be explained as the result of a weakness in the linkage between α2 β1 integrins and talin.

Rigidity dependent spreading has been shown previously to involve a different set of components on collagen and fibronectin (Jiang et al., 2006; Kostic et al., 2006; Wang, et al., 2003). In the case of fibronectin, there is evidence of a β3 integrin dependence involving the receptor-like protein phosphatase α (RPTPα) and the Src-family kinase, Fyn (Kostic et al. 2006). RPTPα and Fyn knockout cells spread to the same extent at early times on soft and rigid fibronectin, but they do sense collagen rigidity and spread to a larger area on rigid collagen (Jiang et al., 2006; Kostic et al., 2006). Focal adhesion kinase (FAK) was previously shown to be involved in collagen rigidity sensing since FAK null cells spread to the same area on soft and rigid collagen (Wang, et al., 2000). However, FAK null cells can sense the rigidity of fibronectin-coated surfaces (Jiang, et al., 2006). The behavior of the ILK null cells is similar to FAK−/− in that they have a defect in the sensing of collagen but not fibronectin (FIGS. 3E and F). This is all consistent with a role for ILK in the activation of β1 integrin.

The observation that ILK−/− cells exhibit increased retrograde flow and do not sense rigidity on collagen, points to the importance of cytoskeletal coupling in early stages of cell motility, the rigidity response, and ECM sensing (FIG. 3). Given the current model, rigidity is thought to be sensed via nascent ECM-integrin-focal adhesion-cytoskeleton coupling events that lead to the mechanical stretching of proteins found at nascent focal contacts. The ability of the cell to transduce force across the plasma membrane through the linkage of ECM-integrin-FA-actin-myosin is also linked to chemical signals via mechanotransduction (Vogel & Sheetz, 2006). Since ILK−/− cells did not sense rigidity on collagen (FIGS. 3E, F), this suggests that the cytoskeletal linkage is necessary to sense, or transduce the rigidity of the substrate and activate the MAPK pathway that is perturbed in ILK−/− cells. Specifically, perhaps it is the weakened actin, focal adhesion and ECM coupling, increased retrograde flow of actin (FIG. 2), that results in less transduction by less protein stretching. That is to say that the reduced traction between integrins, focal adhesion proteins and the cytoskeleton in ILK null cells, manifested by increased actin and myosin retrograde flow, allows for the sustained activation of actin polymerization characteristic of initial spreading or 'P1' (Dobereiner, et al., 2004), or initial fast cell spreading. Moreover, the ability of ILK−/− cells to sense rigidity on fibronectin (FIGS. 3E and F) coated surfaces indicates that ILK is not necessary for the initial coupling of fibronectin to the cell's cytoskeleton in β3-integrin dependent sensing (Kostic and Sheetz, 2006). Interestingly, when collagen-coated magnetic beads are subjected to 1 nN oscillatory forces, they are displaced by twice as much on ILK−/− than on ILK+/+ MEFs' (FIG. 5). This larger displacement further indicates that the ECM-integrin-FA-actin linkage is weakened. Furthermore, the ability of the cell to stretch the ECM-actin linkage more in the absence of ILK supports the idea that the protein complex at the focal adhesion is stabilized by ILK.

The observations on collagen and β1-ILK mediated interactions, highlight the fact that significant focal adhesion size deficits and increases in retrograde flow velocities in ILK null cells leads to mislocalization of myosin (FIG. 3), focal adhesion proteins (FIGS. 1 and 4), reduced force generation (FIG. 5), slower migration and reduced collagen contraction (FIG. 5). This study points to ILK as an important molecular component in the mechanical linkage between β1 integrins and the adhesion complex. Finally, the decreased strength of the integrin-adhesion protein linkage has important cellular consequences such as reduced levels and mislocalization of phosphorylated scaffold proteins and signaling molecules such as phosphorylated (Y118) paxillin, phosphorylated (Y165) p130Cas, phosphorylated (T183/Y185) JNK, and phosphorylated (T204/Y204) ERK (FIG. 6). Since phosphorylated paxillin and p130Cas (Turner, 2000; Defillippi, et al., 2006; Ishibe, et al., 2004) have previously been shown to act as scaffolds and substrates for MAPK's, among other signaling molecules (Cabodi, et al., 2010; Wu and Dedhar, 2001), the reduced cytoskeleton coupling and increased retrograde flow could explain the effects on downstream signaling and growth.

Materials and Methods

Cell Culture: The ILK+/+ and ILK−/− mouse embryonic fibroblast cell lines were a kind gift for R. Fassler (Sakai, et. Al., 2003), and were maintained in DMEM high glucose (Gibco-Invitrogen) supplemented with 10% fetal bovine serum, 100 IU/ml of penicillin-Streptomycin, 2 μM of L-Glutamine, and 2 μM of HEPES (Gibco-Invitrogen). Cultures were kept at 60% confluence at 37° C. in a 5% CO2 incubator. Prior to experiments cells were prepared by trypsinizing with Trypsin Like Enzyme (Gibco-Invitrogen), washed with soybean trypsin inhibitor, centrifuged at 1000 rpm for 5 minutes, and resuspended in phenol red- and serum-free DMEM (Gibco-Invitrogen). Next, cells were incubated for 20 minutes at 37° C. in suspension, and plated on substrates in serum-free media for observation. Constructs and transfection: ILK-GFP, and ILK-PBS-GFP were generous gifts from C. E. Turner (Nikolopoulos, and Turner, 2001). Actin-GFP, myosin-light chain-GFP, talin-GFP, paxillin-GFP, and p130Cas-GFP were described in (Giannone, et al., 2007). DNA constructs were transfected into ILK+/+ and ILK−/− cells using Fugene (Roche) transfection system. Roughly 2-3 μg of DNA and 8-12 μl of fugene were used per reaction ($10^5$ cells). Cover slip-coating and bead coating: Cover glasses were washed 2 hours in 20% nitric acid and then silanized by exposure to gaseous 1,1,1,3,3,3-Hexamethyldisilazane (Sigma). Silanized cover slips or cultures dishes were coated with 10 μg/ml rat tail collagen type I, dissolved in 0.2% Acetic Acid in 1M PBS overnight at 37° C. For live-imaging, cells were sealed in a live imaging chamber and mounted onto a motorized 37° C. stage. DIC and TIRF images were taken on an Olympus BX50 fluorescence microscope with a 60×, N.A. 1.45 objective. Silica beads (100 μl of 2.7-μm) (Dynal Biotech) were washed with 0.1M carbonate buffer and 0.02 M phosphate buffer sequentially before being incubated in 750 μl 2% carbodimide/phosphate buffer for 3 h at room temperature. The beads were then washed with 0.1 M borate buffer. Silica beads were then treated with cyanogen bromide (Technote #205, Bangs Laboratories) and incubated with 10 ug/ml collagen, fibronectin or laminin, in 0.2% Acetic Acid in 1M PBS for collagen and 1M PBS for fibronectin and laminin, overnight at 4° C. and stored in 1 μg/ml of albumin from chicken egg white (Sigma). Magnetic Bead Assay: To apply forces to magnetic beads, a previously described magnetic tweezers apparatus (Tanase et al., 2006) was used. Briefly, an electromagnet with a sharpened ferromagnetic core was used to apply a strong magnetic field gradient, generating a force on the beads. The force exerted by the tweezers was calibrated from the velocity of beads in liquids of known viscosity measured as a function of the tip-bead distance and applied current. For force measurements, fibronectin and collagen coated beads were deposited on cover slips silanized with 1,1,1,3,3,3,-hexamethyldisilazane (Aldrich) and coated with 10 μg/mL collagen (Roche) for 2 h at 37° C. Cells were then trypsinized, resuspended in DMEM high glucose (Gibco-Invitrogen) supplemented with 2 μM of L-Glutamine, and 2 μM of HEPES (Gibco-Invitrogen) for 30 min at 37° C. for recovery, and plated on the coverslips. The system was then mounted on a motorized 37° C. stage on an Olympus IX81 fluorescence microscope. DIC images and videos were taken with a 60× objective and a Cascade II CCD camera (Photometrics) at a frequency of 12.8 Hz.

TIRF and retrograde velocity measurements: To follow the dynamics of paxillin-GFP, p130CasGFP, actin-GFP, MLC-GFP, and talin-GFP in cells, time-lapse images were captured with a cooled CCD camera (Roper Scientific) attached to an Olympus IX81 inverted microscope (objective, Olympus TIRF PlanApo 60×/1.45 oil; imaging software, SimplePCI) coupled to the 488-nm excitation light from an Inova argon-ion laser. Five second time-lapsed images were taken. For retrograde bead measurements, cells were plated onto collagen (10 μg/ml)-coated coverslips preloaded with laminin or collagen-coated 2.7-μm silica beads and spread at 37° C. Two second time-lapse images of beads transported centripetally on the surface of spreading cells were captured on an IX81 Olympus inverted microscope (objective, Olympus PlanApo 60×/1.45 oil; cooled CCD camera, Roper Scientific; imaging software, SimplePCI).

Chemicals, and antibodies: The following antibodies were used: a mouse monoclonal antibody (mAb) against paxillin (BD Transduction Laboratories), a mouse mAb against p130Cas (BD Transduction Laboratories), a mouse mAb against Src (Upstate Biotechnology), a mouse mAb against FAK (Chemicon), a rabbit polyclonal antibody against vinculin (Abcam), an affinity purified polyclonal rabbit phospho-paxillin (Y118), an affinity purified polyclonal rabbit anti-phoshoY165Cas antibody (Cell Signaling Technology, Beverly, Mass.), an affinity-purified rabbit polyclonal phosphoY416-Src kinase family antibody (Cell Signaling Technology), an affinity purified rabbit polyclonal phospho Y397-Focal Adhesion Kinase (pFAK) (Biosource), an affinity purified mouse polyclonal anti-phospho p44/p42 (T202/Y204), an affinity purified mouse polyclonal anti-phospho pJNK (T183/Y185), an affinity purified mouse polyclonal anti-MLC (Cell Signaling Technology), and affinity purified mouse polyclonal anti-phosphoMLC (Ser18,19), a goat anti-rabbit immunoglobulin (Ig) conjugated with Alexa 647 (Molecular Probes, a goat anti-rabbit Ig conjugated with Alexa 488 (Molecular Probes), and goat anti-mouse Ig conjugated with Alexa 568 (Molecular Probes), horseradish peroxidase-conjugated anti-mouse and anti-rabbit antibodies (Amersham). For antibody inhibition experiments, a cyclic-peptide specific for $\alpha V\beta 3$ (Bachem) at 7.5 ug/ml, an inhibitory $\beta 1$ antibody, clone 6S6, (Millipore) at 5 ug/ml, an inhibitory $\alpha 2\beta 1$ antibody clone Hal/29 (BD Biosciences) at 5 ug/ml, and an inhibitory $\alpha 5\beta 1$ antibody, clone BMC5 (Millipore) at 5 ug/ml were used. Cells were trypsinized, counted, and incubated with inhibitory antibody in suspension for 15 minutes and allowed to spread on either 10 ug/ml collagen or 10 ug/ml fibronectin coated glass. Cells were fixed at 30 minutes after plating, washed with PBS and spread cells were counted.

Western blot quantification: Cells in culture were rinsed once with PBS and lysed directly in RIPA buffer. For time-lapse western blotting, transfected cells were trypsinized and incubated in suspension for 20 min before being plated on collagen-coated culture dishes. At the indicated times, cells were washed once with PBS and lysed in RIPA. All cell lysates were combined with 4× loading buffer and boiled before loading onto 4-20% gradient bis acrylamide gels (Lonza). Protein was then transferred to Optitran reinforced nitrocellulose membrane (Whatman). The membrane was blocked with 5% dry milk-PBST, and incubated with primary antibody overnight at 4° C. The membrane was then incubated for 1 hour at room temperature with anti-mouse or anti-rabbit-HRP (Jackson Laboratories). The signal was detected with ECL western blotting detecting reagents (Amersham Biosciences) on Kodak BioMax XAR film. Signal quantification was performed with NIH ImageJ.

Immunohistochemistry: Fibroblast cells were plated onto collagen coated coverglasses (10 µg/ml). After incubation for the described time, cells were fixed in 3.7% formaldehyde and permeabilized with 0.1% Triton. Cells were then incubated in PBS-1% BSA to block non-specific antibody-antigen interaction. Cells were then incubated with primary antibodies for 1 h followed by washing with PBS-1% BSA and incubated with appropriate fluorescent secondary antibodies. Fluorescent signals from all samples were visualized by confocal microscopy, acquired using a Fluoview confocal microscope (Olympus, Melville, N.Y.). DIC images of the cells plated on polyacrylamide substrates were recorded with a cooled CCD camera attached to an Olympus IX81 equipped with a 60× objective. Analysis of acquired images was performed with the image analysis program, ImageJ (by W. Rasband, NIH, Bethesda, Md.; http://rsb.info.nih.gov/ImageJ).

Force generation measurements, collagen contraction: The polydimethylsiloxane (PDMS) micro-posts were prepared and characterized as described previously (Cai, et al., 2006). The dimension of the PDMS micro-posts was 2 µm in diameter, 3 µm center-to-center, and 7 µm in height. To coat posts with collagen, arrays of posts were immersed in 10 µg/ml of collagen or fibronectin solution for 1 hr at 37° C. and then washed with DPBS. Then, cells were plated on the posts in a 37° C. incubator for 5-30 min. The tips of the posts were visualized with a LUCPIanFI 40×/0.60 air objective in bright-field mode on an IX71 Olympus inverted microscope (cooled CCD camera, Roper Scientific; imaging software, SimplePCI). A multiple-particle tracking program was used to analyze the displacement of the posts. Briefly, this multiple particle-tracking program calculated the position of each post for an acquired image. This routine was based on the fact that, in bright-field microscopy, micro-posts acted as wave-guides and appeared bright, whereas the background appeared dark. To identify positions of micro-posts with good accuracy the center of mass of the corresponding bright pixels was determined (Cai, Y., et al., 2006). Collagen gels of specified densities were prepared as to the manufacturers specifications (BD Biosciences). An equal number of cells were seeded and the gel was immersed in culture media for indicated times. Rigidity response assay: The collagen and full-length FN-coated polyacrylamide substrates were prepared as described previously (Pelham and Wang, 1997). The flexibility of the substrate was manipulated by maintaining the total acrylamide concentration at 10% while varying the bis-acrylamide component between 0.4% (rigid) and 0.03% (soft; E=0.2 N/m2×10^4, and E=1.8 N/m2×10^4, respectively; Engler et al., 2004). The uniformity of FN and collagen coating on the substrate surface was examined using scanning electron microscopy. Statistical Analysis:

Data sets exhibiting a normal distribution were subjected to an unpaired. Student T-test. Data sets displaying non-Gaussian distributions were subjected to a Mann-Whitney test. A value of P<0.05 was considered statistically significant. All errors are given as 1 standard deviation (SD).

Example 3

$\beta 1$ and $\beta 3$ Integrin Engagement Rescues Spreading, Growth & Proliferation on Soft Surfaces.

Abstract

Cell function is regulated in large part by extracellular stimuli, including soluble and adhesive factors that bind to cell-surface receptors. Recent evidence suggests that mechanical properties of the extracellular matrix, particularly rigidity, can also mediate cell signaling, proliferation, differentiation and migration. Often pathological states, such as oncogenesis, allow cells to circumvent mechanical cues otherwise necessary for the regulation of motility, growth and proliferation. Termed rigidity sensing, or the matrix rigidity response, wild-type fibroblasts require a substrate rigidity of ~3 kPa or higher to spread and proliferate. Here it is presented that engagement of both collagen and fibronectin receptors are necessary for focal adhesion formation and cell spreading on typically unpermissive soft (~0.5 kPa) surfaces. Furthermore, $\beta 1$ and $\beta 3$ integrins, and ILK are necessary for focal adhesion formation on soft surfaces. The recruitment of paxillin and FAK allows for enhanced focal adhesion clustering and increased FA-actin coupling leading to sufficient traction forces at the leading edge on soft surfaces to sustain spreading. It is proposed that the engagement of $\beta 1$ and $\beta 3$ leads to an increase in focal adhesion coupling to the cytoskeleton, or intracellular traction force. Activation of both integrins enable cells to reinforce and stabilize focal adhesions, activate ERK, the PI3K-Akt pathway and translation on an, otherwise unpermissive soft substrate.

Collagen and Fibronectin Rescues Cell Spreading on Soft Surfaces Allowing for Growth and Proliferation.

Figure 14A:
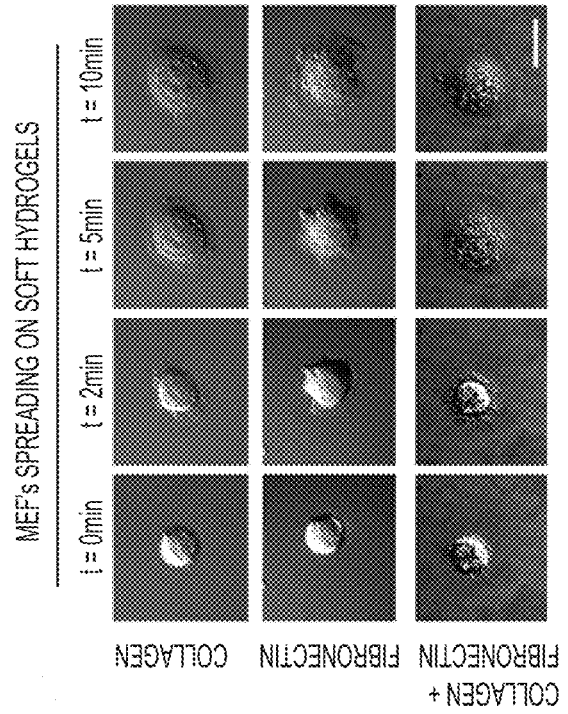
FIG. 14. Coating soft hydrogels with 10 ug/ml collagen and 10 ug/ml fibronectin rescues spreading and proliferation. Wild type Mouse Embryonic Fibroblasts (MEF's) were trypsinized, incubated at 37° C. in suspension for 20 minutes and allowed to spread on soft (0.05 kPa) or rigid (1.8 kPa) bis-acrylamide hydrogels coated with either collagen, fibronectin, or collagen+fibronectin in serum free media. (A) Time-lapse DIC images show wild type MEF's do not spread on soft surfaces coated with 10 ug/ml collagen or 10 ug/ml fibronectin, while MEF's spread within 10 minutes on soft hydrogels coated with 10 ug/ml collagen plus 10 ug/ml fibronectin. (B) Time-lapse DIC images show wild type MEF's spread within 10 minutes on rigid gels coated with 10 ug/ml collagen, 10 ug/ml fibronectin, 10 ug/ml collagen plus 10 ug/ml fibronectin. (C) MEF's were spread on indicated substrates for 30 minutes, fixed and imaged via DIC. Summary quantification of spread cell areas show cells spread to wildtype areas on soft gels coated with collagen and fibronectin. (D) ~$10^5$ cells were plated on indicated substrates, trypsinized and counted at indicated time points. Cells plated on soft collagen and fibronectin did not proliferate, while cells plated on soft collagen plus fibronectin were able to proliferate as cells plated on rigid substrates. Data represent mean±SEM from a minimum of three individual experiments. A Student's t-test was used for statistical analyses, *=P<0.05. Normal, wild type cells exhibit what is termed the rigidity response. That is to say, wild type cells do not spread, grow, or proliferate on soft substrates. Cancer cells have been shown to circumvent this regulatory process, in that oncogenic cells are able to spread, grow and proliferate on soft (~0.05 kPa) substrates. In order to culture a wide range of cancer cells derived from biopsies or explants in vitro one needs to determine the ideal substrate to culture the cells on. Coating soft substrates with collagen and fibronectin rescues the rigidity response with normal wild type cells. That is to say, wild type cells are able to spread on soft surfaces coated with collagen and fibronectin. This serves as a model system to ensure and give the best chance for in vitro culturing of cancer cells. ILK+/+ cells were plated on soft and rigid substrates coated with collagen and fibronectin, stained for paxillin as a focal adhesion marker. Cells are able to spread on soft substrates coated with collagen and fibronectin but unable to spread soft substrate coated with collagen and soft substrates coated with fibronectin. Cells plated on rigid collagen and fibronectin, soft collagen and fibronectin, rigid fibronectin, rigid collagen, grow and proliferate faster, respectively.
Figure 14B:
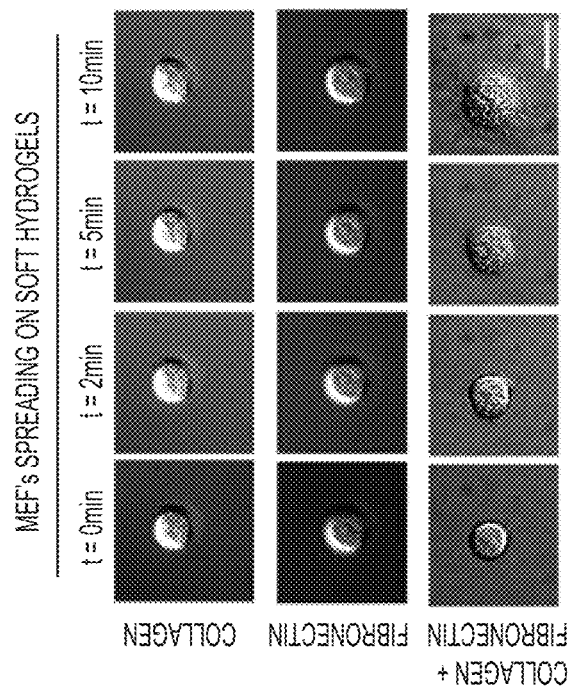
Figure 14C:
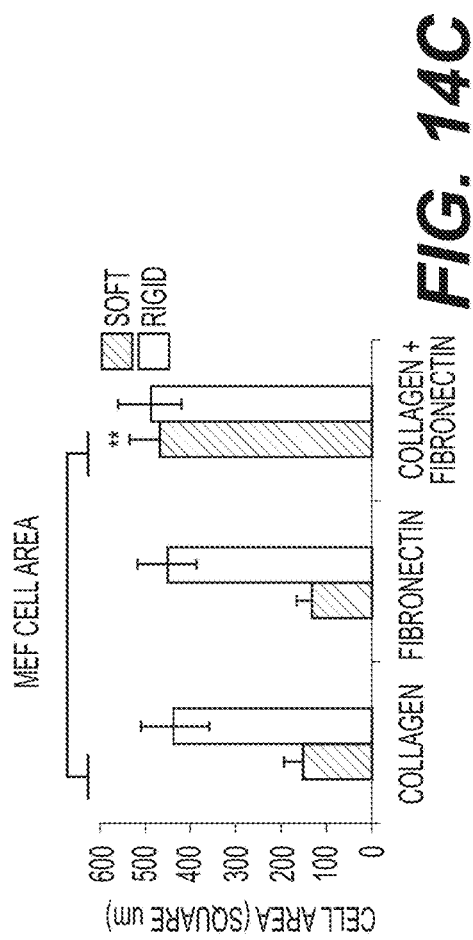
Figure 14D:
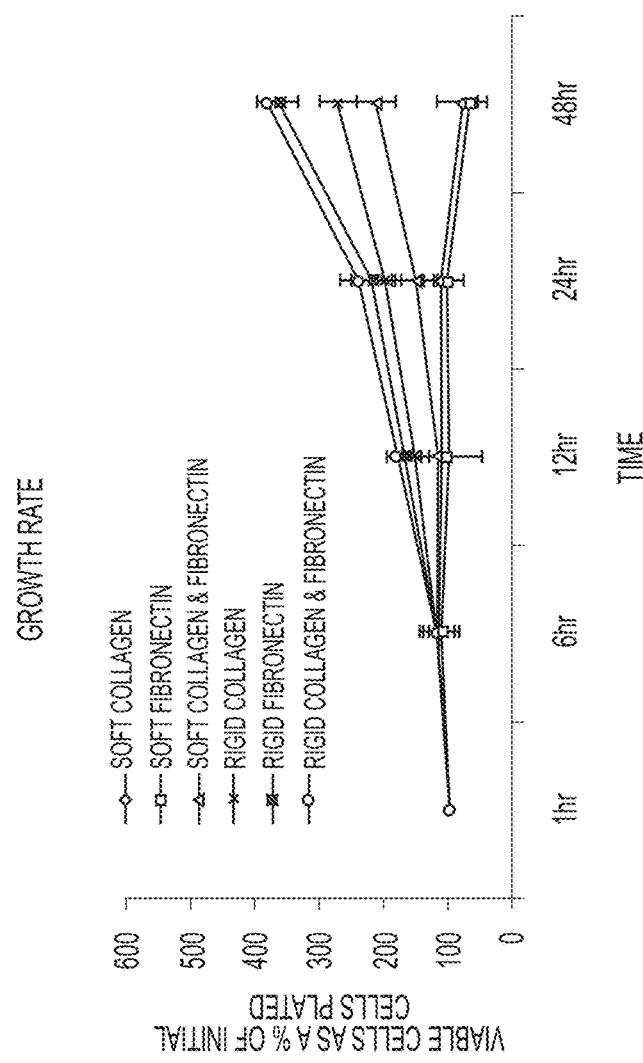
Figure 15A:
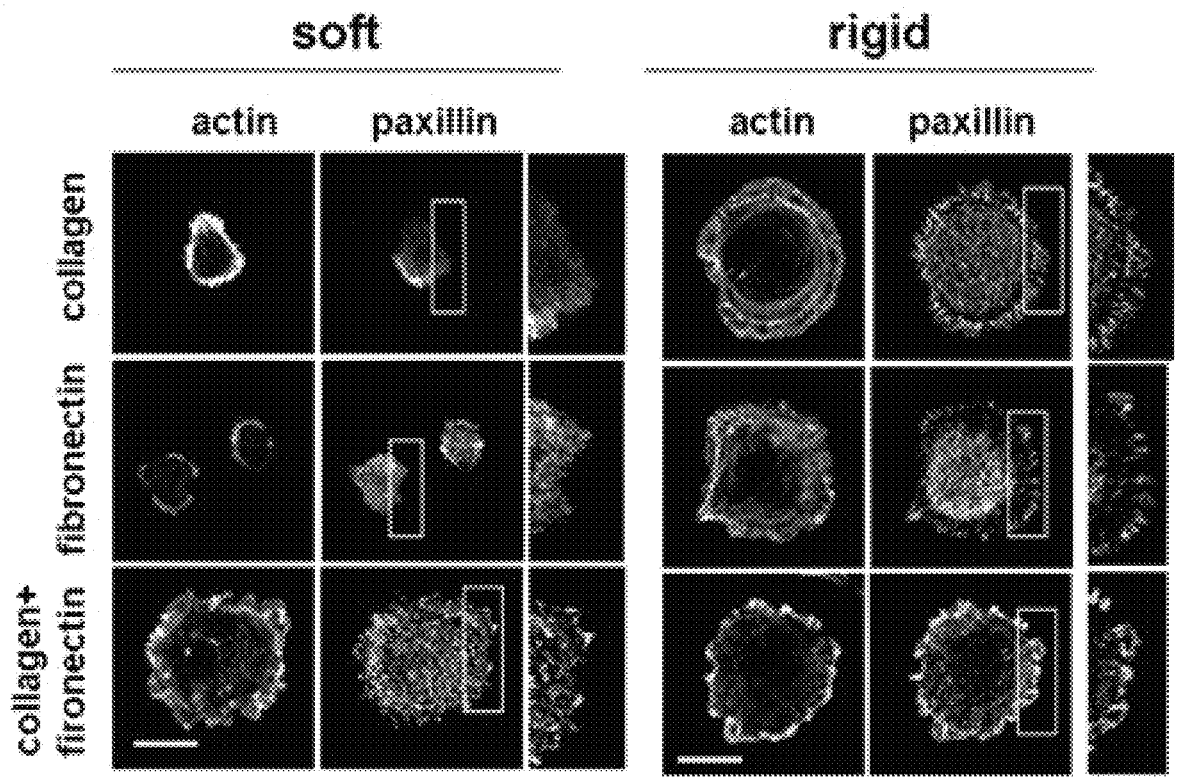
FIG. 15. Cells spread on soft collagen+fibronectin coated substrates, exhibit similar focal adhesion size and actin retrograde flow velocity as cells spread on rigid substrates coated with collagen or fibronectin. (A) Cells were plated for 60 minutes on indicated ECM conditions, fixed, stained for actin and paxillin and imaged via confocal microscopy. (B) Summary quantification of focal adhesion size and determined by paxillin staining. A Student's t-test was used for statistical analyses, *=P<0.05. Cells plated on rigid collagen and fibronectin, soft collagen and fibronectin, rigid fibronectin, rigid collagen, exhibit larger focal adhesions respectively. Interestingly, this observation taken with the observation that cells plated on rigid collagen and fibronectin, soft collagen and fibronectin, rigid fibronectin, rigid collagen, grow and proliferate faster, respectively, supports the assertion that cells with larger focal adhesions grow faster. (C) Phase contrast images of cells (inset) plated on pillars coated with indicated proteins. Hexagonal outline allow individual pillar displacement to be visualized. (D) Summary quantification of pillar displacement on pillars coated with indicated ECM protein.
Figure 15B:
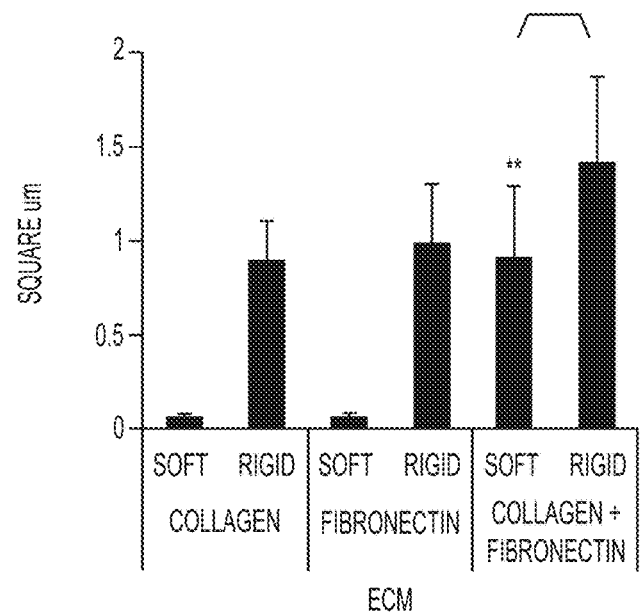
Figure 15C:
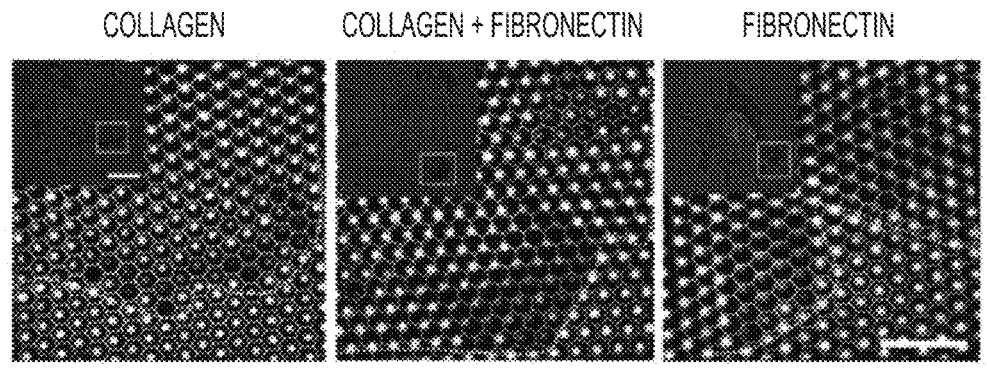
Figure 15D:
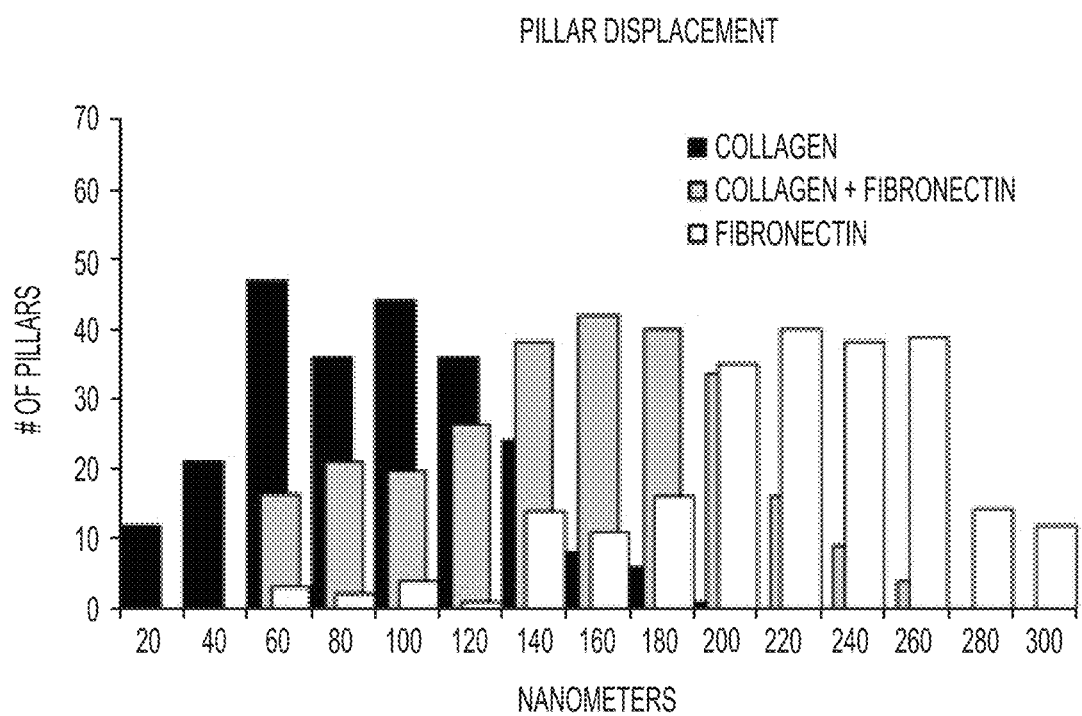

Extracellular matrix (ECM) proteins bind to specific integrin receptors on the cell surface (Gianotti and Ruoslahti, 1999), causing formation of integrin-cytoskeleton bonds that are reinforced by force-dependent recruitment of focal-contact proteins. Reinforcement of the integrin-cytoskeleton bonds is crucial for the response to the matrix rigidity (Choquet et al., 1997; Giannone et al., 2004; Kostic and Sheetz, 2006). To test the hypothesis that increased integrin engagement would rescue spreading of wild-type mouse embryonic fibroblasts (MEF's) on soft surfaces, soft bis-acrylamide hydrogels (~0.05 kPa) were coated with 10 ug/ml collagen type I and 10 ug/ml fibronectin (Col type I+FN). In contrast to wildtype MEF's plated on soft hydrogels coated with 10 ug/ml collagen type I (Col type I) and soft hydrogels coated with 10 ug/ml fibronectin (FN), MEF's plated on Col type I+FN spread to 433 um$^2$ (±76 um). When MEF's were plated on soft Col type I and soft FN, they spread to a reduced area of 153 um$^2$ (±41 um), and 132 um$^2$ (±34 um), respectively (FIG. 14, A and C). Further it was investigated if Col type I+FN rescued and sustained growth on soft substrates. Cells plated on soft Col type I+FN exhibited a doubling time of 43 hours. Cells coated on soft Col type I or soft FN were unable to grow or proliferate (FIG. 14D).

β1 and β3 Integrins are Necessary to Rescue Spreading on Soft Substrates

Figure 17A:
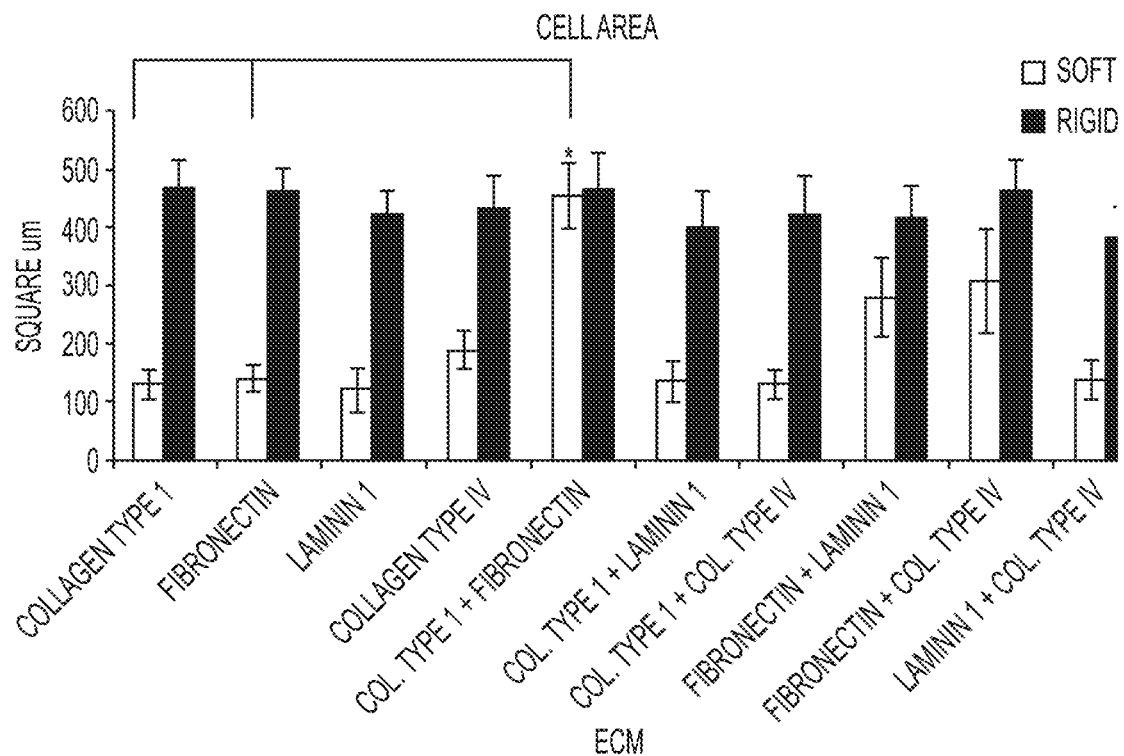
FIG. 17. ECM screen and inhibitory antibody treatment show $\beta 1$ and $\beta 3$ integrins are necessary for spreading on soft and rigid substrates coated with 10 ug/ml collagen, 10 ug/ml fibronectin, and 10 ug/ml collagen+fibronectin. Cells were incubated in suspension with indicated antibodies for 15 minutes prior to plating on indicated ECM condition. (A) Cells were plated on soft and rigid hydrogels coated with indicated ECM pair combinations. Collagen type I+FN was the only ECM pair that rescued spreading on soft surfaces. (B) Blocking $\alpha 2$ integrins rescues spreading on collagen coated soft surfaces, while blocking $\beta 1$ and $\alpha 2$ $\beta 1$ inhibits spreading on collagen coated rigid surfaces. (C) Blocking $\alpha V$ integrins rescues spreading on fibronectin coated soft surfaces, while blocking $\beta 3$ integrins with a $\beta 3$ antibody and cyclic-RGD peptide inhibits spreading on fibronectin coated rigid substrates. (D) Blocking $\beta 1$, and $\alpha 2$ $\beta 1$ integrins inhibited spreading on collagen+fibronectin coated soft and rigid surfaces and blocking $\beta 3$ integrins inhibited spreading on soft collagen+fibronectin. Data represent mean±SEM from a minimum of three individual experiments. A Student's t-test was used for statistical analyses, *=P<0.05. $\beta 1$ integrins are necessary for the rescue of spreading on soft surfaces coated with 10 ug/ml collagen and 10 ug/ml fibronectin suggesting that $\beta 1$ is sufficient for activation of actin polymerization, and adhesion formation Perhaps $\beta 3$ integrins are necessary for the rigidity response And that is why blocking $\beta 3$ is still permissive for spreading on Soft surfaces.
Figure 17B:
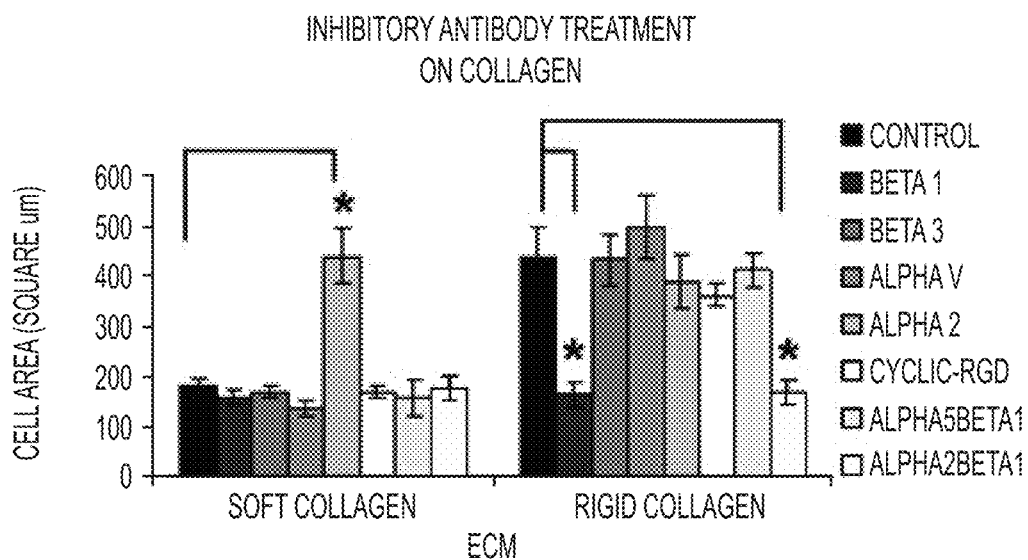
Figure 17C:
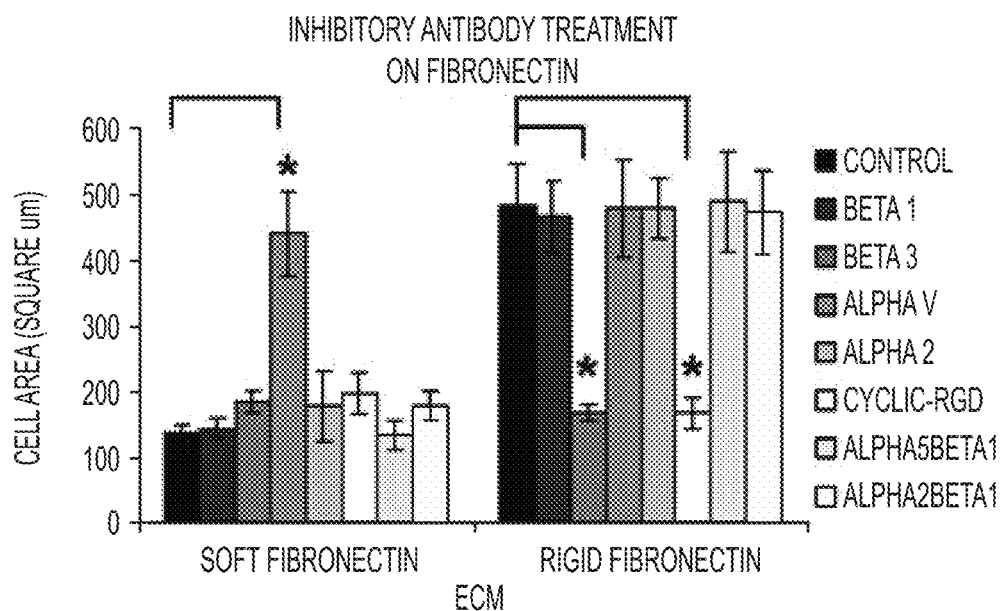
Figure 17D:
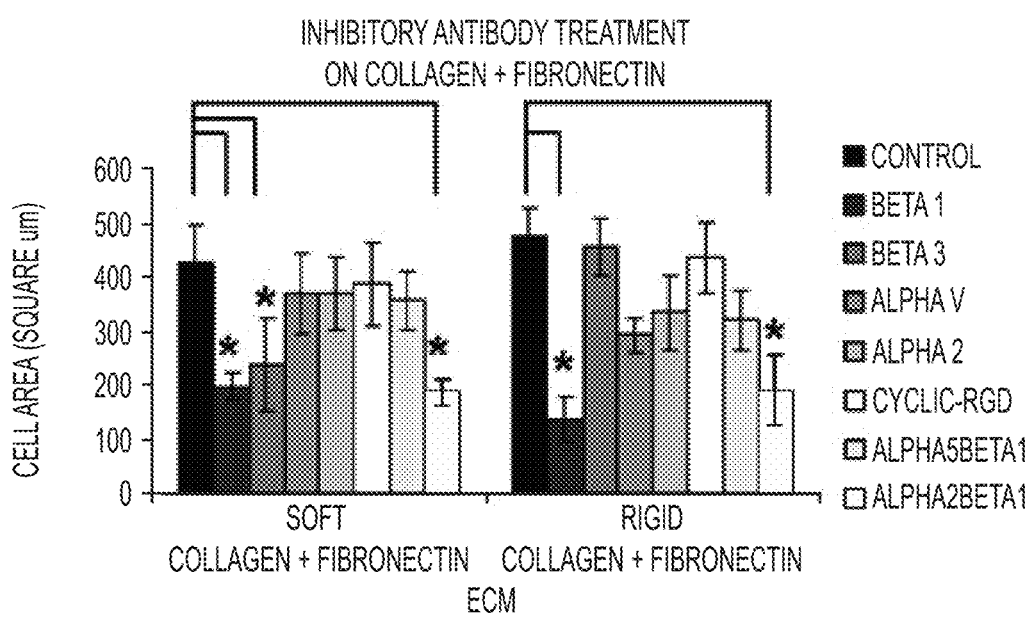
Figure 18A:
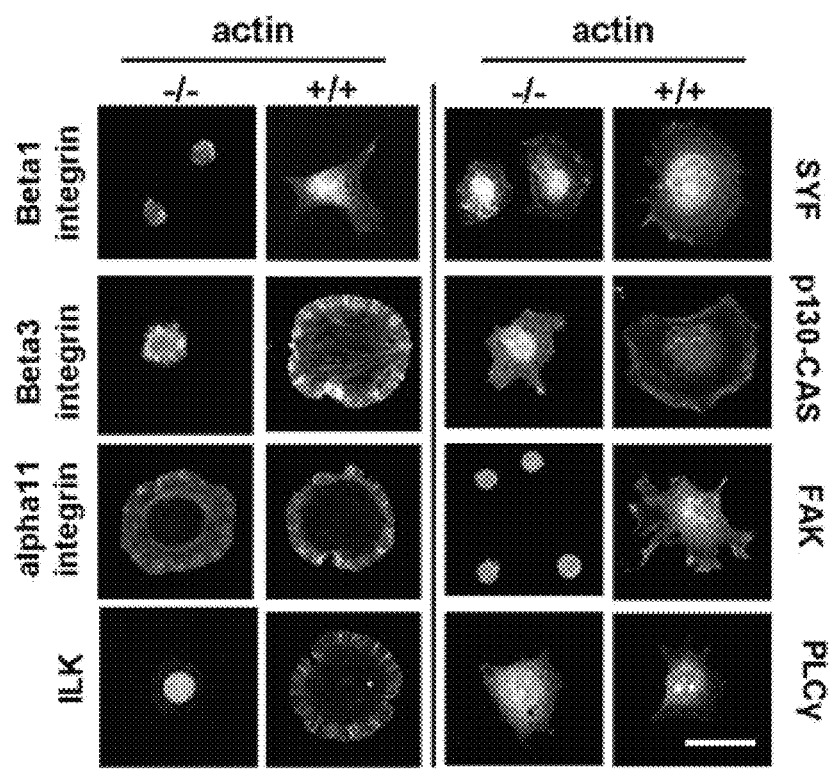
FIG. 18. Knockout and inhibitor screen identify molecules involved in the signaling pathway necessary for spreading and growth on collagen and fibronectin. (A) Knockout cell lines were plated on indicated substrates for 60 minutes, fixed, stained for actin, and imaged via confocal microscopy. (B) Summary quantification of cell areas show that $\beta 1$ integrin, $\beta 3$ integrin, Integrin Linked Kinase (ILK), Src family kinases, RPTP$\alpha$, and Focal Adhesion Kinase are necessary for spreading on soft substrates coated with 10 ug/ml collagen+fibronectin. Data represent mean±SEM from a minimum of three individual experiments. A Student's t-test was used for statistical analyses, *P<0.05. Knock Out cell screen implicates proteins implicated in cancer progression—$\beta 1$ integrin, ILK, FAK, Src, Yes or Fyn, and Cas—are also needed for the collagen and fibronectin rigidity response.
Figure 18B:
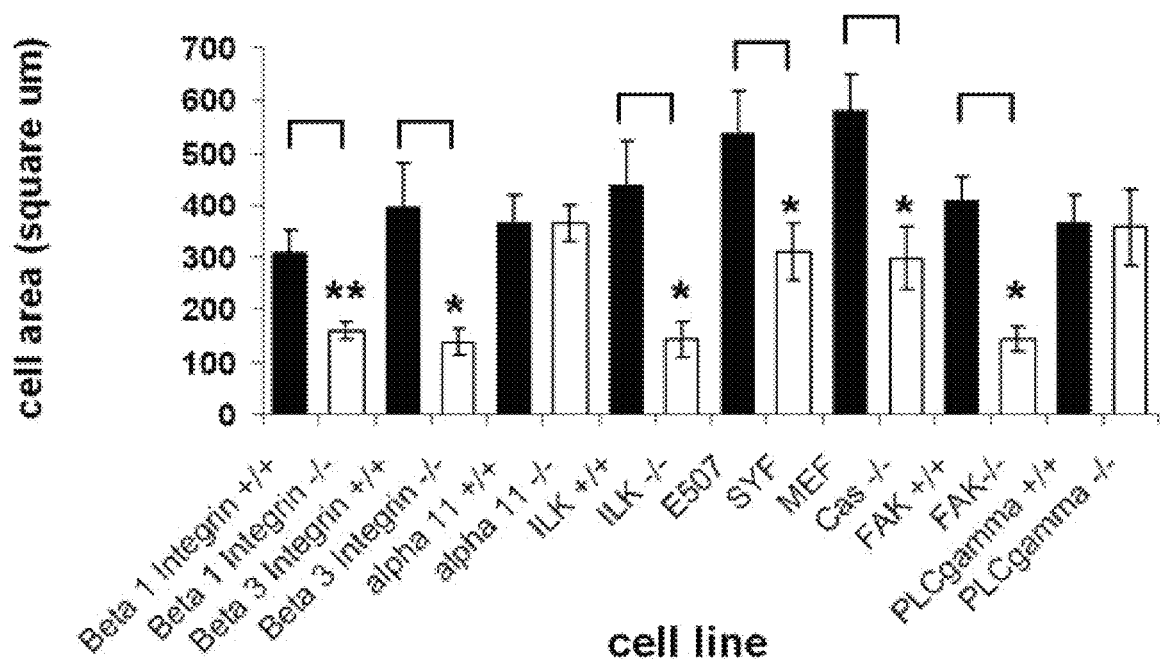

To determine if other ECM combinations could rescue spreading on soft surfaces, ECM coated soft and rigid control surfaces with paired combinations of collagen type I (Col type I), collagen type IV (Col type IV), fibronectin (FN), laminin (LN) (FIG. 17A). Interestingly, Col type I+FN was the only ECM combination that rescued spreading on soft surfaces. As the other ECM engagements involved only β1 engagements, and Col type I and FN involved engagement of β1 and β3 integrins, it was hypothesized that it was the engagement of β1 and β3 that enabled spreading on soft surfaces. To further confirm that it was the engagement of both β1 and β3 integrins that rescued spreading on soft surfaces, soft surfaces were coated with Col type I+RGD peptide, and Col type I+FNIII (FIG. 22), and found that cells were still able to spread on soft surfaces (FIG. 22). After treating cells with inhibitory antibodies, it was confirmed that both β1 and β3 were needed to spread on soft surfaces. Interestingly, blocking α2 and αV integrins on collagen and fibronectin, respectively, rescued spreading on soft surfaces, while blocking β1 and β3 integrins inhibited spreading on rigid collagen and fibronectin surfaces respectively (FIG. 17). Blocking β1 or (β3 integrins inhibited spreading on soft surfaces coated with Col type I+FN as did blocking α2β1 but not α5β1. Moreover, β1 integrin is necessary for spreading on rigid surfaces coated with Col type I and FN, while β3 integrin is not.

Cells Interacting with Collagen+Fibronectin Exhibit Enhanced FA-Actin Coupling.

To confirm that engagement of β1 and β3 integrins were involved in focal adhesion formation and development, cells were stained for paxillin to measured focal adhesion size on soft and rigid surfaces coated with Col type I, FN, and Col type I+FN. Cells plated on soft surfaces coated with Col type I and FN, exhibited average focal adhesion sizes of 0.09 um$^2$ (±0.02) and 0.1 um$^2$ (±0.02) respectively, while cells spread on soft surfaces coated with Col type I+FN, exhibited average focal adhesion sizes of 0.9 um$^2$ (±0.18), similar to rigid surfaces coated with Col type I or FN alone (FIG. 15). Due to the observed large focal adhesion size on Col type I+FN coated substrates it was hypothesized that engagement of β1 and β3 integrins resulted in greater FA-actin coupling, and measured actin retrograde flow velocity. Consistent with these observations that focal adhesion size was increased, actin retrograde flow velocity was decreased in cells spread on surfaces coated with Col type I+FN. Cells plated on soft surfaces coated with Col type I, or FN exhibited actin retrograde flow velocities of 189 nm/sec (±46 nm/sec) and 121 nm/sec (±45 nm/sec) respectively (FIG. 16). When cells were plated on Col type I+FN coated soft surfaces cells exhibited similar actin retrograde flow velocities as if they were plated on rigid surfaces. Cells plated on soft Col type I+FN exhibited an average actin retrograde flow velocity of 42 nm/sec±15 nm/sec.

Traction Force Index Correlates with Spreading and Proliferation

As it was observed that the engagement of β1 and β3 integrins resulted in larger focal adhesions and slower actin retrograde flow on soft surfaces, it was postulated that the increase in FA-actin coupling was responsible for the observed ability to spread and proliferate independent of rigidity. To better understand and quantify FA-actin coupling an index termed the Traction Force Index (TFI) was introduced. The TFI is defined as the average focal adhesion size divided by the average actin retrograde flow velocity. By taking DIC and TIRF time-lapse images of MEF's transfected with paxillin-GFP, actin retrograde flow velocity and focal adhesion size of individual cells was able to be measured. Consistent with these previous observations, cells that were able to spread and proliferate exhibited larger focal adhesions and slower actin retrograde flow velocities—the resulting TFI, focal adhesion size (um2)/actin retrograde flow velocity (um/sec), for cells that spread and proliferate was greater than 10 um×sec (FIG. 7). Cells with TFIs<10 um×sec are unable to spread, presumably due to the fact they are not able to generate the sufficient external and internal traction forces necessary to develop and sustain focal adhesion formation (FIG. 7).

Early Traction Forces are Greater on Fibronectin, Collagen and Fibronectin and Collagen Respectively To better understand the β1 and β3 mediate interaction, traction forces generated on soft substrates coated with Col type I, FN, and Col type I+FN was measured. To do this, a pillar assay using PDMS 0.5 um diameter, 1.8 um height pillars, was employed. Cells were plated after being in suspension for 20 minutes in serum-free media and images were taken at 1 Hz. Interestingly, at early time points during the time rigidity is sensed by the cell, pillars coated with Col type I were displaced an average of 81 nm (±3), pillars coated with Col type I+FN were displaced on average 153 nm (±41), and pillars coated with FN were displaced an average of 223 nm (±61) (FIG. 15). This result is surprising and suggests that α2B1 integrins transmit less force during early time points of spreading than αVβ3.

P13K-Rock1-Akt Pathway and Ca++ Signaling are Necessary for Spreading and Proliferation on Collagen+Fibronectin Using knock-out mouse embryonic fibroblast (MEF) cell lines, the other molecules that may be involved in β1, and β3 integrin mediated rigidity-independent signaling was probed. Consistent with these previous results, MEFs with β1 or β3 integrins were unable to spread on Col type I+FN, while cells null for α11 integrin were able to spread. The β1 binding protein Integrin-Linked Kinase (ILK) was also necessary for spreading, as were members of the Src-family kinases, p130Cas, and Focal Adhesion Kinase (FAK). PLCγ was not necessary for spreading or proliferation on soft surfaces coated with Col type I+FN (FIG. 19). In addition to the knockout cell line screen they sensitivity of spreading and proliferation on soft surfaces coated with Col type I+FN to small molecule inhibitors of the PI3K-Akt pathway was looked at (FIG. 19). Inhibitors of L&T-type Ca++ channel, PI3K, Rock1, and Akt all blocked spreading and proliferation. Surprisingly, an inhibitor of translation also blocked spreading and proliferation.

Phosphorylation of FAK and Paxillin is Enhanced in Cells Spread on Collagen+Fibronectin Compared to Cells Spread on Collagen or Fibronectin As observed, increased focal adhesion formation on soft substrates coated with Col type I+FN, the aim was to confirm that focal adhesion markers known to be associated with focal adhesion formation and stabilization were activated. To look at relative levels of phospho-(Y397)-FAK and phospho-(Y118)-paxillin on soft substrates coated with Col type I, FN, and Col type I+FN By western blot analysis was employed. Consistent with these previous observations of focal adhesion size, and the knockout cell line screen, it was observed elevated levels of phospho-(Y397)-FAK and phospho-(Y118)-paxillin at 60 minute and 120 minute time points on soft Col type I+FN, but not on soft Col type I or soft FN coated substrates (FIG. 20).

Engagement of Collagen and Fibronectin Activates PI3K-Akt Pathway and Translation As it was observed that spreading and proliferation was sensitive to the PI3K-Akt pathway and the translation inhibitor cyclohexamide, activated phospho-species of Akt, p70S6 kinase and the translational activator p90RSK1 were probed. Interestingly, β1 and β3 integrin engagement was sufficient to activate Akt, p70S6 kinase and p90RSK1 (FIG. 21). It was observed by western analysis at 12 and 24 hour time points, Phospho-(S473)-Akt, Phospho-(T389)-p70S6K, and Phospho-(T359/S363)-p90RSK1 existed in cells plated on soft substrates coated with Col type I+FN but not in cells plated on soft substrates coated with Col type 1 or FN alone. Finally, the MAP kinase ERK, was also phosphorylated at the 12 hour and 24 hour time points on soft Col type I+FN while it was not on soft Col type 1 or soft FN.

Discussion

Here it is reported that a novel integrin pathway is sufficient to activate actin-mediated cell spreading and sustain growth and proliferation independent of substrate rigidity. The rigidity response is a coordinated molecular process that underlies many cellular functions including cell growth and transformation. Soft matrices inhibit normal cell growth, while oncogenic transformation enables cells to grow on soft hydrogels. Previous studies have reported on integrin signaling on substrates with far greater rigidities up to 45 GPa (glass). As rigidities relevant to physiological conditions range from 0.05 kPa (brain), 0.5-5 kPa (inside cell layers) 3-7 kPa (connective tissue), ~55 kPa (bone), this study highlights cytoskeletal activation and integrin-mediated signaling under relevant physiological conditions. By various ECM pair combinations, inhibitory antibodies and knock out cell lines it was shown that both β1 and β3 integrins were necessary for cytoskeletal activation, growth, and proliferation on 0.5 kPa surfaces (FIGS. 17 and 18).

Figure 7B:
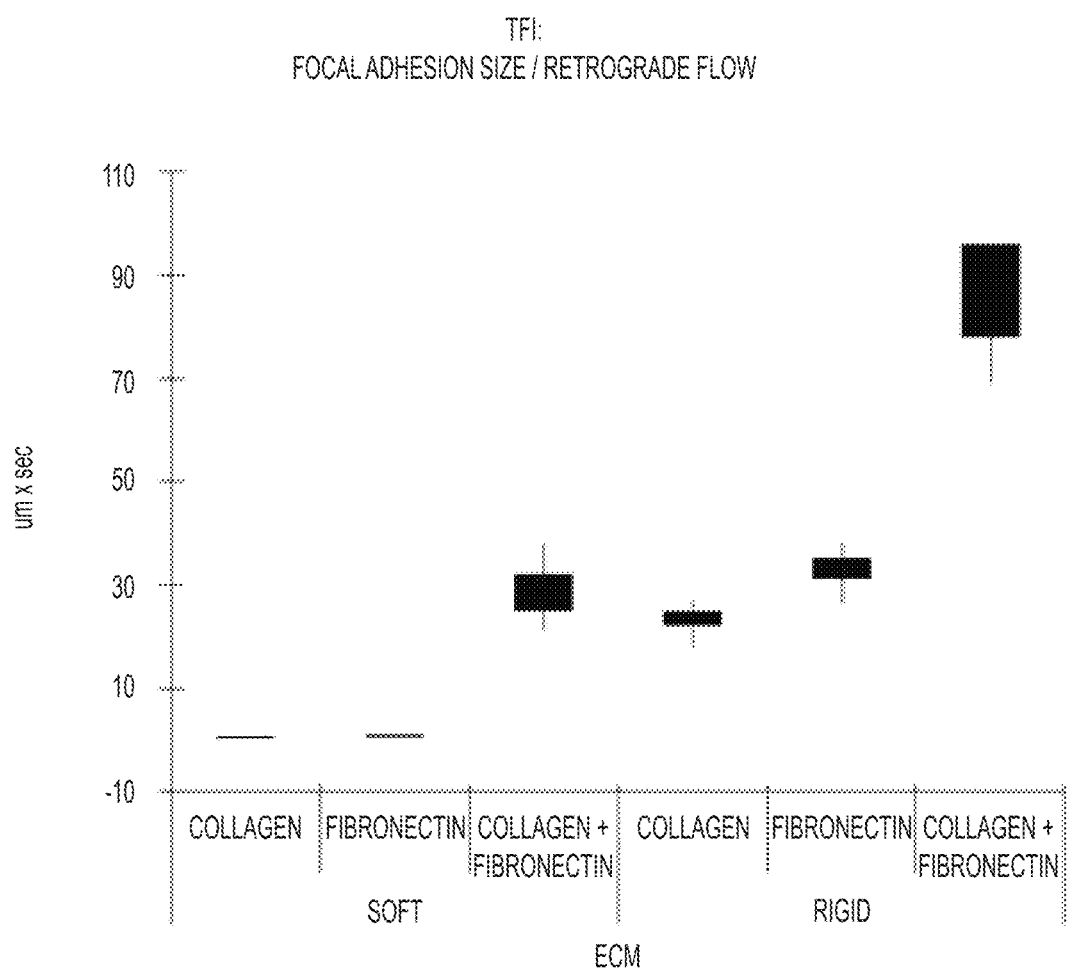
Figure 7C:
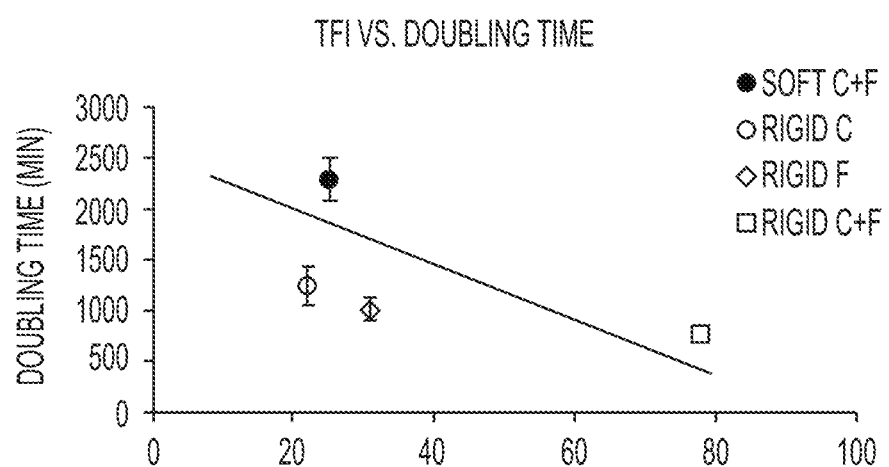

As cell spreading and proliferation on 2D surfaces requires focal adhesion formation, and focal adhesions (FA) require tension to grow and to be maintained, it is postulated that the cells spread on soft substrates coated with Col type I+FN were able to couple FA's with the actin cytoskeleton (FIGS. 7 and 14). Consistent with this hypothesis given the observed larger focal adhesions and slower actin retrograde flow on soft surfaces coated with Col type I+FN than soft surfaces coated with Col type I or FN alone. Moreover, cells plated on soft Col type I+FN exhibited FA sizes and actin retrograde flow speeds similar to cells plated on rigid surfaces coated with Col type I and FN alone (FIGS. 15 and 16). It is concluded that the engagement of both β1 and β3 integrins leads to larger focal adhesions and slower actin retrograde flow than when β1 or β3 are engaged with their component ECM molecule alone. As it was observed that larger focal adhesion size and slower actin retrograde flow velocity are characteristic of increased FA-actin coupling and important for spreading and proliferation on substrates of physiologically relevant moduli, the Traction Force Index (TFI) is introduced as a means to describe the degree of, and quantitatively characterize, FA-actin coupling. It is defined that the TFI as the ratio of average focal adhesion size (um$^2$) of a cell line on a given substrate divided by average actin retrograde flow speed (um/sec) on a given substrate. On soft substrates coated with Col type I, FN, and Col type I+FN it was calculated the respective TFIs to be: 0.27, 0.5, and 25.0 (FIG. 7). As cells were unable to spread and proliferate on soft Col type I and soft FN, it suggests a TFI of less than 10 um×sec is an indicator of low focal adhesion-actin coupling and suggestive of unpermissive intracellular spreading and growth biochemical states. Similarly, on rigid substrates coated with Col type I, FN, and Col type I+FN was calculated the respective TFI's to be: 22.4, 31.5, and 78.3 (FIG. 7B). It is suggested that a greater TFI indicates a greater degree of coupling and correlates with faster growth (FIG. 7C).

Previously the data has shown that a decrease in FA-actin coupling leads to spreading on soft surfaces and mislocalization of ERK and JNK. In ILK depleted cells, coupling was decreased and as a result leads to increased retrograde flow of paxillin, p130Cas, and signaling molecules such as FAK, Src, ERK, and JNK (FIG. 6). The mislocalization of FA proteins also lead to altered modification states of ERK and JNK. It is then postulated that it was the altered FA-actin coupling responsible for slower growth and proliferation of ILK depleted cells. In this report it is shown that there is a correlation with TFI, as a measure of FA-actin coupling, and growth and proliferation. By modulating FA size using substrates coated with different ECM combinations and rigidities, it was possible to modulate the level of FA-actin coupling. As focal adhesions grew in size, actin retrograde flow reduced in speed, and growth and proliferation increased.

Previously, early and late force measurements for fibronectin have been made, while only measurements in late spreading on collagen have been made. In this investigation it is reported that the initial traction force generated on collagen is greatly reduced compared to fibronectin (FN) for cells with nascent ECM-FA contacts interacting with pillars. Cells interacting with collagen coated pillars were able to displace 0.5 um diameter pillars an average of 81 nm (±39) while cells interacting with FN coated pillars displace the pillars an average of 223 nm (±61). This suggests that the initial contacts mediated by α2β1 for collagen are coupled less to the actin cytoskeleton or do not activate the actomyosin networks to the same level as the initial αVβ3 integrins for FN. Interestingly, contrary to this hypothesis, the average pillar displacement for pillars coated with Col type I+FN were no greater than pillars coated with FN alone. Pillars coated with Col type I+FN were displaced an average of 153 nm (±41). This intermediate value could be due to the fact that α2β1 integrins interfere with or cancel out the larger activity of αVβ3 mediated force generation or that pillars were not uniformly coated and the ensemble average is an average of pillars coated with either Col type I or FN. An alternate interpretation of this result takes into account that cells plated on Col type I+FN exhibit slower actin retrograde flow velocities than cells plated on Col type I or FN alone. The observed increase in FA-actin coupling with cells plated on Col type I+FN could suggest that some of the traction force generated by the acto-myosin machinery may be absorbed in the intracellular FA-actin contacts and not transmitted to the external integrin-ECM bond or the acto-myosin network is not activated to the same level as on FN alone. If this is the case, if FA-actin bonds dissipate some of the force generated by the acto-myosin contractile machinery, this could also provide an explanation for the engagement of Col type I+FN to rescue spreading. By generating more force on FAs, or engaging the molecular clutch at the appropriate level, the cell is able to achieve the molecular stretch and displacement needed for activation of protein complexes and spreading. It is the increase in intracellular traction forces that allows for spreading and proliferation as well as the reduced traction force.

To verify that other MEFs were able to spread on soft surfaces coated with Col type I+FN, and to identify molecular components that are involved in the signaling pathway, a knockout cell line screen was employed. Of the eight knock out lines examined, it was found that α11 integrins and PLCγ were not necessary for cell spreading and proliferation, while Integrin-Linked Kinase (ILK), Src-family kinases, p130Cas, and Focal Adhesion Kinase are necessary for spreading on Col type I+FN. Consistent with this previous data, it was also observed that β1 and β3 are both necessary for spreading and proliferation on soft Col type I+FN, supporting their coordinated role in initiating spreading and proliferation.

Previously integrins have been shown to activate numerous pathways. Either acting in concert with growth factor receptors or on substrates with rigidity moduli ~100 fold greater, integrins have been shown to activate MAPK pathways and survival PI3K pathway. In this investigation it is shown that integrins, independent of rigidity, can activate ERK, the PI3K-Akt-p70S6Kinase pathway and the regulator of translation, p90RSK1. This data supports the idea that engagement of β1 and β3 integrins allows for the activation of survival and growth pathways independent of rigidity, and delineates a novel integrin-mediated-biochemical pathway towards actin polymerization, translation, growth and proliferation.

In addition to activating FA proteins such as Phospho-(Y397)-FAK, and Phospho-(118)-paxillin, allowing for focal adhesion turnover and growth, engagement of β1 and β3 integrins allows for activation of phospho-(T202/y204)-ERK, phospho-(S473)-Akt, phospho-(T389)-p70S6Kinase, and the translational activator phospho-(T359/S363) p90RSK1. Consistent with the knock out cell line screen, Integrin-Linked Kinase, a known activator of Akt and substrate for PI3K is necessary for spreading and proliferation on soft Col type I+FN. Furthermore, Akt's downstream activator p70S6Kinase is activated upon engagement of β1 and β3 integrins. Interestingly, the 90 kDa ribosomal S6 kinases (p90S6K) is a member of the family of widely expressed serine/threonine kinases characterized by two unique, functional kinase domains (Smith et al., 1999) and a C-terminal docking site for extracellular signal-regulated kinases (ERKs) (Dalby et al., 1998). Several sites both within and outside of the RSK kinase domain, including Ser380, Thr359, Ser363, and Thr573, are important for kinase activation. RSK1 is activated via coordinated phosphorylation by MAPKs, by autophosphorylation, and by phosphoinositide-3-OH kinase (PI3K) in response to many growth factors, polypeptide hormones, and neurotransmitters (Fisher and Blenis, 1998). Here it is shown that engaged β1 and β3 integrin is sufficient to activate this regulator of translation.

This example demonstrates a novel integrin signaling pathway. Previous studies have reported on integrin signaling on substrates with rigidities >8 kPa. In this study, it has been shown that engagement of α2β1 and αVβ3 integrins is sufficient to activate spreading and proliferation independent of substrate rigidity. As integrins have been shown to be deregulated in pathological states such as cancer, this cell based assay system can be used as a model system to probe and investigate solely integrin mediated signaling. In addition to identifying a model system to explore integrin-based signaling, the results show that 10 ug/ml Col type I+FN is sufficient to induce focal adhesion formation and FA-actin cytoskeleton coupling. In an effort to better characterize the FA-actin coupling necessary for spreading and growth, the Traction Force Index (focal adhesion size/actin retrograde flow velocity) was introduced. The Traction Force Index correlates with spreading and growth proliferation. Finally, engagement of α2β1 and αVβ3 integrins is shown, leading to increased focal adhesion-actin coupling (and a larger TFI) on surfaces, is sufficient to activate the MAPK, ERK, Akt, p90S6K and the translational regulator p70RSK1.

Materials and Methods

Cell Lines, Antibodies and Reagents

Mouse fibroblast cells (B1 Integrin$^{+/+}$, B1 Integrin$^{-/-}$, B3 Integrin$^{+/+}$, B3 Integrin–/–, α11$^{+/+}$, α11$^{-/-}$, ILK$^{+/+}$, ILK$^{-/-}$, E507, SYF, RPTPα$^{+/+}$, p130Cas$^{-/-}$, FAK$^{+/+}$, FAK$^{-/-}$, PLCγ$^{+/+}$, PLCγ$^{-/-}$) were maintained at 37° C. and 5% CO$_2$ in Dulbecco's Modified Eagle's medium (Invitrogen) supplemented with 10% fetal bovine serum (Invitrogen), 2 mM L-glutamine, 50 μg/ml streptomycin, and 50 units/ml penicillin. The following antibodies were used: a mouse monoclonal antibody (mAb) against paxillin (BD Transduction Laboratories), a mouse mAb against FAK (Chemicon), an affinity purified polyclonal rabbit phospho-paxillin (Y118), an affinity purified polyclonal rabbit anti-phoshoY165Cas antibody (Cell Signaling Technology, Beverly, Mass.), an affinity-purified rabbit polyclonal phosphoY416-Src kinase family antibody (Cell Signaling Technology), an affinity purified rabbit polyclonal phospho Y397-Focal Adhesion Kinase (P-FAK) (Biosource), an affinity purified mouse polyclonal anti-phospho p44/p42 (T202/Y204), an affinity purified polyclonal rabbit anti-phospho-(S473)-Akt p70S6Kinase (Cell Signaling Technology), an affinity purified polyclonal rabbit anti-phospho-(T389)-p70S6Kinase (Cell Signaling Technology), an affinity purified polyclonal rabbit anti-phospho-(T359/5363) p90RSK1 p70S6Kinase (Cell Signaling Technology), a goat anti-rabbit immunoglobulin (Ig) conjugated with Alexa 647 (Molecular Probes, a goat anti-rabbit Ig conjugated with Alexa 488 (Molecular Probes), and goat anti-mouse Ig conjugated with Alexa 568 (Molecular Probes), horseradish peroxidase-conjugated anti-mouse and anti-rabbit antibodies (Amersham). For antibody inhibition experiments, a cyclic-peptide specific for αVβ3 (Bachem) at 7.5 ug/ml, an inhibitory β1 antibody, clone 6S6, (Millipore) at 5 ug/ml, an inhibitory α2β1 antibody clone Hal/29 (BD Biosciences) at 5 ug/ml, and an inhibitory α5β1 antibody, clone BMC5 (Millipore) at 5 ug/ml were used. Cells were trypsinized, counted, and incubated with inhibitory antibody in suspension for 15 minutes and allowed to spread on either 10 ug/ml collagen or 10 ug/ml fibronectin coated glass. Cells were fixed at 30 minutes after plating, washed with PBS and spread cells were counted.

Cell Spreading on Polyacrylamide Substrates and Microscopy

The polyacrylamide substrates were prepared as described previously (Discher et al., 2005). The flexibility of the substrate was manipulated by maintaining the total acrylamide concentration at 8% while varying the bis-acrylamide components between 0.4% (rigid surface) and 0.03% (soft surface). The uniformity of FN coating on the substrate surface was examined by coating the gels with Alexa 568 labeled FN and observed by immunofluorescence microscopy. The uniformity of Col type I coating on the surface was examined by SEM. Phase contrast images were recorded with a cooled charge-coupled device camera attached to an Olympus IX81 equipped with a 10× objective. The spread area of individual cells was quantified with Image J software. At least 50 cells were counted for each cell line under each condition.

Immunohistochemistry and Confocal Microscopy

Fibroblast cells were plated onto Col type I, FN, or Col type I+FN-coated polyacrylamide hydrogels (10 μg/ml). After incubation for the described time, cells were fixed in 3.7% formaldehyde and permeabilized with 0.1% Triton. Fixed cells were incubated with primary antibodies (described above) for 1 h followed by washing and incubation with appropriate fluorescent secondary antibodies (also described above). Fluorescent signals from all samples were visualized by confocal microscopy.

Fibroblasts were transfected with β3 Integrin-GFP and plated as described in Spreading assays. Cells were fixed 30 min after plating in 4% PFA for 20 min and permeabilized with 0.2% Triton X-100. Cells were incubated with monoclonal described above for 1 h followed by detection with Alexa-labeled (488, 568, and 647 nm) secondary antibodies. Samples were further analyzed by confocal microscopy (Fluoview 300; Olympus).

DIC and TIRF, and Bright-Field Microscopy of Cell Spreading

Coverslips were prepared as previously described (Cai et al., 2006). Cells were trypsinized, resuspended in serum free culture medium, and then incubated for ~40 minutes at 37° C. with or without inhibitor or antibody treatment. For TIRF microscopy of cell-spreading, cells were transfected with paxillin-GFP. TIRF and DIC time-lapse sequential cell images were captured with an Olympus IX81 inverted microscope (objective, Olympus TIRF PlanApo 60×/1.45 oil; imaging software, SimplePCI) coupled to the 488-nm excitation light from an Inova argon-ion laser. Bright-field images of pillar tips were captured with a LUCPlanFI 40× air objective on an Olympus IX81 inverted microscope. All microscopes were equipped with cooled CCD cameras (Roper Scientific) and temperature control boxes.

Traction Force Measurements

The polydimethylsiloxane (PDMS) micro-posts were prepared and characterized as described previously (Cai et al., 2006). The dimension of the PDMS micro-posts was 0.5 μm in diameter, 1 μm center-to-center, and 1.8 μm in height. To coat posts with fibronectin, arrays of posts were immersed in 10 μg/ml of Col type I, FN, or Col type I+FN solution for 1 hr at 37° C. and then washed with DPBS. Then, cells were plated on the posts in a 37° C. incubator. The tips of the posts were visualized with a LUCPlanFI 40×/0.60 air objective in bright-field mode on an IX71 Olympus inverted microscope (cooled CCD camera, Roper Scientific; imaging software, SimplePCI). A multiple-particle tracking program was used to analyze the displacement of the posts. Briefly, this multiple particle-tracking program calculated the position of each post for an acquired image. This routine was based on the fact that, in bright-field microscopy, micro-posts acted as wave-guides and appeared bright whereas the background appeared dark. Positions of micro-posts were identified with good accuracy by determining the center of mass of the corresponding bright pixels. Although each micro-post in a square array would be the intersection of a row and a column of the matrix, each micro-post belonged to three rows with angles of 60° and 120° between them in a hexagonal lattice. To determine the rest position of a given covered micro-post, the computer program located the positions of the uncovered posts belonging to the same row and fitted them linearly. The unbent position of the pillar was estimated as the intersection of two lines, given by the rows to which it belongs.

Western Blot Analysis

Cells in culture were rinsed once with PBS and lysed directly in RIPA buffer. For time-lapse western blotting, transfected cells were trypsinized and incubated in suspension for 20 min before being plated on collagen-coated culture dishes. At the indicated times, cells were washed once with PBS and lysed in RIPA. All cell lysates were combined with 4× loading buffer and boiled before loading onto 4-20% gradient bis-acrylamide gels (Lonza). Protein was then transferred to Optitran reinforced nitrocellulose membrane (Whatman). The membrane was blocked with 5% dry milk-PBST, and incubated with primary antibody overnight at 4° C. The membrane was then incubated for 1 hour at room temperature with anti-mouse or anti-rabbit-HRP (Jackson Laboratories). The signal was detected with ECL western blotting detecting reagents (Amersham Biosciences) on Kodak BioMax XAR film. Signal quantification was performed with NIH ImageJ.

Image and Statistical Analysis

Cell area measurement was performed using the particle analysis function in ImageJ. Force measurement was performed as described previously (Cai et al., 2006). Force mapping was done using a custom function in Igor. All statistical analyses were performed using a Student's t-test tool.

Example 4

Summary of Molecular Dynamics Governing Growth & Migration

Cell spreading and motility involve physical linkages between the extracellular matrix (ECM), integrins and the cytoskeleton. Numerous proteins compose the subcellular structures termed focal adhesions involved in ECM-cell linkages. Paramount to focal adhesion (FA) formation is integrin activation. This process involves intra-molecular dynamics and inter-molecular interactions resulting in protein oligomerization and focal adhesion formation. Focal adhesions form proximal to the leading edge on similar temporal and spatial scales as the actin cytoskeletal dynamics that regulate protrusive and retraction forces involved in motility events. Before this investigation and the data presented herein, it was unclear how FAs and actin interact and what mechanistic function FA-actin interactions may have on motility events. In examples 2 and 3 data is presented that demonstrates the effects of altered FA-actin dynamics on ECM sensing, rigidity sensing, force generation, and signal generation. The data presented advances the current understanding of these cellular processes by supporting a more dynamic model where catch-slip focal adhesion-actin flow interactions regulate FA protein localization, the physical linkages between the ECM and cell, as well as survival and growth signaling at the leading edge.

Integrin adaptor or binding proteins are important players in physical and biochemical emergent properties resulting from ECM-cell interactions. ECM-cell interactions are thought to be involved in numerous physiological and disease processes such as development, wound healing, cell transformation, metastasis, and tissue fibrosis (Vogel & Sheetz, 2006). ECM-cell interactions are thought to play a role is these diverse processes by regulating basic processes such as survival and growth signal generation, traction force generation, cytoskeletal re-organization and migration (Cabodi et al., 2010).

The leading edge of the cell is an important cellular zone where ECM-cell contacts form. Mediated by integrins, ECM-cell contacts involve the oligomerization of numerous proteins (Zaidel-Bar, 2007) that form focal adhesions. A subset of these proteins can be described as structural or catalytic adaptor proteins. Structural adaptor proteins can be defined as proteins that function to link ECM and cytoskeletal proteins together (i.e. talin and filamin), while catalytic adaptor proteins can be defined as focal adhesion proteins that mediate protein linkages that facilitate protein modification and downstream signaling (i.e. p130Cas and Src).

ECM-cell cytoskeletal linkages are thought to be constructed via intermolecular bonds between ECM molecules—integrins—FA proteins and—actin. Previous investigations have proposed a model in which ECM-FA linkages are mediated by stable stress fibers. While this model is consistent with data from long-term ECM-cell interactions, the architecture and dynamics of early ECM-cell linkages is still unclear. Moreover, at early time points during ECM-cell interactions, or during migration, stable stress fibers are not observed at the leading edge suggesting an alternative model.

In experiments with migratory cells, actin motion can be identified as the drift of fluorescent speckles of actin-gfp in the actin mesh over FAs. For different cell types, it has been found that the slower the actin retrograde flow, the faster the cell protrusion, suggesting that the growing actin network pushes the cell forward if sufficiently stalled at FAs (Mitchison et al., 1988; Lin et al., 1995; Jurado et al., 2005). These findings have led to the suggestion that FAs can act as molecular clutches. It is thought that as the clutch engages, retrograde flow slows down and protrusion is increased (Wang 2007; Giannone et al., 2009) In the previous examples, data is presented that shows that actin rearward flow at the leading edge can regulate focal adhesion protein localization on the order of microns. This mislocalization results in altered modification states of these proteins, as well as altered rigidity response, altered force generation on collagen, and altered downstream signaling effecting translation, growth, and proliferation. These observations highlight how varying levels of clutch engagement regulates the localization and modification of FA proteins.

The previous discussion presents data that contributes to a better temporal and spatial understanding of ECM-cell interactions. The molecular mechanisms that mediate ECM-cell interactions can be described as the following steps: 1. adhesion, 2. rigidity sensing, 3. FA formation and actin polymerization, 4. force generation, and 5. downstream signaling. Advances in the understanding of these five molecular steps are discussed in more detail below.

Adhesion: ECM Sensing, Integrin Activation and Cooperation

Adhesion is primarily thought to involve integrin activation via the binding of integrins to ECM molecules such as collagen or fibronectin. Interestingly, it has been known for sometime that different integrins mediate cell-ECM interactions for different ECM molecules i.e. $\alpha2\beta1$ integrins are known to bind collagen while, $\alpha v\beta3$ integrins bind fibronectin (Hynes, 2002). Moreover, it has been observed that as cells spread on fibronectin, $\alpha v\beta3$ integrins mediate early fibronectin interactions, while $\alpha5\beta1$ integrins mediate later stage interactions. In light of this observation, a current area of interest is to better understand the different molecular mechanisms involved in ECM sensing, or in other words, how do cells sense different biochemical components of the ECM. The previous examples show that different molecular mechanisms involved in the interactions between cells with different ECM molecules such as collagen and fibronectin. Specifically it is observed that ILK null cells are unable to maintain linkages mediated by $\beta1$ integrins (FIGS. 3 and 5). When cells are spread on collagen coated substrates, ILK null cells exhibit increased actin rearward flow, an indication of weaker FA-actin coupling (FIG. 3A). In contrast when cells are spread on fibronectin, early $\alpha v\beta3$ interactions appear normal, but later stage $\alpha5\beta1$ integrin interactions are unable to sustain the contractile forces generated by the cell and adhesions are retracted (FIG. 3B). Specifically, the observations that ILK null cells are unable to contract early in spreading on collagen, resulting in an inability to spread their cytoplasm (FIG. 3), and their ability to spread their cytoplasm while retracting late forming adhesions on fibronectin suggests a functional difference in ILK's role in sensing collagen and fibronectin (FIG. 3).

Example 3 shows that engagement of both collagen and fibronectin receptors are sufficient for adhesion formation and cell spreading on typically unpermissive soft (~0.5 kPa) surfaces. Furthermore, $\beta1$, $\beta3$ integrins, and ILK are necessary for focal adhesion formation on soft surfaces. The recruitment of paxillin and FAK allows for enhanced focal adhesion clustering and increased FA-actin coupling leading to sufficient traction forces at the leading edge on soft surfaces to sustain spreading. Engagement and clustering of $\beta1$ and $\beta3$ integrins leads to an increases adhesion and FA coupling to the cytoskeleton, that enable cells to reinforce and stabilize focal adhesions, activate ERK, the PI3K-Akt pathway and translation on soft substrates.

Upon ECM-cell interactions, adhesion and clustering of integrins results in recruitment of adaptor proteins. Integrin adaptor proteins have been classified into three categories—adaptors that have a mainly structural function, adaptors that fulfill a scaffolding function by providing binding sites for additional focal-adhesion proteins, and adaptors that have catalytic activity. Structural adaptors, including talin, kindling, filamin and tensin, bind to F-actin and therefore couple integrins to the cytoskeleton directly, allowing for traction force mediated motility events. Catalytic adaptors, such as focal adhesion kinase (FAK), Src, and protein phosphatase 2A (PP2A), are thought be involved in the propagation of signal-transduction pathways from adhesion sites. Data presented in example 2 identifies integrin-linked kinase (ILK), as a structural adaptor necessary for maintaining $\beta1$integrin-cytoskeletal linkages, endoplasm spreading, adhesion reinforcement, force generation and collagen contractions (FIGS. 1-7). Interestingly, the observations in example 2 & 3 that activated forms of proteins such as Src, FAK are mislocalized towards the interior of the leading edge identifies integrin-linked kinase as a scaffold adaptor, necessary for catalytic adapter localization (FIGS. 4-6).

All adaptors, by definition, bind to other protein partners including integrins. It is thought that there is significant functional crossover between adaptors due to the nature of the other interactions these proteins have. For example, talin and paxillin can both recruit FAK to focal adhesions (Chen et al., 1995; Hildebrand et al., 1995; Tachibana et al., 1995); FAK can also interface with the actin cytoskeleton through an interaction with the actin-regulatory Arp2-Arp3 (Arp2/3) complex (Serrels et al., 2007). Also, on fibronectin, ILK can connect integrins to F-actin by binding to the actin-binding proteins α- and β-parvin (Nikolopoulos and Turner, 2000; Nikolopoulos and Turner, 2001; Yamaji et al., 2004). The data supports the idea that ILK can connect integrins to f-actin on collagen via paxillin (FIGS. 3 and 7). Moreover, the differences in the way ILK null cells sense collagen versus fibronectin suggest that ILK plays a different functional role in forming linkages between fibronectin and collagen. The model moving forward is that ILK preferentially mediates β1 integrin interactions, as opposed to β3 integrins. The examples presented herein highlight ILK's role in α2β1 integrins binding to collagen and α5β1 integrins binding to fibronectin (FIGS. 3, 5 & 12). Taken with these observations that ILK null cells are able to sense rigidity on fibronectin, but not collagen, and exhibit different focal adhesion dynamics on collagen and fibronectin (FIG. 3), these observations support the idea that ILK mediated integrin activation occurs in an ECM specific manner.

Towards a better understanding of integrin specific molecular mechanism of ECM-cell contacts, the different roles of α and β integrin subunits in focal adhesion formation and composition can be investigated. One way to investigate the specific roles of α and β subunits would be to create chimera proteins. For example switching α2 and αV intra- and extracellular domains would be an interesting experiment to better understand how α2 integrins mediate collagen interactions and how αV integrins mediate fibronectin interactions. By expressing such chimeras in cells, one may observe different affinities to ECM molecules, altered recruitment of FA proteins, and differences in higher order processes such as rigidity sensing, force generation and migration. As more is understood and documented about β-integrin function, investigation into α-integrin's role in focal adhesion ontogeny would be of increasing interest.

Rigidity Response

After a cell adheres to the ECM via integrin receptors, and integrins are activated, the cell tests the local rigidity of the substrate. Examples 2 & 3 demonstrate this process. For example, one difference in ILK's role in linking β1 interacting collagen but not β3 interacting fibronectin is illustrated by FIG. 3, which shows that ILK null cells spread on soft collagen while they are unable to spread on soft fibronectin.

Cellular mechanosensitivity plays an important role in the growth, proliferation and function of cells during the development, maintenance, and pathology of tissues (Bershadsky et al., 2003; Discher et al., 2005; Huang and Ingber, 1999; Jaalouk and Lammerding, 2009; Nelson et al., 2005; Peyton et al., 2007; Wozniak and Chen, 2009). It is thought that the cytoskeleton of cells are composed of actin-myosin stress fibers that actively pull on the surrounding matrix or neighboring cells and generate internal and external traction forces (Bershadsky et al., 2003). Moreover, it is thought that the general purpose of these forces is to provide cells with a means of actively sensing and responding to mechanical properties such as the geometry, topography, and rigidity of the environment (Schwarz & Bischofs, 2005; Vogel & Sheetz, 2006).

Data presented in Examples 2 and 3 provide evidence for a different model of rigidity sensing. An alternate model of the rigidity response is useful because rigidity sensing is thought to occur early in the cell spreading process before stable stress fibers are present in the cell. The preliminary observation that spreading is rescued on soft surfaces when Mouse Embryonic Fibroblasts are treated with blebbistatin provides better understanding of the rigidity response. This observation suggests that when myosin, or contractile activity is inhibited, cells are able to spread on soft surfaces (0.05 kPa). Taken with the observation that reduced coupling and contractile activity in ILK null cells allow cells to spread on soft collagen, suggests that the degree of FA-actin coupling at the leading edge during spreading may be involved in the rigidity response. It is important to note that ILK null cells, while they spread on soft coated collagen, did not reinforce their focal adhesions and did not undergo the transition to a contractile phase of spreading because large rates of actin rearward flow were observed. While not being limited to any particular mechanism of action, it is believed that the lack of FA-actin coupling that allows ILK null cells to spread on soft surfaces. Conversely, when FA-actin coupling was increased by increasing ligand availability, slower actin retrograde flow and spreading on soft surfaces was measured. By coating soft polyacrylamide gels with 10 ug/ml of both collagen and fibronectin, both spreading on soft surfaces as well as contractile activity and growth and proliferation on soft surfaces were rescued. Given these observations a model in which the degree of FA-actin coupling during spreading allows for rigidity sensing by the cell was developed. Decreased FA-actin rearward flow coupling as observed in the ILK null cells circumvents the rigidity sensing mechanisms allowing for spreading, but prevents contractile activity and growth. Increased FA-actin coupling during spreading allows for spreading as well as contractile activity and growth on soft surfaces. In other words it is the level of FA-actin coupling to the rearward flow of actin that allows for rigidity sensing and not the physical interaction, and active contraction of stress fibers on FAs These studies, established a serum free experimental method for investigating cellular responses to integrin interactions and substrate rigidity. Specifically, this investigation implicates ILK as a protein involved in collagen rigidity sensing. Furthermore, these examples show an integrin based mechanism that rescues spreading and growth on soft surfaces (FIG. 15) as well as the importance of actin rearward flow and FA-actin coupling with regards to rigidity sensing. Interestingly, these observations contribute to the mechanistic understanding of cancer cells ability to circumvent the rigidity response. The data presented in examples 2 & 3 suggest a model where the interaction of nascent FAs interacting with actin rearward flow as the mechanism of the rigidity response. This is in contrast to the model that supports stable stress fibers at focal adhesions mediating the rigidity response. Interestingly, the observation that cells were able to spread on soft surfaces (FIGS. 3, 14, and 15) coated with collagen and fibronectin proved to be dependent on ILK, suggesting that ILK plays a role in the engagement and cooperation of β1 and β3 integrins in their ability to allow for FA-actin coupling, cell spreading and proliferation on collagen & fibronectin coated soft surfaces. This observation is consistent with the previous results suggesting that ILK is necessary for β1 integrin function. Finally, the observation that ILK null cells still sense rigidity on fibronectin but do not sense rigidity on collagen, provides more functional evidence supporting ILK's differential role in collagen and fibronectin sensing.

Force Generation

As mentioned in relation to the rigidity response, cells are constantly probing, pushing and pulling on the surrounding extracellular matrix (ECM). These cell generated forces drive cell migration and tissue morphogenesis and maintain the intrinsic mechanical structure of tissues and the cells they are composed of (Dembo et al., 1999; Keller et al., 2003). Such forces not only guide mechanical and structural events, but also trigger signaling pathways that promote functions ranging from proliferation to stem cell differentiation (Huang et al., 1998; McBeath et al., 2004). Therefore, precise measurements of the spatial and temporal nature of these forces are essential to understanding when and where mechanical events come to play in both physiological and pathological settings.

Early work, mainly from the laboratory of Burridge, has suggested that stress fibers represent cytoplasmic units of actin-myosin-mediated contractile activity (Burridge et al., 1981). Phosphorylation of the myosin light chain (MLC), leading to stress fiber contraction, is thought to be regulated by MLC kinase (MLCK) in response to elevated levels of intracellular Ca2+. In recent years, the work of several laboratories has suggested that the tension produced by stress fibers, regulated by Rho-kinase (ROCK)-mediated inhibition of myosin phosphatase, is the primary mechanism necessary for all force generation events.

The present examples describe various conditions of FA protein and actin rearward flow coupling, and how it regulates specific early force generation events, and investigates the relationship between actin retrograde flow and stress fiber formation. Actin rearward flow localizes myosin to ~3 um inward from the leading edge (FIG. 3G-J). This rearward localization of myosin results in rearward localization of stress fibers (FIG. 3-G-J). Specifically the observations support a model that at early time points of cell-ECM interaction force can be generated by the dynamic interaction of FAs and actin rearward flow and support a catch-slip bond model where FA proteins dynamically bind and release actin as it flows rearward. For example under periods of small focal adhesion size, actin rearward flow in MEFs exhibit rates approaching 130 nm/sec, this rate is indicative of large internal forces within the focal complex or adhesion thereby mechanically disrupting physical bonds within the growing focal complex. These internal forces prevent stable ECM-cytoskeletal interaction and linkages between the integrins and structural adaptors necessary for traction force generation. Moreover the data shows that structural adapter proteins such as talin undergo conditions of high actin retrograde flow moves rearward (FIG. 7), further supporting the idea that proteins necessary for ECM-actin linkages are mislocalized and unable to mediate the physical linkages necessary for cellular tractions forces. These observations move the current body of evidence closer to a detailed spatial and temporal understanding of how actin and FA protein flow within the lamellipodia effect force generation, actin-myosin localization, and stress fiber generation. Taken with the observations of focal adhesion formation on soft surfaces (FIG. 14), a more dynamic picture of ECM-actin linkages emerges in contrast to a model where stable stress fibers are involved in early ECM-cytoskeletal linkages and force generation events.

The work with ILK knockout cells show that ILK is necessary to maintain early force bearing contacts with collagen, and late force bearing interactions with fibronectin (FIG. 3). The binding of integrins to the ECM induces them to cluster into focal complexes, which can mature into larger focal adhesions in the case of α5β1 integrin binding to fibronectin (Geiger et al., 2001), and α2β1 integrin binding to collagen. Force measurements on collagen have not been reported in mouse embryonic fibroblasts. Cells null for ILK were unable to generate as much force on collagen, displacing collagen coated pillars ~3× less compared to wild-type cells (FIG. 6) and unable to contract collagen gels (FIG. 5). Moreover, when an external oscillatory force was applied to magnetic beads coated with collagen or fibronectin, ILK null cells were unable to reinforce collagen coated beads, while fibronectin beads were reinforced, suggesting that the linkage between collagen in force bearing adhesion complexes was disrupted without ILK, while the linkage between fibronectin and the adhesion complex was not (FIG. 5). Finally, it is demonstrated that ILK is necessary for migration, wound closure and collagen contraction, physiological events important for many force mediated processes such as development, wound healing, and ECM maintenance (FIG. 5).

Focal Adhesions Formation & Signal Generation

To date, most of the work done on focal adhesion formation and dynamics has been based on fibronectin interactions. The investigation described above details the interactions and dynamics of focal adhesions and actin on collagen and collagen plus fibronectin. This example identifies differences between β1 and β3 integrin interactions (FIGS. 3 & 7) and FA formation on collagen and fibronectin and provides evidence to support a more informative model and understanding of integrin activation, focal adhesion formation, and actin dynamics on substrates of physiologically relevant rigidities FIGS. 14-22). Interestingly, data presented in examples 2 & 3 supports a model that actin dynamics can regulate the subcellular localization of focal adhesion proteins, their modification state, and protein interactions necessary for FA formation and cellular processes such as rigidity sensing (FIGS. 3 & 14), force generation (FIGS. 5 & 15), migration (FIG. 5) and signaling events important for translation, growth and proliferation (FIGS. 4, 6, 20, & 21).

As actin dynamics at the leading edge are spatially and temporally coordinated with focal adhesion formation, maturation and dynamics, one may posit that actin dynamics plays a role in integrin activation, focal adhesion ontogeny and vice versa. Both molecular ensembles, the actin cytoskeleton and the focal adhesions are very dynamic, with all components being in a state of continuous flow and turnover. It is thought that internally or externally derived forces up to a few nano-Newtons per adhesion appear to promote the growth of adhesions in their direction (Balaban et al., 2001, Tan et al., 2003; Riveline 2001). FA size and post-forces were observed to be correlated in fibroblasts (Balaban et al., 2001; Tan et al., 2003). Consistent with these observations, on fibronectin, FA size depends on the local stiffness of the ECM (Katz 2000, Choquet et al., 1997) inhibition of myosin II, and thus contractility of the actin cytoskeletal network, reduces FAs.

Varying the rigidity of the substrate experimentally confirmed these findings on collagen and identified ILK as the molecule directly downstream of the β1 mediated molecular pathway involved in that reinforcement process (FIGS. 17-19). Models that account for force-induced anisotropic growth have been developed (Shemesh, et al., 2005; Nicolas et al., 2005) and suggest that tension-induced variations in protein density shift the balance between adsorption of new proteins and the energy cost of elastic distortions at the front and rear of a FA.

In the absence of ILK, focal adhesion protein flow is increased, namely talin, paxillin, and p130Cas, thereby limiting their availability to contribute to the functional roles they play in adhesion, force generation, and downstream signaling (FIGS. 3-9). Specifically, increased actin retrograde flow, as a result of weak integrin-actin coupling, resulted in less force generation, migration and growth (FIGS. 3-5, 12-15). Conversely, increased focal adhesion size, and integrin-actin coupling, resulted in a slower actin retrograde flow, greater localization of paxillin, and p130Cas in focal adhesions and greater force generation (FIGS. 5 & 15) as well as growth and proliferation on otherwise unpermissive substrates.

An increased flow of actin, myosin and FA proteins decreases a cells ability to localize proteins at adhesions and generate force (FIG. 1-7) and the accumulation of proteins necessary for downstream signaling. The flow of actin is directed from the leading edge to the cell's center (Wang et al., 1985), and its speed tends to be significantly higher close (within a few microns) to the leading edge of the cell (Ponti et al., 2004). Actin retrograde speeds from ~120 um/sec to ~40 um/sec were observed in the MEF's interacting with glass coated collagen. Interestingly differences in retrograde flow speed as cells were plated on different rigidities suggests differences in the level of FA-actin coupling. This observation shows that actin retrograde flow effects the ability to localize FA proteins and for cells to generate forces at the contact points of FAs and the ECM, and localize proteins necessary for downstream signaling.

Methods for evaluating the dynamics of individual protein species include fluorescence speckle microscopy (FSM), in which only a small portion of the molecules are tagged and followed, and image correlation spectroscopy, in which distinct directional drifts of fluorescence probes are detected. Both methods indicate that there is a range of protein mobility. This was consistent with protein dynamics using TIRF on collagen in wild-type mouse embryonic fibroblasts. Moreover, integrin binding proteins such as ILK are necessary to couple the ECM protein collagen to actin, and the lack of coupling leads to increased flow of actin and subsequently the flow of focal adhesion proteins (FIGS. 4-7). Reducing coupling can induce increased rearward flow of focal adhesion proteins was the first of its kind and adds important information to the current model of focal adhesion mediated force generation and signal generation.

In wild type cells, focal adhesion proteins that are most closely associated with integrins are nearly immobile, while those that are most closely associated with actin filaments are highly mobile (Hu et al., 2007; Brown et al., 2006; Wang, 2007) intermediate behaviors are also seen. Upon deletion or inactivation of integrin binding FA proteins, most FA proteins, either proximal or distal to the integrin in their binding, flow at relatively faster rates depending on their affinity to actin (FIGS. 3-5).

From these observations the data support a catch/slip bond formation model of actin and focal adhesion dynamics at the leading edge. Focal adhesion proteins, with varying affinities to actin, interact with the dynamic actin network and move reward at increasing speeds as their affinity to actin increases and coupling decreases (FIGS. 4-6, 12, -18). The working model is supported by the observations that the motions of different molecules in FAs correlate to varying degrees with the motions of actin filaments (Hu et al., 2007), which suggests that layers of FA and cytoskeletal components can slip relative to each other consistent with the model that describes FAs as molecular clutches. Data in the ILK cell line system and with substrates of increasing rigidity and ECM concentration support the model of FAs as clutches. As FAs increase in size, either with the presence of ILK or increasing rigidity and ECM concentration, actin rearward flow decreases and traction force increases (FIGS. 1-7, 12-17). Interestingly, as FAs grow, and actin retrograde flow decreases, the localization of signaling molecules in FAs necessary for translation, growth and proliferation increases (FIGS. 3-8, 21, 22).

The above examples show that actin retrograde flow can alter the localization and modification state of ERK, JNK, and proteins that regulate translation (i.e. p90RSK1, and p70S6K). The observation that mislocalization of paxillin and p130Cas by actin results in the mislocalization and altered modification of ERK, JNK (FIG. 6) and regulators of translation (FIGS. 21 & 22) suggests that actin dynamics, via the mislocalization of catalytic adaptors and signaling proteins, do not only alter force generation events but also alter downstream signaling and activation states of proteins important for cellular functions such as transcription activation.

ECM-cell interactions contribute important information on molecular mechanisms related to many cellular and tissue functions such as development, differentiation, and wound healing as well as disease states such as epithelial-born cancers, cardiac hypertrophy, kidney fibrosis and engineering problems such as organogenesis and neuronal regeneration. An understanding of the molecular mechanism involved in ECM-cell interactions and its regulation of emerging properties such as rigidity sensing, force generation and growth and proliferation provides insight, and molecular targets for the discovery of novel biomarkers, and important therapeutics.

Using model cancer cell line systems and cancer cells, it is reported here the effects of reduced focal adhesion-actin coupling in cells and demonstrate focal adhesion (FA) proteins such as p130Cas, paxillin and talin exhibit faster rearward flow in the context of lower extracellular matrix-FA-actin coupling. It is shown that a certain level of FA-actin coupling is necessary for the activation and stabilization of integrin mediated adhesions, the rigidity response, traction force, and signal generation. In the model cells investigated, the linkage of the integrin to actin is mediated by the size and composition of FAs and is related to the speed of the actin retrograde flow. Thus, FA-actin coupling and their relative dynamics is important for focal adhesion formation, reinforcement, substrate traction and the localization and activation of signaling proteins that regulate growth, proliferation, survival, transcription, translation, endocytosis, exocytosis, migration, invasion, and motility events. As focal adhesion size varies, allowing for various levels of ECM-FA-actin coupling, regulation of signaling molecules involved in the aforementioned processes are modulated.

One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety.

What is claimed is:

1. A method for determining a property of a cell, comprising:
   (a) disposing the cell on a matrix material including one or more of fibronectin, collagen type I, laminin, vitronectin, and collagen type IV;
   (b) imaging the cell as it changes due to interaction with the matrix material to evaluate a value or change in two or more biomarkers in the cell, wherein the two or more biomarkers of the cell comprise a Focal Adhesion Size (FAS) and an Actin Retrograde Flow Speed (RFS); and wherein the two or more biomarkers further include measuring one or more oncogenic biochemical variables, wherein the oncogenic biochemical variables selected from the group consisting of, a Western titrated average of P-FAK (Y397), a Western titrated average of P-PAX(S181), a Western titrated average of P-p130Cas (Y165), a Micron Scale ELISA average of a protein of interest, NFkappaB transcription average, a Ratio of Tyrosine Phosphorylated Adhesion Kinase to Focal Adhesion Phosphatase, an ECM Composition of Dissassociated Tissue, an Immuno-stain of PhosphoProtein, an mRNA Localization Intensity, a Ratio of NFKappaB transcription factor and p53 activation state, a Ratio of STAT transcription factor and p53 activation state, and combinations thereof; and
   (c) measuring the value or change in the two or more biomarkers characteristic of the change in the cell as it interacts with the matrix material;
   (d) calculating two or more quantifiable metrics based on a mathematical expression using the measurement of the value or change in the two or more biomarkers, including the oncogenic biochemical variables; and
   (e) outputting a result of the calculating two or more quantifiable metrics that permits a determination of a potential of the cell, and wherein the potential of the cell is a future growth characteristic of the cell, an oncogenic potential of the cell or a metastatic potential of the cell;
   and the calculating comprises a traction force index (TFI) and correlates with at least one of the oncogenic potential of the cell type and the metastatic potential of the cell, wherein the mathematical expression is defined by FAS/RFS.

2. A method for determining a property of a cell, comprising:
   (a) disposing the cell on a matrix material including one or more of fibronectin, collagen type I, laminin, vitronectin, and collagen type IV;
   (b) imaging the cell as it changes due to interaction with the matrix material to evaluate a value or change in two or more biomarkers in the cell, wherein the two or more biomarkers of the cell comprise a Focal Adhesion Size (FAS) and an Actin Retrograde Flow Speed (RFS); and wherein the two or more biomarkers further include, measuring one or more oncogenic biochemical variables, wherein the oncogenic biochemical variables selected from the group consisting of an ILK expression level, a Western titrated average of P-FAK (Y397), a Western titrated average of P-PAX (S181), a Western titrated average of P-p130Cas (Y165), a Micron Scale ELSA average of a protein of interest, NFkappaB transcription average, a Ratio of Tyrosine Phosphorylated Adhesion Kinase to Focal Adhesion Phosphatase, an ECM Composition of Dissassociated Tissue, an Immuno-stain of PhosphoProtein, an mRNA Localization Intensity, a Ratio of NFKappaB transcription factor and p53 activation state, a Ratio of STAT transcription factor and p53 activation state, and combinations thereof; and
   (c) measuring the value or change in the two or more biomarkers characteristic of the change in the cell as it interacts with the matrix material;
   (d) calculating two or more quantifiable metrics based on a mathematical expression using the measurement of the value or change in the two or more biomarkers, including the oncogenic biochemical variables; and
   (e) outputting a result of the calculating two or more quantifiable metrics that permits a determination of a potential of the cell, and wherein the potential of the cell is a future growth characteristic of the cell, an oncogenic potential of the cell or a metastatic potential of the cell;
   and the calculating comprises a traction force index (TFI) and correlates with at least one of the oncogenic potential of the cell type and the metastatic potential of the cell, wherein the mathematical expression is defined by FAS/RFS.

* * * * *